United States Patent [19]

Narisada et al.

[11] Patent Number: 4,861,913
[45] Date of Patent: Aug. 29, 1989

[54] BICYCLIC SULFONAMIDE DERIVATIVES

[75] Inventors: Masayuki Narisada, Osaka; Mitsuaki Ohtani, Nara; Fumihiko Watanabe, Nara; Sanji Hagishita, Nara; Kaoru Seno; Susumu Kamata, both of Hyogo; Nobuhiro Haga, Osaka; Tatsuo Tsuri, Hyogo; Tadahiko Tsushima; Kenji Kawada, both of Osaka, all of Japan

[73] Assignee: Shionogi & Co., Ltd., Osaka, Japan

[21] Appl. No.: 927,823

[22] Filed: Nov. 5, 1986

[30] Foreign Application Priority Data

Nov. 18, 1985 [JP] Japan ................. 60-259154
Feb. 13, 1986 [JP] Japan ................. 61-30130
May 19, 1986 [JP] Japan ................. 61-115599
Jun. 3, 1986 [JP] Japan ................. 61-129011
Jul. 17, 1986 [JP] Japan ................. 61-169257

[51] Int. Cl.$^4$ .......................... C07C 143/72
[52] U.S. Cl. .......................... 562/427; 546/269;
546/293; 549/23; 549/57; 549/90; 549/397;
549/463; 549/546; 560/12; 560/13; 560/118;
560/120; 562/500; 562/502
[58] Field of Search ........... 560/12, 13, 118, 120;
562/427, 500, 502; 546/269, 293; 549/463

[56] References Cited

U.S. PATENT DOCUMENTS 3,988,362 10/1976 Bernauer et al. ............ 260/471 C
4,389,413 6/1983 Hamanaka et al. ............ 562/427 X
4,458,091 7/1984 Jones et al. .................. 562/427 X
4,647,585 3/1987 Loots et al. .................. 562/427 X
4,654,357 3/1987 Nakane ..................... 549/463 X

FOREIGN PATENT DOCUMENTS 2004327 9/1970 Fed. Rep. of Germany .

OTHER PUBLICATIONS

Watanabe, et al.; C.A. 108: 111866e.

Primary Examiner—Joseph Paul Brust
Attorney, Agent, or Firm—Wenderoth, Lind & Ponack

[57] ABSTRACT

Bicyclic sulfonamido derivatives represented by the formula:

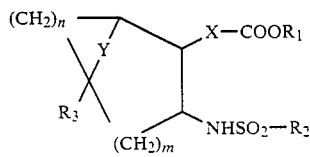

wherein $R_1$ is a hydrogen or lower alkyl; $R_2$ is an alkyl, substituted or unsubstituted arly, aralkyl or hetelocycle; $R_3$ is a hydrogen or methyl; X is an alkylene or alkenylene which may be substituted by a fluorine atom or atoms an may contain an oxygen, sulfur and/or phenylene in the chain; Y is straight or branched alkylene or alkenylene, oxygen, or sulfur; m is 0 or 1; and n is 0, 1 or 2, or their salt, said derivatives being useful as anti-thrombotic, anti-vasoconstricting, and anti-bronchoconstricting drugs.

13 Claims, No Drawings

BICYCLIC SULFONAMIDE DERIVATIVES

BACKGROUND OF THE INVENTION

1. Field of the Invention

The present invention relates to new compounds used as medicines for improving symptoms caused by thromboxane. Moreover, this invention relates to compounds as represented by the general formula (I) and their salts, which are used as antithrombotic, anti-vasoconstricting, and anti-bronchoconstricting drugs.

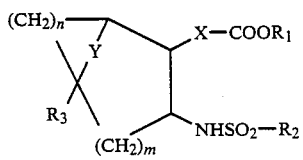  (I)

wherein $R_1$ is hydrogen or lower alkyl; $R_2$ is alkyl, substituted or unsubstituted aryl, aralkyl or heterocycle; $R_3$ is hydrogen or methyl; X is alkylene or alkenylene which may be substituted by a fluorine atom or atoms and may contain an oxygen, sulfur and/or phenylene in the chain; Y is straight or branched alkylene or alkenylene, oxygen, or sulfur; m indicates 0 or 1; and n indicates 0, 1 or 2, or its salt.

In detail, the compounds of this invention can be represented by the following general formulae.

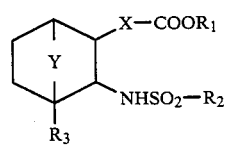  (IA)

When m is 0; and n is 2.

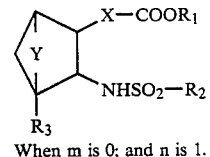  (IB)

When m is 0; and n is 1.

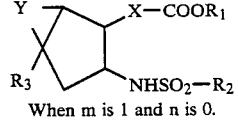  (IC)

When m is 1 and n is 0.

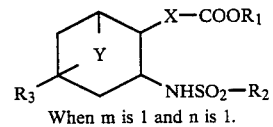  (ID)

When m is 1 and n is 1.

wherein $R_1$, $R_2$, $R_3$, X and Y each is as defined above.

In more detail, the compounds of this invention can be represented by the following general formulae (Ia) to (Ih).

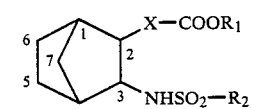  (Ia)

When $R_3$ is hydrogen; Y is methylene; m is 0; and n is 2.

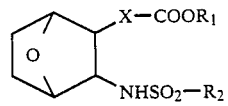  (Ib)

When $R_3$ is hydrogen; Y is oxygen; m is 0; and n is 2.

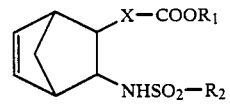  (Ic)

When $R_3$ is hydrogen; Y is vinylene; m is 0; and n is 1.

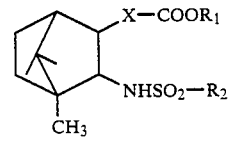  (Id)

When $R_3$ is methyl; Y is dimethylmethylene; m is 0; and n is 2.

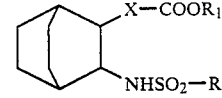  (Ie)

When $R_3$ is hydrogen; Y is ethylene; m is 0; and n is 2.

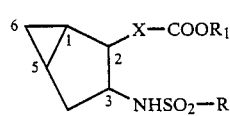  (If-a)

When $R_3$ is hydrogen; Y is methylene; m is 1; and n is 0.

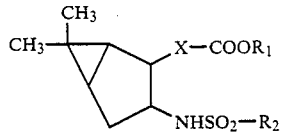  (If-b)

When $R_3$ is hydrogen; Y is dimethylmethylene; m is 1; and n is 0.

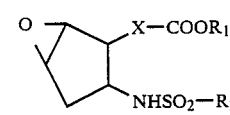  (Ig-a)

When $R_3$ is hydrogen; Y is oxygen; m is 1; and n is 0.

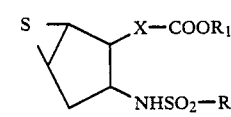  (Ig-b)

When $R_3$ is hydrogen; Y is sulfur; m is 1; and n is 0.

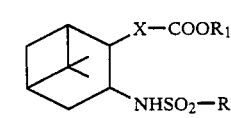  (Ih)

When $R_3$ is hydrogen; Y is dimethylmethylene; m is 1; and n is 1.

wherein $R_1$ $R_2$ and X each is as defined above.

When thrombin acts on platelets, cyclooxygenase is activated. By activation of cyclooxygenase, thromboxane A₂ is produced enzymatically in platelets, vessel wall, and various other cells, from arachidonic acid through prostaglandins G$_2$ and H$_2$. This product has various potent physiologic or pathogenic actions. In particular, the potent platelet agglutination action and the action constricting the smooth muscle of bronchi, and of coronary, cerebral and pulmonary arteries, etc. are considered to be the factors which relate to the onset and progress of such circulatory and respiratory diseases as angina pectoris, myocardial infarction, cerebral infarction, and bronchial asthma. Moreover, it is said that the strong action occurs even at a concentration of $10^{-10}$–$10^{-11}$M. Therefore, increasing attention has been paid to the development of thromboxane A$_2$ antagonists or inhibitors as anti-thrombotics, anti-vasoconstrictives or anti-bronchoconstrictives. Inhibitors, however, have some problems: in view of the fact that they influence on prostaglandins which bear various important roles as well as thromboxane A$_2$, and uncontrollable thromboxane-like harmful effects are caused by accumulated substrates such as prostaglandins H$_2$. So, development of antagonists has especially been sought.

The inventors succeeded in the synthesis of the bicyclic sulfonamide derivatives represented by the general formula (I), and found that these new compounds have potent activity as thromboxane A$_2$ receptor antagonists, and are chemically and biochemically stable. The present invention was based on these findings.

2. Description of the Prior Art

The general course of atherosclerosis, which is regarded as the main risk factor of myocardial infarction and cerebral infarct, begins in the arterial intima with mucoid accumulation and fibroblast formation, progressively followed by degeneration, lipid and cholesterol deposition, and destruction and atheromasia of the intima tissue, with gradual formation of high-degree and localized hypertrophy in the intima. The atherosclerosis has long been regarded to be caused by thrombuse formation and fibrin deposition, but recent discoveries of thromboxane A$_2$ (TXA$_2$) by Samuelsson et al. and prostacyclin (PGI$_2$) by Vane et al. have revealed an interaction between platelets and vessel wall. Platelets are said to play an important role in the onset and progress of atherosclerosis. Therefore, it is now recognized that the use of antithrombotic drugs, particularly drugs which inhibit platelet agglutination, are effective for the treatment of atherosclerotic diseases.

In addition to the conventional antithrombotic drugs such as heparin and coumarin compounds, certain types of prostaglandins are known to have a potent platelet agglutination inhibitory action. From these facts, prostaglandin derivatives have attracted much attention as possible antithrombotic drugs. For example, analogues of prostaglandin E$_1$ and I$_2$ receptor agonists have been developed. Since thromboxane A$_2$ shows potent platelet agglutination and vasoconstriction action, thromboxane A$_2$ synthesis inhibitors, such as cyclooxygenase inhibitors and thromboxane synthetase inhibitors, and thromboxane A$_2$ receptor antagonists, have been developed. The thromboxane A$_2$ receptor antagonists include 13-APA [Venton D. L. et al., J. Med. Chem., 22, 824 (1979)], PTA$_2$ [Lefer A. M. et al., Proc. Natl. Acad. Sci. U.S.A., 76, 2566, (1979)], BM-13177 ]Lefer A. M. et al., Drugs of Today, 21, 283 (1985)], SQ-29548 [Ogletree et al., J. Pharmacol. Exp. Ther., 34, 435, (1985)], and the compounds as disclosed in U.S. patent application No. 259154/1985.

SUMMARY

Bicyclic sulfonamide derivatives represented by the formula:

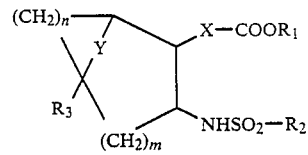

wherein R$_1$ is a hydrogen or lower alkyl; R$_2$ is an alkyl, substituted or unsubstituted aryl, aralkyl or heterocycle; R$_3$ is a hydrogen or methyl; X is an alkylene or alkenylene which may be substituted by a fluorine atom or atoms and may contain a oxygen, sulfur and/or phenylene in the chain; Y is straight or branched alkylene or alkenylene, oxygen, or sulfur; m indicates 0 or 1; and n indicates 0, 1 or 2, or their salts are provided in this invention. Said compounds are used as antithrombotic, antivasconstricting, and anti-bronchoconstricting drugs.

DESCRIPTION OF THE PREFERRED EMBODIMENTS

The following definitions are given for various terms used throughout this specification.

The term "lower alkyl" means a straight or branched alkyl of C$_1$–C$_5$, for example, methyl, ethyl, n-propyl, isopropyl, butyl, pentyl and so forth. The term "alkyl" means a straight or branched alkyl of C$_1$–C$_{10}$, for example, methyl, ethyl, propyl, isopropyl, butyl, sec-butyl, pentyl, isopentyl, hexyl, heptyl, octyl, nonyl, decyl, and so forth. The term "aryl" includes aromatic ring radicals such as phenyl, naphthyl or the like polycyclic aromatic hydrocarbon groups. The term "aralkyl" means the above-mentioned alkyl substituted by the above-mentioned aryl at an optional position. The term "heterocycle" means nitrogen-, oxygen- and/or sulfur-containing 5- or 6-membered one, e.g., furyl, thienyl, oxazolyl, pyridyl, pyrimidyl, benzimidoyl and the like. The substituents on the aryl, aralkyl or heterocycle include lower alkyl (e.g., methyl, ethyl), lower alkoxy (e.g., methoxy), nitro, hydroxy, carboxy, cyano, amino, lower alkylamino (e.g., methylamino), lower dialkylamino (e.g., dimethylamino) whose two alkyl groups may be different from each other, alkanoylamino (e.g., acetamide), halogens (e.g., chloro, fluoro) and so forth. The term "alkanoyl" means those of C$_1$–C$_3$ such as formyl, acetyl, propionyl and so forth. The halogens includes fluorine, chlorine, bromine and iodine. One or more of those substituents may be located at any possible position of the group. The term "alkylene" means a C$_1$–C$_7$ alkylene, for example, methylene, ethylene, trimethylene, tetramethylene, pentamethylene, hexamethylene, heptamethylene, or the like. The term "alkenylene" means a group having one or more double bonds in the above-mentioned C$_2$–C$_7$ alkylene, e.g., vinylene, 1-propenylene, 2-propenylene, 1-butenylene, 2-butenylene, 3-butenylene, 1,2-butadienylene, 1,3-butadienylene, 1-pentenylene, 2-pentenylene, 3-pentenylene, 4-pentenylene, 1,2-pentadienylene, 1,3-pentadienylene, 1,4-pentadienylene, 2,3-pentadienylene, 2,4-pentadienylene, 1-hexenylene, 2-hexenylene, 3-hexenylene, 4-hexenylene, 5-hexenylene, 1,2-hexadienylene, 1,3-hexadienylene, 1,4-hexadienylene, 1,5-hexadienylene, 2,3-hexadienylene, 2,4-hexadienylene, 2,5-hexadienylene, 3,4-hexadienylene, 3,5-hexadienylene, 4,5-hexadienylene, 1-heptenylene, 2-heptenylene, 3-heptenylene, 4-heptenylene, 5-heptenylene, 6-heptenylene, 1,2-heptadienylene, 1,3-heptadienylene, 1,4-heptadienylene, 1,5-heptadienylene, 1,6-heptadienylene, 2,3-heptadienylene, 2,4-heptadienylene, 2,5-heptadienylene, 2,6-heptadienylene, 3,4-heptadienylene, 3,5-heptadienylene, 3,6-heptadienylene, 4,5-heptadienylene, 4,6-heptadienylene, 4,5-heptadienylene, 4,6-heptadienylene, 5,6-heptadienylene, or the like. The "branched alkylene" means such as dimethylmethylene, methylethylmethylene, diethylmethylene, and the like.

In the above definition, preferable $R_1$ is hydrogen or lower alkyl, e.g., methyl, ethyl, or n-propyl. Preferable $R_2$ alkyl, e.g., methyl, ethyl, propyl, isopropyl, butyl, sec-butyl, pentyl, isopentyl, hexyl, heptyl, octyl, nonyl, decyl, and so forth, substituted or unsubstituted aryl, e.g., phenyl, o-tolyl, m-tolyl, p-tolyl, 4-ethylphenyl, 4-pentylphenyl, 4-carboxyphenyl, 4-acetylphenyl, 4-(N,N-dimethylamino)phenyl, 4-nitrophenyl, 4-hydroxyphenyl, 4-methoxyphenyl, 4-fluorophenyl, 4-chlorophenyl, aralkyl, e.g., benzyl, phenethyl, naphthyl, or heterocycle, e.g., pyridyl. $R_3$ is hydrogen or methyl. Preferable X is a 2-butenylene, hexamethylene, 2-hexenylene, 1-fluoro-2-hexenylene, trimethylenethioethylene, ethylenethiotrimethylene, phenylenoxymethylene, 2-propenylene-m-phenylene, or the like. Preferable Y is a methylene, ethylene, vinylene, dimethylmethylene, oxygen or sulfur.

Illustrative of the compounds (I) of the invention are as follows:

5(Z)-7-(endo-3-Methanesulfonamidobicyclo[2.2.1]hept-exo-2-yl)-5-heptenoic acid
5(Z)-7-(endo-3-Hexanesulfonamidobicyclo[2.2.1]hept-exo-2-yl)-5-heptenoic acid
5(Z)-7-(endo-3-Benzenesulfonamidobicyclo[2.2.1]hept-exo-2-yl)-5-heptenoic acid
5(Z)-7-[endo-3-(4-Methoxybenzenesulfonamido)bicyclo[2.2.1]hept-exo-2-yl]-5-heptenoic acid
5(Z)-7-[endo-3-(4-Nitrobenzenesulfonamido)bicyclo[2.2.1]hept-exo-2-yl]-5-heptenoic acid
5(Z)-7-[endo-3-(4-Dimethylaminobenzenesulfonamido)bicyclo[2.2.1]hept-exo-2-yl]-5-heptenoic acid
5(Z)-7-[endo-3-(o-Toluenesulfonamido)bicyclo[2.2.1]hept-exo-2-yl]-5-heptenoic acid
5(Z)-7-[endo-3-(p-Toluenesulfonamido)bicyclo[2.2.1]hept-exo-2-yl]-5-heptenoic acid
5(Z)-7-[endo-3-(m-Toluenesulfonamido)bicyclo[2.2.1]hept-exo-2-yl]-5-heptenoic acid
5(Z)-7-[endo-3-(4-Ethylbenzenesulfonamido)bicyclo[2.2.1]hept-exo-2-yl]-5-heptenoic acid
5(Z)-7-[endo-3-(4-Pentylbenzenesulfonamido)bicyclo[2.2.1]hept-exo-2-yl]-5-heptenoic acid
5(Z)-7-[endo-3-(4-Carboxybenzenesulfonamido)bicyclo[2.2.1]hept-exo-2-yl]-5-heptenoic acid
5(Z)-7-[endo-3-(4-Hydroxybenzenesulfonamido)bicyclo[2.2.1]hept-exo-2-yl]-5-heptenoic acid
5(Z)-7-[endo-3-(4-Fluorobenzenesulfonamido)bicyclo[2.2.1]hept-exo-2-yl]-5-heptenoic acid
5(Z)-7-[endo-3-(4-Chlorobenzenesulfonamido)bicyclo[2.2.1]hept-exo-2-yl]-5-heptenoic acid
5(Z)-7-[endo-3-Phenylmethanesulfonamidobicyclo[2.2.1]hept-exo-2-yl]-5-heptenoic acid
5(Z)-7-[endo-3-(2-Phenylethanesulfonamido)bicyclo[2.2.1]hept-exo-2-yl]-5-heptenoic acid
5(Z)-7-[endo-3-(2-Naphthalenesulfonamido)bicyclo[2.2.1]hept-exo-2-yl]-5-heptenoic acid
5(Z)-7-[endo-3-(2-Pyridinesulfonamido)bicyclo[2.2.1]hept-exo-2-yl]-5-heptenoic acid
7-[endo-3-Benzenesulfonamidobicyclo[2.2.1]hept-exo-2-yl]-heptanoic acid
3(Z)-5-[endo-3-Benzenesulfonamidobicyclo[2.2.1]hept-exo-2-yl]-3-pentenoic acid
3(Z)-5-[endo-3-(4-Chlorobenzenesulfonamido)bicyclo[2.2.1]hept-exo-2-yl]-3-pentenoic acid
3(Z)-5-[endo-3-(p-Toluenesulfonamido)bicyclo[2.2.1]hept-exo-2-yl]-3-pentenoic acid
3(Z)-5-[endo-3-(4-Fluorobenzenesulfonamido)bicyclo[2.2.1]hept-exo-2-yl]-3-pentenoic acid
3(Z)-5-[endo-3-(4-Carboxybenzenesulfonamido)bicyclo[2.2.1]hept-exo-2-yl]-3-pentenoic acid
3-[3-(endo-3-Benzenesulfonamido)bicyclo[2.2.1]hept-exo-2-yl]-1(Z)-1-propenyl]benzoic acid
3-[3-(endo-3-Benzenesulfonamido)bicyclo[2.2.1]hept-exo-2-yl]-1(E)-1-propenyl]benzoic acid
4-(endo-3-Benzenesulfonamidobicyclo[2.2.1]hept-exo-2-yl)phenoxyacetic acid
7-(endo-3-Benzenesulfonamidobicyclo[2.2.1]hept-exo-2-yl)-4-thiaheptanoic acid
7-(endo-3-Benzenesulfonamidobicyclo[2.2.1]hept-exo-2-yl)-5-thiaheptanoic acid
5(Z)-7-(endo-3-Benzenesulfonamidobicyclo[2.2.1]hept-exo-2-yl)-7-fluoro-5-heptenoic acid
5(Z)-7-(endo-3-Benzenesulfonamidobicyclo[2.2.1]hept-5-enexo-2-yl)-5-heptenoic acid
5(Z)-7-(exo-3-Benzenesulfonamido-4,7,7-trimethylbicyclo[2.2.1]hept-endo-2-yl)-5-heptenoic acid
5(Z)-7-(endo-3-Benzenesulfonamidobicyclo[2.2.1]hept-endo-2-yl)-5-heptenoic acid
5(Z)-7-(exo-3-Benzenesulfonamidobicyclo[2.2.1]hept-endo-2-yl)-5-heptenoic acid
5(Z)-7-(exo-3-Benzenesulfonamidobicyclo[2.2.1]hept-exo-2-yl)-5-heptenoic acid
5(Z)-7-(exo-3-Benzenesulfonamido-7-oxabicyclo[2.2.1]hept-endo-2-yl)-5-heptenoic acid
5(Z)-7-(exo-3-Benzenesulfonamido-7-oxabicyclo[2.2.1]hept-exo-2-yl)-5-heptenoic acid
5(Z)-7-(endo-3-Benzenesulfonamido-7-oxabicyclo[2.2.1]hept-exo-2-yl)-5-heptenoic acid
5(Z)-7-(endo-3-Benzenesulfonamido-7-oxabicyclo[2.2.1]hept-endo-2-yl)-5-heptenoic acid
5(Z)-7-(exo-3-Benzenesulfonamidobicyclo[2.2.2]oct-endo-2-yl)-5-heptenoic acid
(1β,2α,3β,5β)-7-5(Z)-(3-Benzenesulfonamidobicyclo[3.1.0]hexan-2-yl)-5-heptenoic acid
(1β,2α,3α,5β)-7-5(Z)-(3-Benzenesulfonamidobicyclo[3.1.0]hexan-2-yl)-5-heptenoic acid
(1α,2α,3β,5α)-7-5(Z)-(3-Benzenesulfonamidobicyclo[3.1.0]hexan-2-yl)-5-heptenoic acid
(1β,2α,3β,5β)-7-5(Z)-(3-Benzenesulfonamido-6,6-dimethylbicyclo[3.1.0]hexan-2-yl)-5-heptenoic acid
(1α,2α,3β,5α)-7-5(Z)-(3-Benzenesulfonamido-6,6-dimethylbicyclo[3.1.0]hexan-2-yl)-5-heptenoic acid
(1α,2α,3β,5α)-7-5(Z)-(3-Benzenesulfonamido-6-oxabicyclo[3.1.0]hexan-2-yl)-5-heptenoic acid
(1α,2α,3α,5α)-7-5(Z)-(3-Benzenesulfonamido-6-oxabicyclo[3.1.0]hexan-2-yl)-5-heptenoic acid
(1β,2α,3β,5β)-7-5(Z)-(3-Benzenesulfonamido-6-oxabicyclo[3.1.0]hexan-2-yl)-5-heptenoic acid
(1β,2α,3α,5β)-7-5(Z)-(3-Benzenesulfonamido-6-oxabicyclo[3.1.0]hexan-2-yl)-5-heptenoic acid
(1β,2α,3β,5β)-7-5(Z)-(3-Benzenesulfonamido-6-thiabicyclo[3.1.0]hexan-2-yl)-5-heptenoic acid (1α,2α,3α,5α)-7-5(Z)-(3-Benzenesulfonamido-6-thiabicyclo[3.1.0]hexan-2-yl)-5-heptenoic acid
(1α,2α,3β,5α)-7-5(Z)-(3-Benzenesulfonamido-6-thiabicyclo[3.1.0]hexan-2-yl)-5-heptenoic acid
5(Z)-7-[endo-3-Benzenesulfonamido-6,6-dimethylbicyclo[3.1.1]hept-exo-2-yl]-5-heptenoic acid
5(E)-7-[endo-3-Benzenesulfonamido-6,6-dimethylbicyclo[3.1.1]hept-exo-2-yl]-5-heptenoic acid
5(Z)-7-[exo-3-Benzenesulfonamido-6,6-dimethylbicyclo[3.1.1]hept-exo-2-yl]-5-heptenoic acid
5(E)-7-[exo-3-Benzenesulfonamido-6,6-dimethylbicyclo[3.1.1]hept-exo-2-yl]-5-heptenoic acid
5(Z)-7-[endo-3-Benzenesulfonamido-6,6-dimethylbicyclo[3.1.1]hept-endo-2-yl]-5-heptenoic acid
5(Z)-7-[exo-3-Benzenesulfonamido-6,6-dimethylbicyclo[3.1.1]hept-endo-2-yl]-5-heptenoic acid and their optically active isomers and their salts.

The salts of the compounds represented by general formula (I) can include, for example, alkali metal salts such as lithium salt, sodium salt, and potassium salt, alkaline earth metal salts, such as calcium salt, ammonium salt, salts with organic bases such as triethylamine, dicyclohexylamine, N-methylmorpholine, and pyridine, and salts with amino acids such as glycine, valine, and alanine.

In the following reaction schemes, the respective compounds are represented by one of the enantiomers in each step. The absolute configuration of the optically active compounds are indicated by the R and S designation in their compound number.

Reaction Scheme I-1

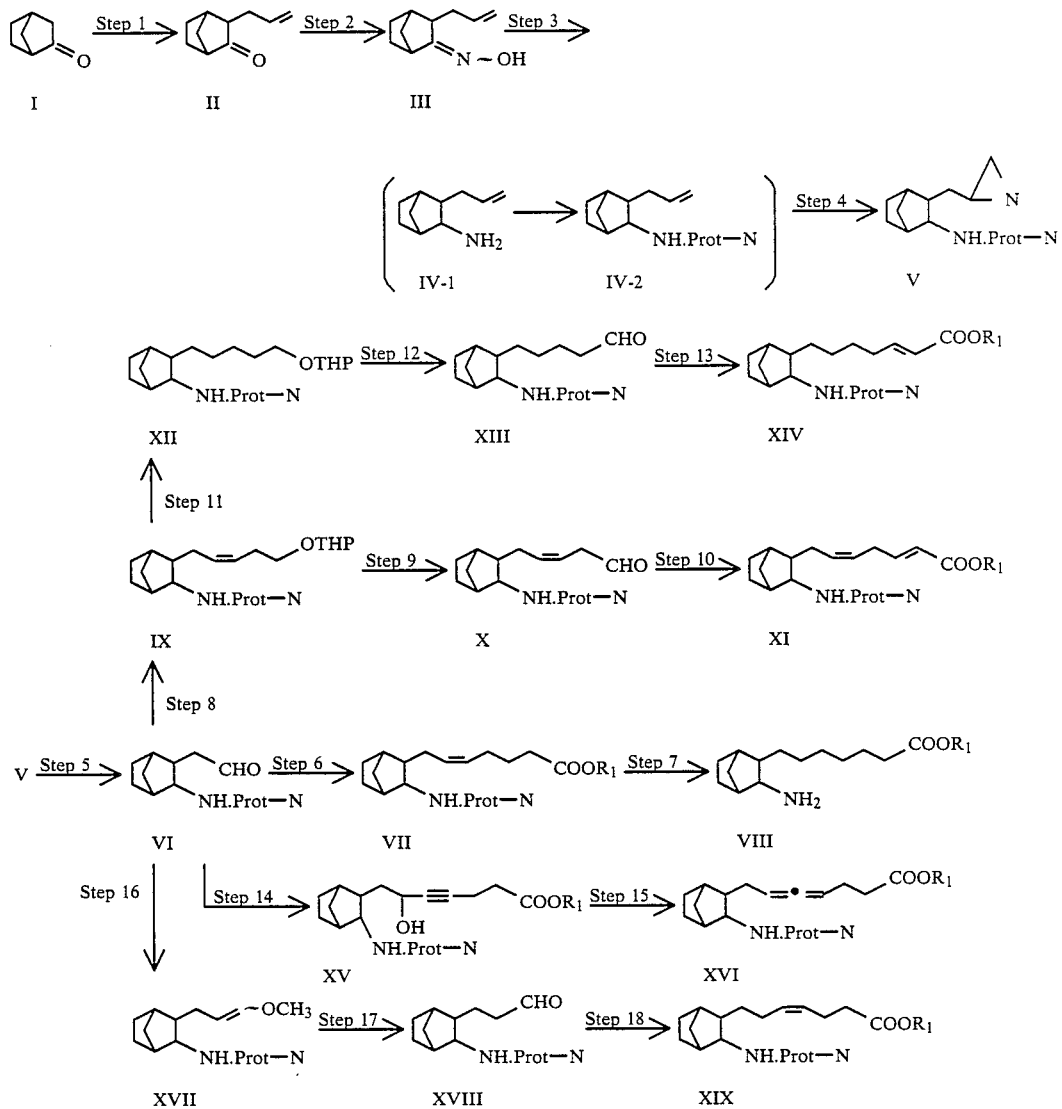

-continued
Reaction Scheme I-1

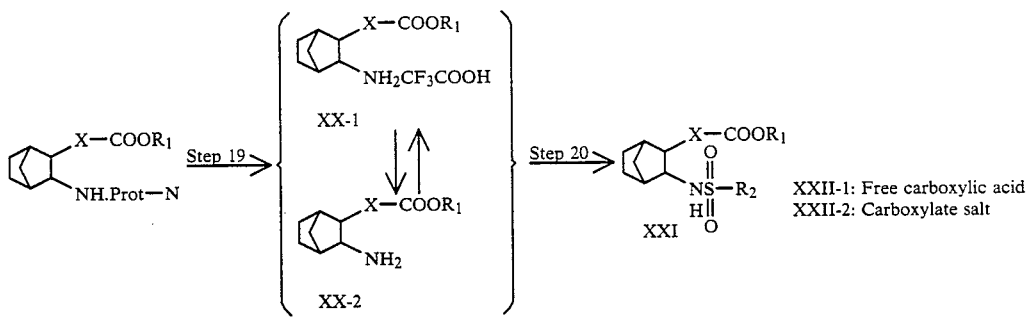

XXII-1: Free carboxylic acid
XXII-2: Carboxylate salt (Step 1)

In this step, an allyl group is introduced into the active methylene of the compound I. An allylating agent such as allyl halide, e.g., allyl chloride, allyl bromide, or allyl iodide, is used in this step. As a catalyst, such as relatively strong base as sodium amide, potassium tert-butoxide, sodium hydride, or lithium diisopropylamide may be used. It is desirable to use as a solvent ethers such as tetrahydrofuran, ether, glyme, or diglyme. The reaction is achieved at a temperature of $-78°$ C. to $25°$ C. for a period of several minutes to several hours.

(Step 2)

In this step, the 3-ketone of the compound II is converted into the oxime. The oxime formation may be carried out using hydroxylamine hydrochloride or sodium hydroxyamidosulfate in the presence of a base. As a base, potassium hydroxide, sodium carbonate, or sodium acetate is used and as a solvent methanol or ethanol is used. The reaction is carried out at room temperature for a period of several tens of minutes to several hours.

(Step 3)

In this step, the oxime III is reduced into the amine IV-1, which is then protected within purification. The reduction may be achieved with a reducing agent such as zinc/hydrochloric acid, stannous chloride/hydrochloric acid, or lithium aluminum hydride in a solvent such as ether, tetrahydrofuran, diglyme, ethanol, or methanol. This reaction is effected at room temperature or under refluxing for several hours. As an aminoprotecting group, those ordinarily used as a protecting group such as benzyloxycarbonyl, tert-butoxycarbonyl, or triphenylmethyl may be used. In this reaction, a base such as pyridine, 4-dimethylaminopyridine, or triethylamine may be added as required. As a solvent, dichloromethane or chloroform may be used and the reaction is carried out at room temperature for a period of several tens of minutes to several hours.

(Step 4)

In this step, the double bond of allyl group of the compound IV-2 is oxidized into epoxide. As an oxidizing agent, a combination of hydrogen peroxide and transition metal, peroxy acid or peroxy acid ester such as performic acid, peracetic acid, perbenzoic acid, monoperphthalic acid, monopermaleic acid, pertrifluoroacetic acid, m-chloroperbenzoic acid, or p-nitroperbenzoic acid may be used. As a solvent, ethers such as ethers, ether or tetrahydrofuran, alcohols such as, methanol or ethanol, or chlorinated hydrocarbons such as dichloromethane or chloroform. The reaction is carried out at $0°$ C. to room temperature for several minutes to several hours (Step 5)

In this step, the epoxide V is converted into the aldehyde VI losing one carbon through the oxidative cleavage of the glycol resulted by hydration. As an oxidizing agent which also serves as a hydrating catayst, periodic acid or orthoperiodic acid may be used. It is desirable to use a solvent which is miscible with water, such as ether, tetrahydrofuran, dioxan, methanol, or ethanol. The reaction is carried out at room temperature for several tens of minutes to several hours. The compound IV-2 may be converted into the compound VI in one step by ozonolysis, which corresponds to the simultaneous reactions of Steps 4 and 5.

(Step 6)

In this step, the aldehyde VI is allowed to react with an ylide to generate a double bond and then, without purification, the resulting compound is esterified in order to protect the carboxy group. The reaction which generates a double bond may be processed in accordance with the conventional Wittig reaction. The ylide used in the reaction is prepared from triphenylphosphine by reaction with a halide of desired alkyl to be condensed such as 5-bromopentanoic acid in the presence of a base. As a base, sodium dimsyl, potassium dimsyl, potassium tert-butoxide, sodium hydride, n-butyl lithium, or diisopropylamide are exemplified. These reaction may be carried out in a solvent such as ether, tetrahydrofuran, n-hexane, or dimethylsulfoxide at room temperature for several hours. The esterification reaction may be achieved in a usual method using diazomethane or dimethyl sulfate with diazabicycloundecene diazabicyclononene (Step 7)

In this step, the double bond of the side chain of the compound VII is reduced by catalytic hydrogenation into a single bond and at the same time the amino-protecting group is removed reductively to give the intermediate amine VIII. The hydrogenation reaction may be achieved with such a catalyst as platinum metal, palladium-carbon, or nickel under usual or moderately increased pressure of hydrogen.

As a solvent, ether, tetrahydrofuran, dioxane, methanol, or ethanol may be used. This reaction may be completed at room temperature within several hours.

(Step 8)

In this step, the aldehyde VI is allowed to react with an ylide to generate a double bond. The ylide used may be prepared from 3-halogenopropanol, of which the hydroxy group is protected, for example, with tetrahydropyranyl, by reacting with triphenylphosphine in the presence of a base. As a halogen, chloro or bromo and as a base, sodium hydride, n-butyl lithium, sodium dimsyl or potassium dimsyl are exemplified. This reaction is carried out in a solvent such as ether, tetrahydrofuran, n-hexane or dimethylsulfoxide at room temperature for several hours.

(Step 9)

In this step, the hydroxy-protecting group of the compound IX is removed by acid hydrolysis and the resulting alcohol is oxidized into the aldehyde. It is desirable to use such an acid catalyst as hydrochloric acid, sulfuric acid or p-toluenesulfonic acid in the acid hydrolysis. As a solvent tetrahydrofuran, methanol, ethanol, acetone, or acetonitrile may be used singly or as a mixture, usually as an aqueous mixture. The reaction is carried out at room temperature or under heating for several minutes to several hours. In the oxidation of the alcohol into the aldehyde, dimethylsulfoxide combined with an appropriate activator may be used as an oxidizing agent. An activator such as thionyl chloride, sulfuryl chloride, phosgen, or oxalyl chloride may be used. If necessary, a base such as triethylamine or diethylmethylamine may be added.

(Step 10)

In this step, the aldehyde X is allowed to react with an ylide to generate a double bond. The reaction may be achieved in accordance with the manner of Step 8 using an ylide or anion prepared from methyl 2-bromoacetate and triphenylphosphine or trialkylphosphonoacetate respectively.

(Step 11)

In this step, the double bond of the side chain of the compound IX is reduced into a single bond. The reaction may be achieved in accordance with the manner of Step 7. In case the amino-protecting group is removed simultaneously with the reduction, the amino group is reprotected with an amino-protecting group such as benzyloxycarbonyl in the presence of a base such as pyridine, 4-dimethylaminopyridine, or triethylamine. The reaction may be carried out in a solvent such as dichloromethane or chloroform at room temperature for several tens of minutes to several hours.

(Step 12)

In this step, the hydroxy-protecting group of the compound X II is removed by acid hydrolysis and then the resulting alcohol is oxidized into aldehyde. This step is achieved in accordance with the same manner as Step 9.

(Step 13)

In this step, the aldehyde X III is allowed to react with an ylide to generate a double bond. This step may be achieved in accordance with the same manner as Step 10.

(Step 14)

In this step, a monosubstituted acetylene metal derivative is added to the aldehyde VI and then the carboxy group is protected by esterification. Dilithium compound of 4-pentynoic acid may be used as a compound to be added. A solvent such as liquid ammonia, ether, tetrahydrofuran, glycol ether, or dimethylformamide may be used. The esterification of carboxylic acid may be achieved by diazomethane in a usual manner.

(Step 15)

In this step, the hydroxy group of the compound X V is acetylated and then the triple bond of the resulting compound is rearranged to the allene X VI. The acetylation is carried out with an acylating agent such as acetic anhydride or acetyl chloride in a solvent as ether, tetrahydrofuran, benzene, or pyridine. A base such as pyridine, triethylamine, 4-dimethylaminopyridine may be added, if necessary. The rearrangement is achieved by reacting the compound with dimethyl copper lithium as an attacking agent followed by hydrolysis of the resulting compound with a catalyst such as hydrochloric acid or hydrobromic acid. If necessary, lithium aluminum hydride may be added.

(Step 16)

In this step, the aldehyde VI is allowed to react with an ylide which is prepared by reacting triphenylphosphine and with a halogenomethyl ether in the presence of a base to give the enol ether X VII. The halogen means chloro or bromo. This step is achieved by reacting in accordance with the manner of Step 8.

(Step 17)

In this step, the enol ether X VII is hydrolyzed with an acid to give the aldehyde X VIII. An acid such as perchloric acid or sulfuric acid is used as an acid catalyst. A solvent such as water or dioxane is used. The reaction is carried out under refluxing for a period of several tens of minutes to several hours.

(Step 18)

In this step, the aldehyde X VIII is allowed to react with an ylide to generate a double bond. The reaction may be achieved in accordance with the manner of Step 8 using an ylide prepared from methyl 4-bromobutanoate or methyl 4-chlorobutanoate by reacting with triphenylphosphine.

(Step 19)

In this step, the amino-protecting group of the compounds VII, IX, X IV, X VI or X IX prepared in Step 6, 10, 13, 15, or 18 respectively is removed to give the amine X X as an intermediate from which the compounds of the present invention are prepared. The reaction is carried out, for example, in a conventional way with trifluoroacetic acid and anisole under warming for several hours. The product may be used in the form of trifluoroacetate salt in the subsequent reaction, but, according to necessity, it may be converted into the free amine X X-2 by treatment with an adequate base such as sodium carbonate or sodium hydrogencarbonate.

(Step 20)

In this step, the free-amine VIII or X X-2, or its salt X X-1 is allowed to react with a substituted sulfonic acid halide in the presence of a base to give the sulfonamide derivatives X X I. As a substituted sulfonic acid halide, which has a substituent as described before, e.g., methanesulfonyl chloride, ethanesulfonyl chloride, propanesulfonyl chloride, butanesulfonyl chloride, pentanesulfonyl chloride, hexanesulfonyl chloride, heptanesulfonyl chloride, octanesulfonyl chloride, benzenesulfonyl chloride, methoxybenzenesulfonyl chloride, nitrobenzenesulfonyl chloride, hydroxybenzenesulfonyl chloride, toluenesulfonyl chloride, ethylbenzenesulfonyl chloride, aminobenzenesulfonyl chloride acetylaminobenzenesulfonyl chloride, or dimethylaminobenzenesulfonyl chloride or the like is exemplified. In the reaction, a base such as pyridine or triethylamine and a solvent such as dichloromethane, chloroform, ether, tetrahydrofuran, or benzene are used.

(Step 21)

In this step, the ester X X I is hydrolyzed into the carboxylic acid X X II-1. The hydrolysis may be carried out in a conventional manner. Hydrochloric acid, sulfuric acid, sodium hydroxide, potassium hydroxide, or barium hydroxide is used as a catalyst. Solvents such as aqueous methanol, aqueous ethanol, aqueous acetone, or aqueous acetonitrile is used. In this step, the compounds of this invention are obtained. According to necessity, the carboxylic acid can be converted into the carboxylate X X II-2 by conventional treatment with a base such as sodium methoxide, sodium hydroxide, potassium hydroxide, calcium hydroxide ammonium hydroxide, methylmorpholine, pyridine, triethylamine, or glycine.

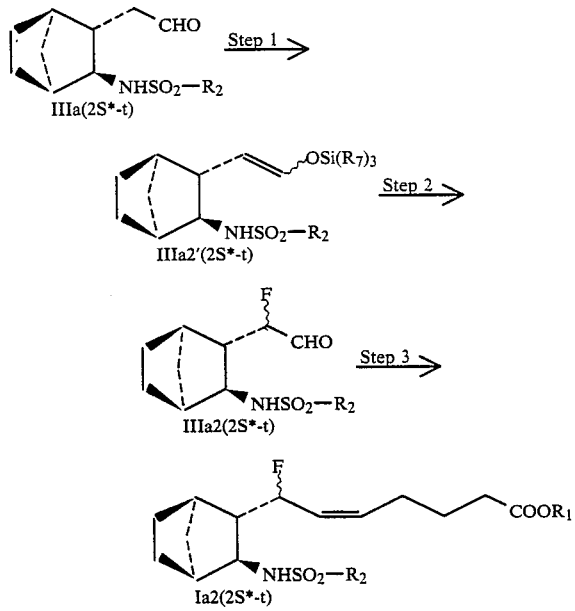

PROCESS I-2

The starting compounds (III a(2S*-t)) may be prepared from the compound IV-1 (see Reaction Scheme I-1) on the reaction with a substituted sulfonic acid chloride and the subsequent epoxidation and oxidation (see Step 5 of Process I-1).

(Step 1)

In this step, the aldehyde III a(2S*-t) is converted into the enol silyl ether III a2'(2S*-t) with a silylating agent in the presence of a base. A base such as Hünig base, diazabicycloundecene or the like may be used. A silylating agent such as trimethylsilyl chloride, dimethyl-tert-butylsilyl chloride, trimethylsilyl triflate, bis(-trimethylsilyl)acetamide or the like is used in a conventional manner (P. Brownbride, Synthesis, 1-28 (1983)). As a solvent, chlorinated hydrocarbon e.g., dichloromethane, ethereal solvent, e.g., diethyl ether, tetrahydrofuran or diglyme, or N,N-dimethylformamide is used. The reaction is achieved completely at room temperature for a day.

(Step 2)

In this step, the enol silyl ether III a2'(2S*-t) prepared from the aldehyde is converted into the α-fluoroaldehyde by reacting with an electrophilic fluoinating agent. As an electrophilic fluorinating agent, xenon difluoride, perchloric fluoride, trifluoromethyl hypofluorite, fluorine gas, acetyl hypofluorite, N-fluoropyridone, N-fluoro-N-alkyl-p-toluenesulfonamide, cesium fluorosulfate or the like is used. As a solvent, chlorinated hydrocarbon, e.g., dichloromethane, or acetonitrile or ethyl acetate may be used. The reaction may be carried out at a temperature of −78° C. to 0° C. or under ice-cooling for several hours.

(Step 3)

In this step, the fluoroaldehyde III a2(2S*-t) is allowed to react with a fluoro-substituted or unsubstituted ylide to give the compound I a2(2S*-t) of the present invention. The reaction with the aldehyde and the ylide may be carried out in a conventional manner for the Wittig reaction. In this step, the bicyclic sulfonamide derivatives possessing fluoride in 2-side chain is prepared. Depending on the reaction conditions the reaction affords either of the Z-form compound alone or a mixture of Z-form and E-form compounds. The fluoro-ylide can be prepared from halide of fluoroalkanoic or alkenoic acid possessing a carboxyl group at the ω-position. The free carboxylic acid I a2-b(2S*-t) of the present invention may be esterified to give the carboxylate ester I a2-a(2*-t) or converted into the carboxylate salt I a2-c(2S*-t) in a conventional manner.

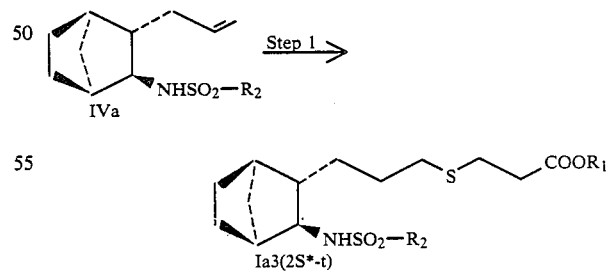

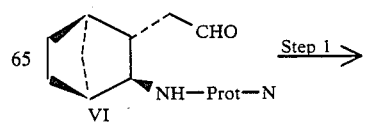

-continued
Reaction Scheme I-3b

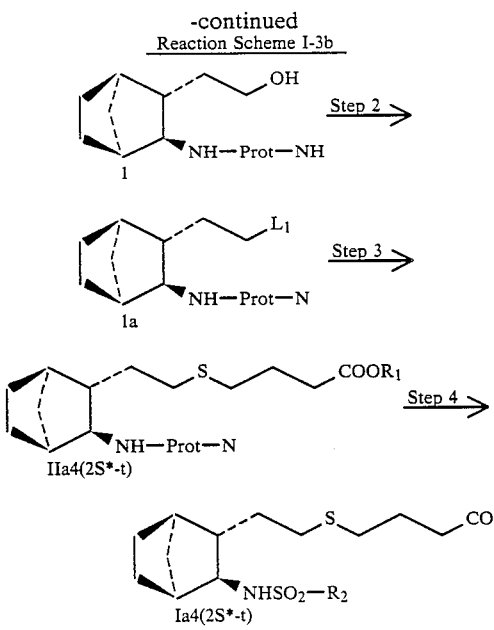

PROCESS I-3a

(Step 1)

In this step, a thiol is added to the double bond of the compound IV a. As the thiol, mercaptoalkanoic acid ester, e.g., 2-mercaptoacetic acid methyl ester, 3-mercaptopropionic acid methyl ester or 4-mercaptobutyric acid methyl ester may be used. As a catalyst, oxygen, peroxide, azobisisobutyronitrile or the like is used. This reaction may be achieved at room temperature for a period of several hours to several tens of hours.

In this step, the carboxylate esters I a3-a(2S*-t) of sulfonamide derivatives, the compounds of the present invention of which the 2-side chain contains sulfur, are prepared. The carboxylate ester is converted into the free carboxylic acid I a3-b(2S*-t) or the carboxylate salt I a3-c(2S*-t) by treating in accordance with the manner of Process I-1, step 21.

PROCESS I-3b

(Step 1)

In this step, the aldehyde VI is reduced to alcohol 1. As a reducing agent, metal hydride, e.g., lithium aluminium hydride, sodium borohydride, sodium bis(2-methoxyethoxy)aluminium hydride, diisobutyl aluminium hydride, lithium trimethoxyaluminium hydride, or lithium-tri-tert-butoxy aluminium hydride may be used. As a solvent, ethereal solvent, e.g., diethyl ether or tetrahydrofuran, or aromatic solvent, benzene or toluene may be exemplified. The reaction is achieved under cooling or at room temperature for a period of several tens of minutes to several hours.

(Step 2)

In this step, the hydroxy group of the compound 1 is converted into a leaving group. As a leaving group, halogen, e.g., chlorine or bromine, or sulfonate, e.g., methanesulfonate, benzenesulfonate or p-toluenesulfonate is exemplified. In the case where the hydroxy group is replaced by a halogen, the compound 1 is allowed to react with a halogenating agent, e.g., hydrogen halide, phosphorus halide, thionyl chloride, and in the case of the sulfonate, the compound 1 is allowed to react with a corresponding sulfonyl chloride in a conventional manner.

(Step 3)

In this step, the compound 1a is allowed to react with a thiol to give the sulfide II a4(2S*-t). As a thiol used in this step, mercapto-alkanoic acid ester or alkenoic acid ester possessing a carboxyl group at the ω-position, e.g., 2-mercaptoacetic acid methyl ester, 3-mercaptopropionic acid methyl ester, 4-mercaptobutyric acid methyl ester, or 5-mercaptopentanoic acid methyl ester is exemplified. A base such as sodium methoxide is used. As a solvent, aprotic solvent, e.g., dimethylformamide, dimethylacetamide, N-methyl-α-pyrrolidone, diethyl ether, tetrahydrofuran, acetone or acetonitrile is used. The reaction is achieved at room temperature or under heating for a period of several tens of minutes to several hours.

(Step 4)

In this step, the compound II a4(2S*-t) is converted into the sulfonamide derivatives, compounds of the present invention. This step is carried out in accordance with Process I-1 steps 19 to 21. In this step, the carboxylate ester I a4-a(2S*-t) of the present invention.

In this step, the carboxylate ester I a4-a(2S*-t) of sulfonamide derivatives, of which the 2-side chain possesses a sulfur atom, the free carboxylic acid I a4-b(2-b(2S*-t), or the carboxylate salt I a4-c(2S*-t) is prepared.

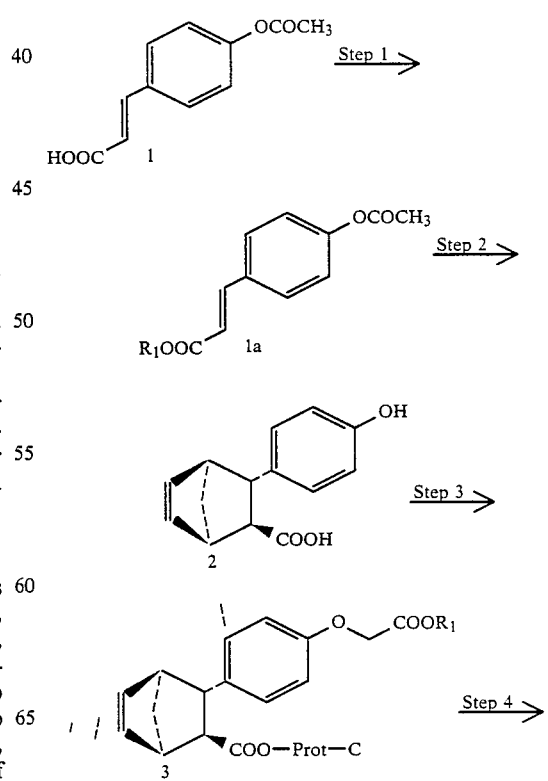

Reaction Scheme I-4

-continued
Reaction Scheme I-4

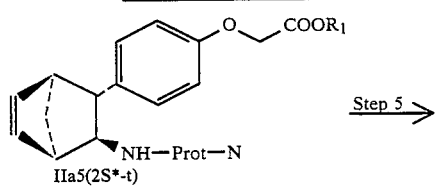
IIa5(2S*-t)

Step 5 →

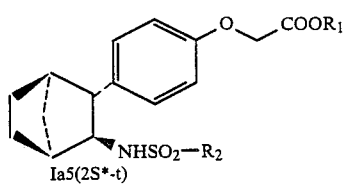
Ia5(2S*-t)

PROCESS I-4

(Step 1)

In this step, the carboxy group of the compound 1 is esterified. The esterification may be carried out by one of the following conventional methods: a method employing diazomethane; and a method employing dimethyl sulfate in the presence of a base such as diazabicyclononene or diazabicycloundecene.

(Step 2)

In this step, the compound 1a is allowed to react with a dienophile to give the compound 2 of six-membered ring system. This reaction is well known as "Diels-Alder reaction" or 4π+2π cycloaddition reaction. The diene generally reacts with the dienophile under atmospheric pressure or higher pressure at room temperature or higher temperature. A variety of catalysts such as zinc chloride, boron trifluoride-etherate, aluminum chloride, titanium tetrachloride or stannic chloride and the other Lewis' acids are usually employed under milder conditions and the adduct is obtained in good yields. Although the reaction is performed without any solvents, if required, organic solvents such as ethereal, e.g., diethyl ether, tetrahydrofuran or diglyme, aromatic solvent, e.g., benzene or toluene, chlorinated hydrocarbon, e.g., dichloromethane or chloroform, alcohol, e.g., methanol, ethanol or propanol, or hydrocarbon, e.g., hexane or heptane may be used.

(Step 3)

In this step, the carboxy group of the compound 2 is protected by esterification and the phenolic hydroxy is alkylated to give the ether 3.

The esterification of the carboxy group may be carried out in a conventional manner; the compound 2 is allowed to react with benzyl alcohol, diphenyldiazomethane, triphenylmethyl chloride, phthalimidomethyl chloride, 4-picolyl chloride, or the like in the presence of a catalyst such as hydrochloric acid, sulfuric acid or triethylamine, if necessary in a solvent such as alcohol, e.g., methanol or ethanol, chlorinated hydrocarbon, e.g., dichloromethane or chloroform, ethereal solvent, e.g., diethyl ether or tetrahydrofuran, or ethyl acetate or dimethylformamide. This reaction may be achieved under warming for a period of several tens of minutes to several hours.

The O-alkylation may be carried out by treating the compound with an alkyl halide. As the alkyl halide used in this reaction, bromoacetic acid methyl ester, bromopropionic acid methyl ester, iodoacetic acid methyl ester, iodopropionic acid methyl ester or the like is exemplified. The reaction is carried out as follows; the compound is converted into the sodium phenolate beforehand, which is treated with the alkyl halide, or the compound is treated with the alkyl halide in the presence of anhydrous potassium carbonate in a solvent such as acetone or methyl ethyl ketone.

(Step 4)

In this step, the carboxy-protecting group of the compound 3 is removed and the resulting carboxy group is converted into the azide, which is then allowed to react with an alcohol to give the urethane II a5(2S*-t). This process can be achieved by the Curtius rearrangement; that is, the reaction of either of the intermediate acid chloride or acid anhydride with sodium azide; the acid chloride is prepared by treating the carboxy group with thionyl chloride, phosphoryl chloride, or phosphorus pentachloride; the acid anhydride is obtained by the reaction of the carboxy group with ethyl chloroformate or isobutoxycarbonyl chloride in the presence of a base catalyst such as triethylamine or 4-dimethylaminopyridine in a solvent such as acetone, dimethylformamide, dimethylsulfoxide, ethyl acetate, or tetrahydrofuran under cooling for a period of several tens of minutes to several hours. The isocyanate can be prepared by refluxing the azide compound in benzene, toluene, or diphenyl ether for a period of several tens of minutes to several hours. The alcohol used in the reaction with the isocyanate includes those giving an urethane which can readily be converted into the desired primary amine, for example, isobutanol, tert-butanol, diisopropylmethanol, cyclopentanol, cyclohexanol, benzyl alcohol, diphenylmethanol, or triphenylmethanol. This reaction can be carried out under refluxing for several hours in a solvent such as benzene, dichloromethane, chloroform, or ethyl acetate in the presence of a base such as triethylamine, 4-dimethylaminopyridine, or 4-pyrrolidinopyridine, as required.

(Step 5)

In this step, the compound II a5(2S*-t) is converted into the sulfonamide derivatives I a5(2S*-t), the compound of the present invention. This step may be carried out in accordance with the manner of Process I-1, Steps 19-21. In this step, the carboxylate ester I a5-a(2S*-t) of the present invention possessing phenyloxy in the 2-side chain; the free carboxylic acid I a5-b(2S*-t); or the carboxylate salt I a5-c(2S*-t) is prepared.

Reaction Scheme I-5

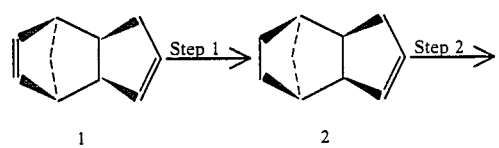

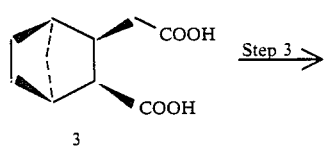

-continued
Reaction Scheme I-5

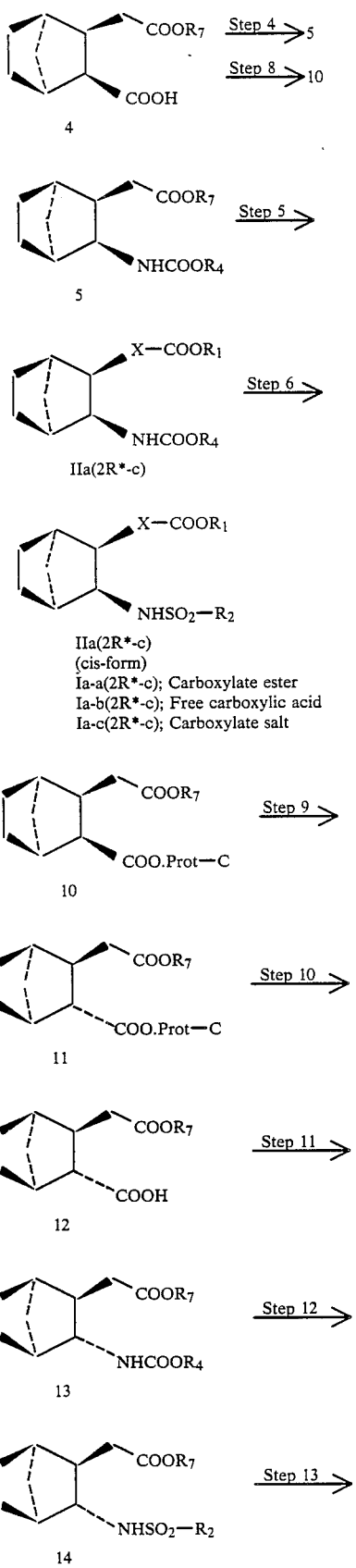

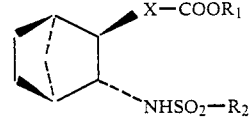

Ia(2R*-t)
(trans-form)
Ia-a(2R*-t); Carboxylate ester
Ia-b(2R*-t); Free carboxylic acid
Ia-c(2R*-t); Carboxylate salt

PROCESS I-5

(Step 1)

In this step, one of the double bonds of the compound 1 is selectively reduced to give the compound 2. Employing palladium, platinum oxide, nickel boride, or chlorotris(triphenylphosphine)rhodium as a reducing agent, and methanol, ethanol, ether, tetrahydrofuran, dioxane, dichloromethane, chloroform, or benzene singly or a mixture as a solvent, the reaction of this step is completed in several tens of minutes to several hours at room temperature.

(Step 2)

In this step, the double bond of the compound 2 is oxidatively cleaved to give aldehyde, which is further oxidized to give dicarboxylic acid 3. The oxidative cleavage of the double bond may be achieved by a conventional method for ozonization and subsequent reductive decomposition of the intermediate ozonide. The ozonization may be carried out in a solvent, for example, benzene, carbon tetrachloride, chloroform, dichloromethane, ether, tetrahydrofuran, ethyl acetate, acetic acid, methanol, ethanol, or water; the reaction is completed in several tens of minutes to several hours under cooling. The reductive decomposition of the ozonide proceeds in water, acetic acid, trifluoromethane, ethyl chloride, or carbon tetrachloride, with zinc dust, sodium iodide, sulfur dioxide, sodium hydrogensulfite, tin (II) chloride, or iron (II) sulfate as a reducing agent, and is completed in several minutes to several hours at room temperature. In the oxidation of the aldehyde into the carboxylic acid, it is appropriate to use an oxidizing agent such as Jones reagent, potassium permanganate, silver oxide or nitric acid together with a catalyst such as sulfuric acid, when necessary. It is desirable to use as solvent in this reaction water or those miscible with water such as acetone, tetrahydrofuran, methanol, and ethanol. The reaction is completed after several hours at room temperature.

(Step 3)

In this step, the compound 3 is converted into the ester 4 in order to protect the 2-carboxymethyl group. For selective protection, the compound 3 is dehydrated into the corresponding acid anhydride, which is then applied to alcoholysis for esterification. The dehydration is performed by heating with a dehydrating agent such as acetic anhydride, trifluoroacetic anhydride, heptanoic anhydride, benzoic anhydride, p-chlorobenzoic anhydride, phosphorus pentoxide, acetyl chloride, thionyl chloride, or sulfonyl chloride, as required. This reaction can be achieved in a solvent such as toluene or xylene by heating for several minutes. The esterification can be achieved by refluxing the acid anhydride for several tens of minutes to several hours in an alcohol such as methanol, ethanol, propanol, isopropanol, butanol, tert-butanol, or in phenol. The reaction can be promoted by adding either an acid such as hydrochloric acid, sulfuric acid, p-toluenesulfonic acid or zinc chloride, or a base such as sodium hydroxide, potassium hydroxide, barium hydroxide, sodium acetate, pyridine, 4-dimethylaminopyridine, or triethylamine.

(Step 4)

In this step, 3-carboxy group of the compound 4 is converted into the azide, which is then rearranged into the isocyanate, which is then allowed to react with an alcohol to yield the urethane 5. This process can be achieved by the Curtius rearrangement; that is, the azide compound is obtained by the reaction of sodium azide with either of the acid chloride or acid anhydride; the acid chloride is prepared by treating the carboxy group with thionyl chloride, phosphoryl chloride, or phosphorus pentachloride; the acid anhydride is obtained by allowing the carboxyl group to react with ethyl chloroformate or isobutoxycarbonyl chloride in the presence of a basic catalyst such as triethylamine or 4-dimethylaminopyridine in a solvent such as acetone, dimethylformamide, dimethylsulfoxide, ethyl acetate, or tetrahydrofuran for several tens of minutes to several hours under cooling. The isocyanate can be prepared by refluxing the azide compound in benzene, toluene, or diphenyl ether for several tens of minutes to several hours. The alcohol which reacts with the isocyanate includes those giving an urethane which might readily yield the desired primary amine, for example, isobutanol, tert-butanol, diisopropylmethanol, cyclopentanol, cyclohexanol, benzyl alcohol, diphenylmethanol, or triphenylmethanol. This reaction can be achieved by several hours reflux in a solvent such as benzene, dichloromethane, chloroform, or ethyl acetate in the presence of a base such as triethylamine, 4-dimethylaminopyridine, or 4-pyrrolidinoyridine, as required.

(Step 5)

In this step, the ester of compound 5 is reduced to an aldehyde, which is allowed to react with an ylide to generate a double bond. The reduction of the ester is carried out in a solvent such as ether, tetrahydrofuran, or toluene in the presence of a reducing agent such as diisobutylaluminum hydride, lithium trimethoxyaluminum hydride, lithium tri-tert-butoxyaluminum hydride; the reaction is completed in several tens of minutes to several hours under cooling. This aldehyde is readily cyclized to form a hemiacetal which is in equilibrium with the aldehyde. The reaction of the aldehyde with an ylide (reaction for double bond formation) is processed in accordance with the conventional Wittig reaction. The ylide used in the reaction is synthesized in the presence of a base from triphenylphosphine on reaction with a halide of alkanoic or alkenoic acid possessing a carboxyl group at the ω-position. As the halide $C_4$–$C_6$ alkanoic or alkenoic acids used for the process, 4-bromobutanoic acid, 4-bromo-2-butenoic acid, 4-bromo-3-butenoic acid, 5-bromopentanoic acid, 5-bromo-2-pentenoic acid, 5-bromo-3-pentenoic acid, 5-bromo-4-pentenoic acid, 6-bromohexanoic acid, 6-bromo-2-hexenoic acid, 6-bromo-3-hexenoic acid, 6-bromo-4-hexenoic acid, 6-bromo-5-hexenoic acid and so on are available. As for the base, sodium hydride, sodium dimsyl, potassium dimsyl, n-butyl lithium, potassium tert-butoxide, or lithium diisopropylamide are cited. This reaction is conducted in a solvent such as ether, tetrahydrofuran, n-hexane, or dimethylsulfoxide, and can be achieved in several hours under cooling or at room temperature. At this stage, the carboxy group is esterified in order to protect it in the succeeding reactions. The esterification may be done by one of the following conventional methods: a method in which the carboxylic acid is allowed to react with an alcohol such as methanol, ethanol, n-propanol, isopropanol, butanol, or pentanol in the presence of a catalyst, as required, such as dried hydrogen chloride, or concentrated sulfuric acid; a method in which the carboxylic acid is transformed into an acid chloride which is allowed to react with an alcohol as cited above in the presence of a base such as metallic magnesium, N,N-dimethylaniline, pyridine, or sodium hydroxide; a method employing diazomethane; and a method employing dimethyl sulfate and diazabicyclononene or diazabicycloundecane.

(Step 6)

In this step, the amino-protecting group of the compound IIa(2R*-c) is removed and the resulting amine is allowed to react with a substituted sulfonic acid halide to give the sulfonamide derivative Ia-a(2R*-c). Removal of the protecting group is achieved by a conventional method with trifluoroacetic acid and anisole under warming for several hours. The product can be used in the form of trifluoroacetate salt in the subsequent process, but, according as necessity, it may be converted into the free amine by treatment with an adequate alkali such as sodium carbonate and sodium hydrogencarbonate. The reaction to give the sulfonamide derivatives is completed in several tens of minutes in a solvent such as dichloromethane, chloroform, ether, tetrahydrofuran, or benzene in the presence of a basic substance such as pyridine or triethylamine at room temperature, using a sulfonic acid halide having a desired substituent such as methanesulfonyl chloride, ethanesulfonyl chloride, propanesulfonyl chloride, butanesulfonyl chloride, pentanesulfonyl chloride, hexanesulfonyl chloride, heptanesulfonyl chloride, octanesulfonyl chloride, benzenesulfonyl chloride, methoxybenzenesulfonyl chloride, nitrobenzenesulfonyl chloride, hydroxybenzenesulfonyl chloride, toluenesulfonyl chloride, ethylbenzenesulfonyl chloride, aminobenzenesulfonyl chloride, acetylaminobenzenesulfonyl chloride, or dimethylaminobenzenesulfonyl chloride. In this process, the sulfonamide derivative is produced in a cis form.

(Step 7)

In this step the ester Ia-a(2R*-c) is hydrolyzed into the carboxylic acid Ia-b(2R*-c). The hydrolysis is carried out by a conventional procedure. Hydrochloric acid, sulfuric acid, sodium hydroxide, potassium hydroxide, or barium hydroxide is used as a catalyst. Solvents such as methanol-water, ethanol-water, acetone-water, or acetonitrile-water are used. In this process the cis-form of free carboxylic acid is obtained. According to necessity, the carboxylic acid can be converted into the cis-form carboxylate Ia-c(2R*-c) by conventionally processing it with an alkali such as sodium methoxide, sodium hydroxide, potassium hydroxide, calcium hydroxide, ammonium hydroxide, methylmorpholine, pyridine, triethylamine, or glycine.

(Step 8)

In this step, the carboxyl group of the compound 4 is esterified for protection in the succeeding reactions. The compound 4 is allowed to react with benzyl alcohol, diphenyldiazomethane, triphenylmethyl chloride, phthalimidomethyl chloride, or 4-picolyl chloride, along with hydrochloric acid, sulfuric acid, or triethylamine as required. This reaction may be conducted in a solvent such as methanol, ethanol, dichloromethane, chloroform, ether, tetrahydofuran, ethyl acetate, or dimethylformamide, and is completed after several tens of minutes to several hours of warming.

(Step 9)

In this step, the cis-form compound 10 is isomerized into the thermodynamically stable trans-form isomer 11. This reaction is achieved in a solvent such as toluene, xylene, dimethylsulfoxide, or dimethylformamide by heating for several days. according as necessity, a catalytic amount of basic substance such as diazabicyclononene, diazabicycloundecane, pyrrolidine-acetate, piperidine-acetate, or triethylamine may be added.

(Step 10)

In this step, the protecting group of the 3-carboxy group of the compound 11 is selectively removed to give the compound 12. This reaction can be achieved in several minutes to several hours under cooling or at room temperature with trifluoroacetic acid, boron fluoride, and so forth. As a solvent, dichloromethane, chloroform, ether, tetrahydrofuran, and anisole are recommended. This process can also be achieved by catalytic reduction using palladium carbon and so on.

(Step 11)

In this step, the carboxylic acid 12 is converted to the urethane 13 through an intermediate isocyanate. The reaction of this step may follow the procedure of Step 4.

(Step 12)

In this step, the compound 13 is hydrolyzed into a primary amine, which is allowed to react with a substituted sulfonic acid halide in the presence of a basic catalyst to give the sulfonamide derivative 14. The reaction of this step may follow the procedure of Step 6.

(Step 13)

In this step, the ester 14 is reduced to an aldehyde, which is further allowed to react with an ylide to generate a double bond. The reaction of this step may follow the procedure of Step 5. In this process the trans-form of sulfonamide derivative Ia-a(2R*-t) is produced.

(Step 14)

In this step, the carboxylate ester Ia-a(2R*-t) is hydrolyzed into the free carboxylic acid Ia-b(2R*-t), which may be processed further with an adequate base to give the carboxylate salt Ia-c(2R*-t). In this process the free trans-form carboxylic acids and their salts are produced. In this process the reaction is achieved according to the procedure of Step 7.

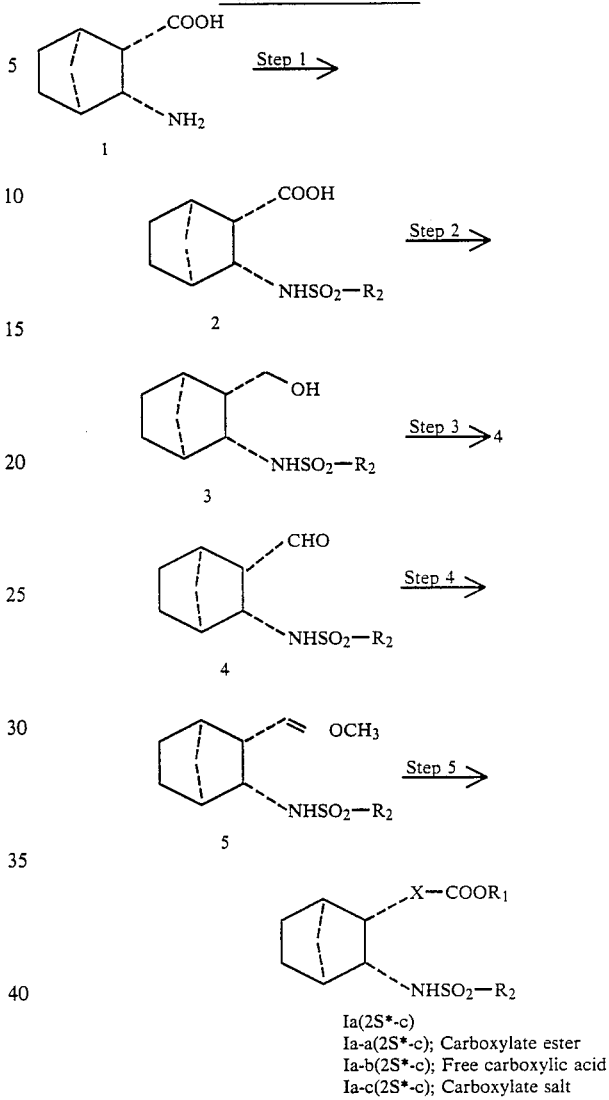

PROCESS I-6

(Step 1)

In this step, the amine 1 is allowed to react with a substituted sulfonic acid halide in the presence of a base to give the sulfonamide derivatives 2. The reaction to give the sulfonamide derivatives is completed in several tens of minutes in a solvent such as chlorinated hydrocarbon, e.g. chloroform or dichloromethane, ether, e.g. ethyl ether or tetrahydrofuran, or aromatic solvent, e.g. benzene, in the presence of a basic substance such as pyridine, triethylamine, potassium hydroxide or sodium hydroxide at room temperature, using a sulfonic acid halide having a desired substituent such as methanesulonyl chloride, ethanesulfonyl chloride, propanesulfonyl chloride, butanesulfonyl chloride, pentanesulfonyl chloride, hexanesulfonyl chloride, heptanesulfonyl chloride, octanesulfonyl chloride, benzenesulfonyl chloride, methoxybenzenesulfonyl chloride, nitrobenzenesulfonyl chloride, hydroxybenzenesulfonyl chloride, toluenesulfonyl chloride, ethylbenzenesulfonyl chloride, aminobenzenesulfonyl chloride, acetylaminobenzenesulfonyl chloride, or dimethylaminobenzenesulfonyl chloride.

(Step 2)

In this step, the carboxylic acid 2 is reduced to an alcohol 3. This step may be carried out with a reducing agent, for example, diborane or metal hydride such as sodium borohydride, lithium aluminum hydride, lithium trimethoxy aluminum hydride, or sodium bis(2-methoxyethoxy)aluminum hydride, in a solvent alcohol such as methanol or ethanol, ether such as ethyl ether or tetrahydrofuran, or aromatic solvent such as benzene under cooling or at room temperature for a period of several tens of minutes to several hours.

(Step 3)

In this step, the alcohol 3 is oxidized into the aldehyde 4. The oxidation may be carried out with chromates such as Jones' reagent, Collins' reagent, pyridinium chlorochromate, pyridinium dichromate in a solvent such as chlorinated hydrocarbon, e.g. chloroform or dichloromethane, ether, e.g. ethyl ether or tetrahydrofuran, or acetone or benzene under cooling or at room temperature for several hours.

(Step 4)

In this step, the carbon number of the side chain of 2-position in the compound 4 is increased to give the compound 5. This reaction may be carried out in accordance with a conventional manner of the Wittig reaction. As a phosphonium salt, such as methoxymethyltriphenylphosphonium chloride or methoxymethyltriphenylphosphonium bromide may be used. As a base, sodium hydride, n-butyl lthium, sodium dimsyl or potassium dimsyl may be use. The reaction is completed in a solvent such as an ether, e.g. ethyl ether or tetrahydrofuran, or n-hexane, dimethylsulfoxide under cooling or at room temperature within a period of several tens of minutes to several hours.

(Step 5)

In this step, the enol ether 5 is hydrolyzed with an acid to give the hemiacetal, equivalent to the aldehyde, which is allowed to react with an ylide to give the compounds of the present invention. In an acid decomposition reaction, formic acid, acetic acid, hydrochloric acid, sulfuric acid, perchloric acid or the like may be used as an acid. As a solvent, aqueous alcohol such as methanol or ethanol, ether such as ethyl ether or tetrahydrofuran, or acetonitrile, dioxane or water may be used. The reaction of the aldehyde with an ylide (reaction for double bond formation) is carried out in accordance with a conventional manner of the Wittig reaction. The phosphonium salt used in the reaction is prepared from triphenylphospine on the reaction with a halide of alkanoic or alkenoic acid possessing a carboxy group at the ω-position in the presence of a base. As the halide of $C_4$–$C_6$ alkanoic or alkenic acids used for this process, 4-bromobutanoic acid, 4-bromo-2-butenoic acid, 4-bromo-3-butenoic acid, 5-bromopentanoic acid, 5-bromo-2-pentenoic acid, 5-bromo-3-pentenoic acid, 5-bromo-4-pentenoic acid, 6-bromohexanoic acid, 6-bromo-2-hexenoic acid, 6-bromo-3-hexenoic acid, 6-bromo-4-hexenoic acid, 6-bromo-5-hexenoic acid and so on are available. As for the base, sodium hydride, sodium dimsyl, potassium dimsyl, n-butyl lithium, potassium tert-butoxide, or lithium diisopropylamine are cited. This reaction is conducted in a solvent such as ether, e.g. ethyl ether or tetrahydrofuran, or n-hexane, toluene or dimethylsulfoxide, under cooling or at room temperature for several hours. When $R_1$ denotes a hydrogen, the compound may be esterified, if necessary. The esterification may be done by one of the following conventional methods: a method for the reaction of the carboxylic acid with an alcohol such as methanol, ethanol, n-propanol, isopropanol, butanol, or pentanol in the presence of a catalyst, as required, such as dry hydrogen chloride, or concentrated sulfuric acid; a method for the transformation of the carboxylic acid into an acid chloride and subsequent reaction with an alcohol as cited above in the presence of a base such as metallic magnesium, N,N-dimethylaniline, pyridine, or sodium hydroxide; a method employing diazomethane; and a method employing dimethylsulfate acid and diazabicyclononene or diazabicycloundecene. In the esterification, the carboxylate ester I a-a(2R*-c) of the present invention may be prepared. The free carboxylic acid I a-b(2S*-c) of the present invention may be prepared by hydrolyzing the carboxylate ester I a-a(2S*-c). The hydrolysis is carried out by a conventional procedure. Hydrochloric acid, sulfuric acid, sodium hydroxide, potassium hydroxide, or barium hydroxide is used as a catalyst. A solvent such as aqueous methanol, ethanol, acetone, or acetonitrile is used. According to necessity, the carboxylic acid I a-b(2S*-c) can be converted into the carboxylate salt I a-c(2S*-c) of the present invention represented by the general formula (I) in a conventional manner on treatment with a base such as sodium methoxide, sodium hydroxide, potassium hydroxide, calcium hydroxide, ammonium hydroxide, methylmorpholine, pyridine, dicyclohexylamine, triethylamine, glycine, valine, or alanine.

Reaction Scheme I-7

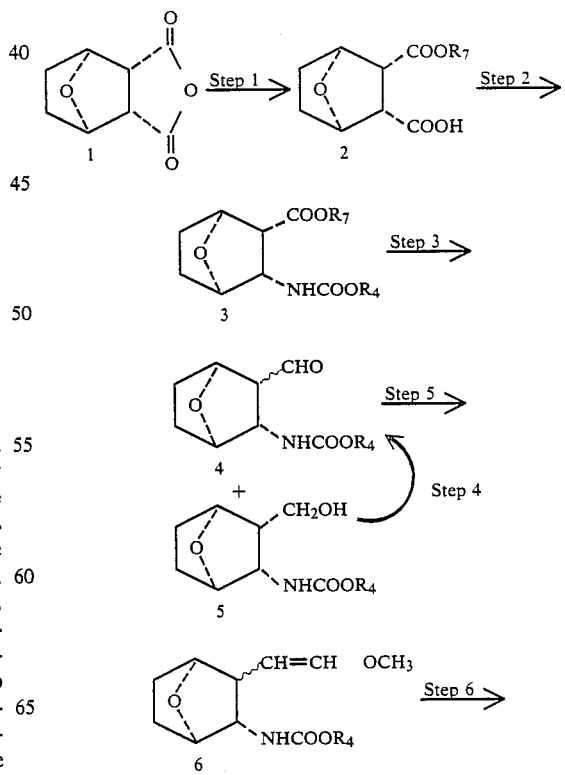

-continued
Reaction Scheme I-7

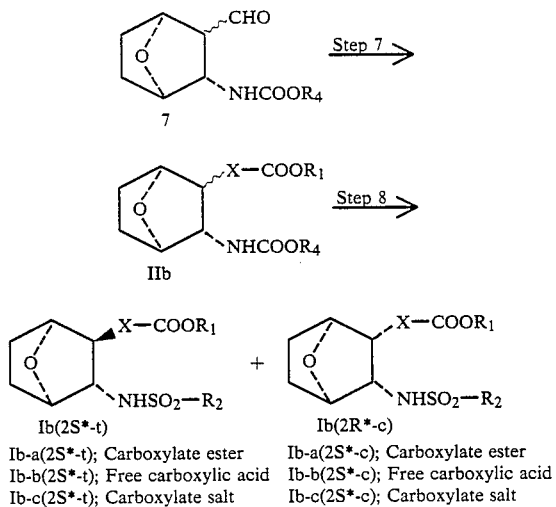

Ib-a(2S*-t); Carboxylate ester
Ib-b(2S*-t); Free carboxylic acid
Ib-c(2S*-t); Carboxylate salt Ib-a(2S*-c); Carboxylate ester
Ib-b(2S*-c); Free carboxylic acid
Ib-c(2S*-c); Carboxylate salt

PROCESS I-7

(Step 1)

In this step, the acid anhydride 1 is esterified by alcoholysis to give the compound 2. The esterification reaction is carried out by refluxing the acid anhydride in an alcohol such as methanol, ethanol, propanol, isopropanol, butanol or tert-butanol, or phenol for a period of several tens of minutes to several hours.

(Step 2)

In this step, 2-carboxy group of the compound 2 is converted into the azide and then into the isocyanate, which is then allowed to react with an alcohol to give the urethane 3. This process can be achieved by the Curtius rearrangement; that is, the azide compound is obtained by the reaction of either of the acid chloride or acid anhydride with sodium azide; the acid chloride is prepared by treating the carboxy group with thionyl chloride, phosphoryl chloride, or phosphorus pentachloride; the acid anhydride is obtained by the reaction of the carboxy group with ethyl chloroformate or isobutoxycarbonyl chloride in the presence of a base catalyst such as triethylamine or 4-dimethylaminopyridine in a solvent such as acetone, dimethylformamide, dimethylsulfoxide, ethyl acetate, or tetrahydrofuran under cooling for a period of several tens of minutes to several hours. The isocyanate can be prepared by refluxing the azide compound in benzene, toluene, or diphenyl ether for a period of several tens of minutes to several hours. The alcohol used in the reaction with the isocyanate includes those giving an urethane which can readily be converted into the desired primary amine, for example, isobutanol, tert-butanol, diisopropylmethanol, cyclopentanol, cyclohexanol, benzyl alcohol, diphenylmethyl, or triphenylmethanol. This reaction can be carried out under refluxing for several hours in a solvent such as benzene, dichloromethane, chloroform, or ethyl acetate in the presence of a base such as triethylamine, 4-dimethylaminopyridine, or 4-pyrrolidinopyridine, as required.

(Step 3)

In this step, the ester of compound 3 is reduced to an aldehyde 4. The reduction is carried out with a reducing agent such as sodium bis(2-methoxyethoxy)aluminum hydride, diisobutyl aluminum hydride, lithium trimethoxyaluminum hydride, lithium tri-tert-butoxyaluminum hydride in an ethereal solvent such as ethyl ether or tetrahydrofuran, or aromatic solvent such as benzene or toluene under cooling or at room temperature for a period of several tens of minutes to several hours. If necessary, in order to control the reducing power, a cyclic amine such as pyrrolidine, N-ethylpiperidine may be added to the reaction medium. In this step, further reduction of the aldehyde 4 sometimes affords the alcohol 5.

(Step 4)

In this step, the alcohol 5 is oxidized into aldehyde 4. The oxidation may be carried out with chromates such as Jones' reagent, Collins' reagent, pyridinium chlorochromate, pyridinium dichromate in a solvent such as dimethylformamide, dimethylsulfoxide, chlorinated hydrocarbons such as chloroform or acetone under cooling or at room temperature for several hours.

(Step 5)

In this step, the aldehyde 4 is allowed to react with an ylide to give an enol ether 6. This reaction may be carried out in accordance with a conventional manner for the Wittig reaction. The ylide prepared from triphenylphosphine and chloromethyl ether or bromoethyl ether in the presence of a base such as sodium hydride, n-butyl lithium, potassium tert-butoxide, lithium diisopropylamine, sodium dimsyl or potassium dimsyl may be used. The reaction is completed in a solvent such as an ether, e.g. ethyl ether or tetrahydrofuran, or n-hexane, toluene, dimethylsulfoxide under cooling or at room temperature within several hours.

(Step 6)

In this step, the enol ether 6 is hydrolyzed with an acid to give the aldehyde 7. As an acid, formic acid, acetic acid, hydrochloric acid, sulfuric acid, perchloric acid or the like may be used. As a solvent, aqueous alcohols such as methanol or ethanol, ethers such as ethyl ether or tetrahydrofuran, or acetonitrile may be used. The reaction may be carried out at room temperature or under warming for a period of several tens of minutes to several hours.

(Step 7)

In this step, the aldehyde 7 is allowed to react with an ylide to give the starting compound II b of the present invention. The reaction of the aldehyde with an ylide (reaction for double bond formation) is carried out in accordance with a conventional manner for the Wittig reaction. The ylide used in the reaction is prepared from triphenylphosphine on the reaction with a halide of alkanoic or alkenoic acid possessing a carboxy group at the ω-position in the presence of a base. As the halide of $C_4$-$C_6$ alkanoic or alkenoic acids used for this process, 4-bromobutanoic acid, 4-bromo-2-butenoic acid, 4-bromo-3-butenoic acid, 5-bromopentanoic acid, 5-bromo-2-pentenoic acid, 5-bromo-3-pentenoic acid, 5-bromo-4-pentenoic acid, 6-bromohexanoic acid, 6-bromo-2-hexenoic acid, 6-bromo-3-hexenoic acid, 6-bromo-4-hexenoic acid, 6-bromo-5-hexenoic acid and so on are available. As for the base, sodium hydride, sodium dimsyl, potassium dimsyl, n-butyl lithium, potassium tert-butoxide, or lithium diisopropylamine are cited. This reaction is conducted in a solvent such as ether, tetrahydrofuran, n-hexane, or dimethylsulfoxide, under cooling or at room temperature within several hours. In this reaction, the product is obtained as the Z-isomer alone or as a mixture of the Z-isomer and E-isomer according to the reaction condition employed. At this stage, the carboxy group is esterified in order to protect it in the succeeding reactions. The esterification may be done by one of the following conventional methods: a method for the reaction of the carboxylic acid with an alcohol such as methanol, ethanol, n-propanol, isopropanol, butanol, or pentanol in the presence of a catalyst, as required, such as dry hydrogen chloride or concentrated sulfuric acid; a method for the transformation of the carboxylic acid into an acid chloride and subsequent reaction with an alcohol as exemplified above in the presence of a base such as metallic magnesium, N,N-dimethylaniline, pyridine, or sodium hydroxide; a method employing diazomethane; and a method employing dimethylsulfate and diazabicyclononene or diazabicycloundecene.

(Step 8)

In this step, the starting compound II b of the present invention is allowed to react in accordance with the manner of the following procedure to give the compounds of the present invention.

In this step, compound II b is allowed to react with a substituted sulfonyl chloride in the presence of a base to give sulfonamide derivatives I b of the present invention. The amino-protecting group may be removed by a conventional method, for example, hydrolysis with an acid such as hydrochloric acid or sulfuric acid, or a base such as sodium hydroxide, potassium hydroxide or barium hydroxide, acid decomposition with trifluoroacetic acid, or hydrogenolysis. The product can be used in the form of ammonium salt in the subsequent process, but, according as necessity, it may be converted into the free amine by treatment with an adequate alkali such as sodium carbonate or sodium hydrogencarbonate. The carboxy group may be esterified in order to protect it in the succeeding reactions. The esterification may be effected by one of the following conventional methods: a method for reacting the carboxylic acid with an alcohol such as methanol, ethanol, n-propanol, isopropanol, butanol, or pentanol in the presence of a catalyst, as required, such as dry hydrogen chloride, or concentrated sulfuric acid; a method for transformation of the carboxylic acid into an acid chloride and subsequent reaction with an alcohol as cited above in the presence of a base such as metallic magnesium, N,N-dimethylaniline, pyridine, or sodium hydroxide; a method employing diazomethane; and a method employing dimethyl sulfate and diazabicyclononene or diazabicycloundecene. The reaction to give the sulfonamide derivatives is completed in several tens of minutes in a solvent such as dichloromethane, chloroform, ether, tetrahydrofuran, or benzene in the presence of a basic substance such as pyridine or triethylamine at room temperature, using a sulfonic acid halide having a desired substituent such as methanesulfonyl chloride, ethanesulfonyl chloride, propanesulfonyl chloride, butanesulfonyl chloride, pentanesulfonyl chloride, hexanesulfonyl chloride, heptanesulfonyl chloride, octanesulfonyl chloride, benzenesulfonyl chloride, methoxybenzenesulfonyl chloride, nitrobenzenesulfoyl chloride, hydroxybenzenesulfonyl chloride, toluenesulfonyl chloride, ethylbenzenesulfonyl chloride, aminobenzenesulfonyl chloride, acetylaminobenzenesulfonyl chloride, or dimethylaminobenzenesulfonyl chloride. In this step, the carboxylate ester I b-a of the present invention can be prepared. Further, the carboxylate ester I b-a may be converted into free carboxylic acid I b-b by hydrolysis in accordance to a conventional procedure. Hydrochloric acid, sulfuric acid, sodium hydroxide, potassium hydroxide, or barium hydroxide is used as a catalyst. Solvent such as aqueous methanol, aqueous ethanol, aqueous acetone or aqueous acetonitrile is used. According as necessity, the carboxylic acid I b-b can be converted into the carboxylate I b-c in a conventional manner on treatment with an alkali such as sodium methoxide, sodium hydroxide, potassium hydroxide, calcium hydroxide, ammonium hydroxide, methylmorpholine, pyridine, triethylamine, glycine, valine or alanine.

In this step, the carboxylate ester ( b-a(2S*-t) of the 2S*-trans-sulfonamide derivatives I b(2S*-t); the free carboxylic acid I b-b(2S*-t) and the carboxylate salt I b-c(2S*-t), and the carboxylate ester I b-a(2R*-c) of 2R*-cis-sulfonamide derivatives I b(2R*-c); the free carboxylic acid I b-b(2R*-c) and the carboxylate salt I b-c(2R*-c) are prepared.

Reaction Scheme I-8

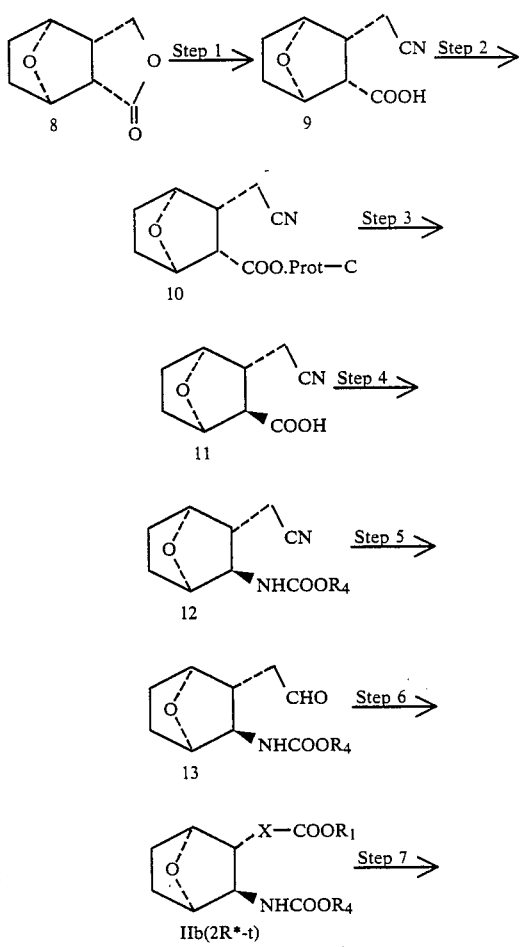

-continued
Reaction Scheme I-8

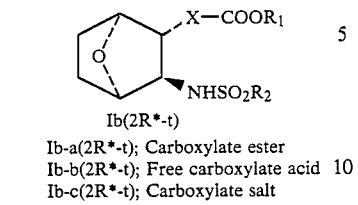

Ib(2R*-t)
Ib-a(2R*-t); Carboxylate ester
Ib-b(2R*-t); Free carboxylate acid
Ib-c(2R*-t); Carboxylate salt

PROCESS I-8

(Step 1)

In this step, the lactone 8 is cleaved with cyano-formation to give the carboxylic acid 9. This reaction may be carried out with metal cyanide such as potassium cyanide, sodium cyanide or copper cyanide as a cyanating agent in a solvent such as dimethylsulfoxide or dimethylformamide under heating for several hours.

(Step 2)

In this step, the carboxy group of the compound 9 is esterified in order to promote the isomerization at the following step. The esterification may be carried out in accordance with a usual method for esterification of carboxy group, that is, for example, a method using alcohol such as methanol, ethanol, propanol, isopropanol or benzyl alcohol, a method using diazomethane or diphenyldiazomethane, or a method using triphenylmethyl chloride, phthalimidomethyl chloride or 4-picolyl chloride. An acid such as hydrochloric acid, sulfuric acid, p-toluenesulfonic acid or a base such as sodium hydroxide, potassium hydroxide, barium hydroxide or triethylamine may be used as a catalyst, as required. The reaction may be carried out in a solvent such as alcohols, methanol or ethanol, ethers, ethyl ether or chlorinated hydrocarbon, e.g. dichloromethane or chloroform, ethyl acetate, or dimethylformamide at room temperature or under warming for a period of several tens of minutes to several hours.

(Step 3)

In this step, the cis-form compound 10 is isomerized to the thermodynamically stable trans-form isomer 11. The reaction may be carried out in a solvent such as alcohol, e.g. methanol or ethanol, ether e.g. ethyl ether or tetrahydrofuran, at room temperature for several hours. If necessary, a base such as sodium hydroxide, potassium hydroxide or barium hydroxide may be added. In the case where a base is added, the ester is hydrolyzed to give the carboxylic acid.

(Step 4)

In this step, 3-carboxy group of the compound 11 is converted into the azide, which is then rearranged into the isocyanate, which is then allowed to react with an alcohol to yield the urethane 12. This step can be achieved by the Curtius rearrangement and carried out in accordance with the manner of Process I-7, Step 2.

(Step 5)

In this step, the cyano group of the compound 12 is reduced to give the aldehyde 13. In this step, diisobutylaluminum hydride is used as a reducing agent. The reaction is completed in a solvent such as an ether, e.g. ethyl ether or tetrahydrofuran, aromatic solvent, e.g. toluene, or hexane under cooling within several hours.

(Step 6)

In this step, the aldehyde 13 is allowed to react with an ylide to give the starting compound II b(2R*-t) of the present invention. The reaction of the aldehyde with an ylide (reaction for double bond formation) is achieved in accordance with a conventional manner for the Wittig reaction. This step may be carried out in accordance with the manner of Process I-7, Step 7.

(Step 7)

In this step, the starting compound II b(2R*-t) is allowed to react in accordance with the manner of Process I-7, Step 8 to give the compounds of the present invention. In this step, the carboxylate ester I b-a(2R*-t) of the 2R*-trans-sulfonamide derivatives I b(2R*-t), the free carboxylic acid I b-b(2R*-t) and the carboxylate salt I b-c(2R*-t) are prepared.

Reaction Scheme I-9

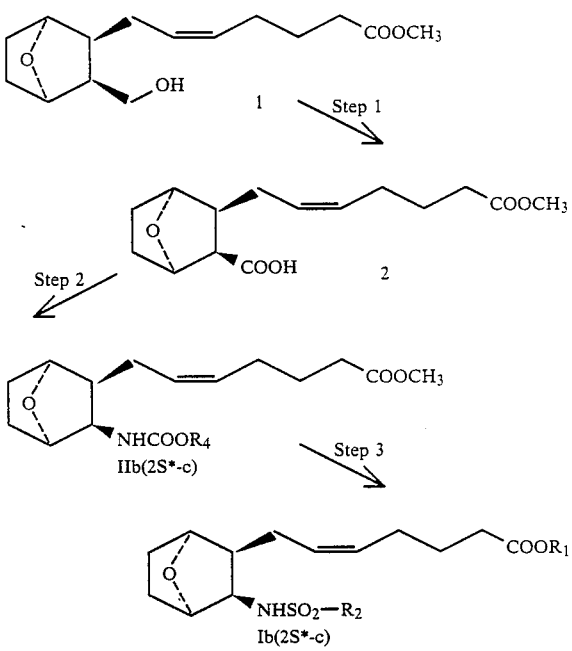

Process I-9

(Step 1)

In this step, the hydroxy group of the compound 1 is oxidized into the carboxy group. The oxidation may be carried out with chromates such as Jones' reagent, Collins' reagent, pyridinium chlorochromate, pyridinium dichromate in a solvent such as dimethylformamide, dimethylsulfoxide, chlorinated hydrocarbons such as chloroform or acetone under cooling or at room temperature for several hours.

(Step 2)

In this step, the carboxy group of the compound 2 is converted into the azide, which is then allowed to react with an alcohol to give the urethane II b(2S*-c). This step is carried out in accordance with the manner of Process I-7, Step 2.

(Step 3)

In this step, the compound II b(2S*-c) is allowed to react in accordance with the manner of Process I-7, Step 8 to give the compound of the present invention. In this step, the carboxylate ester I b-a(2S*-c) of the 2S-cis-sulfonamide derivatives; the free carboxylic acid I b-b(2S*-c); or the carboxylate salt I b-b(2S*-c) is prepared.

Reaction Scheme II

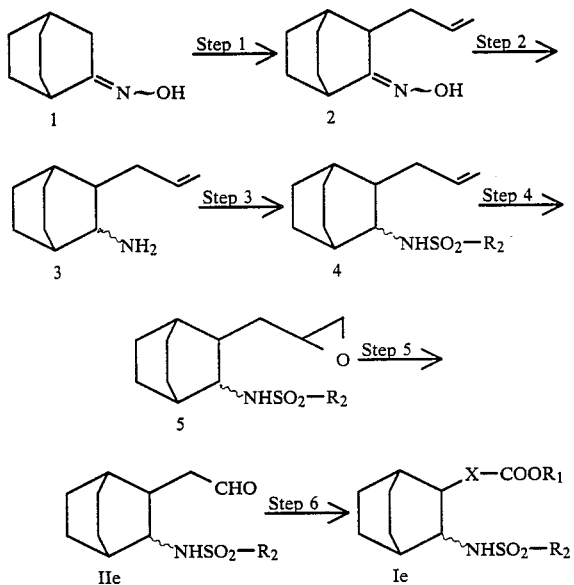

PROCESS II

(Step 1)

In this step, an allyl group is introduced into the 2-position of the compound 1. An allylating agent such as allyl halide, e.g., allyl chloride, allyl bromide or allyl iodide, or allyl sulfonate is used in this step. As a catalyst, such a relatively strong base as n-butyl lithium, sodium amide, potassium tert-butoxide, sodium hydride, or lithium diisopropylamide may be used. As a solvent, ether, such as diethyl ether, tetrahydrofuran, glyme, or diglyme is exemplified. The reaction is achieved at a temperature of −78° C. to 25° C. within a period of several minutes to several hours.

(Step 2)

In this step, the oxime 2 is reduced to the amine 3. As a reducing agent, lithium aluminium hydride, zinc or stannous chloride is exemplified. As a solvent, alcohol such as methanol or ethanol, or ether such as diethyl ether or tetrahydrofuran is exemplified. This step also achieved by catalytic hydrogenation with a catalyst such as platinum or palladium, or reduction with metal sodium in an alcohol solvent.

In this step, a mixture of two stereoisomers of which the 3-side chain has α and β configurations is prepared.

(Step 3)

In this step, the amine 3 is converted into the sulfonamide derivatives 4. This step may be carried out in accordance with the manner of Process I-6, Step 1.

(Step 4)

In this step, the double bond of allyl group of the compound 4 is oxidized into the epoxide 5. As an oxidizing agent, a combination of hydrogen peroxide and transition metal, or peroxy acid or peroxy acid ester such as performic acid, peracetic acid, perbenzoic acid, monoperphthalic acid, monopermaleic acid, pertrifluoroacetic acid, m-chloroperbenzoic acid, or p-nitroperbenzoic acid may be used. As a solvent, ether such as diethyl ether or tetrahydrofuran, alcohol such as, methanol or ethanol, or chlorinated hydrocarbon such as dichloromethane or chloroform may be used. The reaction is carried out at a temperature of 0° C. to room temperature for a period of several minutes to several hours.

(Step 5)

In this step, the epoxide 5 is converted into the aldehyde II e losing one carbon through the hydration and the subsequent oxidative cleavage of the resulting glycol. As an oxidizing agent which also serves as a hydrating catalyst, periodic acid or orthoperiodic acid may be used. It is desirable to use a solvent which is miscible with water, such as ether, e.g., diethyl ether, tetrahydrofuran, dioxane, alcohol, e.g., methanol, ethanol. The reaction is carried out at room temperature for a period of several tens of minutes to several hours.

In this step, the aldehyde II e, the starting compounds prepared.

(Step 6)

In this step, the compound II e is allowed to react in accordance with the manner of Process I-7, Step 7 to give the compound of the present invention.

In this reaction, the free carboxylic acid I e-b can be prepared. If necessary, the carboxylic acid I e-b may be esterified. The esterification may be carried out in accordance to the method described in Process I-7, Step 8. In this esterification, the carboxylate ester I e-a of the present invention can be prepared. Moreover, the free carboxylic acid I e-b may be converted into the carboxylate salt I e-c by treating in accordance to Process I-7, Step 8.

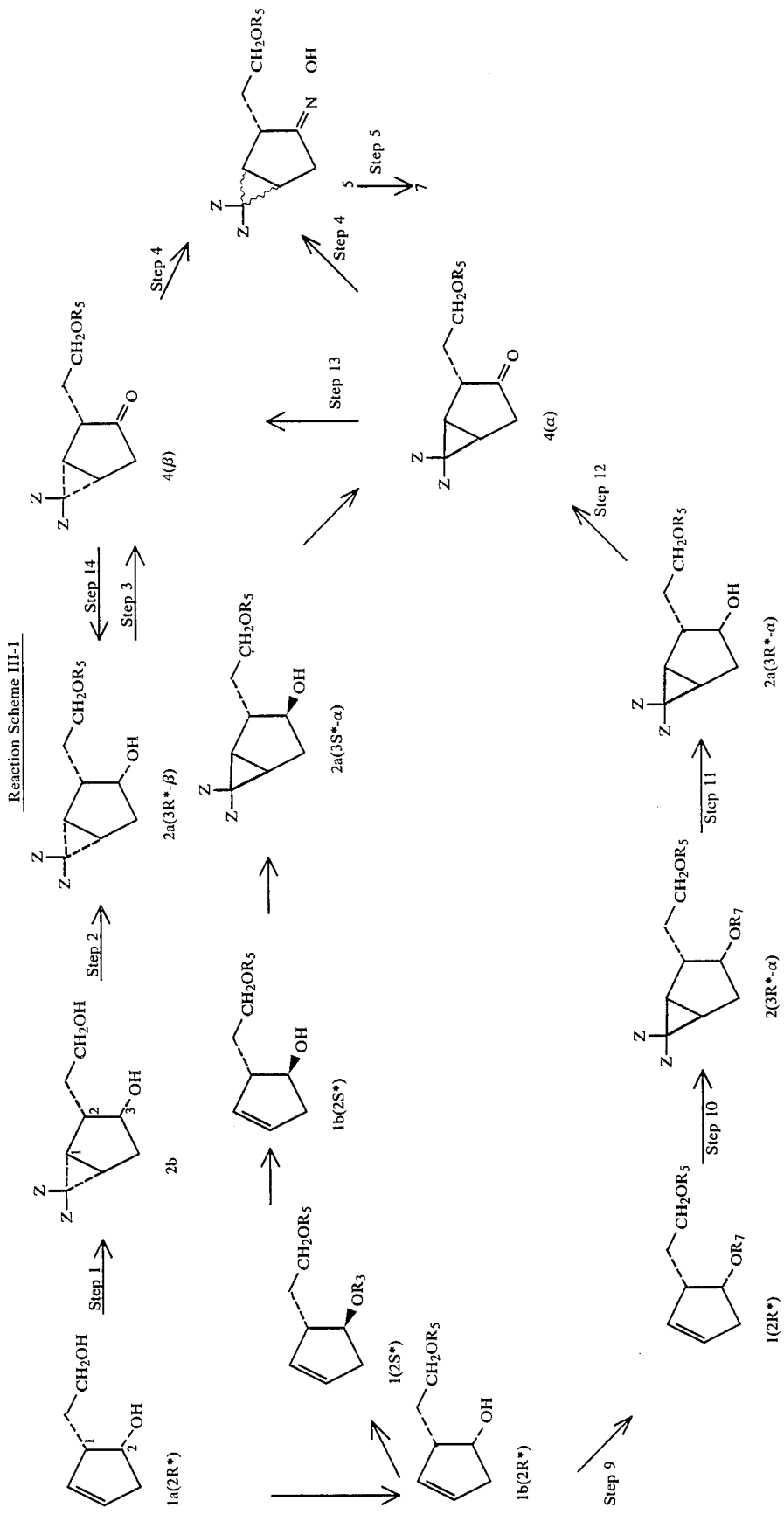
Reaction Scheme III-1

Reaction Scheme III-1

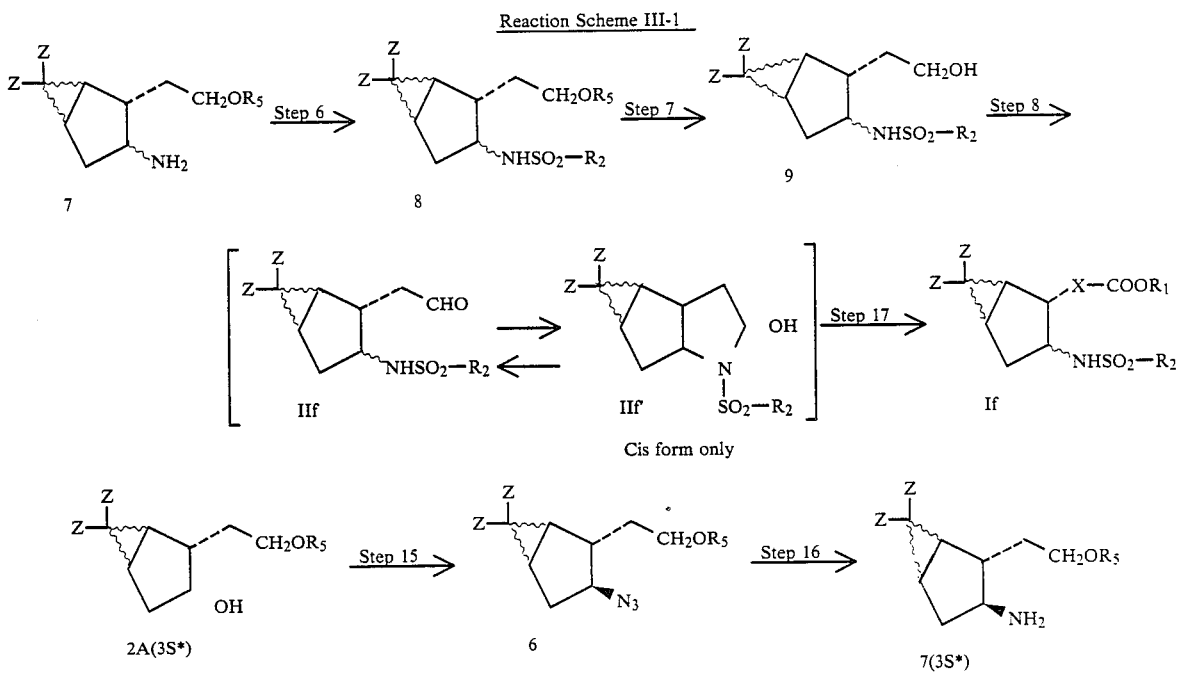

Cis form only

PROCESS III-1

(Step 1)

In this step, a methylene group is introduced between the $C_4$–$C_5$ carbon atoms of the compound 1a(2R*). As a methylene donor agent, the Simmons-Smith agent or its analog prepared from methylene iodide and zinc-copper couple, zinc-silver couple, diethylzinc or ethylzinc iodide, or diazomethane and zinc halide, respectively, is used. As a solvent, ethers such as diethyl ether, tetrahydrofuran, glyme or diglyme may be used. The reaction is completed at room temperature or under heating within several hours. In this step, the methylene group is introduced to the same side as that of the 3-hydroxy.

(Step 2)

In this step, the hydroxy of hydroxyethyl of the compound 2b is protected. As compounds forming a protecting group, methoxymethyl chloride, benzyloxymethyl chloride, benzyl chloride, triphenylmethyl chloride, trimethylsilyl chloride, bistrimethylsilylacetamide, dimethyl-tert-butylsilyl chloride or the like may be exemplified. The reaction may be carried out in a conventional manner in the presence of a base such as triethylamine or pyridine, if necessary, with a catalyst such as dimethylaminopyridine. As a solvent, ethers such as diethyl ether or tetrahydrofuran, or chlorinated hydrocarbons such as dichloromethane or chloroform may be exemplified.

This step may be carried out prior to Step 1.

(Step 3)

In this step, the 3-hydroxy group of the compound 2a(3R*-β) is oxidized. As an oxidizing agent, chromate-type agents such as Jones' reagent, Collins' reagent, pyridinium chlorochromate or pyridinium dichromate, or dimethylsulfoxide combined with sulfur trioxide, trifluoroacetic anhydride, methanesulfonic anhydride, thionyl chloride or oxalyl chloride or the like may be used. In a case where dimethylsulfoxide is used as an oxidizing agent, a tertiary amine such as triethylamine or pyridine may be used as a decomposing agent. As a solvent, according to the property of the agent, a chlorinated hydrocarbon such as chloroform or dichloromethane, ether such as diethyl ether, tetrahydrofuran, or dimethylsulfoxide may be used. The reaction may be carried out under cooling or at room temperature within several hours.

(Step 4)

In this step, the 3-ketone of the compound 4(β) is converted into the oxime. The oxime formation is carried out with hydroxylamine hydrochloride or sulfate in the presence of a base such as sodium hydroxide, potassium hydroxide or sodium carbonate. As a solvent, an alcohol such as methanol or ethanol may be exemplified.

(Step 5)

In this step, the oxime 5 is reduced to the amine 7. This step may be achieved by reducing the oxime 5 into the imine, which is then converted into the amine 7. As a reducing agent for reducing the oxime 5 to the imine, a combination of a disulfide such as diphenyldisulfide or dibenzyldisulfide with phosphines such as n-tributylphosphine, trimethoxyphosphine, triethoxyphosphine, or triphenylphosphine may be used. As a solvent, an ether such as diethyl ether or tetrahydrofuran may be used. The reaction may be carried out under cooling for several hours. As a reducing agent for reducing the imine to the amine 7, lithium aluminum hydride, sodium borohydride, sodium cyanoborohydride or the like may be exemplified. As a solvent, an alcohol such as methanol or ethanol, or ether such as diethyl ether or tetrahydrofuran may be exemplified. In this step, the 3-side chain can be located in either of α or β configuration dependent on the property of the agent used.

(Step 6)

In this step, the amine 7 is converted into the sulfonamide derivatives 8. The reaction to the sulfonamide derivatives is completed in several tens of minutes in a solvent such as chlorinated hydrocarbon, e.g. dichloromethane or chloroform, ether, e.g. ethyl ether or tetrahydrofuran, or aromatic solvent, e.g. benzene, in the presence of a basic substance such as pyridine or triethylamine at room temperature, using a sulfonic acid halide having a desired substituent such as methanesulfonyl chloride, ethanesulfonyl chloride, propanesulfonyl chloride, butanesulfonyl chloride, pentanesulfonyl chloride, hexanesulfonyl chloride, heptanesulfonyl chloride, octanesulfonyl chloride, benzenesulfonyl chloride, methoxybenzenesulfonyl chloride, nitrobenzenesulfonyl chloride, hydroxybenzenesulfonyl chloride, toluenesulfonyl chloride, ethylbenzenesulfonyl chloride, aminobenzenesulfonyl chloride, acetylaminobenzenesulfonyl chloride, or dimethylaminobenzenesulfonyl chloride. If necessary, 4-dimethylaminopyridine may be used as a catalyst.

(Step 7)

In this step, the hydroxy-protecting group of the compound 8 is removed. The reaction condition for removal of the protecting group is variable according to the group. In a case of lower alkyl which has a substituent such as alkoxymethoxy, aralkyloxymethoxy, or aralkyloxy, the reaction is carried out by treating the compound 8 with an acid, for example, organic acid such as formic acid, acetic acid, propanic acid, butyric acid, oxalic acid or malonic acid, or mineral acid such as hydrochloric acid, hydrobromic acid or sulfuric acid. In a case of aralklyoxy, the reaction may also be achieved by catalytic hydrogenation. For the reaction to proceed smoothly, a solvent may be used. As a solvent, water, alcohol such as methanol or ethanol, or ether such as diethyl ether, tetrahydrofuran or dioxane may be used singly or as a mixture. The reaction may be achieved at room temperature or under heating for a period of several hours to several tens of hours. In the case where the protecting group is trilower alkylsilyl, the reaction is easily achieved on the treatment with triethylammonium fluoride in a nonaqueous solvent, or with an acid or base in an aqueous solvent. An acid used in the reaction includes is hydrogen fluoride or those exemplified before, and as a base, hydroxide such as sodium hydroxide, potassium hydroxide or calcium hydroxide, or carbonate such as sodium carbonate or potassium carbonate may be exemplified. As a solvent, aqueous ether such as diethyl ether, tetrahydrofuran or dioxane, or aqueous alcohol such as methanol or ethanol may be used. The reaction may be carried out in a conventional manner.

In addition, depending on the reaction conditions, the ester compound may be obtained, which may be hydrolyzed in the presence of a base, if necessary. As a base, a hydroxide such as sodium hydroxide, potassium hydroxide or calcium hydroxide, or carbonate such as sodium carbonate or potassium carbonate may be exemplified. As a solvent, an alcohol such as methanol or ethanol, ether such as diethyl ether or tetrahydrofuran, or dimethylsulfoxide may be used singly or in a mixture. The reaction may be achieved at room temperature or under heating within several hours.

(Step 8)

In this step, the hydroxy compound 9 is oxidized into the aldehyde II f. This step may be carried out in accordance with the manner of Step 3. The aldehyde prepared in this step is in equilibrium with the cyclic hemiacetal II f' when it is in a cis form. The prepared aldehyde II f in this step, included in the starting compounds of the present invention, has the methylene which is attached to the same side as that of the 2-side chain.

The compound of which the methylene is located in the opposite side to the 2-side chain is prepared as follows. First, the hydroxy of the hydroxyethyl group of the starting compound 1a(2R*) is protected in accordance with the manner of Step 2 to give the compound 1b(2R*). The inversion of the 2-hydroxy gives the compound 1b(2S*), which may be used as a starting material.

The inversion reaction may be achieved by reacting the compound 1b(2R*) with the carboxylic acid compound in the presence of, for example, the Mitsunobu agent which is a combination of triphenylphosphine with diethyl azodicarboxylate. As the carboxylic acid compound, an aliphatic carboxylic acid such as formic acid, acetic acid, propionic acid or pivalic acid, or aromatic carboxylic acid such as benzoic acid or phenylacetic acid may be exemplified. As solvent, aromatic solvents such as benzene, chlorinated hydrocarbons such as chloroform or dichloromethane, or ethers such as diethyl ether or tetrahydrofuran may be exemplified. The reaction may be achieved under cooling or at room temperature for a period of several tens of minutes to several hours. The inversion reaction may also be carried out with calcium peroxide or cesium acetate. In this case, the hydroxy may be previously mesylated in a conventional method. As a solvent, dimethylsulfoxide, dimethylformamide, dimethoxyethane, diethyl ether or the like may be exemplified. As a solubilizing agent, 18-Crown-6 may be added. In the case where the hydroxy group has been esterified, the ester may be hydrolyzed in the presence of a base. The hydrolysis may be carried out in accordance with the manner of the ester hydrolysis with a base as mentioned in the Step 7.

The succeeding reaction may be carried out in accordance with the manner of Step 1 and Steps 3 to 8 to give the aldehyde II f as a starting compound, of which the methylene is located in the same side as that of the 2-side chain. The starting compounds of the present invention which are substituted by methyl, halogen or trifluoromethyl at the 6-position may be prepared as follows.

(Step 9)

In this step, the 2-hydroxy of the compound 1b(2R*) is acylated to be protected. As an acylating agent, acetic anhydride, acetyl chloride, pivaloyl chloride, benzoyl chloride or the like may be exemplified. As a solvent, aromatic one such as benzene, toluene or pyridine may be used. As a base, triethylamine or pyridine may be added and, if necessary, as a catalyst, 4-dimethylaminoprydine may be added. The reaction is achieved at room temperature within several hours.

(Step 10)

In this step, a substituted methylene is introduced into between the $C_1$–$C_5$ carbon atoms of the compound 1(2R*). A halocarbene derived from chloroform, bromoform, or dibromodifluoromethane on the treatment with a base such as sodium hydroxide, potassium hydroxide, potassium fluoride or n-butyl lithium, or from sodium chlorodifluoroacetate or lithium chlorodifluoroacetate by heating may be added to the double bond. As a solvent, chlorinated hydrocarbon such as chloroform or dichloromethane may be exemplified. If necessary, the reaction may be carried out in a two phase medium between water and a nonaqueous solvent. As a phase transfer catalyst, triethylbenzylammonium chloride or triethylbenzylammonium bromide or the like may be used. The compound of which the 6-position is substituted by fluoro, methyl or trifluoromethyl is prepared from the above prepared chloro- or bromo-compound by the reaction with potassium fluoride, silver fluoride or antimony fluoride, or with dimethyl copper lithium, dimethylthiocyanate copper lithium or dimethylcyano copper lithium, if necessary, followed by treatment with methyl iodide, or by the reaction with trifluoromethyl iodide or bistrifluoromethyldiazomethane in the presence of a copper catalyst. As a solvent, ether such as diethyl ether or tetrahydrofuran, or hexamethylphosphoramide may be used singly or as a mixture.

(Step 11)

In this step, the 3-hydroxy-protecting group of the compound 2(3R*-α) is removed by hydrolysis. The reaction may be carried out in a conventional method. As a solvent, alcohol such as methanol or ethanol, ether such as diethyl ether or tetrahydrofuran, or water may be used singly or as a mixture. If necessary, a base catalyst such as sodium hydroxide or barium hydroxide may be used.

(Step 12)

In this step, the 3-hydroxy of the compound 2a(3R*-α) is oxidized into the ketone (4(α). This step is carried out in accordance with the manner of Step 3.

The compound 4(α) prepared in this step is successively treated in accordance with the manner of Steps 4 to 8 to give the aldehyde II f of which the methylene is located in the opposite side of the 2-side chain.

(Step 13)

In this step, the compound 4(α) is converted into the compound 4(β) in the presence of a base. As a base, a strongly basic substance such as diazabicyclononene, diazabicycloundesene, triethylamine, or potassium tert-butoxide is exemplified. As a solvent, dimethylsulfoxide ior dimethylformamide, aromatic solvent such as toluene or xylene is exemplified. This step is achieved by carrying out the reaction at room temperature or under heating for a period of several hours to several tens of hours and then adding the reaction mixture to a cold acidic nonaqueous solvent such as formic acid, acetic acid or propionic acid.

The compound 4(β) prepared in this step is converted into the aldehyde IIf, of which the methylene is located in the same side as that of the 2-side chain, by treating in accordance with the manner of Steps 4 to 8, successively.

(Step 14)

In this step, the ketone 4(β) is reduced to the hydroxy compound 2a(3R*-β). As a reducing agent, lithium aluminium hydride, lithium triethoxyaluminium hydride, lithium tri-tert-butoxyaluminium hydride, sodium borohydride or the like may be used. As a solvent, ether such as diethyl ether or tetrahydrofuran, alcohol such as methanol or ethanol, or water may be used according to the property of the agent.

(Step 15)

In this step, the hydroxy compound 2a(3R*) [2a(3R*-β) or 2a(3R*-α)] prepared in Steps 11 or 14 is converted into the azide. Before carrying out the azide formation reaction, the hydroxy compound 2a(3R*) is sulfonated in the presence of triethylamine or pyridine. As a sulfonating agent, p-toluenesulfonyl chloride, methanesulfonyl chloride, trifluorosulfonic anhydride or the like is exemplified. As a solvent, chlorinated hydrocarbon such as chloroform or dichloromethane, ether such as diethyl ether or tetrahydrofuran, acetone, dimethylformamide, dimethylsulfoxide, or ethyl acetate may be used. The reaction is achieved under cooling within a period of several minutes to several hours. If necessary, a catalyst such as 4-dimethylaminopyridine may be added. The azide compound 6 is prepared from the intermediate thus prepared by the reaction with sodium azide or lithium azide in a solvent such as hexamethylphosphoramide, dimethylformamide, dimethylsulfoxide, or diphenyl ether under heating for a period of several tens of minutes to several hours.

(Step 16)

In this step, the azide 6 is reduced to the amine 7(3S*). As a reducing agent, triphenylphosphine, lithium aluminium hydride, triethylamine-hydrogen sulfide, triethylamine-mercaptane, or the like is exemplified. As a solvent, alcohol such as methanol or ethanol, ether such as diethyl ether or tetrahydrofuran is exemplified. The reaction is achieved at room temperature or under heating within several hours. This step may also be carried out by catalytic hydrogenation with a catalyst such as platinum or palladium.

The amine 7(3S*) prepared in this step is allowed to react in accordance with the manner of Steps 6 to 8 successively to give the aldehyde IIf, one of the starting compounds of the present invention, of which the 2- and 3-side chain are in relation of trans each other.

(Step 17)

In this process, aldehyde IIf is allowed to react with an ylide to give the compounds If of the present invention. The reaction of the aldehyde with an ylide (reaction for double bond formation) is carried out in accordance with a conventional manner of the Wittig reaction. The ylide used in the reaction is synthesized in the presence of a base from triphenylphosphine on reaction with a halide of alkanoic or alkenoic acid possessing a carboxyl group at the ω-position. As the halide of $C_4$–$C_6$ alkanoic or alkenoic acids used for this process, 4-bromobutanoic acid, 4-bromo-2-butenoic acid, 4-bromo-3-butenoic acid, 5-bromopentanoic acid, 5-bromo-2-pentenoic acid, 5-bromo-3-pentenoic acid, 5-bromo-4-pentenoic acid, 6-bromohexanoic acid, 6-bromo-2-hexenoic acid, 6-bromo-3-hexenoic acid, 6-bromo-4-hexenoic acid, 6-bromo-5-hexenoic acid and so on are available. As for the base, sodium hydride, sodium dimsyl, potassium dimsyl, n-butyl lithium, potassium tert-butoxide, or lithium diisopropylamide are cited. This reaction is conducted in a solvent such as ether, tetrahydrofuran, n-hexane, or dimethylsulfoxide, and can be achieved in several hours under cooling or at room temperature. In this reaction, the free carboxylic acid If-a can be prepared. Depending to the reaction condition the Z-form or a mixture of the Z-form and E-form is produced. If necessary, the carboxylic acid If-b may be esterified. The esterification may be carried out in accordance to the method described in Process I-7, Step 8. In this esterification, the carboxylate ester If-a of the present invention can be prepared. Moreover, the free carboxylic acid If-b may be converted into the carboxylate salt If-c by treating in accordance with Process I-7, Step 8.

(Step 4)

In this step, the hydroxy-protecting group is removed. This step is carried out in accordance with the manner of Process III-1, Step 7.

(Step 5)

In this step, the double bond iof the compound 5a is oxidized into epoxide 6. This step is carried out in ac-

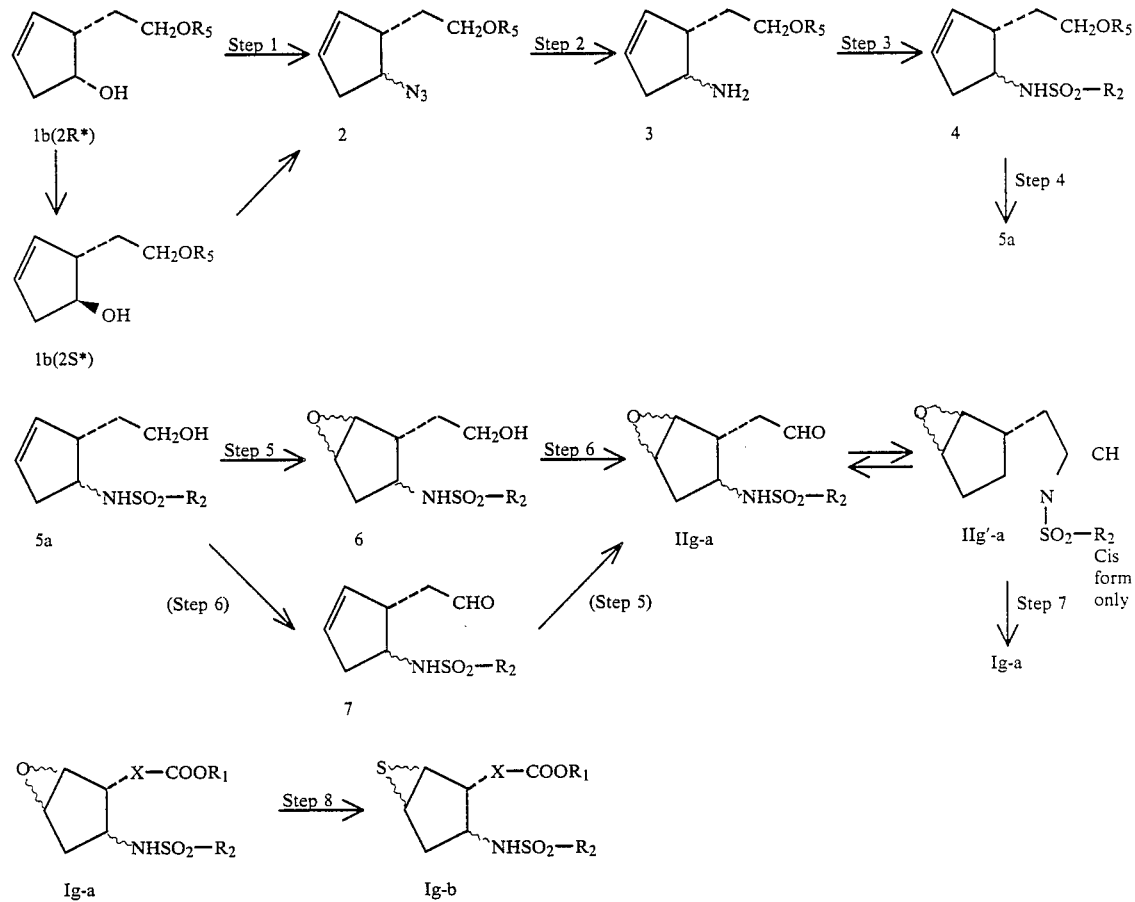

Reaction Scheme III-2 cordance with the manner of Process I-1, Step 4.

(Step 6)

In this step, the hydroxy of the compound 6 is oxidized into the aldehyde IIg. This step may be carried out in accordance with the manner of Process III-1, Step 3. The aldehyde prepared in this step is in equilibrium with the cyclic hemiacetal IIg'. The aldehyde IIg prepared in this step has the 3-side chain which is in relation of cis configuration with the 2-side chain.

In addition, this step may be carried out in advance of Step 5.

The aldehyde IIg has the 3-side chain which is in relation of trans configuration with the 2-side chain is prepared as follows. First, the 2-hydroxy of the compound 1b(2R*) is inversed in accordance with the method for the inversion reaction described in Process III-1. Then, the compound 1b(2S*) may be allowed to react in accordance with the manner of Process III-2, Steps 1 to 6.

PROCESS III-2

(Step 1)

In this step, the hydroxy group of the compound 1b(2R*) is converted into the azide. This step is carried out in accordance with the manner of Process III-1, Step 15.

(Step 2)

In this step, the azide 2 is reduced into the amine 3. This step is carried out in accordance with the manner of Process III-1, Step 16.

(Step 3)

In this step, the amine 3 is converted into the sulfonamide derivatives 4. This step is carried out in accordance with the manner of Process III-1, Step 6.

(Step 7)

In this step, aldehyde IIg-a (or IIg'-a) is allowed to react with an ylide to give the compound Ig-a of the present invention. This step may be carried out in accordance with a manner of Process III-1, Step 17.

In this step, the carboxylate ester Ig-aa of the present invention, the free carboxylic acid Ig-ab or the carboxylate salt Ig-ac is prepared.

(Step 8)

In this step, the epoxide Ig-a is converted into epi-sulfide Ig-b. This step may be carried out as follows. First, the epoxide Ig-a is converted into α-hydroxy-thiocyanate by treating with thiocyanic acid in an ethereal solvent such as diethyl ether or tetrahydrofuran at room temperature for several hours and then the resulting hydroxy group is converted into a leaving group. Subsequently, the thiocyanate moiety is hydrolyzed with a base such as potassium hydroxide in a mixture such as diethyl ether/methanol or diethyl ether/ethanol at room temperature or under heating for a period of several tens of minutes to several hours. As the leaving group used in this step, a substituted sulfonate, e.g., methanesulfonate, benzenesulfonate, p-toluenesulfonenate or the like is exemplified. The epi-sulfide prepared in this step has a configuration opposite to that of the starting epoxide.

In this step, the free carboxylic acid Ig-bb of the present invention is prepared. The free carboxylic acid Ig-bb may be converted into the carboxylate ester Ig-ba or salt Ig-bc in accordance with the manner of Process I-7, Step 8.

Reaction Scheme IV-1

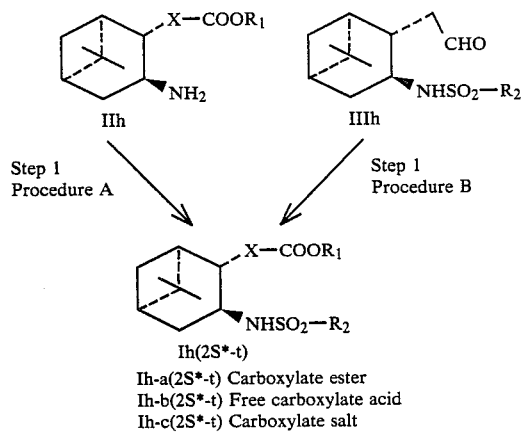

PROCESS IV-1

PROCEDURE-A (Step 1)

In this step, the starting compound IIh(2S*-t) of the present invention is allowed to react in accordance with the manner of Process I-7, Step 8 to give the compound of the present invention. In this step, the carboxylate ester Ih-a(2S*-t) of the 2S*-trans-sulfonamide derivatives Ih(2S*-t); the free carboxylic acid Ih-b(2S*-t) and the carboxylate salt Ih-c(2S*-t) can be prepared.

PROCEDURE B (Step 1)

In this step, the starting compound IIIh(2S*-t) of the present invention is allowed to react in accordance with the manner of Process III-1, Step 17 to give the compounds of the present invention. In this step, the carboxylate ester Ih-a(2S*-t) of the 2S*-trans-sulfonamide derivatives Ih(2S*-t); the free carboxylic acid Ih-b(2S*-t) and the carboxylate salt Ih-c(2S*-t) can be prepared.

Reaction Scheme IV-2

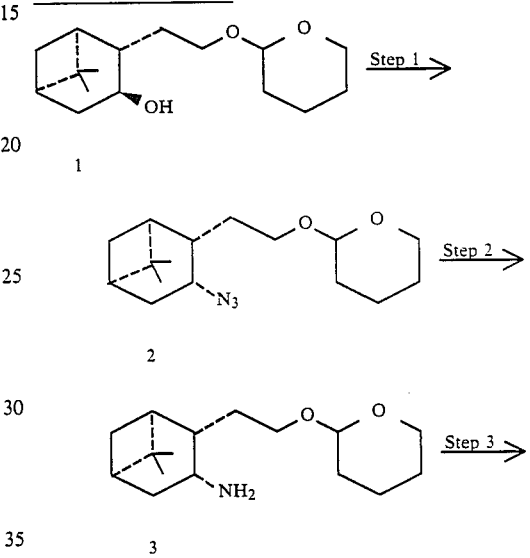

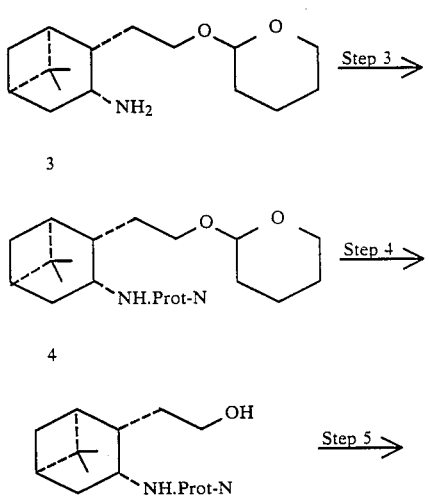

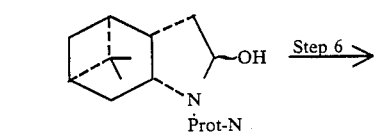

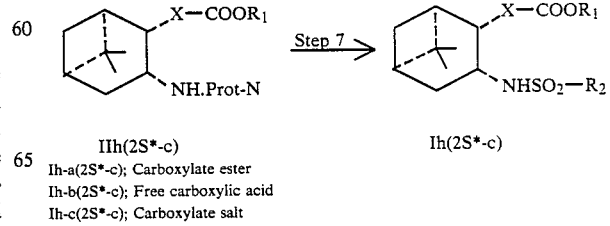

IIh(2S*-c)
Ih-a(2S*-c); Carboxylate ester
Ih-b(2S*-c); Free carboxylic acid
Ih-c(2S*-c); Carboxylate salt Ih(2S*-c)

PROCESS IV-2

(Step 1)

In this step, the 3-hydroxy group of the compound 1 is converted into the azide. Firstly, a chloride or a sulfonyl compound is prepared as a intermediate. The hydroxy compound 1 is converted into the chloride on the reaction with thionyl chloride or into the alternative intermediate in the reaction with p-toluenesulfonyl chloride, methanesulfonyl chloride or trifluoromethanesulfonic anhydride or the like in a solvent such as chlorinated hydrocarbon, e.g. chloroform or dichloromethane, ether, e.g. ethyl ether or tetrahydrofuran, acetone, dimethylformamide, dimethylsulfoxide, or ethyl acetate under cooling for a period of several minutes to several hours. The intermediate prepared in such a manner is heated with sodium azide in a solvent such as hexamethylphosphoramide, dimethylformamide, dimethylsulfoxide, or diphenyl ether for a period of several tens of minutes to several hours to give the azide compound 2.

(Step 2)

In this step, the azide compound 2 is reduced to give the amine 3. The reaction may be carried out with a metal hydride compound such as lithium aluminium hydride ir triphenylphosphine as a reducing agent in a solvent such as ether, e.g. ethyl ether or tetrahydrofuran at room temperature or under heating for several hours.

(Step 3)

In this step, an amino-protecting group is introduced into the amine 3. The amine may be allowed to react, for example, with trifluoroacetic anhydride, trifluoroacetyl chloride, benzyloxycarbonyl chloride or triphenylmethyl chloride in the presence of a base such as triethylamine, pyridine or sodium hydrogencarbonate in a solvent such as chlorinated hydrocarbon, e.g. chloroform or dichloromethane or aromatic solvent, e.g. benzene or toluene. The reaction may be carried out at room temperature or under heating for a period of several tens of minutes to several hours.

(Step 4)

In this step, the hydroxy-protecting group is removed by acid hydrolysis. The reaction may be carried out in accordance with the usual method or hydrolysis using such catalyst as acetic acid, hydrochloric acid, sulfuric acid, or p-toluenesulfonic acid in a solvent such as aqueous alcohol, e.g. methanol or ethanol, or aqueous ether, e.g. ethyl ether or tetrahydrofuran.

(Step 5)

In this step, the alcohol 5 is oxidized into an aldehyde. The reaction may be achieved by a method using dimethylsulfoxide in combination with trifluoroacetic acid, thionyl chloride or oxalyl chloride, or in a method using a chromate oxidizing agent such as Jones' reagent, Collins' reagent, pyridinium chlorochromate, or pyridinium dichromate. As a solvent, chlorinated hydrocarbon such as chloroform or dichloromethane may be used. This aldehyde is cyclized easily to form the hemiacetal 6.

(Step 6)

In this step, the hemiacetal 6 is allowed to react with an ylide to give the starting compound IIh(2S*-c) of the present invention. This step may be carried out in accordance with the manner of the Wittig reaction described in Process I-7, Step 7.

(Step 7)

In this step, the starting compound IIh(2S*-c) of the present invention is allowed to react in accordance with the manner of Process I-7, Step 8 to give the compound of the present invention. In this step, the carboxylate ester Ih-a(2S*-c) of the 2S*-trans-sulfonamide derivatives Ih(2S*-c), the free carboxylic acid Ih-b(2S*-c) and the carboxylate salt Ih-c(2S*-c) can be prepared.

Reaction scheme IV-3

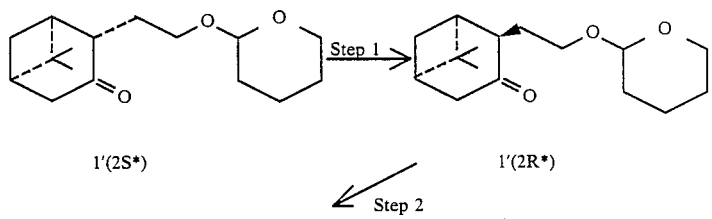

Reaction scheme IV-3

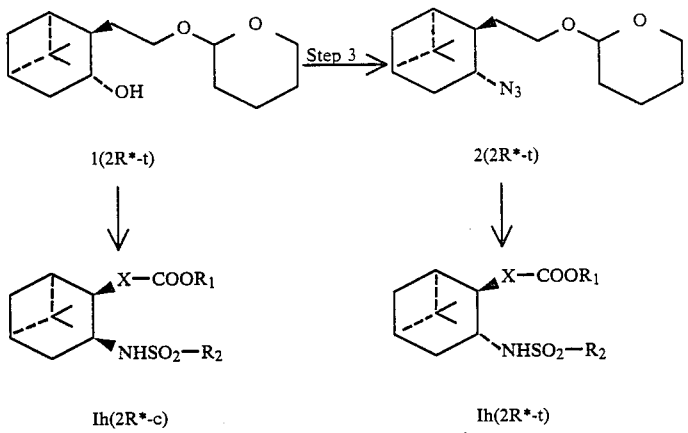

PROCESS IV-3

(Step 1)

In this step, the compound 1'(2S*) is isomerized into the compound 1'(2R*). This reaction is achieved in a solvent such as alcohol, e.g., methanol or ethanol, ether, e.g., diethyl ether or tetrahydrofuran, aromatic solvent, e.g., toluene or xylene, or dimethylsulfoxide or dimethylformamide at room temperaure or under heating for a period of several hours to several tens of hours. According to necessity, a catalyticamount of basic substance such as diazabicyclononene, diazabicycloundecene, pyrrolidine-acetate, piperidine-acetate, sodium methoxide, potassium tert-butoxide, lithium diisopropylamide, triethylamine or the like may be added.

(Step 2)

In this step, the ketone 1'(2R*) is reduced to alcohol 1(2R*-c). As a reducing agent, metal hydride, e.g., lithium aluminum hydride, lithium trimethoxyaluminum hydride, lithium tri-tert-butoxyaluminum hydride, lithium borohydride, or sodium borohydride is exemplified. As a solvent, dry alcohol, e.g., methanol or ethanol, or dry ethereal solvent, e.g., diethyl ether or tetrahydrofuran is used. The reaction may be carried out under cooling or heating within several hours.

The alcohol 1(2R*-t) prepared in this step is allowed to react in accordance with the manner of Process IV-2, Steps 1 to 7 to give the compounds of the present invention. The carboxylate ester Ih-a(2R*-c) of the 2R-cis-sulfonamide derivatives, the free carboxylic acid Ih-b(2R*-c) or the carboxylate salt Ih-c(2R*-c) is prepared.

(Step 3)

In this step, the hydroxy of the compound 1(2R*-t) is converted into the azide which has the same configuration as that of the hydroxy. First, under Mitsunobu condition, that is, in the presence of ethyl azodicarboxylate and triphenylphosphine, the compound 1(2R*-t) is allowed to react with a nucleophile to give the intermediate for the azide-formation. As the nucleophile, methyl bromide, methyl iodide, methyl p-toluenesulfonate, methyl benzenesulfonate, methyl methanesulfonate, zinc p-toluenesulfonate, zinc benzenesulfonate, zinc methanesulfonate, lithium p-toluenesulfonate, lithium benzenesulfonate, lithium methanesulfonate or the like may be exemplified. As a solvent, ethereal solvent, e.g., diethyl ether or tetrahydrofuran, or benzene may be used. The reaction may be carried out under cooling or at room temperature for several hours. In this reaction, the compound 1(2R*-t) is respectively converted into the corresponding sulfonate or halogenide with inverted configuration.

The intermediate is allowed to react with sodium azide to give the azide 2(2R*-t) in a solvent such as hexamethylphosphoramide, dimethylformamide, dimethylsulfoxide or diphenyl ether under heating for a period of several tens of minutes to several hours.

The azide 2(2R*-t) prepared in this step is allowed to react in accordance with the manner of Process IV-2, Steps 2 to 7 to give the compounds of the present invention. The carboxylate ester Ih-a(2R*-t) of the 2R-trans-sulfonamide derivatives, the free carboxylic acid Ih-b(2R*-t) or the carboxylate salt Ih-c(2R*-t) is prepared.

In the reaction schemes, $R_1$, $R_2$, $R_3$, or X each is as defined before. $R_4$ is diisopropylmethyl, isobutyl, tert-butyl, cyclopenyl, benzyl, diphenylmethyl, or triphenylmethyl. $R_5$ is a hydroxy-protecting group such as methoxymethyl, benzyloxymethyl, benzyl, triphenylmethyl, trimethylsilyl or the like. $R_6$ is an alkanoyl or aroyl, such as formyl, acetyl, propionyl, pivaloyl, benzoyl, or phenylacetyl. $R_7$ is a hydrogen or a straight or branched alkyl such as methyl, ethyl, n-propyl, isopropyl, butyl or tert-butyl, or benzyl. $L_1$ is a leaving group such as halogene, e.g., chlorine or bromine, or sulfonate, e.g., methanesulfonate, benzenesulfonate or p-toluenesulfonate. Z is a hydrogen or methyl. THP is tetrahydro-2-pyranyl. Prot-N is an ordinarily used amino-protecting group such as trifluoroacetyl, benzyloxycarbonyl, tert-butoxycarboxyl or triphenylmethyl. Prot-C is a carboxyl-protecting group such as methyl, ethyl, propyl, isopropyl, tert-butyl, benzyl, diphenylmethyl, triphenylmethyl, phthalimido or 4-picolyl. The wavy line indicates the compound is a mixture of the epimers, or of α or β configuration.

The salts of the compounds represented by general formula (I) is as defined before.

The following examples and physical constants are included to explain the embodiment of the present invention in more detail, but these are not intended to limit the scope of the invention.

In the following Examples, the respective compounds are represented by one of the enantiomers in each step. The absolute configuration of the optical

EXAMPLE I-1

EXAMPLE 1

Preparation of dl-2-allyl-bicyclo[2.2.1]heptane-3-one

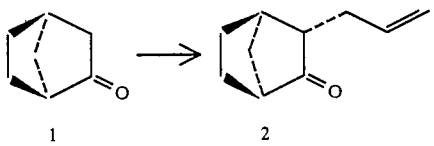

According to the method described in the literature [Tetr. Lett. 21, 1897 (1980)] the compound 2 is prepareded as follow.

To a solution of 21.0 ml (0.15M) of diisopropylamine in 50 ml of tetrahydrofuran (hereinafter, abbreviated to THF) is dropwise added 94.0 ml (0.15M) of n-butyl lithium (1.6M in n-hexane) at −30° C., which is stirred a −20° C. for 15 minutes. Separately, a solution of 16.5 g (0.15M) of norcamphor 1 (Aldrich) in 100 ml of THF is prepared and the solution of lithium diisopropylamide prepared above is added thereto at −78° C., to which 14.3 ml (1.05M×1.1) of allyl bromide is added at −78° C. The reaction mixture is stirred and slowly warmed up to 20° C. over a 1.5 hour period. The mixture solution is evaporated under reduced pressure until its volume become about 100 ml. Ether is added to the remaining mixture and then 300 ml of 2N hydrochloric acid added. The organic layer collected is dried over anhydrous sodium sulfate, and evaporated under reduced pressure. The residue is distilled under reduced pressure to give 17.0 g of the titled compound 2 as a distillate with b.p. 88°-98° C./15 mmHg in 75.6% yield. Colorless oil, (lit; liquid, b.p. 92° C./10 mmHg).

EXAMPLE 2

Preparation of 2-allyl-3(E)-hydroxyimino-bicyclo[2.2.1]heptane 3a and 2-allyl-3(Z)-hydroxyimino-bicyclo[2.2.1]heptane 3b

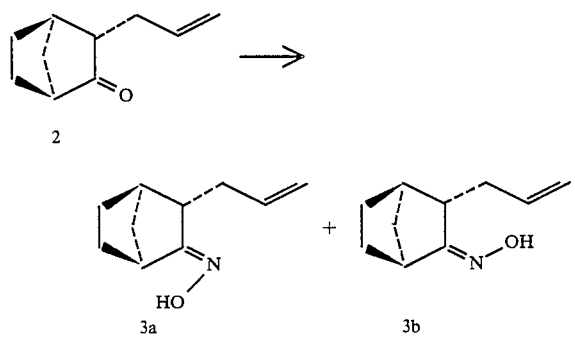

To 60 ml of methanol are added 6.00 g (40 mM) 2-allylbicyclo[2.2.1]heptane-2-one 2, 5.56 g (80 mM) of hydroxylamine hydrochloride and 4.49 g (80 mM) of powderly potassium hydroxide at 0° C., and the mixture is stirred at 25° C. for 30 minutes. The reaction mixture is then distributed between ether and 0.1N hydrochloric acid, and the organic layer is washed with water, dried over anhydrous sodium sulfate and evaporated under reduced pressure. The residue is chromatographed on a silica-gel (hereinafter abbreviated to SiO$_2$) column [Merck, Lobar C; eluted with n-hexane-ethyl acetate (95:5) (hereinafter, ethyl acetate is abbreviated to AcOEt)] to give 3.76 g of the 3(E)-oxime 3a as an early eluate in 56.71% yield. Colorless oil.

$^1$H-NMR(CDCl$_3$) δppm: 1.03∼1.90 (m, 7H), 1.90∼2.60 (m, 4H), 3.50 (br.s, 1H), 4.86∼5.25 (m, 2H), 5.60–6.18 (m, 1H).

IR(CHCl$_3$) νmax: 3590, 3285, 3140, 3080, 1680, 1640 cm$^{-1}$.

Anal. Calcd. for C$_{10}$H$_{15}$NO: (%): C 72.67, H 9.17, N 8.48, Found: (%): C 72.38, H 9.14, N 8.49.

The late eluate gives 2.02 g of the 3(Z)-oxime in 30.64% yield. Colorless oil.

$^1$H-NMR(CDCl$_3$) δppm: 1.15∼2.00 (m, 7H), 2.15∼3.15 (m, 5H), 4.90∼5.22 (m, 2H), 5.60∼6.12 (m, 1H).

IR(CHCl$_3$) νmax: 3590, 3280, 3140, 3085, 1678, 1641 cm$^{-1}$.

Anal. Calcd. for C$_{10}$H$_{15}$NO: (%): C 72.67, H 9.17, N 8.48, Found: (%): C 72.45, H 9.26, N 8.21.

EXAMPLE 3

2-Allyl-3-benzyloxycarbonylamino-bicyclo[2.2.1]heptane

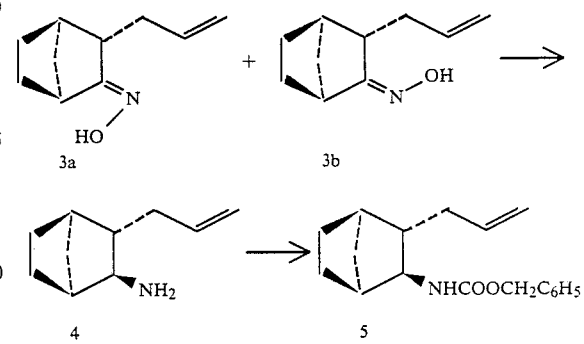

To a solution of 6.26 g (37.9 mM) of 2-allyl-3(E)-hydroxyimino-bicyclo[2.2.1]heptane 3a in 60 ml of dry THF is added 1.44 g (3.79 mM) of lithium aluminum hydride, and the mixture is refluxed for 1.5 hours. After being decomposed with addition of water, as usual, the reaction mixture is extracted with AcOEt and then with diluted hyrochloric acid. The aqueous laer is then washed with AcOEt, then alkalined with 0.1N-sodium hydroxyide(hereinafter abbreviated to NaOH) aqueous solution, and then extracted with AcOEt. The extract is dried over anhydrous sodium sulfate (hereinafter abbreviated to Na$_2$SO$_4$) and evaporated under reduced pressure. Without further purification, 4.4 g (29.1 mM) of the resulting amine 4 is dissolved immediately in 30 ml of dichloromethane (hereinafter abbreviated to CH$_2$Cl$_2$), to which are added 2.87 ml (29.1 mM×1.2) of pyridine and 5.0 ml (29.1×1.2) of benzyloxycarbonyl chloride at 0° C., and the mixture is stirred at the same temperature for 30 minutes. The reaction mixture is distributed between CH$_2$Cl$_2$ and 0.2N hydrochloric acid, and the organic layer is dried over anhydrous sodium sulfate and concentrated under reduced pressure. The residue is chromatographed on a SiO$_2$ column [Merck, Lobar C; eluted with n-hexane-AcOEt (9:1)] to give 4.27 g of the titled compound 5 in 39.5% in yield. Colorless columnar crystals, mp. 60°-61° C.

IR(CHCl₃) νmax: 3430, 1715, 1505 cm⁻¹.

¹H-NMR(CDCl₃) δppm: 0.74~1.89 (m, 7H), 1.90~2.30 (m, 3H), 2.43 (br.s, 1H), 3.53 (t, d, J=4, 7 Hz, 1H), 4.80 (br.s, 1H), 4.91 (m, 1H), 5.09 (s, 2H), 5.50~6.00 (m, 1H), 7.36 (s, 5H).

Anal. Calcd. for C₁₈H₂₃NO₂: (%): C 75.74, H 8.14, N 4.91 Found: (%): C 75.84, H 8.10, N 4.95.

Reduction of 3.37 g (20.4 mM) of 2-allyl-3(Z)hydroxyliminobicyclo[2.2.1]heptane 3b with lithium aluminum hydride in the same manner as mentioned above, also affords 2.2 g of amine 4 which further yields 2.13 g of the titled compound 5 in 40.0% yield. IR and NMR spectrum of the compounds 4 and 5 prepared from the Z-isomer are the same as those prepared from the E-isomer.

EXAMPLE 4

2-(2,3-Epoxypropyl)-3-benzyloxycarbonylaminobicyclo[2.2.1]heptane

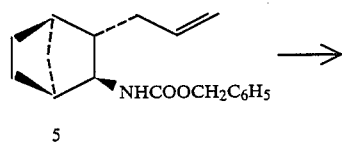

5

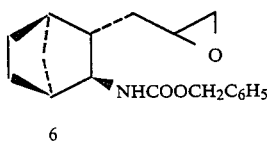

6

To a solution of 6.8 g (23.8 mM) of 2-allyl-3-benzyloxycarbonylaminobicyclo[2.2.1]heptane 5 in 150 ml of CH₂Cl₂ is added 10.3 g (23.8 mM×2) of m-chloroperbenzoic acid at 0° C. and the mixture is stirred at 20° C. for 3 hours. The resulting crystals are removed by filtration and the filtrate is washed successively with 10% aqueous solution of sodium thiosulfate, 5% aqueous solution of sodium hydrogencarbonate and water, dried over Na₂SO₄, and then concentrated under reduced pressure. The residue is chromatographed on a SiO₂ column [Merck; Lobar C; eluted with n-hexane-AcOEt (4:1)] to give 7.17 g of the titled compound 6 in 100% yield. Colorless oil.

IR(CHCl₃) νmax: 3455, 1717, 1505, 1479, 1456 cm⁻¹.

¹H-NMR(CDCl₃) δppm: 1.00~1.85 (m, 9H), 2.05 (br.s, 1H), 2.40 (br.s, 1H), 2.43 (m, 1H), 2.70 (m, 1H), 2.89 (m, 1H), 3.55 (m, 1H), 4.90 (m, 1H), 5.06 (s, 2H), 7.32 (s, 5H).

Anal. Calcd. for C₁₈H₂₃NO₃.0.1H₂O (%): C 71.29, H 7.72, N 4.62, Found (%): C 71.27, H 7.47, N 4.57.

EXAMPLE 5

Methyl 7-[2(S*)-2-exo-3-endo-(3-benzyloxycarbonylamino)bicyclo[2.2.1]hept-2-yl]-5(Z)-heptenoate acid 8

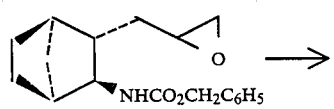

6

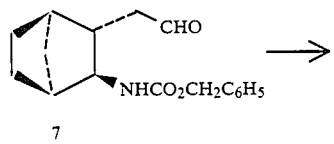

7

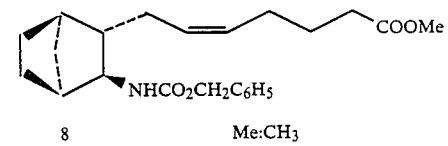

8          Me:CH₃

To a solution of 4.52 g (15 mM) of the epoxide 6 in 50 ml of dioxane is added 15 ml of aqueous solution containing of 6.84 g (30 mM) of periodic acid dihydrate at 25° C. and the mixture is stirred for 4 hours at the same temperature. AcOEt is added, and the mixture is washed with water, dried over Na₂SO₄, and evaporated to give 3.97 g of the aldehyde 7.

To 100 ml of dimethyl sulfoxide (hereinafter abbreviated to DMSO) is added 2.88 g (13.8 mM×6×0.9) of sodium hydride (60% in mineral oil) at 25° C., and the mixture is stirred at 70° C. until no hydrogen gas is evolved (about 1.5 hours). To the solution is added at 18° C. 17.8 g (13.8 mM×3×0.97) of 5-carboxybutyltriphenylphosphonium bromide which is prepared from triphenylphosphine and 5-bromopentanoic acid, and then 40 ml of DMSO added, and the mixture is stirred for 20 minutes at 20° C.

To this mixture is added a solution of 3.97 g of the above prepared aldehyde 7 in 60 ml of DMSO at 18° to 20° C., and the mixture is stirred at 25° C. for 4 hours. The reaction mixture is allowed to stand overnight, then diluted with AcOEt, washed with 0.1N hydrochloric acid, and then with water, dried over sodium sulfate, and evaporated under reduced pressure. The residue is dissoluved in 50 ml of AcOEt, to which a distilled diazomethane ether solution is added in the usual manner for esterification. The solvent is evaporated under reduced pressure and the rediue is chromatographed on a SiO₂ column [Merck, Lobar C; eluted with n-hexane/AcOEt (9:1)] to give 2.80 g of the titled compound 8 in 48.4% yield (from the epoxide). Colorless oil.

IR(CHCl₃) νmax: 3450, 1721, 1602, 1501, 1453, 1437 cm⁻¹.

¹H-NMR(CDCl₃) δppm: 1.00~1.85 (m, 9H), 1.85~2.30 (m, 5H), 2.30 (t, J=7 Hz, 2H), 2.40 (br.s, 1H), 3.50 (t, d, J=4, 7 Hz, 1H), 3.63 (s, 3H) 4.93 (d, J=7 Hz, 1H), 5.09 (s, 2H), 5.36 (m, 2H), 7.34 (s, 5H).

Anal. Calcd. for C₂₃H₃₁NO₄: (%): C 71.65, H 8.12, N 3.63, Found: (%): C 71.60, H 7.95, N 3.71.

EXAMPLE 6

Methyl 7-[(3-aminobicyclo[2.2.1]hept-2-yl)]-5-heptenoate 10

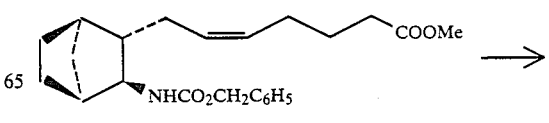

8

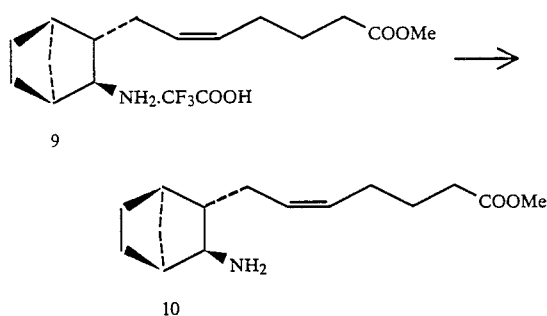

9

10

A mixture of 771 mg (2 mM) of the compound 8, 10 ml of trifluoroacetic acid and 2 ml of anisole is heated at 45° C. for 3 hours. The reaction mixture is evaporated under reduced pressure. Benzene is added to the residue and evaporated. This procedure is repeated 3 times. The resulting residue is rinsed well with petroleum ether and evaporated under reduced pressue to give 500 mg of the trifluoroacetate salt 9 as a light brown oil in 99.6% yield.

This compound may be used in the next reaction even in the form of salt.

$^1$-NMR(CDCl$_3$) δppm: 1.10~2.50 (m, 15H), 2.32 (t, J=7 Hz, 2H), 3.08 (m, 1H), 3.68 (s, 3H), 5.40 (m, 2H), 7.60 (br, 2H), 8.85 (br, 1H).

IR(CHCl$_3$) νmax: 3100 br, 2560 br, 1779, 1725, 1675, 1522, 1436 cm$^{-1}$.

This salt 9 is distributed between water and ether and then the aqueous layer is collected and washed with ether, alkaline with sodium carbonate aqueous solution, and extracted with AcOEt. The AcOEt layer is washed with water, dried over Na$_2$SO$_4$ and evaporated to give 330 mg of the amine 10 in 65.7% yield.

IR(CHCl$_3$) νmax: 3400 br, 1728, 1600, 1583 cm$^{-1}$.

$^1$H-NMR(CDCl$_3$) δppm: 1.00~2.35 (m, 17H), 2.30 (t, J=7 Hz, 2H), 2.73 (m, 1H), 3.64 (s, 3H), 5.40 (m, 2H).

EXAMPLE 7

Methyl 5Z-7-[3-phenylsulfonamidobicyclo[2.2.1-]hept-2-yl]-5-heptenoate and Methyl 5Z-7-[3-hexylsulfonamidobicyclo[2.2.1]hept-2-yl]-5-heptenoate

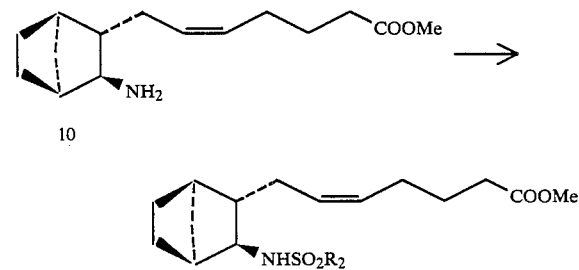

10

11; R = C$_6$H$_5$
13; R = C$_6$H$_{13}$

To a solution of 140 mg (0.557 mM) of the amine 10 in 3 ml of CH$_2$Cl$_2$ is added 155 μl (0.557 mM×2) of triethylamine and 107 μl (0.557 mM×1.5) of benzenesulfonyl chloride at 0° C., and the mixture is stirred at 23° C. for 15 minutes. The reaction mixture is diluted with AcOEt and washed with 0.1N hydrochloric acid, and then successively, with water, 5% sodium hydrogencarbonate aqueous solution and water, and dried over Na$_2$SO$_4$. The solvent is evaporated under reduced pressure and the residue is chromatographed on a SiO$_2$ column [Merck, Lobar A; eluted with n-hexane-AcOEt (9:1)] to give 188 mg of the benzenesulfonamide 11 in 86.2% yield. Colorless oil.

IR(CHCl$_3$) νmax: 3375, 1725, 1158, 1090 cm$^{-1}$.

$^1$H-NMR(CDCl$_3$) δppm: 0.80~2.10 (m, 15H), 2.17(br.s, 1H), 2.26 (t, J=7 Hz, 2H), 3.02 (m, 1H), 3.67 (s, 3H), 5.20 (m, 2H), 7.40~7.65 (m, 3H), 7.83~8.03 (m, 2H).

Anal. Calcd. for C$_{21}$H$_{29}$NO$_4$S (%): C 64.41, H 7.48, N 3.58, S 8.19, Found (%): C 64.51, H 7.48, N 3.61, S 7.87.

n-Hexylsulfonyl chloride is used in the place of the above-mentioned benzenesulfonyl chloride to give hexylsulfonamide 13 in 42.3% yield. Pale yellow oil.

$^1$H-NMR(CDCl$_3$) δppm: 0.89 (t, J=7 Hz, 3H), 1.00~2.25 (m, 22H), 2.30 (t, J=7 Hz, 2H), 2.35 (br.s. 1H), 2.85~3.06 (m, 2H), 3.22 (t, d, J=4, 7 Hz, 1H), 3.65 (s, 3H), 4.73 (d, J=7 Hz, 1H), 5.39 (m, 2H).

IR(CHCl$_3$) νmax: 3400, 3295, 1730, 1458, 1437, 1409 cm$^{-1}$.

Anal. Calcd. for C$_{21}$H$_{37}$NO$_4$S: (%): C 63.11, H 9.35, N 3.51, S 8.02, Found (%): C 62.98, H 9.29, N 3.56, S 7.72.

EXAMPLE 8

7-[3-Phenylsulfonamidobicyclo[2.2.1]hept-2-yl]-5-heptenoic acid and its sodium salt 12

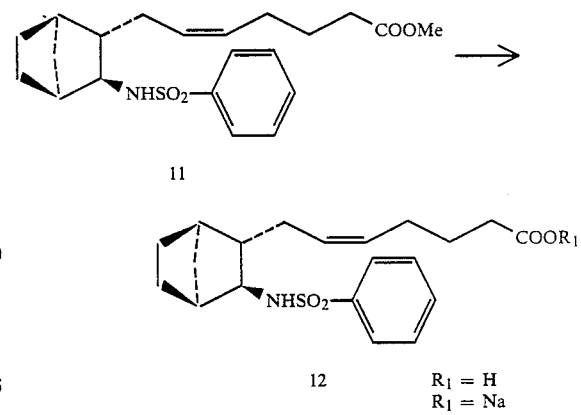

12  R$_1$ = H
    R$_1$ = Na

To a solution of 150 mg (0.383 mM) of the ester 11 in 2.0 ml of methanol is added 0.77 ml (0.383 mM×2) of 1 N sodium hydroxide aqueous solution at 23° C. and the mixture is allowed to stand overnight at the same temperature. The reaction mixture is distributed between ether and water, and the aqueous layer is acidified with hydrochloric acid and extracted with AcOEt. The organic layer is washed with water, dried over Na$_2$SO$_4$, and evaporated under reduced pressure. The resulting crude crystals are recrystallized from ether and n-hexane to give 126 mg of the carboxylic acid 12 in 87.5% yield. Colorless prisms.

Mp. 85°-86° C.

IR νmax: 3380, 3550~2500, 1710, 1160, 1090 cm$^{-1}$.

$^1$H-NMR(CDCl$_3$) δppm: 0.85~2.30 (m, 15H), 2.31(t, J=7 Hz, 2H), 3.00 (t, d, J=4, 7 Hz, 1H), 5.20 (m, 2H), 5.69 (d, J=7 Hz, 1H), 7.43~7.70 (m, 3H), 7.83~8.10 (m, 2H), 9.52 (br.s, 1H).

Anal. Calcd. for C$_{20}$H$_{27}$NO$_4$S (%): C 63.62, H 7.22, N 3.71, S 8.49, Found (%): C 63.67, H 7.15, N 3.71, S 8.36.

Sodium salt of compound 12

Anal. Calcd. for C20H26NO4SNa H2O: (%): C 59.46, H 6.61, N 3.47, S 7.94, Na 5.69, Found (%): C 59.26, H 6.60, N 3.59, S 7.95, Na 5.63.

$^1$H-NMR(D$_2$O ext TMS) δppm: 1.40~2.65 (m, 17H), 3.36 (m, 1H), 5.53 (m, 2H), 8.00~8.39 (m, 5H).

IR(KBr) νmax: 3390br, 3270, 1560, 1445, 1408 cm$^{-1}$.

The following ester 13 is hydrolyzed in the same manner as mentioned above to give the carboxylic acid 14.

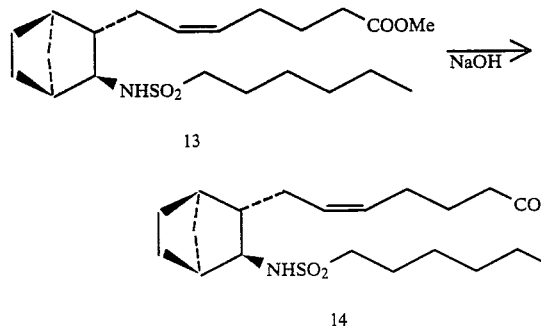

Yield 97.8%, Colorless oil.

IR(CHCl$_3$) νmax: 3380, 3500~2450, 1710, 1142 cm$^{-1}$.

$^1$H-NMR(CDCl$_3$) δ: 0.88 (t, J=7 Hz, 3H), 1.00~2.25 (m, 22H), 2.33 (br.s, 1H), 2.34 (t, J=7 Hz, 2H), 2.85~3.10 (m, 2H), 3.20 (t, d, J=4, 7 Hz, 1H), 4.85 (d, J=7 Hz, 1H), 5.39 (m, 2H), 8.30 (br.s, 1H).

EXAMPLE 9

Methyl 5Z-7-[3-methanesulfonamidobicyclo[2.2.1]hept-2-yl]-5-heptenoate

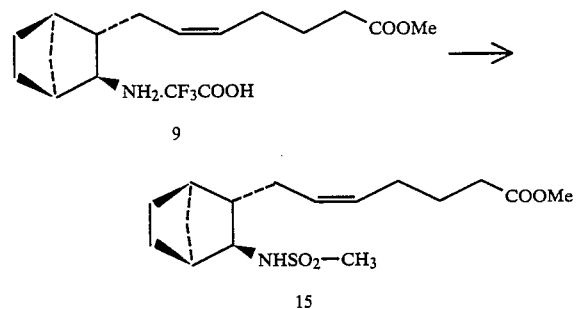

To a solution of 129 mg (0.35 mmole) of the starting material 9 is added 148 μl (3×0.35 mmole) of triethylamine and then 41 μl (1.5×0.35 mmole) of methanesulfonyl chloride under ice-cooling in an atmosphere of nitrogen, and the mixture is stirred at room temperature for 30 minutes. The reaction mixture is poured into a mixture of AcOEt and 0.2N hydrochloric acid. The AcOEt layer is washed with 5% sodium hydrogencarbonate and water, dried over magnesium sulfate, and evaporated. The oily residue is applied to chromatography on a column of 8 g of SiO$_2$ (containing 10% of water). The eluate with benzene-AcOEt is collected and evaporated to give 85 mg of the titled compound 15 as an oily residue in 73.7% yield.

Anal. Calcd. for C$_{16}$H$_{27}$NO$_4$S.0.05C$_6$H$_6$: (%) C 58.72, H 8.25, N 4.20, S 9.62, (%): C 58.71, H 8.13, N 4.27, S 9.18.

IR(CHCl$_3$)νmax: 3400, 3302, 1730.5 cm$^{-1}$.

$^1$H-NMR(CDCl$_3$)δppm: 1.00~2.13 (m, 15H), 2.32 (t, J=7 Hz, 2H), 2.95 (s, 3H), 3.23 (m, 1H), 3.67 (s, 3H), 4.99 (d, J=7 Hz, 1H), 5.41 (m, 2H).

EXAMPLE 10

Methyl 5Z-7-[3-p-methoxybenzenesulfonamidobicyclo[2.2.1]hept-2-yl]-5-heptenoate

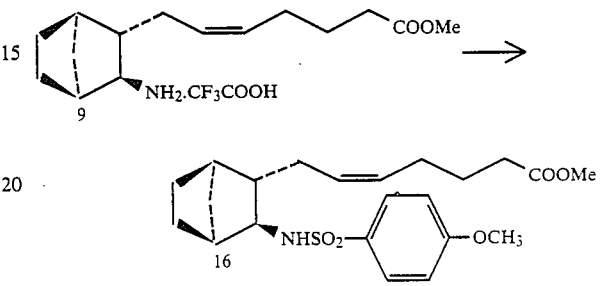

To a solution of 129 mg (0.35 mmole) of the starting material 9 in 2 ml of CH$_2$Cl$_2$ is added 148 μl (3×0.35 mmole) of triethylamine and then 108 mg (1.5×0.35 mmole) of p-methoxybenzenesulfonyl chloride in an atmosphere of nitrogen under ice-cooling, and the mixture is stirred at room temperature for an hour. The reaction mixture is distributed between AcOEt and 0.2N hydrochloric acid. The AcOEt layer is washed with 5% sodium hydrogencarbonate and water, dried over magnesium sulfate, and evaporated under reduced pressure. The oily residue is chromatographed on a column of 8 g of SiO$_2$ (containing 10% wter). The eluate with benzen-AcOEt (9:1) is collected and evaporated to give 104 mg of the aimed product 16 as an oily material in 70.5% yield.

Anal. Calcd. for C$_{22}$H$_{31}$NO$_5$S.0.15C$_6$H$_6$: (%): C 63.48, H 7.42, N 3.23, S 7.40, Found (%): C 63.24, H 7.33, N 3.28, S 6.99.

IR(CHCl$_3$)νmax: 3385, 3282, 1730, 1599, 1580, 1499 cm$^{-1}$.

$^1$H-NMR(CDCl$_3$)δppm: 0.87~2.15 (m, 15H), 2.25 (t, J=7 Hz, 2H), 2.95 (m, 1H), 3.65 (s, 3H), 3.85 (s, 3H), 5.20 (m, 3H), 6.94 (A$_2$B$_2$q, A part J=9 Hz 2H), 7.81 (A$_2$B$_2$q, B part J=9 Hz, 2H).

EXAMPLE 11

Methyl 5(Z)-7-[3-p-Nitrobenzenesulfonamidobicyclo[2.2.1]hept-2-yl]heptenoate

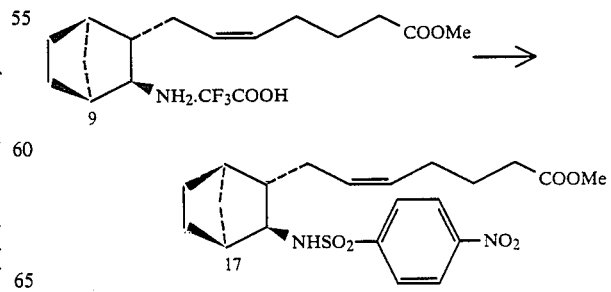

To a solution of 205 mg (0.56 mmole) of the starting material 9 in 3 ml of CH$_2$Cl$_2$ is added 235 μl (3×0.56 mmole) of triethylamine and then 186 mg (1.5×0.56 mmole) of p-nitrobenzenesufonyl chloride in an atmosphere of nitrogen under ice-cooling, and the mixture is stirred at room temperature for 30 minutes. The reaction mixture is poured into a mixture of AcOEt and 0.2N hydrochloric acid. The AcOEt layer is washed with 5% sodium hydrogencarbonate aqueous solution and water, dried over magnesium sulfate, and evaporated under reduced pressure. The oily rediue is applied to chromatography on a column of 10 g of $SiO_2$ (containing 10% of water) and the eluate with benzene-AcOEt (20:1) is collected and evaporated to give 130 mg of the titled compound as an oily residue in 53% yield.

Anal. Calcd. for $C_{21}H_{28}N_2O_6S.0.2C_6H_6$: (%): C 58.96, H 6.51, N 6.20, S 7.09, Found (%): C 58.91, H 6.51, N 6.14, S 6.53.

IR(CHCl$_3$)$\nu$max: 3400, 3295, 1731, 1610, 1534 cm$^{-1}$.

NMR(CDCl$_3$)$\delta$ppm: 1.02~2.17 (m, 15H), 2.28 (t, J=7 Hz, 2H), 3.06 (m, 1H), 3.69 (s, 3H), 5.23 (m, 2H), 5.72 (d, J=6 Hz, 1H), 8.12 (A$_2$B$_2$q, A part J=9 Hz, 2H), 8.37 (A$_2$B$_2$q, B part J=9 Hz, 2H).

EXAMPLE 12

5Z-7-[3-Methanesulfonamidobicyclo[2.2.1]hept-2-yl]-5-heptenoic acid and its sodium salt 18

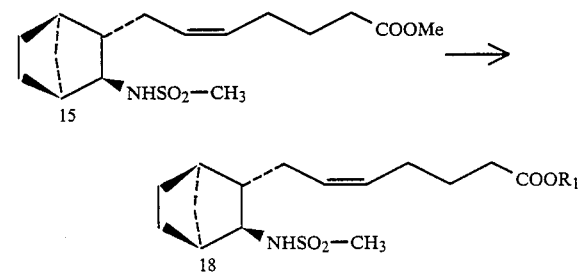

$R_1 = H$
$R_1 = Na$

To a solution of 71 mg (0.22 mmole) of the starting material 15 in 1.2 ml of methanol is added 431 μl (2×0.22 mmole) of 1N sodium hydroxide and the mixture is stirred at 23° C. for 4 hours. The reaction mixture is poured into a mixture of AcOEt and 0.2N hydrochloric acid. The AcOEt layer is washed with saturated sodium chloride aqueous solution and dried over magnesium sulfate and evaporated under reduced pressure to give 65 mg of the carboxylic acid 18 as an oily product in 93.6% yield.

$^1$H-NMR(CDCl$_3$)$\delta$ppm: 1.02~2.37 (m, 15H), 2.35 (t, J=7 Hz, 2H), 2.95 (s, 3H), 3.22 (m, 1H), 5.20 (d, J=6 Hz, 1H), 5.40 (m, 2H).

To a solution of 65 mg (0.206 mM) of this carboxylic acid 18 in 1 ml of methanol is added 806 μl (0.9×0.206 mM) of 0.23N sodium methoxide, and the mixture is allowed to stand for 5 minutes, and evaporated. The residue is dissolved in 1.5 ml of water, and freeze-dried to give 69 mg of the titled compound 18 as white powder in 99% yield.

Anal. Calcd. $C_{15}H_{24}NO_4SNa.0.25H_2O$: (%): C 52.69, H 7.22, N 4.10 S 9.38, Na 6.72, Found (%): C 52.74, H 7.17, N 3.91 S 9.34, Na 6.92.

IR(KBr)$\nu$max: 3400br, 3245, 1636sh, 1560, 1450, 1404 cm$^{-1}$.

$^1$H-NMR(d-MeOH)$\delta$ppm: 1.08~2.35 (m, 17H), 2.92 (s, 3H), 3.18 (m, 1H), 3.43 (m, 2H).

EXAMPLE 13

5Z-7-[3-p-Methoxybenzenesulfonamidobicyclo[2.2.1-]hept-2-yl]-5-heptenoic acid and its sodium salt 19

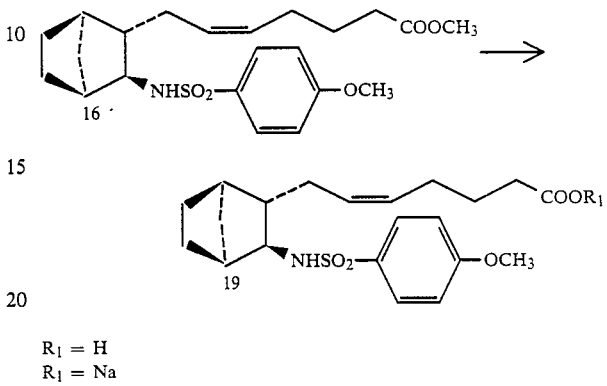

$R_1 = H$
$R_1 = Na$

To a solution of 84 mg (0.2 mmole) of the starting material 16 in 1.2 ml of methanol is added 398 μl (2×0.2 mmole) of 1N NaOH and the mixture is stirred at 23° C. for 7 hours. The reaction mixture is poured into AcOEt-0.2N hydrochloric acid and distributed. The AcOEt layer is washed with saturated sodium chloride aqueous solution, dried over magnesium sulfate and evaporated under reduced pressure to give 81 mg of the oily residue 19 (carboxylic acid) in 99% yield.

$^1$H-NMR(CDCl$_3$)$\delta$ppm: 0.95-2.12 (m, 15H), 230 (t, J=7 Hz, 2H), 2.97 (m, 1H), 3.84 (s, 3H), 5.25 (m, 3H), 6.94 (A$_2$B$_2$q, A part J=9 Hz, 2H), 7.78 (A$_2$B$_2$q, B part J=9 Hz, 2H), 9.19 (brs, 1H).

To a solution of 81 mg of the above prepared carboxylic acid 19 in 1 ml of methanol is added 782 μl (0.9×0.2 mmole) of 0.23N sodium methoxide, and the mixture is allowed to stand for 5 minutes. The reaction mixture is evaporated and the residue is dissolved in 1.5 ml of water and lyophilized to give 81 mg of the titled compound 19 as white powder in 94% yield.

Anal. Calcd. for $C_{21}H_{28}NO_5SNa.0.25H_2O$: (%): C 58.12, H 6.62, N 3.23, S 7.39, Na 5.30, Found (%): C 58.14, H 6.61, N 3.31, S 7.20, Na 5.39.

IR(KBr)$\nu$max: 3400 br, 3280, 1640 sh, 1598, 1576, 1560 br, 1500, 1458, 1439, 1405 cm$^{-1}$.

$^1$H-NMR(d-MeOH)$\delta$ppm: 0.87~2.13 (m, 15H), 2.12 (t, J=7 Hz, 2H), 2.89 (m, 1H), 3.87 (s, 3H), 5.21 (m, 2H), 7.07 (A$_2$B$_2$q, A part J=9 Hz, 2H), 7.81 (A$_2$B$_2$q, B part J=9 Hz, 2H).

EXAMPLE 14

5Z-7-[3-p-Nitrobenzenesulfonamidobicyclo[2.2.1-]hept-2-yl]-5-heptenoic acid and its sodium salt 20

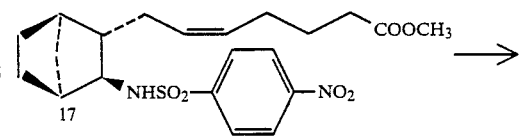

-continued

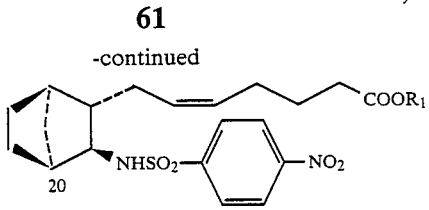

$R_1 = H$
$R_1 = Na$

To a solution of 117 mg (0.268 mmole) of the starting compound 17 in 1 ml of methanol is added 536 μl (2×0.268 mmole) of 1N potassium hydroxide and the mixture is stirred at 23° C. for 24 hours. The reaction mixture is distributed between AcOEt and 0.2N hydrochloric acid. The AcOEt layer is washed with saturated sodium chloride aqueous solution, dried over magnesium sulfate, and evaporated under reduced pressure to give 109 mg of the oily residue 20 (carboxylic acid) in 96.2% yield.

$^1$H-NMR(CDCl$_3$)δppm: 1.0~2.13 (m, 15H), 2.32 (t, J=7 Hz, 2H), 3.06 (m, 1H), 5.22 (m, 2H), 5.69 (d, J=7 Hz, 1H), 8.08 (A$_2$B$_2$q A part J=9 Hz, 2H), 8.35 (A$_2$B$_2$q B part J=9 Hz, 2H), 9.86 (brs, 1H).

To a solution of 109 mg of the above prepared carboxylic acid 20 in 1.5 ml of methanol is added 1 ml (0.9×0.26 mM) of 0.23N sodium methoxide and the mixture is allowed to stand for 5 minutes. The reaction mixture is evaporated under reduced pressure and the residue is dissolved in 1.5 ml of water and freeze-dried to give 107 mg of the titled compound 20 as white powder in 92.6% yield.

Anal. Calcd. for C$_{20}$H$_{26}$N$_2$O$_6$SNa: (%): C: 54.04, H: 5.67, N: 6.30, S: 7.21, Na: 5.17, Found (%): C: 54.08, H: 5.98, N: 6.16, S: 7.03, Na: 4.54.

IR(KBr)νmax: 3385br, 1650sh, 1605, 1560, 1529, 1400 cm$^{-1}$.

$^1$H-NMR(d-MeOH)δppm: 1.05~1.92 (m, 15H), 2.11 (t, J=7 Hz, 2H), 3.00 (m, 1H), 5.15 (m, 2H), 8.08 (A$_2$B$_2$q A part J=9 Hz, 2H), 8.40 (A$_2$B$_2$q B part J=9 Hz, 2H).

EXAMLES 15 to 29

The following compounds are prepared in the same manner as mentioned above.

TABLE 1

[Structure: bicyclic compound with COOR₁ chain and NHSO₂—R₂ substituent]

| Compd. No. | R₁ | R₂ | Mp. (°C) | Elementary Analysis (Molecular Formula) Calcd. (%) Found (%) | IR ν max cm⁻¹ | NMR δ ppm |
|---|---|---|---|---|---|---|
| 21 | —CH₃ | 4-N(CH₃)₂-C₆H₄— | 94~98 | $C_{23}H_{34}N_2O_4S$<br>C:63.56 H:7.89 N:6.45 S:7.38<br>C:63.20 H:7.84 N:6.40 S:7.16 | (CHCl₃)<br>3390, 1730.5, 1600, 1514, 1149, 1098. | 0.93~2.15(m,15H), 2.25(t,J = 7Hz,2H), 2.95(m,1H), 3.00(s,6H), 3.65(s,3H), 4.98(d,J = 7Hz,1H), 5.20(m,2H), 6.63(A₂B₂—q,Apart,J = 9Hz,2H), 7.68(A₂B₂—q,Bpart,J = 9Hz,2H). |
| 22 | H | 4-N(CH₃)₂-C₆H₄— | | $C_{22}H_{31}N_2O_4SNa$<br>C:58.70 H:7.13 N:6.22 S:7.12<br>C:59.00 H:7.09 N:6.33 S:7.24 | (KBr)<br>3430, 3260, 1600, 1564, 1518, 1409, 1369, 1311, 1146, 1097. | 0.93~2.15(m,15H), 2.30(t,J = 7Hz,2H), 2.96(m,1H), 3.02(s,6H), 5.24(m,2H), 6.65(A₂B₂—q,Apart,J = 10 Hz,2H), 7.70(A₂B₂—q,Bpart,J = 10Hz,2H), 9.15(br.s, 1H). |
| 23 | Na | 4-N(CH₃)₂-C₆H₄— | | $C_{22}H_{31}NSO_4$<br>C:65.15 H:7.71 N:3.45 S:7.91<br>C:65.10 H:7.68 N:3.54 S:7.58 | (CHCl₃)<br>3390, 1730.5, 1600, 1158, 1093. | 0.89~2.15(m,15H), 2.10(t,J = 7Hz,2H), 2.85(m,1H), 3.02(s,6H), 5.16(m,2H), 6.24(A₂B₂—q,Apart,J = 10 Hz,2H), 7.13(A₂B₂—q,Bpart,J = 10Hz,2H). |
| 24 | —CH₃ | 4-CH₃-C₆H₄— | | | | 0.98~2.15(m,15H), 2.25(t,J = 7Hz,2H), 2.40(s,3H), 2.95(m,1H), 3.64(s,3H), 5.18(m,2H), 5.42(d,J = 7 Hz,1H), 7.27(A₂B₂q-Apart,J = 8Hz,2H), 7.77(A₂B₂q-B part,J = 8Hz,2H). |
| 25 | H | 4-CH₃-C₆H₄— | | | | 0.96~2.13(m,15H), 2.31(t,J = 7Hz,2H), 2.40(s,3H), 2.97(m,1H), 5.20(m,2H), 5.67(d,J = 7Hz,1H), 7.29 (A₂B₂q-Apart,J = 8Hz,2H), 7.78(A₂B₂q-Bpart,J = 8Hz, 2H), 9.91(br.s,1H). |
| 26 | Na | 4-CH₃-C₆H₄— | | $C_{21}H_{28}NSO_4Na\cdot 0.56H_2O$<br>C:59.55 H:6.93 N:3.31 S:7.57<br>Na:5.43<br>C:59.79 H:6.94 N:3.42 S:7.27<br>Na:5.36 | (KBr)<br>3420, 3285, 1560, 1490, 1318, 1154, 1092. | 0.08~2.01(m,17H), 2.34(s,3H), 2.75(m,1H), 2.92 (m,1H), 5.24(m,2H), 7.17(A₂B₂q-Apart,J = 8Hz,2H), 7.77(A₂B₂q-Bpart,J = 8Hz,2H). |
| 27 | —CH₃ | 2-CH₃-C₆H₄— | | $C_{22}H_{31}NO_4S\cdot 0.1C_6H_6$<br>C:65.66 H:7.71 N:3.39 S:7.76<br>C:65.43 H:7.75 N:3.33 S:7.50 | (CHCl₃)<br>3395, 3300, 1730, 1600, 1458, 1436, 1317, 1155, 1067. | 0.90~2.15(m,15H), 2.27(t,J = 7Hz,2H), 2.67(s,3H), 2.98(m,1H), 3.67(s,3H), 5.20(m,2H), 5.47(d,J = 7 Hz,1H), 7.35(m,3H), 8.02(m,1H). |

TABLE 1-continued

[Structure shown at top of table: bicyclic compound with COOR₁ group and NHSO₂—R₂ substituent]

| Compd. No. | R₁ | R₂ | Mp. (°C.) | Elementary Analysis (Molecular Formula) Calcd. (%) Found (%) | I R ν max cm$^{-1}$ | NMR δ ppm |
|---|---|---|---|---|---|---|
| 28 | H | 2-CH₃-C₆H₄ | | | | 0.97~2.15(m,15H), 2.21(t,J = 7Hz,2H), 2.65(s,3H), 2.97(m,1H), 5.20(m,2H), 5.45(d,J = 7Hz,1H), 7.37 (m,3H), 8.00(m,1H). |
| 29 | Na | 2-CH₃-C₆H₄ | | C₂₁H₂₈NO₄SNa·0.6H₂O C:59.44 H:6.94 N:3.30 S:7.56 Na:5.42 C:59.42 H:6.87 N:3.26 S:7.50 Na:5.48 | (KBr) 3435, 3300, 1564, 1412, 1316, 1157. | 0.80~2.18(m,17H), 2.63(s,3H), 3.04(m,2H), 5.24 (m,2H), 7.30(m,3H), 7.97(m,1H). |
| 30 | —CH₃ | 4-CH₂CH₃-C₆H₄ | 69~72 | C₂₃H₃₃NO₄S C:65.84 H:7.93 N:3.34 S:7.64 C:65.82 H:7.86 N:3.47 S:7.53 | (CHCl₃) 3395, 3285, 1730, 1600, 1095, 1054. | 0.87~2.15(m,15H), 1.24(t,J = 7Hz,3H), 2.25(t,J = 7 Hz,2H), 2.70(q,J = 7Hz,2H), 2.97(m,1H), 3.65(s, 3H), 5.20(m,3H), 7.30(A₂B₂—q,Apart,J = 8Hz,2H), 5.78(d,J = 7Hz,1H), 7.31(A₂B₂—q,Apart,J = 8Hz, 2H), 7.79(A₂B₂—q,Bpart,J = 8Hz,2H). |
| 31 | H | 4-CH₂CH₃-C₆H₄ | | | | 1.06~2.16(m,15H), 1.24(t,J = 7Hz,3H), 2.30(t,J = 7 Hz,2H), 2.70(q,J = 7Hz,2H), 2.98(m,1H), 5.19(m, 2H), 5.78(d,J = 7Hz,1H), 7.31(A₂B₂—q,Apart,J = 8Hz, 2H), 7.82(A₂B₂—q,Bpart,J = 8Hz,2H), 10.69(s,1H). |
| 32 | Na | 4-CH₂CH₃-C₆H₄ | | C₂₂H₃₀NO₄SNa·H₂O C:61.28 H:7.11 N:3.25 S:7.44 C:61.10 H:7.06 N:3.33 S:7.42 | (KBr) 3430, 3280, 1685sh, 1458, 1408, 1155, 1095. | 1.08~2.20(m,17H), 1.24(t,J = 7Hz,3H), 2.72(q, J = 7Hz,2H), 2.88(m,1H), 5.15(m,2H), 7.37(A₂B₂q-A part,J = 8Hz,2H), 7.77 (A₂B₂q-Bpart,J = 8Hz,2H). |
| 33 | —CH₃ | 4-CH₂(CH₂)₃CH₃-C₆H₄ | | C₂₆H₃₉NO₄S C:67.64 H:8.52 N:3.03 S:6.95 C:67.47 H:8.43 N:3.06 S:6.82 | (CHCl₃) 3395, 3285, 1730, 1601, 1094, 1055. | 0.81~2.15(m,24H), 2.26(t,J = 7Hz,2H), 2.66(t,J = 7 Hz,2H), 2.92(m,1H), 3.65(s,3H), 5.17(m,2H), 5.51 (d,J = 7Hz,1H), 7.28(A₂B₂q-Apart,J = 8Hz,2H), 7,80 (A₂B₂q-Bpart,J = 8Hz,2H). |

TABLE 1-continued

[Structure: cyclohexane with two substituents — one bearing CH₂-CH=CH-CH₂-COOR₁ chain, the other bearing NHSO₂—R₂]

| Compd. No. | R₁ | R₂ | Mp. (°C) | Elementary Analysis (Molecular Formula) Calcd. (%) Found (%) | IR ν max cm⁻¹ | NMR δ ppm |
|---|---|---|---|---|---|---|
| 34 | H | $\text{CH}_2(\text{CH}_2)_3\text{CH}_3$ — C₆H₄ |  |  |  | 0.80~2.15(m,24H), 2.32(t,J = 7Hz,2H), 2.68(t,J = 7 Hz,2H), 3.02(m,1H), 5.22(m,2H), 5.38(d,J = 7Hz, 1H), 7.30(A₂B₂q-Apart,J = 8Hz,2H), 7.81(A₂B₂q-B part,J = 8Hz,2H), 9.86(br.s,1H). |
| 35 | Na | $\text{CH}_2(\text{CH}_2)_3\text{CH}_3$ — C₆H₄ |  | C₂₅H₃₆NO₄SNa.0.4H₂O C:62.97 H:7.78 N:2.94 S:6.73 C:63.24 H:7.78 N:3.01 S:6.42 | (KBr) 3400, 3280, 1695, 1564, 1455, 1430, 1410, 1155, 1094. | 0.82~2.20(m,26H), 2.68(t,J = 7Hz,2H), 2.90(m,1H), 5.15(m,2H), 7.33(A₂B₂q-Apart,J = 8Hz,2H), 7.76(A₂B₂q-Bpart,J = 8Hz,2H). |
| 36 | —CH₃ | COOH—C₆H₄ |  | C₂₂H₂₉NO₆S.0.2C₆H₆ C:61.76 H:6.74 N:3.10 C:61.84 H:6.84 H:6.90 N:3.33 | (CHCl₃) 3385, 3280, 2650, 2530, 1725, 1700.5, 1602, 1575, 1162, 1089. | 0.90~2.17(m,15H), 2.29(t,J = 7Hz,2H), 3.07(m,1H), 3.69(s,3H), 5.23(m,2H), 5.57(d,J = 7Hz,1H), 8.03 (A₂B₂q-Apart,J = 8Hz,2H), 8.25(A₂B₂q-Bpart,J = 8Hz,2 H), 9.35(s,1H). |
| 37 | H | COOH—C₆H₄ |  | C₂₁H₂₇NO₆S.0.4H₂O C:58.83 H:6.54 N:3.27 S:7.48 C:59.14 H:6.44 N:3.35 S:7.15 | (KBr) 3420, 3270, 2660, 1704, 1602, 1503, 1526, 1165, 1091. | 1.08~2.13(m,15H), 2.23(t,J = 7Hz,2H), 3.00(m,1H), 5.17(m,2H), 7.48(A₂B₂q-Apart,J = 8Hz,2H), 7.76(A₂B₂q-Bpart,J = 8Hz,2H). |
| 38 | Na | COONa—C₆H₄ |  | C₂₁H₂₅NO₆SNa₂.1.5H₂O C:51.21 H:5.73 N:2.84 S:6.51 C:51.31 H:5.75 N:2.98 S:6.42 | (KBr) 3420, 3295, 1600, 1560, 1427sh, 1402, 1161, 1090. | 1.05~2.64(m,17H), 3.43(m,1H), 2.62(m,2H), 8.40(A₂B₂q-Apart,J = 8Hz,2H), 8.50(A₂B₂q-Bpart,J = 8 Hz,2H). |
| 39 | Na | OH—C₆H₄ |  | C₂₀H₂₆NO₅SNa.0.8H₂O C:55.88 H:6.47 N:3.26 S:7.46 Na:5.35 C:55.84 H:6.39 N:3.30 S:7.45 Na:5.32 | (KBr) 3380br, 3270, 1588, 1555, 1500, 1150, 1091. | (D₂O + EXT.TMS): 1.45~2.67(m,17H), 3.27(m, 1H), 5.62(m,2H), 7.45(A₂B₂q-Apart,J = 8Hz, 2H), 8.17(A₂B₂q-Bpart,J = 8Hz,2H). |
| 40 | Na | F—C₆H₄ |  | C₂₀H₂₅FNO₄SNa.0.5H₂O C:56.59 H:6.17 F:4.48 N:3.30 S:7.55 Na:5.42 C:56.57 H:5.97 F:4.55 N:3.29 S:7.79 Na:5.75 | (KBr) 3420, 3282, 1591, 1562, 1495, 1169, 1153, 1093. | (D₂O + EXT.TMS): 1.46~2.65(m,17H), 3.36(m, 1H), 5.64(m,2H), 7.22(m,2H). |

TABLE 1-continued

[Structure: bicyclic ring with CH2-CH=CH-CH2-COOR1 chain and NHSO2-R2 substituent]

| Compd. No. | R1 | R2 | Mp. (°C.) | Elementary Analysis (Molecular Formula) Calcd. (%) Found (%) | IR ν max cm$^{-1}$ | NMR δ ppm |
|---|---|---|---|---|---|---|
| 41 | —CH3 | 3-methylphenyl | | $C_{22}H_{31}NO_4S \cdot 0.8H_2O$<br>C:62.92 H:7.82 N:3.34 S:7.64<br>C:63.02 H:7.60 N:3.38 S:7.28 | (CHCl3)<br>3395, 3300, 1731, 1603, 1154, 1098, 1088. | (CDCl3): 0.77~2.02(m,15H), 2.27(t,J = 7Hz, 2H), 2.42(s,3H), 2.99(m,1H), 3.67(s,3H), 5.23(m,3H), 7.36(m,2H), 7.72(m,2H). |
| 42 | Na | 3-methylphenyl | | $C_{21}H_{28}NO_4SNa \cdot 1.2H_2O$<br>C:57.96 H:7.04 N:3.22 S:7.37<br>Na:5.28<br>C:57.88 H:6.72 N:3.23 S:7.32<br>Na:5.34 | (KBr)<br>3430, 3280, 1562, 1409, 1321, 1303, 1153, 1097, 1088. | (D-methanol): 1.08~2.18(m,17H), 2.42(s, 3H), 2.90(m,1H), 5.14(m,2H), 7.40(m,2H), 7.69(m,2H). |
| 43 | H | phenyl | | $C_{20}H_{26}NO_4SNa \cdot 0.5H_2O$<br>C:58.80 H:6.66 N:3.43 S:7.85<br>Na:5.63<br>C:58.82 H:6.59 N:3.45 S:7.74<br>Na:5.86 | (KBr)<br>3420, 3280, 1561, 1446, 1410, 1318, 1154, 1092. | (D2O + EXT.TMS): 1.07~2.61(m,17H), 3.35(m, 1H), 5.60(m,2H), 8.27(m,3H), 8.33(m,2H). [[α]D + 14.3 ± 0.5(24° C. C = 1.012% CH3OH)] |

Optically active compd.

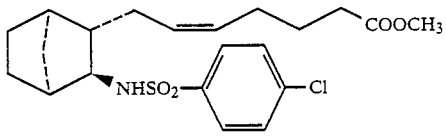

Anal. Calcd. (%) for C_{21}H_{28}NO_{4}SCl.0.1C_{6}H_{6}: C: 59.80 H: 6.65 N: 3.23 S: 7.39 Cl: 8.17, Found (%): C: 59.70 H: 6.60 N: 3.24 S: 7.02 Cl: 8.33.

IRνmax (CHCl_{3}) cm$^{-1}$: 3400, 3290, 1733, 1590, 1578, 1164, 1098, 1089.

NMRδppm (CDCl_{3}): 0.95–2.18 (m, 15H), 2.29 (t, J=7 Hz, 2H), 3.00 (m, 1H), 3.69 (s, 3H), 5.02 (d, J=7 Hz, 1H), 5.28 (m, 2H), 7.49 (A_{2}B_{2}q, A part, J=10 Hz, 2H), 7.84 (A_{2}B_{2}q, B part, J=10 Hz, 2H).

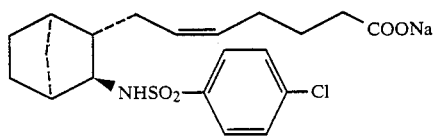

Anal. Calcd. (%) for C_{20}H_{25}NO_{4}SClNa.0.5H_{2}O: C: 54.23 H: 5.92 N: 3.16 S: 7.24 Cl: 8.01 Na: 5.19, Found (%): C: 54.45 H: 6.04 N: 3.25 S: 6.90 Cl: 7.89 Na: 5.13.

IRνmax (KBr) cm$^{-1}$: 3410 br, 1640, 1560, 1160, 1196, 1086.

NMRδppm (d-Methanol): 1.10–2.22 (m, 17H), 2.94 (m, 1H), 5.20 (m, 2H), 7.57 (A_{2}B_{2}q, A part, J=10 Hz, 2H), 7.86 (A_{2}B_{2}q, B part, J=10 Hz, 2H).

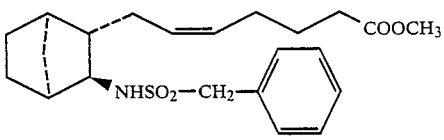

Anal. Calcd. (%) for C_{22}H_{31}NO_{4}S.0.12C_{6}H_{6}: C: 65.76 H: 7.71 N: 3.38 S: 7.73, Found (%): C: 65.59 H: 7.68 N: 2.86 S: 7.41.

IRνmax (CHCl_{3}) cm$^{-1}$: 3390, 1730, 1150, 1126.

NMRδppm (CDCl_{3}): 0.81–2.10 (m, 15H), 2.30 (t, J=7 Hz, 2H), 3.18 (m, 1H), 3.63 (s, 3H), 4.20 (s, 2H), 4.84 (d, J=7 Hz, 1H), 5.40 (m, 2H), 7.39 (s, 5H).

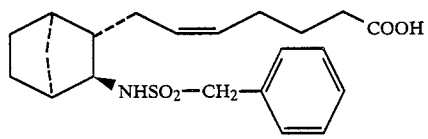

NMRδppm (CDCl_{3}): 0.89–2.41 (m, 17H), 3.17 (m, 1H), 4.20 (s, 2H), 5.04 (d, J=7 Hz, 1H), 5.39 (m, 2H), 7.39 (s, 5H), 10.18 (brs, 1H).

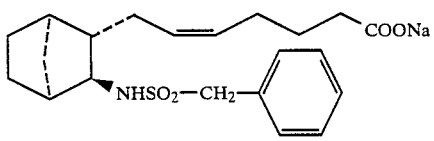

Anal. Calcd. (%) for C_{21}H_{28}NO_{4}SNa.0.4H_{2}O: C: 59.95 H: 6.90 N: 3.33 S: 7.62 Na: 5.46, Found (%): C: 60.18 H: 6.89 N: 3.29 S: 7.51 Na: 5.31.

IRνmax (KBr) cm$^{-1}$: 3405, 3280, 1561, 1430 sh, 1411, 1316, 1150, 1125.

NMRδppm (CDCl_{3}): 0.95–2.30 (m, 17H), 3.09 (m, 1H), 4.20 (s, 2H), 5.37 (m, 2H), 7.32 (s, 5H).

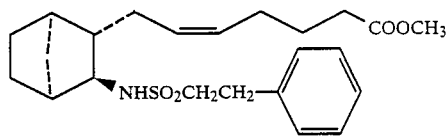

Anal. Calcd. (%) for C_{23}H_{33}NO_{4}S: C: 65.84 H: 7.93 N: 3.34 S: 7.64, Found (%): C: 65.90 H: 7.84 N: 3.38 S: 7.38.

IRνmax (CHCl_{3}) cm$^{-1}$: 3390, 3295, 1730, 1604, 1498, 1144, 1072, 1054.

NMRδppm (CDCl_{3}): 1.02–2.09 (m, 15H), 2.29 (t, J=7 Hz, 2H), 3.20 (m, 5H), 3.65 (s, 3H), 4.94 (d, J=7 Hz, 1H), 5.37 (m, 2H), 7.24 (m, 5H).

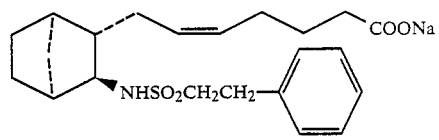

Anal. Calcd. (%) for C_{22}H_{30}NO_{4}SNa.0.3H_{2}O: C: 61.03 H: 7.12 N: 3.24 S: 7.41 Na: 5.31, Found (%) C: 60.97 H: 7.06 N: 3.37 S: 7.46 Na: 5.62.

IRνmax (KBr) cm$^{-1}$: 3425, 3295, 1562, 1455, 1499.5, 1407, 1312, 1146, 1080, 1059.

NMRδppm (d-Methanol): 1.15–2.32 (m, 17H), 3.19 (m, 5H), 5.38 (m, 2H), 7.25 (s, 5H).

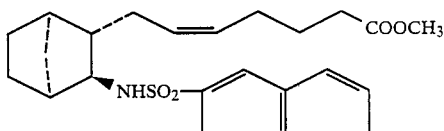

Anal. Calcd. (%) for C_{25}H_{31}NO_{4}S.0.1H_{2}O: C: 67.72 H: 7.09 N: 3.16 S: 7.23, Found (%): C: 67.64 H: 6.88 N: 3.04 S: 6.93.

IRνmax (CDCl_{3}) cm$^{-1}$: 3395, 1732, 1156, 1132, 1076.

NMRδppm (CDCl_{3}): 1.05–2.23 (m, 17H), 3.05 (m, 1H), 3.65 (s, 3H), 5.10 (m, 2H), 5.64 (d, J=7 Hz, 1H), 7.60 (m, 2H), 7.97 (m, 4H), 8.50 (s, 1H).

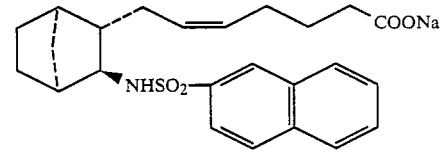

Anal. Calcd. (%) for C_{24}H_{28}NO_{4}SNa.0.4H_{2}O: C: 63.11 H: 6.36 N: 3.07 S: 7.02 Na: 5.03, Found (%): C: 63.18 H: 6.27 N: 3.20 S: 6.83 Na: 4.96.

IRνmax (KBr) cm$^{-1}$: 3360, 3285, 1562, 1407, 1316, 1153, 1130, 1075.

NMRδppm (d-MeoH): 1.03–2.20 (m, 17H), 2.97 (m, 1H), 5.02 (m, 2H), 7.64 (m, 2H), 8.00 (m, 4H), 8.43 (s, 1H).

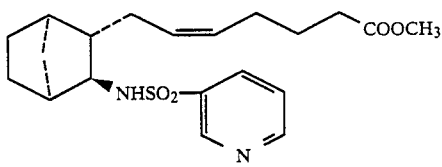

Anal. Calcd. (%) for $C_{20}H_{28}N_2O_4S \cdot 1/10\ C_6H_6$: C: 61.97 H: 7.17 N: 6.97 S: 7.97, Found (%): C: 61.71 H: 7.30 N: 6.80 S: 7.76.

IRνmax (CHCl$_3$) cm$^{-1}$: 3390, 3290, 1730, 1577, 1168, 1107.

NMRδppm (CDCl$_3$): 1.02–2.26 (m, 15H), 2.27 (t, J=7.0 Hz, 2H), 3.03 (m, 1H), 3.65 (s, 3H), 5.22 (m, 2H), 5.87 (d, J=7.0 Hz, 1H), 7.44 (m, 1H), 8.17 (m, 1H), 8.78 (m, 1H), 9.09 (m, 1H).

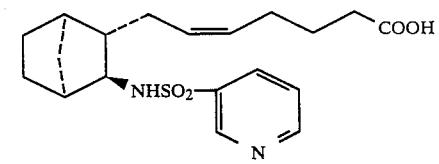

NMRδppm (CDCl$_3$): 1.02–2.22 (m, 15H), 2.33 (t, J=7 Hz, 2H), 3.05 (m, 1H), 5.23 (m, 2H), 5.94 (d, J=7 Hz, 1H), 7.51 (d.d, J=5 Hz, 8 Hz, 1H), 8.25 (m, 1H), 8.85 (m, 1H), 9.17 (brs, 1H), 9.73 (brs, 1H).

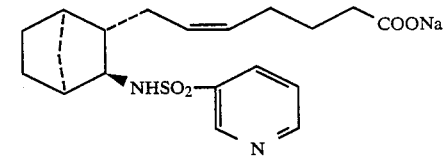

Anal. Calcd. (%) for $C_{19}H_{25}N_2O_4SNa \cdot 0.03H_2O$: C: 56.90 H: 6.30 N: 6.99 S: 8.00, Found (%): C: 57.07 H: 6.38 N: 7.07 S: 8.15.

IRνmax (KBr) cm$^{-1}$: 3420, 3260, 3080, 1698, 1570, 1413, 1320, 1166, 1106.

NMRδppm (d-MeOH): 1.12–2.16 (m, 15H), 2.14 (t, J=7 Hz, 2H), 2.97 (m, ppm 1H), 5.14 (m, 2H), 7.10 (d,d, J=5 Hz, 8 Hz, 1H), 8.25 (m, 1H), 8.76 (m, 1H), 8.99 (brs, 1H).

EXAMPLE 30

Sodium 7-[2(S*)-2-exo-3-endo-3-benzenesulfonaimido-bicyclo[2.2.1]hept-2-yl]-5-heptanoate I al-ac(2S*-t)

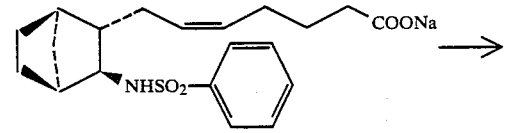

12a

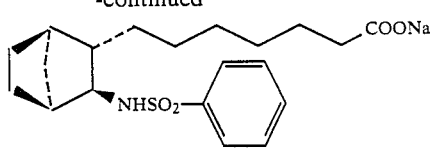

I al-ac(2S*–t)

Compound 12a (200 mg) in methanol (5 ml) is hydrogenated on 10% palladium-carbon (700 mg) in hydrogen atmosphere for 20 minutes. After removed of the catalyst by filtration, the filtrate is freeze-dried to give I al-ac(2S*-t) as a colorless powder (189 mg).

Anal. Calcd. (%) for $C_{20}H_{28}NO_4SNa$, $0.7H_2O$: C, 58.00; H, 7.16; N, 3.38; S, 7.74; Found (%): C, 58.12; H, 7.02; N, 3.49; S, 7.57.

IR(KBr) νmax: 3400, 3270, 1564, 1488, 1412, 1322, 1156 cm$^{-1}$.

$^1$H-NMR(D$_2$O+EXT-TMS) δppm: 1.5–2.67 (m, 21H), 3.30 (m, 1H), 8.07 (m, 3H), 8.63 (m, 2H).

EXAMPLE 31

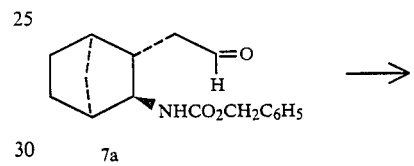

7a

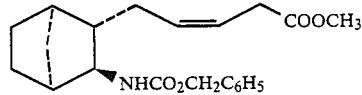

II a6(2S*—t)

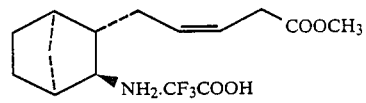

44

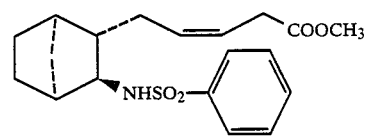

Ia6-aa(2S*—t)

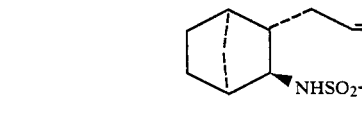

Ia6-ac(2S*—t)

(1) Preparation of II a6(2S*-t)

Sodium hydride (2.43 g, 60% purity, 60.9 mM) was suspended in 74 ml of dry DMSO at room temperature. The mixture was heated at 75° C. for 50 minutes under stirring, cooled with ice-water to 15° C.

To the solution was added 13.03 g of 2-carboxyethyl-triphenylphosphonium bromide (32.8 mM) at 15° C.

The mixture was stirred for 10 minutes at the same temperature. A solution of aldehyde 7a, prepared in I-1, Example 5 (3.24 g, 11.28 mM) in dry DMSO (14 ml) was added to the solution, which was stirred for 1.5 hours at room temperature and partitioned between ethyl acetate and 1N-HCl. The organic solution was washed with water, dried over magnesium sulfate and concentrated in vacuo. The residue was chromatographed on silica gel (elution with ethyl acetate) to afford oily product, which was treated with diazomethane in ether. Separation by chromatography on silica gel (elution with 20% ethyl acetate in n-hexane) afforded oily product II a6(2S*-t) (2.47 g, 61.3%).

IR $\nu$max (CHCl$_3$) cm$^{-1}$: 3445, 1720.

NMR $\delta$ppm (CDCl$_3$): 0.90–2.40 (m, 11H), 3.05 (m, 2H), 3.47 (m, 1H), 3.63 (s, 3H), 4.88 (m, 1H), 5.06 (s, 2H), 5.54 (m, 2H), 7.33 (s, 5H).

(2) Preparation of I a6-aa(2S*-t)

A solution of II a6(2S*-t) (1.27 g, 3.55 mM) in 5 ml of anisole and 20 ml of trifluoroacetic acid was stirred for 4 hours at 45° C. The reaction mixture was concentrated in vacuo and rinsed with n-hexane to give a oily residue. To a solution of the oily residue in dichloromethane (10 ml), triethylamine (2.24 ml, 8.9 mM) and benzenesulfonyl chloride (0.68 ml, 5.3 mM) were added under stirring at $-20°$ C. After stirring for 30 minutes at the same temperature, the reaction mixture was partitioned between ethyl acetate and 1N-HCl.

The organic solution was washed with 5% aqueous sodium bicarbonate solution, water, dried over magnesium sulfate and concentrated in vacuo. The residue was chromatographed on silica gel (elution with 20% ethyl acetate in n-hexane) to afford I a6-aa(2S*-t) (804 mg, 62.5%).

Anal. Calcd. for (%) $C_{19}H_{25}NO_4S$: C: 62.78 H: 6.93 N: 3.85 S: 8.82, Found (%): C: 62.62 H: 6.97 N: 3.72 S: 8.70.

IR $\nu$max (CHCl$_3$) cm$^{-1}$: 3390, 3280, 1733, 1160, 1093.

NMR $\delta$ppm (CDCl$_3$): 0.85–2.00 (m, 10H), 2.18 (brs, 1H), 2.94 (d, J=7 Hz, 2H), 2.98 (m, 1H), 3.68 (s, 3H), 5.01 (d, J=7 Hz, 1H), 5.27–5.58 (m, 2H), 7.43–7.61 (m, 3H), 7.82–7.95 (m, 2H).

(3) Preparation of I a6-ac(2S*-t)

Methyl ester I a6-aa(2S*-t) was saponified and freeze-dried by the usual method to give I a6-ac(2S*-t).

Anal. Calcd. (%) for $C_{18}H_{22}NO_4SNa \cdot 0.8H_2O$: C: 56.03 H: 6.17 N: 3.63 S: 8.31, Found (%): C: 55.86 H: 6.04 N: 3.57 S: 8.36.

IR $\nu$max (KBr) cm$^{-1}$: 3400 br, 3280, 1630 sh, 1565, 1448, 1400 sh, 1388, 1318, 1157, 1093.

NMR $\delta$ppm (D$_2$O+EXT.TMS): 1.48–2.50 (m, 11H), 3.22 (m, 3H), 5.73 (m, 2H), 8.03 (m, 3H), 8.30 (m, 2H).

EXAMPLES 32 TO 35

The following compounds, shown in Table 2, were prepared from the compound 44 in accordance with the manner of Example 31 (2) and (3).

TABLE 2

(No. 1)

| $R_2$ | $^1$HNMR (CDCl$_3$): $\delta$ppm |
|---|---|
| —⟨phenyl⟩—Cl | 0.85~2.05 (m, 10H), 2.16 (brs, 1H), 2.96 (d, J = 7Hz, 2H), 3.00 (m, 1H), 3.68 (s, 3H), 5.14 (d, J = 7Hz, 1H), 5.20~5.65 (m, 2H), 7.46 (A$_2$B$_2$type, Apart, J = 8Hz, 2H), 7.82 (A$_2$B$_2$type, Bpart, J = 8Hz, 2H) |
| —⟨phenyl⟩—CH$_3$ | 0.80~2.00 (m, 10H), 2.16 (brs, 1H), 2.41 (s, 3H), 2.92 (d, J = 7Hz, 2H), 2.96 (m, 1H), 3.66 (s, 3H), 5.17 (d, J = Hz, 1H), 5.23~5.55 (m, 2H), 7.29 (A$_2$B$_2$type, Apart, J = 8Hz, 2H), 7.75 (A$_2$B$_2$type, Bpart, J = 8Hz, 2H) |
| —⟨phenyl⟩—F | 0.86~2.06 (m, 10H), 2.15 (brs, 1H), 2.96 (d, J = 7Hz, 2H), 2.98 (m, 1H), 3.67 (s, 3H), 5.18~5.54 (m, 2H), 5.56 (d, J = 7Hz, 1H), 7.08~7.30 (m, 2H), 7.84~9.03 (m, 2H) |
| —⟨phenyl⟩—OCOCH$_3$ | 0.86~2.02 (m, 10H), 2.16 (brs, 1H), 2.32 (s, 3H), 2.96 (d, J = 7Hz, 2H), 2.97 (m, 1H), 3.67 (s, 3H), 5.17~5.60 (m, 2H), 5.61 (d, J = 7Hz, 1H), 7.25 (A$_2$B$_2$type, Apart, J = 8Hz, 2H), 7.93 (A$_2$B$_2$type, Bpart, J = 8Hz, 2H) |

(No. 2)

| $R_2$ | $^1$HNMR (CDCl$_3$): $\delta$ppm |
|---|---|

TABLE 2-continued

| | |
|---|---|
| 4-Cl-phenyl | 0.90~2.05 (m, 10H), 2.13 (brs, 1H), 2.80~3.15 (m, 3H), 5.20~5.65 (m, 2H), 5.54 (d, J = J = 8Hz, 1H), 7.46 (A$_2$B$_2$type, Apart, J =8Hz, 2H), 7.81 (A$_2$B$_2$type, Bpart, 2H), 9.20 (brs, 1H) |
| 4-CH$_3$-phenyl | 0.85~2.00 (m, 10H), 2.16 (brs, 1H), 2.41 (s, 3H), 2.80~3.20 (m, 3H), 5.15~5.63 (m, 3H), 7.27 (A$_2$B$_2$type, Apart, J = 8Hz, 2H), 7.77 (A$_2$B$_2$type, J = 8Hz, 2H), 9.31 (brs, 1H) |
| 4-F-phenyl | 0.88~2.03 (m, 10H), 2.16 (brs, 1H), 2.90~3.18 (m, 3H), 5.18 (d, J = 7Hz, 1H), 5.25~5.65 (m, 2H), 6.59 (brs, 1H), 7.09~7.28 (m, 2H), 7.82~7.98 (m, 2H) |
| 4-OH-phenyl | 0.98~2.00 (m, 10H), 2.13 (brs, 1H), 2.80~3.13 (m, 3H), 5.25~5.62 (m, 2H), 6.91 (A$_2$B$_2$type, Apart, J = 8Hz, 2H) 7.73 (A$_2$B$_2$type, Bpart, J = 8Hz, 2H) | d$_4$-Methanol

EXAMPLES 36 AND 37

The following compounds are prepared from the aldehyde, prepared in I-2, Example 40 (2), by reacting with 3-methoxycarbonylbenzyl triphenylphosphonium bromide in the same manner as I-1, Example 31.

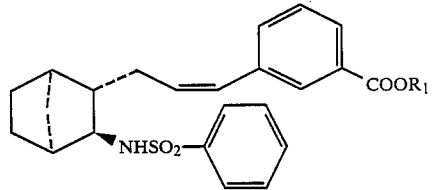

1 R$_1$=CH$_3$

Anal. Calcd. (%) for C$_{24}$H$_{27}$NO$_4$S.0.1H$_2$O: C: 67.45 H: 6.42 N: 3.28 S: 7.50, Found (%): C: 67.34 H: 6.46 N: 3.34 S: 7.34.

IR νmax (CHCl$_3$) cm$^{-1}$: 3400, 3285, 1605, 1584, 1165, 1095.

NMR δppm (CDCl$_3$): 1.05-2.13 (m, 11H), 3.05 (m, 1H), 3.92 (s, 3H), 5.27-5.70 (m, 2H), 6.30 (d, J=11.5 Hz, 1H), 7.40 (m, 5H), 7.90 (m, 4H).

R$_1$; H
mp. 160°-162° C.

Anal. Calcd. (%) for C$_{23}$H$_{25}$NO$_4$S.0.1H$_2$O: C: 67.13 H: 6.12 N: 3.40 S: 7.79, Found (%): C: 66.92 H: 6.24 N: 3.34 S: 7.64

IR νmax (KBr) cm$^{-1}$: 3435, 3270, 2605, 2560, 1688, 1607, 1581, 1158, 1093.

NMR δppm (CDCl$_3$): 1.03-2.25 (m, 11H), 3.05 (m, 1H), 4.97 (d, J=7 Hz, 1H), 5.50 (t of d J=7 Hz, 11.5 Hz, 1H), 6.20 (br, 1H), 6.33 (d, J=11.5 Hz, 1H), 7.47 (m, 5H), 7.90 (m, 4H).

EXAMPLE 37

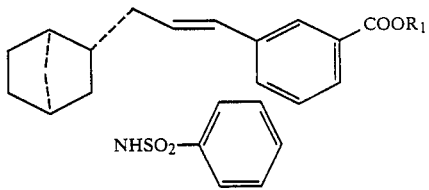

R$_1$; CH$_3$

Anal. Calcd. (%) for C$_{24}$H$_{27}$NO$_4$S.0.1H$_2$O: C: 67.45 H: 6.42 N: 3.28 S: 7.50, Found (%): C: 67.41 H: 6.56 N: 3.22.

IR νmax (CHCl$_3$) cm$^{-1}$: 3390, 3280, 1720, 1601, 1583, 1161, 1093, 965.

NMR δppm (CDCl$_3$): 1.08-2.16 (m, 11H), 3.08 (m, 1H), 3.92 (s, 3H), 5.46 (d, J=7 Hz, 1H), 5.90-6.36 (m, 2H), 7.49 (m, 5H), 7.90 (m, 4H).

R$_1$; Na

Anal. Calcd. (%) for C$_{23}$H$_{24}$NO$_4$SNa.0.1H$_2$O: C: 61.18 H: 5.80 N: 3.10 S: 7.10 Na: 5.09, Found (%): C: 61.38 H: 5.83 N: 3.10 S: 7.36 Na: 4.69.

IR νmax (KBr) cm$^{-1}$: 3425, 3285, 1608, 1590, 1560, 1449, 1430, 1390, 1163, 1156, 1095, 967.

NMR δppm (d-MeOH): 1.12-2.18 (m, 11H), 3.00 (m, 1H), 6.15 (m, 2H), 7.23-7.90 (m, 9H).

I-1

EXAMPLE 38

In the same manner as I-7, Example 47 the following compounds Ic are prepared from norborn-5-ene-2,3-dicarboxylic anhydride [Aldrich].

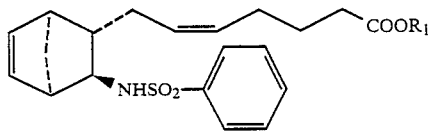

Ic (2S*-t)

| $R_1$ | Appearance | Physical Constants |
|---|---|---|
| —$CH_3$ | Colorless oil | $^1$HNMR (CDCl$_3$): δ2.27 (t, J = 7Hz,2H), 2.46 (br.s,1H), 2.71 (br.s,1H), 3.32 (td,J = 4,9Hz,1H), 3.65 (s,3H), 4.52 (d, J = 9Hz,1H), 5.05–5.45 (m,2H), 5.80–6.40 (m,2H), 7.40–8.05 (m,5H). Anal. Calcd. for C$_{21}$H$_{27}$NO$_4$S.H$_2$O: C; 61.88, H; 7.18, N; 3.44, S; 7.87. Found: C; 61.86, H; 6.86, N; 3.22, S; 7.74. |
| —H | | $^1$HNMR (CDCl$_3$): δ0.85–2.25 (m,9H), 2.32 (t,J = 7Hz,2H) 2.45 (br.s,1H), 2.70 (br.s,1H), 3.32 (td,J = 9Hz,1H), 4.71 (d, J = 9Hz,1H), 5.08–5.43 (m,2H),5.80–6.40 (m,2H), 7.43–8.00 (m,5H), 8.50 (3br.s, 1H). Anal. Calcd. for C$_{20}$H$_{25}$NO$_4$S: C; 63.96, H; 6.72, N; 3.73, S; 8.54. Found: C; 64.23, H; 6.86, N; 3.64, S; 8.36. |
| —Na | Colorless powder | |

I-1

EXAMPLE 39

In the same manner as I-1, Example 1 to 14 the following compounds Id are prepared from (+)-camphor-[Aldrich].

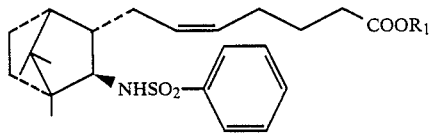

Id(2S-t)

[The configuration at each asymmetric centers of (+)-camphor are retained in the final product.]

| $R_1$ | Appearance | Physical Constants |
|---|---|---|
| —$CH_3$ | Colorless gum | $^1$HNMR (CDCl$_3$): δ0.71 (s,3H), 0.80 (s, 3H), 0.88 (s,3H), 2.27 (t,J = 7Hz,2H), 2.58 (dd,J = 5, 9Hz,1H), 3.68 (s,3H),5.01 (d,J = 9Hz, 1H), 5.05–5.25 (m,2H), 7.40–8.05 (m,5H). Anal. Calcd. for C$_{24}$H$_{35}$NO$_4$S: C; 66.47, H; 8.15, N; 3.23, S; 7.39. Found: C; 66.27, H; 8.06, N; 3.22, S; 7.15 |
| —H | Colorless gum | $^1$HNMR (CDCl$_3$): δ0.71 (s,3H), 0.79 (s,3H), 0.87 (s,3H), 2.31 (t,J = 7Hz,2H), 2.58(dd,J = 5, 9Hz,1H), 5.17 (d,J = 9Hz,1H), 4.95–5.40 (m,2H), 7.40–8.10 (m,5H), 9.36 (br.s,1H), Anal. Calcd. for C$_{23}$H$_{33}$NO$_4$S: C; 65.83, H; 7.94, N; 3.34, S; 7.64. Found: C; 65.49, H; 7.76, N; 3.41, S; 7.37. |
| Na | Colorless powder | |

I-2

EXAMPLE 40

(1) Preparation of 5b

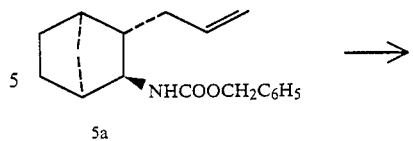

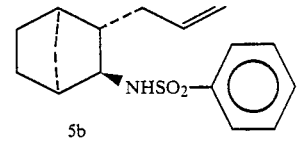

A solution of 2.85 g (10 mM) of compound 5a, prepared in I-1 Example 3, in anisole (10 ml) and trifluoroacetic acid (30 ml) was stirred for 4 hours at 45° C. The reaction mixture was concentrated in vacuo. To a solution of the residue in 30 ml of CH$_2$Cl$_2$, triethylamine (4.18 ml; 10 mM×3) and benzenesulfonyl chloride (1.90 ml; 10 mM×1.5) were added at 0° C.

The mixture was stirred for 30 min at 0° C., partitioned between AcOEt and 1NHCl. The AcOEt solution was washed with water, dried over Na$_2$SO$_4$ and concentrated in vacuo. Separation of the residue by column chromatography [SiO$_2$ 50 g, eluted with 10% AcOEt in n.hexane] gave 1.89 g (65%) of compound 5b as colorless prisms. mp 84°–87° C. IR νmax(CHCl$_3$) (cm$^{-1}$): 3395, 3285, 1642, 1449, 1157, 1094. $^1$HNMR(CDCl$_3$): δppm 1.00–2.15 (m, 11H), 3.02 (m, 1H), 4.78 (m, 2H), 5.50 (m, 2H), 7.55 (m, 3H), 7.93 (m, 2H).

(2) Preparation of 7b

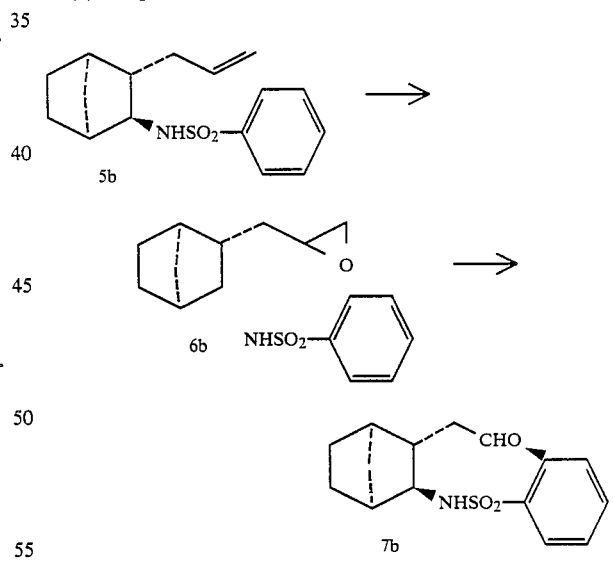

To a solution of compound 5b (1.00 g, 3.43 mM) in 15 ml of CH$_2$Cl$_2$, was added m-chloroperbenzoic acid (purity 80%; 1.48 g, 6.86 mM) at 0° C. The mixture was stirred for 2.5 hours at 25° C., washed with 10% aqueous sodium thiosulfate and 5% aqueous sodium bicarbonate. The organic solution was concentrated in vacuo and gave the crude epoxide. To a solution of the epoxide in 22 ml of dioxane, periodic acid (1.56 g; 6.86 mM) and 4 ml of water were added at 25° C. The mixture was stirred for 3 hours at 25° C., poured into water and extracted with AcOEt. The AcOEt solution was washed with water, dried over Na$_2$SO$_4$, concentrated in vacuo and gave 1.00 g (100%) of compound 7b as a colorless oil. ¹H-NMR (CDCl₃): δppm 1.25–2.35 (m, 11H), 2.85 (m, 1H), 5.68 (d, J=10 Hz, 1H), 7.45 (m, 3H), 7.83 (m, 2H), 9.52 (s, 1H).

(3) Preparation of 2(S*)-2-exo-3-endo-(2-trimethylsilyloxy)-vinyl-3-benzenesulfonamidobicyclo[2.2.1]heptane III a2 (2S*-t).

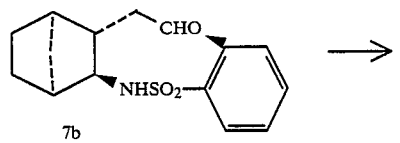

7b

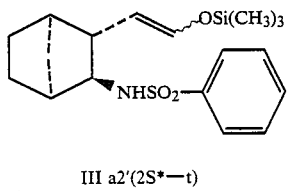

III a2'(2S*—t)

Trimethylsilylation of 7b was conveniently achieved as follows. Into the well stirred solution of trimethylsilyl chloride (1.13 g, 9 mmol) in dichloromethane (8 ml) was quickly added trimethylamine (1.25 ml, 9 mmol) at 0° C. Complex formation was completed within 10 minuits. Then, the aldehyde 7b (852 mg, 2.93 mmol) dissolved in 1.5 ml of dichloromethane was added dropwise to this mixture over 5 minuits. The reaction temperature was gradually raised to room temperature and the mixture was kept well stirred overnight to effect the progress of the reaction, as precipitation of triethylamine hydrochloride made the reaction heterogeneous. After nmr spectroscopic confirmation of the entire consumption of 7b, the solvent was completely evaporated under reduced pressure to leave an crude solid mixture. The mixture was repeatedly trituated with dry pentane to separate the desired enol trimethylsilyl ether from triethylamine hydrochloride. Evaporation of pentane from the organic layer gave an nearly pure crystalline residue (915 mg, 86%) of the desired product III a2'(2S*-t). As III a2'(2S*-t) was easily hydrolyzed in an aqueous work-up or column chromatography, it was used for the subsequent reaction without further purification.

NMR: δppm (CDCl₃) 0.13–0.17 (two s, 9H), 1.0–2.35 (m, 9H), 3.03 (m, 1H), 4.28 (dd, J=6 Hz, J=9 Hz, 1H), 4.95 (m, 1H), 5.97 (dd, J=6 Hz, J=1.5 Hz, 1H), 7.43–7.63 (m, 3H), 7.77–7.97 (m, 2H).

(4) Preparation of 2(S*)-2-exo-3-endo-2-formyl-fluoromethyl-3-bensenesulfonamidobicyclo[2.2.1]heptane III a2(2S*-t)

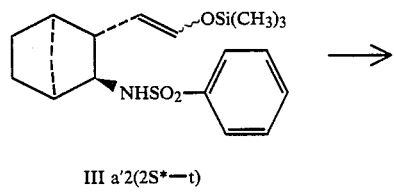

III a'2(2S*—t)

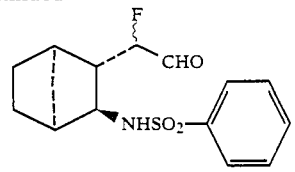

III a2(2S*—t)

Into the well stirred solution of III a'2(2S*-t) (365 mg, 1 mmol) in either dichloromethane or acetonitrile (1.5 ml) was added all at once crystalline xenon fluoride (253 mg, 1.48 mmol) at 0° C. After a short induction period, the reaction started smoothly with the evolution of gaseous xenon. As the gas evolution weakened, the temperature was raised to room temperature and maintained for 2 hours to complete the reaction. Then, the resulting pale yellow solution was poured into cold water and extracted three times with ethyl acetate. The organic layer was dried over magnesium sulfate and evapolated under reduced pressure to leave an oily residue. The nmr spectrum of this residue showed two characteristic aldehyde signals which appeared in the same intensity at δ9.51 and 9.68 with vicinal F-H coupling constants 5.8 Hz and 6.5 Hz, respectively, clearly suggesting the formation of the desired fluorinated aldehyde as two isomeric mixtures. Thus formed fluorinated aldehyde was separated from other minor by-products such as the compound III a'2(2S*-t) and other unidentified ones by silica gel column chromatography using toluene-ethyl acetate mixture as an eluent to afford the oily aldehyde III a2(2S*-t) (132 mg, 45%). The structure of III a2(2S*-t) was clearly proved by 19F-nmr spectrum as shown below.

19F-NMR: δ from C₆F₆ (CDCl₃) +31 ppm (dm. J=43 Hz) and +38 ppm (Oct., J=43 Hz, J=26 Hz, J=6 Hz).

(5) Preparation of methyl 7-[2(S*)-2-exo-3-endo-3-benzenesulfonamidobicyclo[2.2.1]heptan-2-yl]-(5Z)-7-fluoro-5-pentenoate I a2-aa(2S*-t)

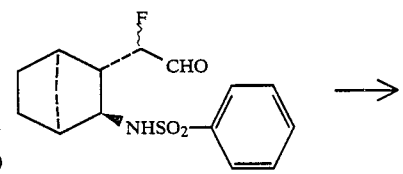

III a2(2S*—t)

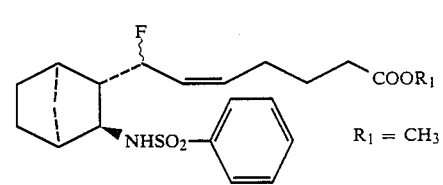

I a2-aa(2S*—t)

The ylide required for this Wittig reaction was prepared according to the well known Corey's method as follows.

Under the nitrogen atmosphere, sodium hydride dispersion (60% oil: 138 mg, 3.4 mmol) was, in sequence, washed with dry pentane, then dried followed by addition of dimethylsulfoxide (3.6 ml), and finally completely dissolved into dimethylsulfoxide at 60°–70° C. to afford the pale yellow solution of methylsulfinyl carbanion. This solution was cooled to 12° C. and then the commercially available 5-(methyl pentenoate)triphenylphosphonium bromide (846 mg, 1.9 mmol) dissolved in dimethylsulfoxide (3.6 ml) was quickly added. Then, the temperature was gradually raised to room temperature and maintained for 20 minutes to effect the ylide formation. The color of the solution turned to be quite reddish brown from pale yellow as ylide was formed. Then, fluorinated aldehyde (175 mg, 0.6 mmol) dissolved in 1.5 ml of DMSO was added into this ylide solution maintained at 12° C. in a few minutes and the temperature was gradually raised to room temperature. The color of the solution was immediately faded away along with the addition of the aldehyde. After 30 minutes, the reaction mixture was poured into cold saturated saline acidified with hydrochloric acid and extracted with ethyl acetate. DMSO was completely washed out from the organic extract by cold water. The organic layer was then dried over magnesium sulfate, filtered, and evaporated solvent under reduced pressure to leave an oily residue. This residue was again dissolved into tetrahydrofuran without purification and esterified with diazomethane. After evaporation of solvents the desired title compound (105 mg, 43%) was easily separated from the resulting product mixture by silica gel column chromatography using toluene-ethyl acetate as an eluent. The compounds was characterized as follows and identified as the desired one.

NMR: δppm (CDCl3); 1.0–2.4 (m, 15H), 3.0–3.5 (m, 1H), 3.6–3.8 (two s, 3H), 4.0–5.0 (m, 1H), 5.0–5.8 (m, 3H), 7.40–7.70 (m, 3H), 7.80–8.10 (m, 2H).

IR: νmax (CHCl3); 3600, 3375, 2950, 1730, 1580, 1440, 1320, 1160, 1095 cm$^{-1}$.

Mass (m/e): 409 (M+), 389, 377, 358, 320, 315, 268, 248, 232, 91, 77 etc.

I-3a

EXAMPLE 41

(1) Preparation of I a3-aa(2S*-t)

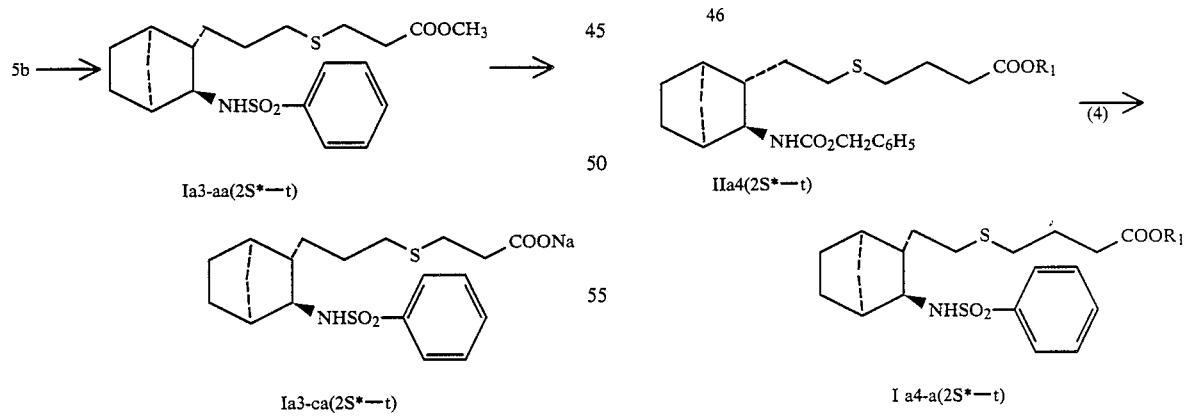

Ia3-aa(2S*—t)

Ia3-ca(2S*—t)

A mixture of 400 mg (1.38 mM) of 5b, prepared in I-2, Example 40, and methyl 3-mercaptopropionate (824 mg, 6.9 mM) was heated at 60° C. overnight with stirring in the presence of azoisobutylonitrile (30 mg).

The mixture was diluted with ethyl acetate, washed with 5% aqueous sodium carbonate solution, water, dried over magnesium sulfate, and concentrated in vacuo. Separation by chromatography on silica gel (elution with 20% ethyl acetate in n-hexane) afforded oil I a3-aa(2S*-t) (236 mg, 41.6%)

Anal. Calcd. (%) for $C_{20}H_{29}NO_4S_2.0.2H_2O$: C: 57.85 H: 7.14 N: 3.37 S: 15.45, Found (%): C: 57.86 H: 6.97 N: 3.47 S: 15.28.

IR νmax (CHCl3) cm$^{-1}$: 3390, 1736, 1159.5, 1092.

NMR δppm (CDCl3): 1.00–2.64 (m, 19H), 3.02 (m, 1H), 3.70 (s, 3H), 5.58 (d, J=7 Hz, 1H), 7.67 (m, 3H), 7.93 (m, 2H).

(2) Preparation of I a3-ca(2S*-t)

Saponification of the methyl ester I a3-aa(2S*-t) (225 mg), followed by freeze-drying in the usual manner gave I a3-ca(2S*-t) (201 mg, 87%).

Anal. Calcd. (%) for $C_{19}H_{26}NO_4S_2Na.0.6H_2O$: C: 53.03 H: 6.37 N: 3.26 S: 14.90, Found (%): C: 53.14 H: 6.29 N: 3.37 S: 14.65.

IR νmax (KBr) cm$^{-1}$: 3425, 3270, 1570, 1449, 1421, 1402, 1160, 1093.

NMR δppm (d-Methanol): 1.00–2.95 (m, 20H), 7.58 (m, 3H), 7.88 (m, 2H).

I-3b

EXAMPLE 42

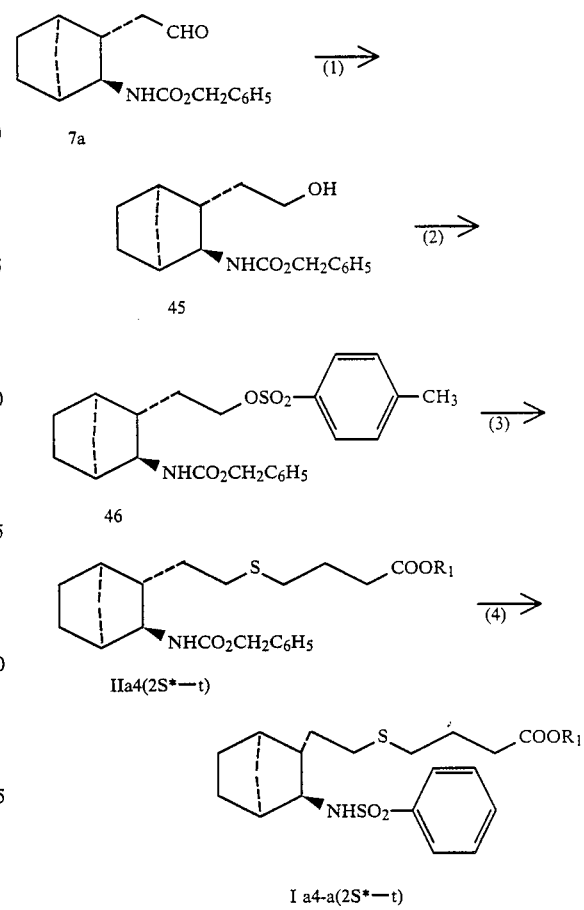

Ia4-aa(2S*—t): R1 = CH3
Ia4-ba(2S*—t): R1 = H
Ia4-ca(2S*—t): R1 = Na (1) Preparation of 45

To a solution of compound 7a, prepared from I-1, Example 5, 2.61 g (9.11 mM) in 20 ml of ethanol, was added 378 mg of sodium borohydride (10 mM) at 0° C. The mixture was stirred for 30 minutes at 0° C., partitioned between AcOEt and 2NHCl. The organic solution was washed with water, dried over Na₂SO₄, concentrated in vacuo. The crude alcohol was purified by chromatography with silica gel [Merck Lobar B, eluted with n.hexane-AcOEt (25%)] and 1.6 g of compound 45 (Yield; 60.6%) was obtained as a colorless gum. ¹HNMR (CDCl₃): δppm 1.00–1.75 (m, 9H), 1.93 (br.s, 1H), 2.40 (br.s, 1H), 2.50 (br.s, 1H, OH), 2.50 (m, 1H), 2.59 (t, J=7 Hz, 2H), 5.05 (s, 2H), 5.15 (br.s, 1H), 7.32 (s, 5H). Anal. Calcd. (%) for C₁₇H₂₃NO₃: C; 70.55, H; 8.03, N; 4.84. Found (%): C; 70.08, H; 7.99, N; 4.90.

(2) Preparation of 46.

To a solution of compound 46, 868 mg (3 mM) in 10 ml of CH₂Cl₂, 572 mg of p-toluenesulfonyl chloride (3 mM) and 291 μl of pyridine (3 mM×1.2) were added at 0° C. The mixture was stirred for 3 h at 20° C. and allowed to stand overnight. The reaction mixture was partitioned between AcOEt and 0.1NHCl. The AcOEt layer was washed with water, dried over Na₂SO₄, concentrated in vacuo and separation by chromatography with silica gel [30 g, eluted with n.hexane-AcOEt (25%)] gave 964 mg of compound 46 (Yield; 72.5%) as a colorless gum. ¹HNMR (CDCl₃): δppm 0.80–1.85 (m, 9H), 1.88 (br.s, 1H), 2.38 (br.s, 1H), 2.40 (s, 3H), 3.41 (td, J=4, 8 Hz, 1H), 4.01 (t, J=7 Hz, 2H), 4.85 (d, J=8 Hz, 1H), 5.05 (s, 2H), 7.28 (A₂B₂q, Apart, J=8 Hz, 2H), 7.38 (s, 5H), 7.75 (A₂B₂q, Bpart, J=8 Hz, 2H). Anal. Calcd. (%) for C₂₄H₂₉NO₅S: C; 64.98; H; 6.60, N; 3.16, S; 7.23. Found (%): C; 65.11, H; 6.53, N; 3.31, S; 6.96.

(3) Preparation of II a4(2S*-t)

To a solution of 290 mg (1.08 mM×2) of methyl 4-mercaptobutyrate, prepared from ethyl 4-bromobutyrate (H-L. Pan and T. L. Fletcher, Chem. & Ind. (London), 546, 1968), in 2 ml of methanol, was added a solution of 4.51 ml of sodium methoxide (1.08 mM×2; 0.479 M/L in MeOH) at 0° C. The mixture was stirred for 15 min at 25° C., concentrated in vacuo, dissolved in 2 ml of DMF. The solution was added to a solution of compound 46, 480 mg (1.08 mM) in 4 ml of THF at 0° C. and the mixture was stirred for 30 min at 25° C. The reaction mixture was partitioned between AcOEt and water and the organic layer was washed with water, dried over Na₂SO₄ and concentrated in vacuo. Separation by chromatography on silica gel [30 g, eluted with n.hexane-AcOEt (10%)] gave 371 mg of compound II a4(2S*-t) as a colorless gum. ¹HNMR (CDCl₃): δ ppm 0.95–2.10 (m, 11H), 2.33–2.65 (m, 7H), 3.52 (td, J=4, 8 Hz, 1H), 3.66 (s, 3H), 4.92 (d, J=8 Hz, 1H), 5.09 (s, 2H), 7.36 (s, 5H). Anal. Calcd. (%) for C₂₂H₃₁NO₄S: C; 65.14, H; 7.72, N; 3.45, S; 7.90. Found (%): C; 65.02, H; 7.77, N; 3.38, S; 7.80.

(4) Preparation of I a4-aa(2S*-t)

500 mg of compound II a4(2S*-t) (1.23 mM) was dissolved in a mixture of 1 ml of anisole and 5 ml of trifluoroacetic acid. The mixture was stirred for 5 hours at 45° C., concentrated in vacuo. The residue was dissolved in 10 ml of CH₂Cl₂ and 512 μl of triethylamine (1.23 mM×3), 235 μl of benzenesulfonyl chloride (1.23 mM×1.5) were added to the solution at 0° C. The mixture was stirred for 15 minutes at 25° C., partitioned between AcOEt and 0.1 NHCl. The organic layer was washed with water, dried over Na₂SO₄ and concentrated in vacuo. Separation by chromatography on silica gel [30 g, eluted with n.hexane-AcOEt (20%)] gave 380 mg of compound I a4-aa(2S*-t) as a colorless gum. ¹H-NMR (CDCl₃): δ ppm 0.90–2.60 (m, 19H), 3.01 (td, J=4, 7 Hz, 1H), 3.69 (s, 3H), 5.13 (d, J=7 Hz, 1H), 7.40–8.05 (m, 5H). Anal. Calcd. (%) for C₂₀H₂₉NO₄S₂: C; 58.35, H; 7.12, N; 3.40, S; 15.58. Found (%): C; 58.39, H; 7.15, N; 3.26, S; 15.35.

(5) Preparation of I a4-ba(2S*-t)

To a solution of compound I a4-aa(2S*-t), 360 mg (0.87 mM) in 5 ml of methanol, was added 1.74 ml of 1NKOH (0.87 mM×2) at 23° C. The mixture was stirred for 8 hours at 23° C., partitioned between ether and water. The aqueous solution was acidified with 2NHCl, extracted with AcOEt. The AcOEt solution was washed with water, dried over Na₂SO₄, concentrated in vacuo, and gave 345 mg of compound I a4-ba(2S*-t) (89.6%) as a colorless gum. ¹HNMR (CDCl₃): δ ppm 1.00–1.65 (m, 11H), 1.75–2.65 (m, 8H), 3.02 (td, J=4, 7 Hz, 1H), 5.38 (d, J=7 Hz, 1H), 7.45–8.05 (m, 5H), 8.80 (br.s, 1H). Anal. Calcd. (%) for C₁₉H₂₇NO₄S₂.0.1C₆H₆: C; 58.07, H; 6.88, N; 3.46 Found (%): C; 58.26, H; 6.92, N; 3.41.

(6) Preparation of I a4-ca(2S*-t)

To a solution of compound I a4-ba(2S*-t), 320 mg (0.72 mM) in 3 ml of methanol, was added a solution of 1.43 ml of sodium methoxide (0.72 mM×0.95; 0.479 M/L in methanol) at 0° C. The mixture was stirred for 10 minutes at 0° C., concentrated in vacuo. The residue was dissolved in 7 ml of water and freeze-dried to afford 302 mg of compound I a4-ca(2S*-t) (100%) as a colorless powder.

I-4

EXAMPLE 43

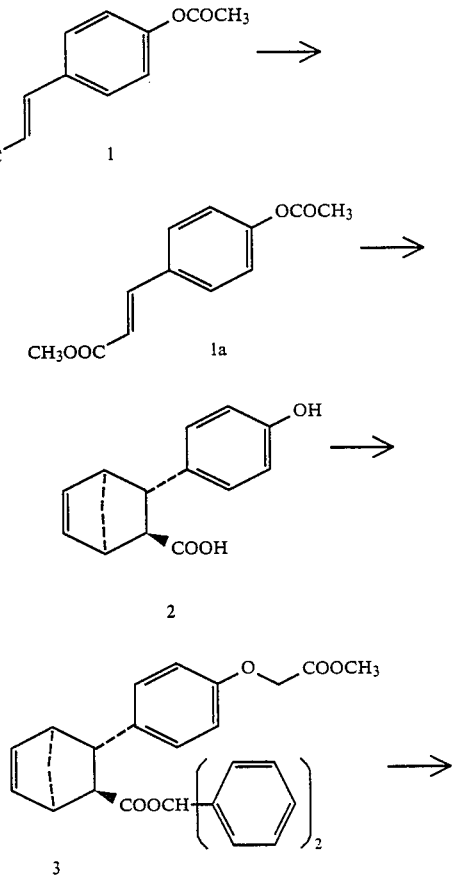

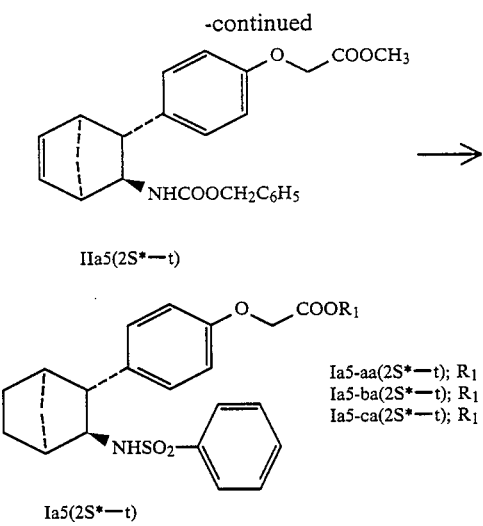

(1) Preparation of 1a

To a suspension of compound 1, 10.3 g (50 mM), prepared from p-hydroxy cinnamic acid by acetylation, in 100 ml of acetone, 8.5 ml (50 mM×1.1) of diazabicycloundecene and 5.2 ml (50 mM×1.1) of dimethylsulfate were added at 0° C. The mixture was stirred for 30 minutes at 25° C., partitioned between AcOEt and 0.2NHCl, and the organic solution was washed with water, dried over $Na_2SO_4$ and concentrated in vacuo to give 8.00 g (Yield 72.7%) of compound 1a as crystalline powder. $^1$HNMR ($CDCl_3$): δ2.29 (s, 3H), 3.78 (s, 3H), 6.38 (d, J=16 Hz, 1H), 7.12 ($A_2B_2$ type, Apart, J=10 Hz, 2H), 7.53 ($A_2B_2$ type, Bpart, J=10 Hz, 2H), 7.67 (d, J=16 Hz, 1H).

(2) Preparation of 2

To a solution of 7.96 ml (36.3 mM×2) of titanium tetrachloride in 90 ml of $CH_2Cl_2$, was added a solution of 21.61 ml (36.3 mM×2) of titanium tetraisopropoxide in 60 ml of $CH_2Cl_2$ at −30° C. Cyclopentadiene (9 ml, 36.3 mM×3) and compound 1a (8.00 g, 36.3 mM) were added to the solution and the mixture was stirred for 6 h at 0° C. The reaction mixture was poured into ice water, extracted with $CH_2Cl_2$. The $CH_2Cl_2$ solution was washed with water, dried over $Na_2SO_4$ and concentrated in vacuo. Separation by column chromatography [$SiO_2$ 120 g, eluted with $CH_2Cl_2$] gave the Diels-Alder adduct, which was hydrolysed as usual with 1N KOH and gave 460 mg (Yield 5.5%) of compound 2 as colorless prisms. Mp 144°–146° C. $^1$HNMR ($CDCl_3$): δ1.40–1.85 (m, 2H), 2.85–3.15 (m, 3H), 3.25 (brs, 1H), 6.00 (brs, 1H), 6.05–6.55 (m, 2H), 6.75 ($A_2B_2$type, Apart, J=9 Hz, 2H), 7.18 ($A_2B_2$type, Bpart, J=9 Hz, 2H), 9.31 (brs, 1H).

(3) Preparation of 3

Compound 2, 450 mg (1.95 mM) was treated with diphenyldiazomethane as usual and the benzhydryl ester was treated with anhydrous potassium carbonate (538 mg, 1.95 mM×2) by refluxing in 10 ml of methyl ethyl ketone for 1 hour.

To the above suspension 203 μl (1.95 mM×1.1) of methyl bromoacetate and 293 mg (1.95 mM) of sodium iodide were added and the mixture was stirred for 4 hours under reflux. The reaction mixture was partitioned between AcOEt and water and the organic layer was washed with water, dried over $Na_2SO_4$ and concentrated in vacuo. Separation of the residue by chromatography [$SiO_2$ 20 g, eluted with 25% AcOEt in n-hexane] gave 700 mg (76.9%) of compound 3 as a colorless gum. $^1$HNMR ($CDCl_3$): δ ppm 1.40–1.88 (m, 2H), 2.90–3.25 (m, 3H), 3.36 (brs, 1H), 3.78 (s, 3H), 4.59 (s, 2H), 5.83–6.45 (m, 2H), 6.82 ($A_2B_2$type, Apart, J=9 Hz, 2H), 6.85 (s, 1H), 7.22 ($A_2B_2$type, Bpart, J=9 Hz, 2H), 7.33 (brs, 10H).

(4) Preparation of II a5(2S*-t)

A mixture of 3 (700 mg, 1.49 mM), anisole (1.4 ml), trifluoroacetic acid (1.4 ml) in 14 ml of $CH_2Cl_2$ was stirred for 30 minutes at 0° C. and concentrated in vacuo to remove trifluoroacetic acid. The residue was treated with triethylamine (296 μl, 1.49 mM×3) and ethyl chloroformate (185 μl, 1.49 mM×1.3) in 10 ml of acetone and 2 ml of water for 20 min at 0° C. To the mixture was added a solution of 145 mg (1.49 mM×1.5) of sodium azide in 3 ml of water. The reaction mixture was stirred for 30 minutes at 0° C. and partitioned between AcOEt and 0.1NHCl.

The organic layer was washed with water, dried over $Na_2SO_4$ and concentrated in vacuo. A solution of the residue in 6 ml of benzene was stirred for 30 minutes under gentle reflux. After evolution of nitrogen, benzyl alcohol (309 μl, 1.49 mM×2) and triethylamine (269 μl, 1.49 mM×1.3) were added to the solution and the mixture was refluxed for 5 hours. The reaction mixture was diluted with AcOEt and washed with 0.2NHCl and water. The organic solution was dried over $Na_2SO_4$ and concentrated in vacuo. Separation by column chromatography [$SiO_2$ 50 g, eluted with 5% AcOEt in benzene] gave 540 mg (89.1%) of compound II a5(2S*-t) as a colorless oil. $^1$HNMR ($CDCl_3$): δ ppm 1.45–1.83 (m, 2H), 2.25 (m, 1H), 2.90 (brs, 1H), 3.06 (brs, 1H), 3.77 (s, 3H), 4.33 (m, 1H), 4.57 (s, 2H), 4.63 (d, J=7 Hz, 1H), 5.05 (s, 2H), 6.06–6.60 (m, 2H), 6.82 ($A_2B_2$type, Apart, J=9 Hz, 2H), 7.23 ($A_2B_2$type, Bpart, J=9 Hz, 2H), 7.31 (brs, 5H).

(5) Preparation of I a5-a(2S*-t)

① Methyl ester I a5-aa(2S*-t)

Catalytic reduction of compound II a5(2S*-t), 204 mg (0.5 mM) in 6 ml of methanol using 10% palladium-carbon (50 mg) as a catalyst gave the saturated amine.

To a solution of the amine in 5 ml of $CH_2Cl_2$, triethylamine (139 μl, 0.5 ml×2) and benzenesulfonyl chloride (83 μl, 0.5 ml×1.3) were added at 0° C. and the mixture was stirred for 15 minutes at 0° C. The reaction mixture was partitioned between AcOEt and 0.1NHCl and the organic layer was washed with water, dried over $Na_2SO_4$ and concentrated in vacuo. Separation by column chromatography [$SiO_2$, Merck Lobar A, eluted with 20% AcOEt in n-hexane] gave 150 mg (72.5%) of compound I a5-aa(2S*-t) as a colorless gum. $^1$HNMR (δ ppm 1.10–1.85 (m, 6H), 2.20 (m, 3H), 3.60 (m, 1H), 3.79 (s, 3), 4.56 (s, 2H), 5.48 (d, J=7 Hz, 1H), 6.67 ($A_2B_2$type, Apart, J=9 Hz, 2H), 6.93 ($A_2B_2$type, Bpart, J=9 Hz, 2H), 7.20–78.5 (m, 5H).

② Free carboxylic acid

Compound I a5-aa(2S*-t), 147 mg (0.35 mM) was hydrolysed as usual using 1N KOH to give 130 mg (92.9%) of compound I a5-ba(2S*-t) as colorless prisms, mp 150°–152° C. $^1$HNMR (acetone-$d_6$): δ ppm 1.00–1.90 (m, 6H), 2.00–2.40 (m, 3H), 3.53 (m, 1H), 4.60 (s, 2H), 6.70 ($A_2B_2$type, Apart, J=9 Hz, 2H), 6.81 (d, J=7 Hz, 1H), 6.97 ($A_2B_2$type, Bpart, J=9 Hz, 2H), 7.25–7.85 (m, 5H).

③ Sodium salt

Treatment of compound I a5-ba(2S*-t), 116 mg (0.289 mM) with sodium methoxide in methanol as usual gave 110 mg (90.2%) of compound I a5-ca(2S*-t) as a colorless powder.

I-5

EXAMPLE 44

(1) Preparation of 8-endo-9-endo-4,7-methano-1,4,5,6,7,8,9-hexahydro-1H-indene 2

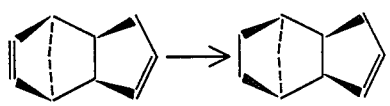

1　　　　　2

According to the method described in Brown, et al., J. Organic Chem., 37, 4098, (1972), selective reduction is carried out as follows:

To a suspension of 9.3 g (37.37 mM) of nickel acetate tetrahydrate in 180 ml of ethanol is added 1.42 g (37.37 mM) of sodium borohydride at 20° C., and the mixture is stirred for 30 minutes. Then, 39.67 g (0.3M) of dicyclopentadiene (Nakarai Chemicals, Ltd.) and 20 ml of ethanol are added thereto. The resulting mixture is catalytically hydrogenated under the usual pressure. The reaction is stopped when 6.72 L (1 eq.) of hydrogen is absorbed. The reaction mixture is distributed between n-pentane and water. The aqueous layer is extracted with n-pentane twice. The extract is mixed with the above n-pentane solution, washed with water, dried over sodium sulfate, and evaporated under reduced pressure at a temperature of 10° C. or less. The residue is distilled under usual pressure to give 33.8 g of the compound 2, (Yield 84.5%). Colorless, semicrystal. bp. 184°~186° C.

$^1$H-NMR(CDCl$_3$): δ ppm 1.00–1.75 (m, 6H), 2.00–2.70 (m, 5H), 2.96 (m, 1H), 5.43–5.85 (m, 2H).

(2) Synthesis of cis-[3-carboxybicyclo[2.2.1]hept-2-yl]-acetic acid

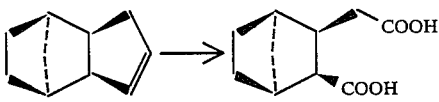

2　　　　　3

A solution of 10.74 g of compound 2 in 200 ml of dichloromethane is subjected to ozonolysis at −78° C. At the same temperature, 50 ml of acetic acid and 25 g of zinc dust are added, and the mixture is gradually warmed up to 20° C. The zinc dust is filtered off and the filtrate is washed with 1% sodium hydrogencarbonate aqueous solution and with water, dried over sodium sulfate, and evaporated under reduced pressure. The residue is dissolved in 200 ml of acetone. To a solution of the residue in 200 ml of acetone is added 36 ml of Jones reagent at 0° C., and the mixture is stirred for 4 hours at 23° C. The reaction mixture is left standing overnight at room temperature and then evaporated under reduced pressure. Ethyl acetate is added to the residue and the resulting solution is washed with water, dried over sodium sulfate, and evaporated under reduced pressure. The residue is crystallized from ether and petroleum ether to give 6.6 g of compound 3 (Yield 41.7%), mp. 133°~136° C.

$^1$H-NMR(CDCl$_3$): δ ppm 1.25–1.75 (m, 6H), 2.05–2.70 (m, 4H), 2.83–3.35 (m, 2H), 10.32 (br.s, 2H).
IR(CHCl$_3$): νmax 2450–3550, 1708 cm$^{-1}$.
Anal. Calcd. for C$_{10}$H$_{14}$O$_4$ (%): C 60.58, H 7.13, Found (%): C 60.47, H 7.05

(3) Synthesis of methly cis-[(3-carboxy)-bicyclo[2.2.1]hept-2-yl]-acetate

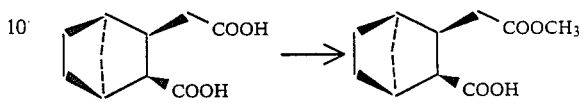

3　　　　　4

A suspension of 7.2 g (36.3 mM) of compound 3 in 40 ml of acetic anhydride in a stream of nitrogen is stirred at 100° C. for 5 minutes to dissolve the compound. At the same temperature, the solution is evaporated under reduced pressure. To the residue 200 ml of toluene is added, which is evaporated under reduced pressure. This operation is repeated twice to completely remove acetic anhydride, and 30 ml of methanol is added to the resulting residue. The mixture is refluxed for 20 minutes. The reaction mixture is evaporated under reduced pressure and subjected to column chromatography [silica-gel: Merck, Lobar column C, developed with chloroform] to give 7.2 g of compound 4, (Yield 93.5%). Light yellow oil.

$^1$H-NMR(CDCl$_3$): δ ppm 1.20–1.80 (m, 6H), 2.15–2.67 (m, 4H), 2.68–3.10 (m, 2H), 3.63 (s, 3H), 10.49 (br.s, 1H).
Anal. Calcd. for C$_{11}$H$_{16}$O$_4$.0.1H$_2$O: (%): C 61.71, H 7.64, Found (%): C 61.79, H 7.38.

(4) Synthesis of methyl cis-[(3-benzyloxycarbonylamino)bicyclo[2.2.1]hept-2-yl]acetate

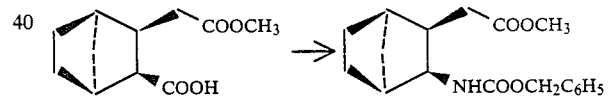

4　　　　　5

To a solution of 4.25 g (20 mM) of compound 4 in 40 ml of acetone is added 10 ml of water, 3.61 ml (20 mM×1.3) of triethylamine, and 2.49 ml (20 mM×1.3) of ethyl chloroformate in a stream of nitrogen at 0° C. The mixture is stirred for 45 minutes at the same temperature. A solution of 19.5 g (20 ml×1.5) of sodium azide in 10 ml of water is added to the reaction mixture at 0° C. and the mixture is stirred for 1 hour at the same temperature. Ether is added to the reaction mixture, which is washed with 0.1N hydrochloric acid, water and saturated sodium chloride solution, dried over sodium sulfate and evaporated under reduced pressure to give an azide compound. A solution of the obtained azide in 50 ml of benzene is refluxed for 1 hour. The reaction mixture is refluxed for 3 hours after the addition of 5 ml of benzyl alcohol and 3.6 ml of triethylamine. After cooled, the resulting mixture is washed with 0.1N hydrochloric acid, dried, and evaporated under reduced pressure. The residue is subjected to column chromatography [silica gel: Merck, Lobar C, developed with benzene-ethyl acetate (5%)] to give 3.75 g of compound 5, (Yield 59.1%).

Colorless prisms, mp. 70° C.

¹HNMR(CDCl₃): δ ppm 1.25–1.63 (m, 6H), 2.07–2.70 (m, 5H), 3.58 (s, 3H), 4.11 (t.d., J=9, 5 Hz, 1H), 4.90 (d, J=9 Hz, 1H), 5.07 (s, 2H), 7.34 (s, 5H).

Anal. Calcd. for C₁₈H₂₃O₄N: (%): C 68.11, H 7.32, N 4.41, Found (%): C 67.96, H 7.29, N 4.53.

(5) Synthesis of methyl cis-5(Z)-7-[(3-benzyloxycarbonylamino)bicyclo[2.2.1]hept-2-yl]-5-heptenoate

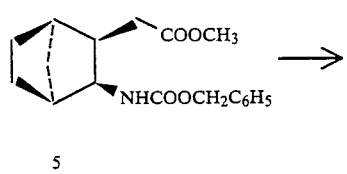

5

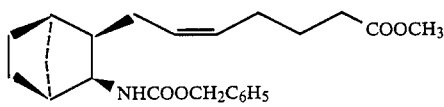

6

To a solution of 1.00 g (3.15 mM) of compound 5 in 10 ml of toluene is added 5.35 ml (3.15 mM×1.7) of diisobutyl aluminum hydride (1.0M in hexane) in a stream of nitrogen at −78° C. and the mixture is stirred for 45 minutes at the same temperature. To the reaction mixture is added 8 ml of 2N hydrochloric acid and the resulting mixture is diluted with ethyl acetate. The organic layer is washed with water and all precipitated substances are filtered off. The filtrate is dried, and concentrated under reduced pressure to give a light yellow oil. Separately, 907 mg (3.15 mM×8×0.9) of sodium hydride (60% in mineral oil) is suspended in 40 ml of dimethylsulfoxide (hereinafter abbreviated to as DMSO). The suspension is stirred for 1.5 hours at 75° C., and after the reaction mixture is cooled to 12° C., a solution of 5.58 g (3.15×4) of 4-carboxybutyl triphenylphosphonium bromide in 10 ml of DMSO is dropwise added thereto. The resulting yellow red solution is stirred for 20 minutes at 20° C., to which the previously obtained hemiacetal, dissolved in 10 ml of DMSO, is added at 20° C. At the same temperature, the mixture is stirred for 2.5 hours. Ethyl acetate is added to the reaction mixture, which is washed with 0.2N hydrochloric acid and water, dried over sodium sulfate, concentrated under reduced pressure. The residue obtained is subjected to column chromatography [silica-gel 25 g, developed with benzene-ethyl acetate (9:1)-(4:1)]. Fractions of carboxylic acid are collected and concentrated under reduced pressure. Then, the residue is dissolved in 5 ml of ethyl acetate and treated with diazomethane in a conventional way to give methyl ester. The product is subjected to column chromatography again [silica gel: Merck, Lobar B, developed with n-hexane-ethyl acetate (9:1)] to give 416 mg of compound 6, (yield 34.3%). Colorless oil.

¹H-NMR(CDCl₃): δ ppm 1.36 (br.s, 6H), 1.55–2.43 (m, 9H), 2.36 (t, J=7 Hz, 2H), 3.62 (s, 3H), 4.03 (m, 1H), 4.90 (d, J=9 Hz, 1H). 5.06 (s, 2H), 5.27 (m, 2H), 7.31 (s, 5H).

IR(CHCl₃): 3440, 1720, 1505 cm⁻¹.

Anal. Calcd. for C₂₃H₃₁NO₄: (%): C 71.65, H 8.12, N 3.63, found (%): C 71.55, H 8.10, N 3.57.

(6) Synthesis of methyl cis-5(Z)-7-[(3-phenylsulfonamido)bicyclo[2.2.1]hept-2-yl]-5-heptenoate

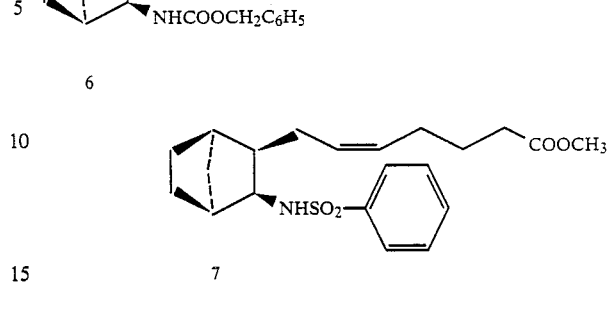

To 200 mg (0.51 mM) of compound 6 is added 0.5 ml of anisole and 3 ml of trifluoroacetic acid. The solution is stirred for 4 hours at 45° C. The reaction mixture is concentrated under reduced pressure, benzene is added to the residue and the mixture is concentrated again. This operation is repeated three times to completely remove trifluoroacetic acid. To a solution of the residue 4 ml of dichloromethane is added 99 μl (0.51 mM×1.5) of benzenesulfonyl chloride and 215 μl (0.51 mM×3) of triethylamine at 0° C., and the mixture is stirred for 15 minutes at 20° C. Ethyl acetate is added to the reaction mixture. The mixture is successively washed with 0.1N hydrochloric acid, water, 1% sodium hydrogencarbonate, and water, dried over sodium sulfate, and concentrated under reduced pressure. The residue is subjected to column chromatography [silica-gel, Merck, Lobar A, developed with n-hexane-ethyl acetate (10%)] to give 160 mg of compound 7, (Yield 80.4%).

Colorless prisms, mp 79° C.

¹H-NMR (CDCl₃): δ1.05–2.25 (m, 15H), 2.29 (t, J=8 Hz, 2H), 3.60 (m, 1H), 3.66 (s, 3H), 5.03 (d, J=9 Hz, 1H), 5.26 (m, 2H), 7.33–7.60 (m, 3H), 7.70–8.00 (m, 2H).

Anal. Calcd. for C₂₁H₂₉NO₄S: (%): C 64.41, H 7.48, N 3.58, S 8.19, Found (%): C 64.82, H 7.24, N 3.51, S 8.05.

(7) Synthesis of cis-5(Z)-7-[(3-phenylsulfonamide)-bicyclo[2.2.1]hept-2-yl]-5-heptenoic acid

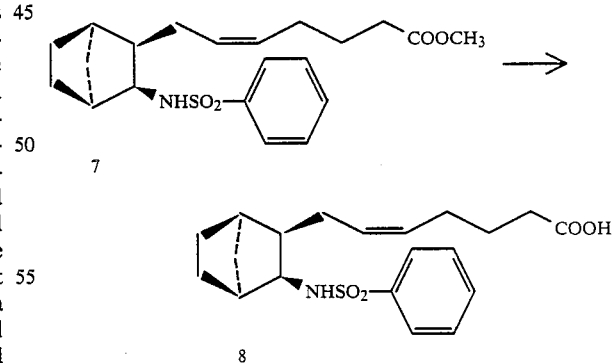

To a solution of 120 mg (0.306 mM) of compound 7 in 2.0 ml of methanol is added 0.61 ml (0.306 mM×2) of 1N potassium hydroxide. The mixture is stirred for 3 hours, and left standing overnight. The solution is distributed between ether and water. To the aqueous layer 0.1N hydrochloric acid is added, which is extracted with ethyl acetate. The ethyl acetate layer is washed with water, dried over sodium sulfate and concentrated under reduced pressure. The residue is crystallized from petroleum ether to give 109 mg of compound 8, (Yield 94.3%).

Colorless pillars, mp. 104–106° C.

$^1$H-NMR(CDCl$_3$): δ1.05–2.25(m, 15H), 2.33(t, J=7 Hz, 2H), 3.63(t.d.,

J=9, 3 Hz, 1H), 5.25(m, 2H), 5.44(d, J=9 Hz, 1H), 7.33–7.70(m, 3H), 7.75–8.03(m, 2H), 9.10(br.s, 1H).

Anal. Calcd. for C$_{20}$H$_{27}$NO$_4$S: (%): C 63.62, H 7.22, N 3.71, S 8.49, Found (%): C 63.46, H 7.17, N 3.65, S 8.26.

(8) Synthesis of sodium cis-5(Z)-7-[(3-phenylsulfonamido)bicyclo[2.2.1]hept-2-yl]-heptenoate

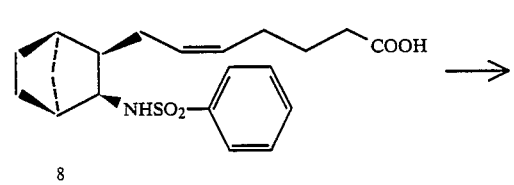

8

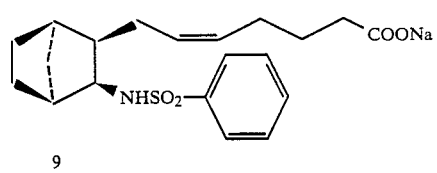

9

To a solution of 97 mg (0.25 mM) of compound 8 in 1 ml of methanol is added 1.08 ml of sodium methoxide (0.219M in methanol) at 0° C. The mixture is stirred for 15 minutes at the same temperature and the reaction mixture is concentrated under reduced pressure. The residue dissolved in 3 ml of water is freeze-dried to give 97 mg of compound 9, (Yield 94.2%). Colorless powder.

$^1$H-NMR (CDCl$_3$+CD$_3$OD): δ1.00–2.35(m, 17H), 3.55(m, 1H), 5.29(m. 2H), 7.40–7.70(m, 3H), 7.75–8.00(m, 2H).

Example 45

(1) Synthesis of methyl cis-[(3-diphenylmethoxycarbonyl)bicyclo[2.2.1]hept-2-yl]-acetate

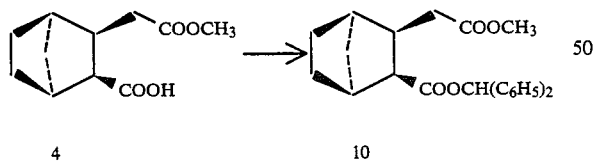

4      10

To a solution of 7.0 g (33 mM) of compound 4 in 30 ml of ethyl acetate is added 6.4 g (33 mM) of diphenyldiazomethane at 20° C. The mixture is stirred for 2 hours at 45° C. The reaction mixture is concentrated under reduced pressure, and the residue is subjected to column chromatography [silica-gel: Merck, Lobar C, developed with n-hexane-ethyl acetate (2%)] to give 7.3 g (58.4%) of compound 10. Colorless oil.

$^1$H-NMR(CDCl$_3$): δ1.15–1.75(m, 6H), 2.10–3.20 (m, 6H), 3.46(s, 3H), 6.79(s, 1H), 7.32(s, 10H).

(2) Synthesis of methyl trans-[(3-diphenylmethoxycarbonyl)bicyclo[2.2.1]hept-2-yl]-acetate

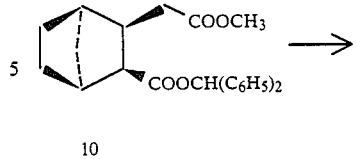

10

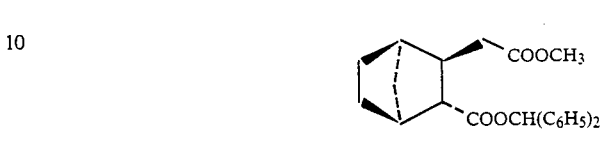

11

To a solution of 5.30 g (14 mM) of compound 10 in 50 ml of toluene is added 2.09 ml (14 mM) of diazabicycloundecene (DBU). The mixture is refluxed under heating for 3 days. After being cooled, the reaction mixture is washed with 0.2N hydrochloric acid and water, dried over sodium sulfate, and concentrated under reduced pressure. The residue is crystallized from petroleum ether to give 3.70 g of compound 11, (Yield 69.8%).

Colorless pillars, mp. 65° C.

$^1$H-NMR(CDCl$_3$): δppm 1.10–1.75(m, 6H), 1.98(m, 1H), 2.13–2.75 (m.5H), 3.49(s, 3H), 6.87(s, 1H), 7.35(s, 10H).

Anal. Calcd. for C$_{24}$H$_{26}$O$_4$: (%): C 76.15, H 6.94, Found (%): C 76.26, H 6.83.

(3) Synthesis of methyl trans-[(3-carboxy)-bicyclo[2.2.1]hept-2-yl]-acetate

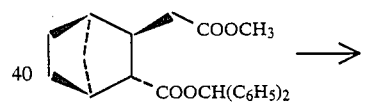

11

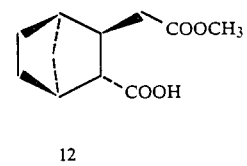

12

To a solution of 3.7 g of compound 11 in 30 ml of dichloromethane is added 7.6 ml of anisole and 7.6 ml of trifluoroacetic acid at 0° C. The mixture is stirred for 1 hour at the same temperature. The reaction mixture is concentrated under reduced pressure and the residue is subjected to column chromatography [silica gel 70 g, developed with chloroform and chloroform-methanol (5%), successively] to give 2.06 g of compound 12 (Yield 98.1%), Colorless oil.

$^1$H-NMR(CDCl$_3$): δppm 1.05–2.00(m, 7H), 2.20–2.70(m, 5H), 3.67(s, 3H), 9.40(br.s, 1H).

Anal. Calcd. for C$_{11}$H$_{16}$O$_4$: (%): C 62.24, H 7.61, Found (%): C 61.96, H 7.48.

(4) Synthesis of trans-[(3-benzyloxycarbonylamino)-bicyclo[2.2.1]hept-2-yl]-acetate

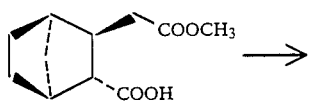

12

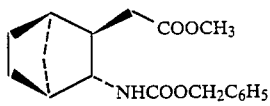

13

To a solution of 2.04 g (9.6 mM) of compound 12 in 20 ml of acetone is added 5 ml of water, 1.73 ml (9.6 mM×1.3) of triethylamine and 1.19 ml (9.6 mM×1.3) of ethyl chloroformate in a stream of nitrogen at 0° C. The mixture is stirred for 45 minutes at the same temperature. To the reaction mixture is added a solution of 0.94 g of sodium azide in 5 ml of water at 0° C., and the resulting mixture is stirred for 1 hour at the same temperature. Ether is added to the mixture, which is successively washed with 0.1N hydrochloric acid, water, and saturated sodium chloride aqueous solution, dried over sodium sulfate, and concentrated under reduced pressure. The residue is dissolved in 30 ml of benzene and refluxed for 1 hour. In addition, 2.5 ml of benzyl alcohol and 1.5 ml of triethylamine are added to the mixture, and refluxed for 3 hours. After being cooled, the reaction mixture is washed with 0.2N hydrochloric acid and concentrated under reduced pressure. The residue is subjected to column chromatography [silica gel; Merck, Lobar B, developed with benzene-ethyl acetate (3%)] to give 2.56 g of compound 13, (Yield 84.0%). Colorless oil.

$^1$H-NMR(CDCl$_3$): δppm 1.05–1.70(m, 6H), 1.93(m, 1H), 2.22(br.s, 3H), 2.34, 2.72(ABq.d., J=16, 8, 7 Hz, 2H), 3.03(m, 1H), 3.64(s, 3H), 4.80(br.s., 1H), 5.09(s, 2H), 7.38(s, 5H).

Anal. Calcd. for C$_{18}$H$_{23}$O$_4$N: (%): C68.11, H 7.32, N 4.41, Found (%): C 67.87, H 7.27, N 4.76.

(5) Synthesis of trans-[3-benzenesulfonamidobicyclo[2.2.1]hept-2-yl]-acetate

13

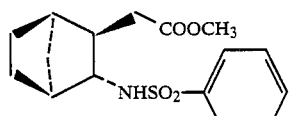

14

A solution of 1.00 g (3.15 mM) of compound 13 in 2.0 ml of anisole and 10 ml of trifluoroacetic acid is stirred in a stream of nitrogen under warming at 45° C. for 4 hours. The trifluoroacetic acid is completely removed (using benzene) under reduced pressure. To the residue dissolved in 15 ml of dichloromethane is added 1.31 ml (3.15 ml (3.15 mM×3) of triethylamine and 603 μl (3.15 mM×1.5) of benzenesulfonyl chloride in a stream of nitrogen at 0° C. The mixture is stirred for 15 minutes at 20° C. After the reaction mixture is concentrated under reduced pressure, ethyl acetate is added thereto. The resulting mixture is washed with 0.2N hydrochloric acid and water, dried over sodium sulfate, and concentrated under reduced pressure. The residue is subjected to column chromatography [silica gel: Merck, Lobar B, developed with n-hexane-ethyl acetate (4:1)] to give 694 mg of compound 14, (Yield 68.2%). Colorless oil.

$^1$H-NMR(CDCl$_3$): δppm 0.77–1.75(m, 6H), 1.75–2.40(m, 5H), 2.47(t, J=5 Hz, 1H), 3.57(s, 3H), 5.35(d, J=5 Hz, 1H), 7.36–7.67(m, 3H), 7.80–8.03(m, 2H).

Anal. Calcd. for C$_{16}$H$_{21}$NO$_4$S.0.2H$_2$O: (%): C 58.75, H 6.61, N 4.28, S 9.80, Found (%): C 58.57, H 6.42, N 4.46, S 9.57.

(6) Synthesis of methyl trans-5(Z)-7-[(3-phenylsulfonamido)bicyclo[2.2.1]hept-2-yl]-5-heptenoate

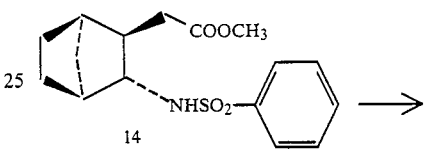

14

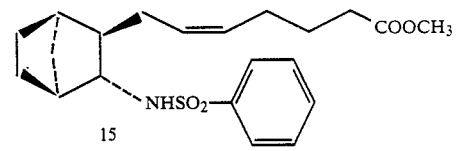

15

To a solution of 530 mg (1.63 mM) of compound 14 in 5 ml of toluene is added 3.26 ml (1.63 mM×1.8) of diisobutylaluminum hydride (1.0M in hexane) in a stream of nitrogen at −78° C. The mixture is stirred for 30 minutes at the same temperature. To the reaction mixture is added 4 ml of 2N hydrochloric acid and 10 ml of ethyl acetate. The ethyl acetate layer is washed with water, dried over sodium sulfate, and then concentrated under reduced pressure to give a the aldehyde as a crude product. Separately, 460 mg (1.63 mM×8×0.9) of sodium hydride (60.0% in mineral oil) is suspended in 15 ml of DMSO. The suspension is warmed at 70° C. for 1.5 hours in a stream of nitrogen, and cooled to 12° C., to which 2.84 g (1.63 mM×4) of 4-carboxybutyl triphenylphosphonium bromide dissolved in 5 ml of DMSO is added. The resulting yellow red solution is stirred for 20 minutes at 20° C. The solution of above prepared aldehyde in 5 ml of DMSO is added to the above solution at 20° C. and the mixture is stirred at the same temperature for 1.5 hours. The reaction mixture is poured into a mixture of 2N hydrochloric acid and ice, and extracted with ethyl acetate. The organic layer is washed with water, dried over sodium sulfate and concentrated under reduced pressure. The residue is subjected to column chromatography [silica gel 15 g, developed with benzene ethyl acetate (9:1)-(4:1)] to give the carboxylic acid as a crude product. The crude carboxylic acid is converted into methyl ester by processing with diazomethane in the conventional way, and 220 mg of compound 15 is given by column chromatography [silica gel, Merck, Lobar A, developed with n-hexane-ethyl acetate (9:1)], (Yield 34.6%). Colorless pillars, mp. 70° C.

$^1$H-NMR(CDCl$_3$): δ0.75-2.40(m, 15H), 2.26(t, J=7 Hz, 2H), 2.55(m, 1H), 3.68(s, 3H), 4.90(d, J=7 Hz, 1H), 5.18(m, 2H), 7.36-7.75(m, 3H), 7.75-8.10(m, 2H).

Anal. Calcd. for C$_{21}$H$_{29}$NO$_4$S: (%): C 64.41, H 7.48, N 3.58, S 8.19, Found (%): C 64.28, H 7.32, N 3.55, S 8.01.

(7) Synthesis of trans-5(Z)-7-[(3-phenylsulfonamido)-bicyclo[2.2.1]hept-2-yl]-5-heptenoic acid

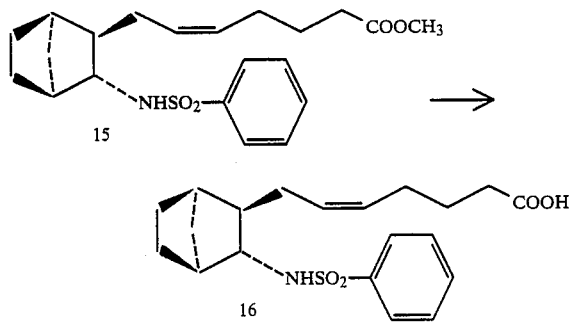

To a solution of 190 mg (0.485 mM) of compound 15 in 3.0 ml of methanol is added 0.97 ml (0.485 mM×2) of 1N potassium hydroxide at 20° C. The mixture is stirred for 2 hours and left standing overnight. The reaction mixture is distributed between ether and water, and the aqueous layer is acidified with 0.2N hydrochloric acid and extracted with ethyl acetate. The ethyl acetate layer is washed with water, dried over sodium sulfate and concentrated under reduced pressure. The resulting crystal is recrystallized from a mixture of ether-pertroleum ether to give 162 mg of compound 16, (Yield 88.5%). Coloreless pillars, mp. 82°-83° C.

$^1$H-NMR(CDCl$_3$): δppm 0.83-2.27(m, 15H), 2.31(t, J=7 Hz, 2H), 2.53(m, 1H), 5.00(d, J=7 Hz, 1H), 5.17(m, 2H), 7.35-7.70(m, 3H), 7.80-8.05(m, 3H).

Anal. Calcd. for C$_{20}$H$_{27}$NO$_4$S: (%): C 63.62, H 7.22, N 3.71, S 8.49, Found (%): C 63.48, H 7.06, N 3.61. S 8.25.

(8) Synthesis of sodium trans-5(Z)-7-[(3-phenylsulfonamido)bicyclo[2.2.1]hept-2-yl]-5-heptenoate

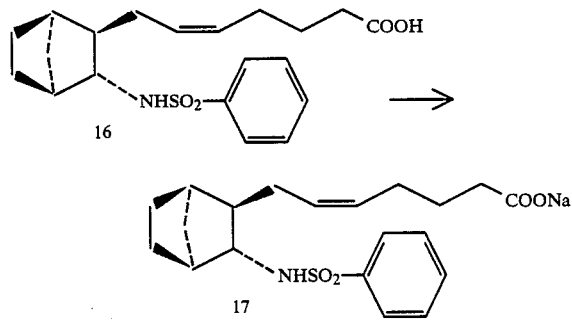

To a solution of 153 ml (0.405 mM) of compound 16 in 1.5 ml of methanol is added 1.85 ml (0.405 mM×0.95) of sodium methoxide (0.219M in methanol) in a stream of nitrogen at 0° C. The mixture is stirred for 15 minutes at the same temperature and the reaction mixture is concentrated under reduced pressure. Then, a solution of the residue dissolved in 1.5 ml of water is freeze-dried to give 158 mg of compound 17, (Yield 97.7%). Colorless powder.

$^1$H-NMR(CDCl$_3$+CD$_3$OD): δppm 0.75-2.25(m, 15H), 2.16(t, J=7 Hz, 2H), 2.42(br.s, 1H), 5.23(m, 2H), 7.40-7.65(m, 3H), 7.80-8.02(m, 2H).

I-6

Example 46

(1) Exo-3-benzenesulfonamido-exo-2-bicyclo[2.2.1]heptan-2-carboxylic acid 2a

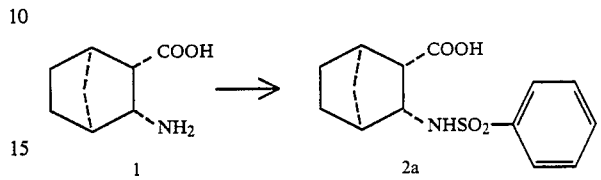

The amino acid 1 (12.42 g (80 mM) which is prepared according to the method described in the literature is dissolved in 100 ml of 10% potassium hydroxide aqueous solution, to which 5.1 ml of phenylsulfonyl chloride is added at 0° C., and the mixture is stirred at the same temperature for 20 minutes. An additional 5.1 ml of phenylsulfonyl chloride (total: 80 mM) is added, and the mixture is stirred at the same temperature for 1 hour. Ether is added, and the mixture is acidified with 2N-hydrochloride acid. The organic layer is washed with water, dried on sodium sulfate and evaporated under the reduced pressure, and the residue is applied to column chromatography [100 g of silica gel; developed with chloroform-methanol (2%-10%)] to give 9.10 g (38.6% yield) of the compound 2a as colourless prisms, mp. 148° C.

$^1$HNMR:(CDCl$_3$)δppm 0.80~2.05(m, 6H), 1.86 (br.s, 1H), 2.49 (br.s, 1H), 2.73(d, J=8 Hz, 1H), 3.66(t, J=8 Hz, 1H), 6.70(d, J=8 Hz, 1H), 7.70(br.s, 1H), 7.37~8.05 (m, 5H).

Anal. Calcd. (%) for C$_{14}$H$_{17}$NO$_4$S: C; 56.92, H; 5.81, N; 4.74, S; 10.85, Founed(%): C; 56.72, H; 5.80, N; 4.74, S; 10.71.

(2) Exo-2-hydroxymethyl-exo-3-benzenesulfonamidobicyclo[2.2.1]heptane 3a

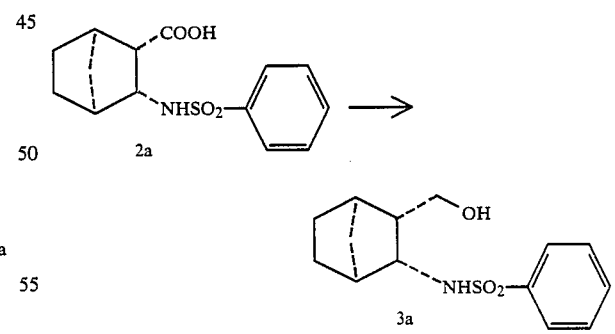

To a solution of 1.18 g (4 mM) of the compound 2a in 10 ml of tetrahydrofuran (hereinafter referred to as THF) is added 16 ml (16 mM) of diborane [1M THF solution; Aldrich] at 0° C., and the mixture is stirred at 20° C. for 4 hours. Ethyl acetate is added, and the mixture is washed with 0.2N-hydrochloric acid and then with water, dried on sodium sulfate, and evaporated under reduced pressure. The residue is applied to column chromatography [50 g of silica gel; developed with benzene-ethyl acetate (9:1-4:1)] to give 700 mg (62.3% yield) of the compound 3a as colourless gummy material.

$^1$HNMR:(CDCl$_3$)δppm 0.80~2.00(m 7H), 2.04 (br.s, 2H), 2.40 (br.s, 1H), 3.30(t, J=8 Hz, 1H), 3.66(m, 2H), 5.81(d, J=8 Hz, 1H), 7.45~8.10(m, 5H).

Anal. Calcd. (%) for C$_{14}$H$_{19}$NO$_3$S: C; 59.75, H; 6.82, N; 4.98, S; 11.39, Found (%): C; 59.93, H; 6.72, N; 4.55, S; 10.94.

(3) Exo-2-formyl-exo-3-benzenesulfonamidobicyclo[2.2.1]heptane 4a

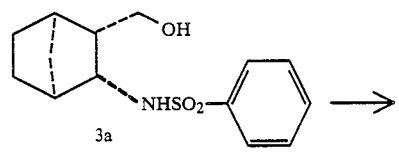

To a solution of 700 mg of the compound 3a in 30 ml of dichloromethane is added 3.2 g of chromic acid pyridine complex at 0° C., and the mixture is stirred for 1 hour. The upper clear solution is collected, and the insoluble material is washed with dichloromethane. The washing is combined with the upper solution and passed through 10 g of silica gel in order to remove inorganic portion, and the eluate is condensed to give 435 mg (62.7% yield) of the compound 4a as colourless gummy material.

$^1$HNMR:(CDCl$_3$)δppm 0.95~1.90(m, 6H), 2.01 (br.s, 1H), 2.50(br.s, 1H), 2.60(d.t, J=8, 1Hz, 1H), 3.61(t.d, J=8, 1 Hz, 1H), 5.62(d, =J8Hz, 1H), 7.35~8.00(m, 5H), 9.56(d, J=1Hz, 1H).

Anal. Calcd. (%) for C$_{14}$H$_{17}$NO$_3$S: C; 60.18, H; 6.15, N; 5.01, S; 11.48, Found (%): C; 60.18, H; 5.99, N; 5.04, S; 11.52.

(4) Exo-2-methoxyethenyl-exo-3-benzenesulfonamidobicyclo[2.2.1]heptane 5a

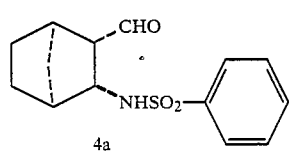

To a suspension of 2.40 g (2 mM×3.5) of methoxymethyltriphenylphosphonium chloride in 20 ml of THF is added 3.75 ml (2 mM×3.0) of n-butyllithium (1.6M n-hexane solution) at −78° C., and the mixture is stirred at 0° C. for 20 minutes. Then, a solution of 558 mg (2 mM) of the aldehyde 4a in 5 ml of THF is added, and the mixture is warmed up to 20° C. over a period of 30 minutes. The reaction mixture is distributed into ethyl acetate and water, and the organic layer is dried on sodium sulfate and evaporated under reduced pressure. The residue is applied to column chromatography [40 g neutral aluminium oxide, grade I; developed with n-hexane -ethyl acetate (10%) ] to give 300 mg (48.8% yield) of the enol ether 5a. This is used in the next reaction, immediately.

(5) 5(Z)-7-[Exo-3-benzenesulfonamidobicyclo[2.2.1]hept-exo-2-yl]-5-heptenoic acid methyl ester Ia-aa(2S*-c)

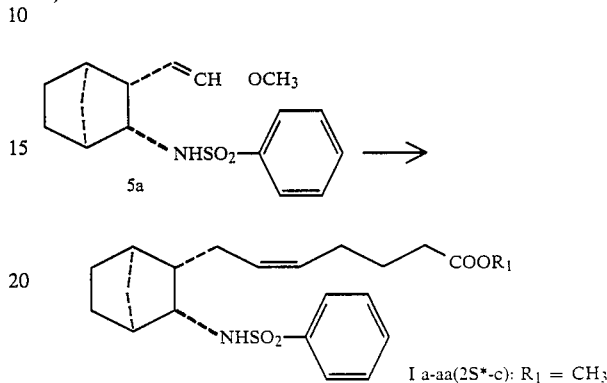

The enol ether 5a (300 mg) is dissolved in 0.5 ml 90% formic acid and allowed to stand at 20° C. for 20 minutes. Ethyl acetate is added, and then 5% sodium bicarbonate aqueous solution added, and the organic layer collected is dried on sodium sulfate and evaporated under reduced pressure to give 270 mg of the aldehyde as colourless foamy material.

Sodium hydride (60% in mineral oil) (460 mg; 0.92 mM×7×2×0.9) is dispersed in 15 ml dimethylsulfoxide (hereinafter referred to as DMSO) and stirred at 70° C. for 1.5 hours. After cooling to 12° C., 2.84 g (0.92 mM×7) of 4-carboxybutyltriphenylphosphonium bromide is added thereto to give an orange solution, to which is added a solution of 270 g of the above-prepared aldehyde in 5 ml of DMSO at 12° C., and the mixture is stirred at 20° C. for 1.5 hours. The reaction mixture is distributed into ethyl acetate and saturated ammonium chloride solution, and the organic layer is washed with water, dried on sodium sulfate and evaporated under reduced pressure. The residue is applied to column chromatography [15 g of silica gel; developed with benzene-ethyl acetate (9:1-2:1)] to give 200 mg of the carboxylic acid. This is dissolved in 5 ml of ethyl acetate, treated with diazomethane in a conventional way for esterification, and purified by column chromatography [silica gel: Merck Lober A; developed with n-hexane-ethyl acetate (4:1)] to give 241 mg (30.8% yield form 4a) of the compound Ia-aa(2S*-c) as colorless gummy material.

$^1$HNMR: (CDCl$_3$) δppm 0.80~2.20 (m, 15H), 2.30 (t, J=7 Hz, 2H), 3.30 (t, J=8 Hz, 1H), 3.67 (s, 3H), 4.80 (d, J=8 Hz, 1H), 5.33 (m, 2H), 7.35~8.03 (m, 5H).

Anal. Calcd. (%) for C$_{21}$H$_{29}$NO$_4$S: C; 64.41, H; 7.48, N; 3.58, S; 8.19, Found (%): C; 64.20, H; 7.32, N; 3.18, S; 8.26.

(6) 5(Z)-7-[Exo-3-benzenesulfonamidobicyclo[2.2.1]hept-exo-2-yl-5-heptenoic acid Ia-ba(2S*-c) and its sodium salt Ia-ca(2S*-c)

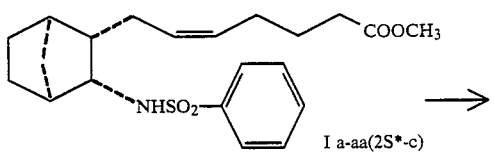

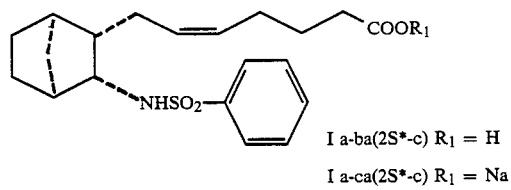

① Carboxylic acid Ia-ba(2S*-c)

To a solution of 210 mg (0.536 mM) of the compound Ia-aa(2S*-c) in 3 ml of methanol is added 1.07 ml (0.536 mM×2) of 1N-potassium hydroxide, and the mixture is stirred at 20° C. for 2 hours and then allowed to stand overnight at the same temperature. Ethyl acetate is added, and the mixture is washed with 0.1N-hydrochloric acid and water, dried on sodium sulfate, and evaporated under reduced pressure to give 203 mg (100% yield) of the compound Ia-ba(2S*-c) as colorless gummy material.

$^1$HNMR: (CDCl$_3$) δppm 0.85~2.23 (m, 15H), 2.36 (t, J=8 Hz, 2H), 3.32 (t, J=8 Hz, 1H), 5.25 (d, J=8 Hz, 1H), 5.36 (m, 2H), 7.40~8.03 (m, 5H), 8.48 (br.s, 1H).

Anal. Calcd. (%) for $C_{20}H_{27}NO_4S.0.1C_6H_6$: C; 64.20, H; 7.23, N; 3.64, S; 8.32, Found (%): C; 64.32, H; 6.92, N; 3.52, S; 8.06.

② The sodium salt Ia-ca(2S*-c)

The compound Ia-ba(2S*-c) is treated with sodium methoxide in a conventional way to give the sodium salt Ia-ca(2S*-c) as colourless powder in 94.7% yield.

I-7

EXAMPLE 47

(1) Monomethyl 2-exo-3-exo-7-oxabicyclo[2.2.1]heptan-2,3-dicarboxylate 2a

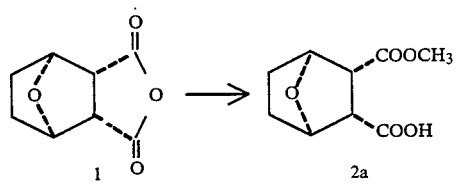

A mixture of 24.3 g of exo-hexahydro-4,7-epoxyisobenzofuran-1,3-dione 1 and 200 ml of dry methanol is heated under refluxing for 18 hours. The reaction mixture is evaporated under reduced pressure to give crystalline residue, which is recrystallized from ethyl acetate to give 27.5 g of the titled compound 2a in 95.1% yield. Mp. 144°~146° C.

IR (Nujol): νmax 1737, 1697 cm$^{-1}$.

NMR (DMSO-d$_6$): δppm 1.52 (4H, s), 2.98 (2H, s), 3.50 (3H, s), 4.66 (2H, s).

Anal. Calcd. (%) for $C_9H_{12}O_5$: C, 54.00; H, 6.04, Found (%): C, 54.04; H, 5.93.

(2) Methyl cis-exo-3-benzyloxycarbonylamino-7-oxabicyclo[2.2.1]heptan-exo-2-carboxylate 3a

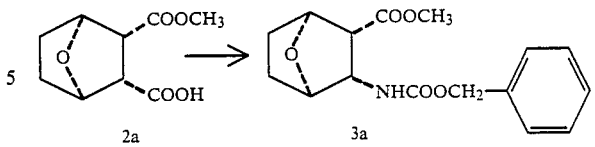

Acetone is added to a mixture of 46.8 g of the carboxylic acid prepared in Example 47 (1) and 42 ml of water until it become a homogeneous solution. Under ice-cooling, a solution of 27.8 g of triethylamine in 490 ml of acetone is added thereto and then a solution of 34.1 g of ethyl chloroformate in 120 ml of acetone is added over a 30 minutes period. The resulting mixture is stirred at 3° C. for 30 minutes, to which is added 80 ml of aqueous solution of 23.2 g of sodium azide under ice-cooling over a 30 minute period. The reaction mixture is stirred at 3° C. for an hour, and poured into ice-cooled water, and the mixture is extracted with ether. The organic layer is washed with a saturated aqueous solution of sodium chloride, dried over magnesium sulfate and evaporated to give an oily residue.

IR (Film): νmax 2130 cm$^{-1}$.

A solution of the above prepared acid azide dissolved in 200 ml of benzene is heated under refluxing for 2 hours. A small amount of the reaction mixture is collected and evaporated under reduced pressure to give an oily substance.

IR (Film): νmax 2230 cm$^{-1}$.

To the remaining reaction mixture is added 12 ml of triethylamine and 25 ml of benzyl alcohol and the mixture is heated under refluxing for 4 hours. The volatile substance is removed by distillation from the reaction mixture under reduced pressure. The residue is crystallized from ether to give 47.2 g of 3a as colorless crystals in 66.1% yield (from the carboxylic acid).

mp. 108° C.

IR (Nujol): νmax 3350, 1728, 1716 cm$^{-1}$.

$^1$H-NMR (CDCl$_3$): δppm 1.3~2.0 (4H, m), 2.95 (1H, d, J=10 Hz), 3.55 (3H, s), 4.2~4.5 (2H, m), 4.79 (1H, d, J=3 Hz), 5.09 (2H, s), 5.50 (1H, d, J=10 Hz), 7.36 (5H, s).

Anal. Calcd. (%) for $C_{16}H_{19}NO_5$: C, 62.94; H, 6.27; N, 4.59, Found (%): C, 62.74; H, 6.09; N, 4.37.

(3) [exo-3-Benzyloxycarbonylamino-7-oxabicyclo[2.2.1]hept-2-yl]formaldehyde 4a and [exo-3-benzyloxycarbonylamino-7-oxabicyclo[2.2.1]hept-exo-2-yl]methanol 5a

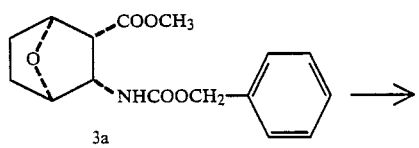
(1)

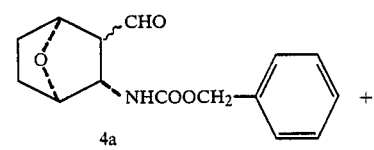

103

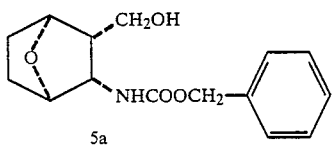
5a

A solution of 5.5 ml of N-methylpiperidine in 14 ml of benzene is added to a 35% solution of sodium bis(2-methoxyethoxy)aluminium hydride in 26 ml of benzene in a stream of nitrogen under ice-cooling. After stirred at 0° C. for 10 minutes, the mixture is added to a suspension of 12.3 g of the ester 3a prepared in Example 47 (2) in benzene under ice-cooling and the resulting mixture is stirred at room temperature for 2.5 hours. Water and then dilute hydrochloric acid are dropwise added to the mixture under ice-cooling. The two layers are separated and the aqueous layer is extracted with ethyl acetate. The organic layers are combined, washed with a saturated aqueous solution of sodium chloride, dried over sodium sulfate, and evaporated under reduced pressure. The residue is chromatographed on 150 g of a silica gel column and eluted with hexane-ethyl acetate (1:1) to give 0.622 g of the starting material 3a in 5.1% yield as an eluate; and further elutate with ethyl acetate gives 4.4 g (43.8% yield) of an about 1:1 mixture of the epimers of the aldehyde derivative containing with about 10% of the starting material in addition to the alcohol derivative 5a. This alcohol derivative is purified by crystallization from ether to give 0.222 g (2.0% yield).

The physical constants of the aldehyde derivative 4a:
$^1$H-NMR (CDCl$_3$): δppm 1.2~2.0 (4H, m), 2.7~3.0 (1H, m), 4.0~4.5 (2H, m), 4.7~4.9 (1H, m), 5.06 (2H, s), 5.5~5.9 (1H, m); 7.30 (5H, s), 9.50 (0.5H, d, J=2 Hz), 9.73 (0.5H, s).

The physical constants of the alcohol derivative 5a:
mp 174°~175° C.
IR (Nujol): νmax 3330, 1685 cm$^{-1}$.
$^1$H-NMR (CDCl$_3$): δppm 1.48 (4H, s), 1.95 (1H, m), 3.19 (1H, d, J=4 Hz), 3.79 (1H, t, J=10 Hz), 4.20 (1H, s), 4.39 (1H, s), 4.50 (1H, t, J=2 Hz), 5.01 (2H, s), 7.11 (1H, d, J=10 Hz), 7.35 (5H, s).

Anal. Calcd. (%) for C$_{15}$H$_{19}$NO$_4$: C, 64.97; H, 6.91; N, 5.05, Found (%): C, 64.73; H, 6.70; N, 5.06.

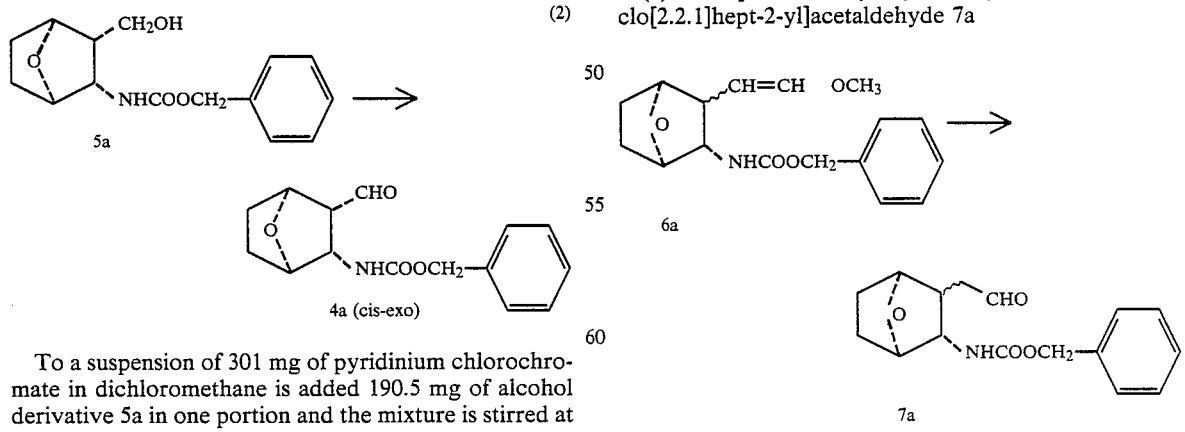

To a suspension of 301 mg of pyridinium chlorochromate in dichloromethane is added 190.5 mg of alcohol derivative 5a in one portion and the mixture is stirred at room temperature for 2 hours. Then, ether is added and the mixture is chromatographed on Florisil [Floridin Co.] and eluted with ether. The eluate is crystallized from benzene to give 138 mg of the cis-exo isomer 4a in 75% yield.

104

Mp. 117°-119° C.
IR(Nujol): νmax 3300, 1706 cm$^{-1}$.
$^1$H-NMR(CDCl$_3$): δppm 1.2~2.0 (4H, m), 2.90 (1H, d, J=9 Hz), 4.3~4.6 (2H, m), 4.93 (1H, m), 5.07 (2H, s), 5.30 (1H, m), 7.36 (5H, s), 9.56 (1H, d, J=2 Hz).

Anal. Calcd. (%) for C$_{15}$H$_{17}$NO$_4$: C, 65.44; H, 6.22; N, 5.09, Found (%): C, 65.55; H, 6.17; N, 4.96.

(4) 2-(2-Methoxyethenyl)-exo-3-benzyloxycarbonylamino-7-oxabicyclo[2.2.1]heptane 6a

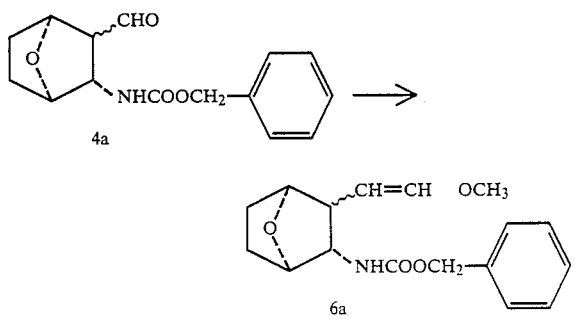

In 100 ml of toluene is suspended 36.6 g of methoxymethyltriphenylphosphonium chloride and the suspension is dried by evaporation of a small amount of toluene. Separately, litiuium diisopropylamide which is prepared from 70 ml of 1.6M solution of n-butyl lithium in hexane, 11.0 g of diisopropylamine and 40 ml of dry tetrahydrofuran at 0° C. in a stream of nitrogen is dropwise added to the above-prepared suspension at 0° C. over a 30 minutes period. The mixture is stirred for 2 hours, to which a solution of 10 g of the aldehyde 4a (prepared in Example 47 (3)) in 20 ml of dry tetrahydrofuran and 20 ml of dry toluene is dropwise added at 0° C. After stirred at 0° C. for 2.5 hours, the reaction mixture is poured into ice-water. The separated aqueous layer is extracted with ethyl acetate. The combined organic layers are washed with saturated sodium chloride aqueous solution, dried over sodium sulfate and evaporated under reduced pressure. The residue is chromatographed on 160 g of a silica gel column and eluted with hexane-ethyl acetate (1:1) to give 6.5 g of the titled compound 6a and 0.9 g of the ester 3a contaminated in Example 47 (3).

(5) 2-[exo-3-Benzyloxycarbonylamino-7-oxabicyclo[2.2.1]hept-2-yl]acetaldehyde 7a A solution of 3.07 g of the ether 6a prepared in Example 47 (4) in 10 ml of 90% formic acid is left standing at room temperature for 2 hours. The solution is poured carefully into a sodium carbonate solution and extracted with dichloromethane. The extract is washed with saturated sodium chloride aqueous solution, drid over sodium sulfate and evaporated under reduced pressure to give 2.8 g of 7a as an oily substance.

IR (Film): νmax 1720 cm$^{-1}$.

(6) Methyl 5(Z)-7-[exo-3-tert-butoxycarbonylamino-7-oxabicyclo[2.2.1]hept-2-yl]-5-heptenoate IIb-b

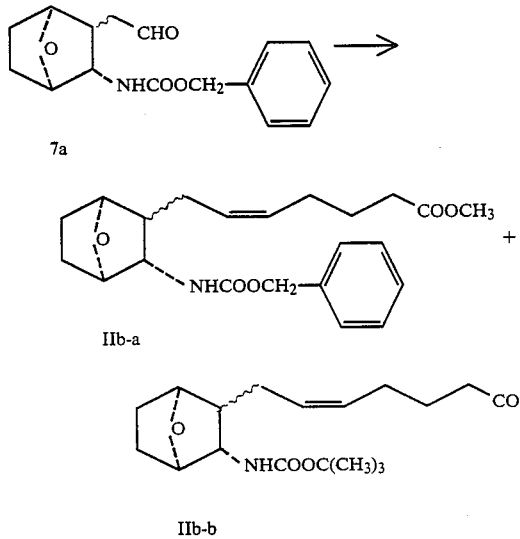

To a suspension of 27.5 g of 4-carboxylbutyltriphenylphosphonium bromide in 50 ml of dry tetrahydrofuran is added 13.9 g of potassium tert-butoxide in one portion at room temperature in a stream of nitrogen. The mixture is stirred at room temperature for 30 minutes, and then a solution of 6.0 g of the aldehyde 7a (prepared in Example 47 (5)) in 20 ml of dry tetrahydrofuran is dropwise added thereto at room temperature. After being stirred at room temperature for 1 hour, the mixture is poured into an oxalic acid aqueous solution. The organic layer is removed and the aqueous layers are extracted with ethyl acetate. The combined organic layers are washed with saturated sodium chloride aqueous solution, dried over sodium sulfate and evaporated under reduced pressure. The residue is chromatographed on 200 g of a silica gel column and eluted with hexane-ethyl acetate (1:1).

A solution of 3.2 g of the resulting crude carboxylic acid in 10 ml of ether is treated with an excess of diazomethane-ether solution. The residue is chromatographed on 90 g of a silica gel column and eluted with hexane-ethyl acetate (2:1) to give 0.95 g of the tert-butoxycarbonyl derivative (hereinafter abbreviated to as BOC derivative ) IIb-b (Yield 13%: from the aldehyde) and 1.25 g of the benzyloxycarbonyl derivative IIb-a (Yield 15.6%: from the aldehyde).

Physical constants of the BOC derivative IIb-b $^1$H-NMR (CDCl$_3$): δppm 1.45 (9H, s), 1.5~1.9 (6H, m), 1.9~2.4(7H, m), 3.25 (1H, dd, J=10, 3 Hz), 3.69 (3H, s), 4.29 (1H, d, J=5 Hz), 4.43 (1H, t, J=5 Hz), 4.75 (1H, m), 5.3~5.5 (2H, m).

Physical constants of the benzyloxycarbonyl derivative IIb-a $^1$H-NMR (CDCl$_3$): δppm 1.3~1.9 (7H, m), 1.9~2.5 (6H, m), 3.30 (1H, dd, J=9, 4 Hz), 3.62 (3H, s), 4.26 (1H, d, J=4 Hz), 4.41 (1H, t, J=4 Hz), 5.06 (2H, s), 4.9~5.2 (1H, m), 5.31 (2H, m), 7.31 (5H, s).

(7) Methyl 5(Z)-7-[exo3-benzenesulfonamido-7-oxabicyclo[2.2.1]hept-endo-2-yl]-5-heptenoate I b-aa(2S*-t)

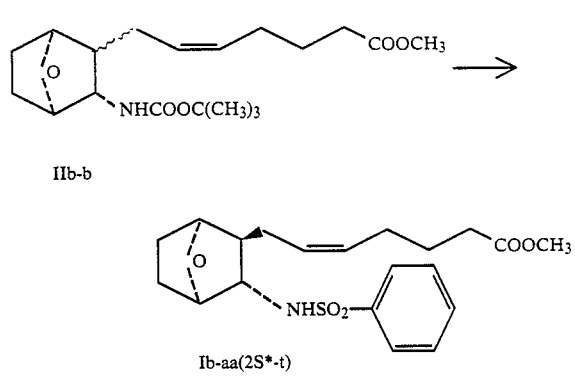

A mixture of 0.675 g of the BOC derivative (II b-b prepared in Example 47 (6)) in 3 ml of trifluoroacetic acid is left standing at room temperature for 1 hour. Then the mixture is concentrated under reduced pressure and hexane is added to the residue. This operation is repeated to remove excess amount of trifluoroacetic acid. To a solution of the above-mentioned salt in 10 ml of dichloromethane is added 0.7 g of triethylamine and then 0.35 g of benzenesulfonyl chloride, the mixture is allowed to stand at room temperature for 1 hour, then diluted hydrochloric acid is added thereto, and then the organic layer is removed. The aqueous layer is extracted with dichloromethane and the collected organic layer is washed with sodium hydrogencarbonate solution and then saturated sodium chloride aqueous solution, dried over sodium sulfate, and evaporated. The residue is chromatographed on 25 g of silica gel and eluted with hexane-ethyl acetate (2:1) to give 0.417 g of the trans-derivative I b-aa(2S*-t) in 55.5% yield.

IR (Film): νmax 3270, 1735, 1162 cm$^{-1}$.

$^1$H-NMR(CDCl$_3$): δppm 1.1~2.4 (13H, m), 2.92 (1H, dd, J=9, 3 Hz), 3.69 (3H, s), 4.12 (1H, d, J=6 Hz), 4.40 (1H, t, J=6 Hz), 5.0~5.4 (3H, m), 7.60 (3H, m), 7.90 (2H, m).

(8) 5(Z)-7-[exo-3-Benzenesulfonamido-7-oxabicyclo[2.2.1]heptendo-2-yl]-5-heptenoic acid I b-ba(2S*-t) and its salt I b-ca (2S*-t)

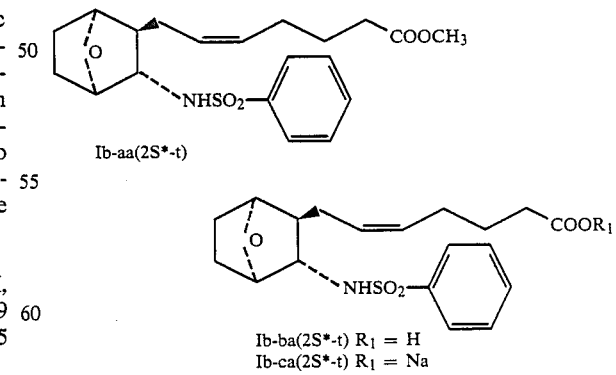

To a solution of 0.366 g of the ester I b-aa(2S*-t) (prepared in Example 47 (7)) in 7.2 ml of methanol is added 7.2 ml of 10% sodium hydroxide solution and the mixture is allowed to stand at room temperature overnight, then acidified with diluted hydrochloric acid, and then extracted with ethyl acetate. The organic layer is washed with saturated sodium chloride aqueous solution, dried over sodium sulfate, and evaporated under reduced pressure to give 348 mg of I b-ba(2S*-t) as an oily substance in 98.6% yield.

IR (Film): $\nu$max 3220, 1708, 1162 cm$^{-1}$.

$^1$H-NMR(CDCl$_3$): $\delta$ppm 1.1~2.5 (13H, m), 2.93 (1H, dd, J=10, 2 Hz), 4.13 (1H, d, J=3 Hz), 4.43 (1H, t, J=2 Hz), 5.20 (2H, m), 5.45 (1H, d, J=10 Hz), 7.56 (3H, m), 7.90 (2H, m), 9.00 (1H, s).

To a solution of 311 mg of the resulting carboxylic acid I b-ba(2S*-t) in methanol is added 2.80 ml of 0.263M solution of sodium methoxide in methanol and the mixture is evaporated under reduced pressure. The residue is dissolved in water and active carbon is added thereto, and the mixture is filtered. The resulting aqueous solution is freeze-dried to give the sodium salt I b-ca(2S*-t) of which the physical constant is as follows.

IR(KBr): $\nu$max 3420, 3260, 1565, 1324, 1159 cm$^{-1}$.

EXAMPLE 48

(1) Methyl 5(Z)-7-[exo-benzenesulfonamido-7-oxabicyclo[2.2.1]hept-exo-2-yl]-5-heptenoate I b-aa(2R*-c)

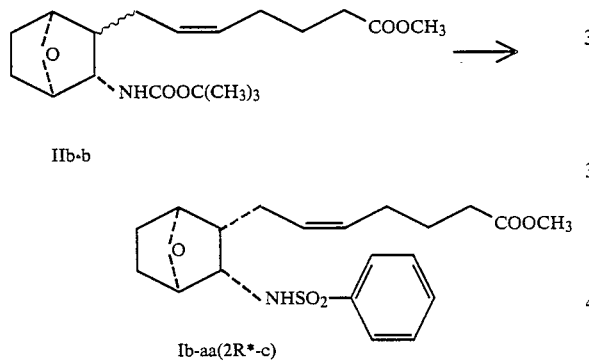

IIb-b

Ib-aa(2R*-c)

The BOC derivative II b-b prepared in Example 47 (6) is treated in the same manner as in Example 47 (7) and an early eluate is crystallized from benzene-hexane to give 15 mg of the cis-derivative I b-aa(2R*-c) in 2% yield. Mp. 93°~94° C.

The physical constants of cis-derivative I b-aa(2R*-c):

IR(KBr): $\nu$max 3420, 3195, 1734, 1165 cm$^{-1}$.

$^1$H-NMR(CDCl$_3$): $\delta$ppm 1.2~2.4 (13H, m), 3.60 (1H, m), 3.70 (3H, s), 3.93 (1H, t, J=2 Hz), 4.16 (1H, t, J=2 Hz), 4.89 (1H, d, J=10 Hz), 5.48 (2H, m), 7.58 (3H, m), 7.89 (2H, m).

(2) 5(Z)-7-[exo-3-Benzenesulfonamido-7-oxabicyclo[2.2.1]hept-exo-2yl]-5-heptenoic acid I b-ba(2R*-c) and its salt I b-ca(2R*-c)

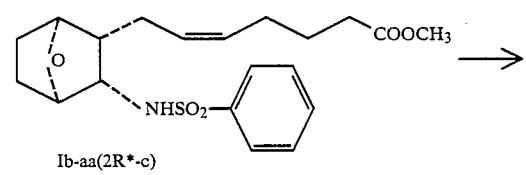

Ib-aa(2R*-c)

-continued

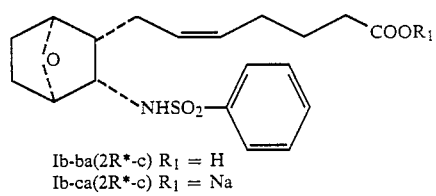

Ib-ba(2R*-c) R$_1$ = H
Ib-ca(2R*-c) R$_1$ = Na

The ester prepared in Example 48 (1) is treated in the same manner as in Example 47 (8) to give the title compound I b-ba(2R*-c).

$^1$H-NMR(CDCl$_3$): $\delta$ppm 1.2~2.5 (13H, m), 3.60 (1H, m), 3.99 (1H, d, J=2 Hz), 4.19 (1H, d, J=2 Hz), 5.36 (2H, m), 5.48 (1H, m), 7.58 (3H, m), 7.90 (2H, m):

The resulting carboxylic acid I b-ba(2R*-c) is treated in the same manner as in Example 47 (8) to give the sodium salt I b-ca(2R*-c) of which the physical constant is as follows.

IR(KBr): $\nu$max 3415, 3270, 1563, 1317, 1157 cm$^{-1}$.

I -8

EXAMPLE 49

(1) Exo-2-cyanomethyl-7-oxabicyclo[2.2.1]heptan-exo-3-carboxylic acid 9

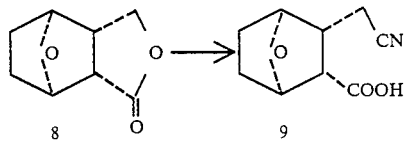

8　　9

A mixture of 4.3 g exo-hexahydro-4,7-epoxyisobenzofuran-1(3H)-one 8, 2.0 g of potassium cyanate and 30 ml of dimethylsulfoxide is heated under stirring at 180° C. for 2 hours. Water is added to the reaction mixture, to which then diluted hydrochloric acid is added carefully to acidify. The mixture is extracted with ethyl acetate and the extract is washed with water, dried over sodium sulfate, and evaporated under reduced pressure. The residue is crystallized from ether to give 2.1 g of the titled compound 9 in 41.6% yield of which physical constants are as follows.

Mp. 124°–126° C.

IR(Nujol): $\nu$max 2325, 1710, 1693 cm$^{-1}$.

$^1$H-NMR(CDCl$_3$): $\delta$ppm 1.6~2.2 (4H, m), 2.47 (2H, s), 2.5~3.0 (2H, m), 4.55 (1H, d, J=4 Hz), 4.86 (1H, d, J=3 Hz), 8.09 (1H, s).

Anal. Calcd. (%) for C$_9$H$_{11}$NO$_3$: C, 59.66; H, 6.12; N, 7.73; Found (%): C, 59.50; H, 6.13; N, 7.76.

(2) 1 Methyl exo-2-cyanomethyl-7-oxabicyclo[2.2.1]heptane-exo-3-carboxylate 10a

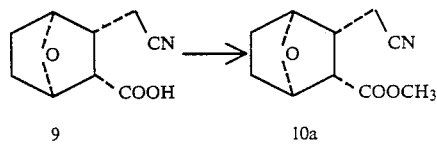

9　　10a

To an ethereal solution of excess amount of diazomethane is added 383 mg of the above carboxylic acid 9 in small portions and the mixture is concentrated under reduced pressure. The residue is purified by chromatography on 10 g of silica gel column and eluted with hexane-ethyl acetate (1:1) to give 330 mg of the titled compound 10a, which is recrystallized from benzene-hexane. The physical constants are as follows. Mp. 88°–89° C.

IR(Nujol): $\nu$max 2319, 1724 cm$^{-1}$. NMR(CDCl$_3$): $\delta$ppm 1.3~2.1 (4H, m), 2.42 (2H, s), 2.4~2.8 (1H, m), 2.83 (1H, d, J=8 Hz), 3.71 (3H, s), 4.50 (1H, d, J=5 Hz), 4.85 (1H, d, J=3 Hz).

Anal. Calcd. (%) for C$_{10}$H$_{13}$NO$_3$: C, 6.84; H, 6.23; N, 7.21; Found (%): C, 6.35; H, 6.67; N, 7.23.

2  Exo-2-cyanomethyl-7-oxabicyclo[2.2.1]heptane-endo-3-carboxylic acid 11

A solution of 5.5 g of the above ester 10a in 50 ml of 10% solution of potassium hydroxide in methanol is stirred at room temperature for 1 hour. The mixture is acidified with diluted hydrochloric acid and then extracted with ethyl acetate. The extract is washed with water, dried over sodium sulfate and evaporated under reduced pressure. The crystalline residue is recrystallized from benzene and then from ether to give 3.95 g the title compound 11 in 77.0% yield, of which the physical constants are as follows. Mp. 103° C.

IR(Nujol): $\nu$max 2240, 1702 cm$^{-1}$.

NMR(CDCl$_3$): $\delta$ppm 1.4~2.1 (4H, m), 2.2~2.8 (4H, m), 4.41 (1H, d, J=3 Hz), 4.85 (1H, d, J=5 Hz), 10.29 (1H, s).

Anal. Calcd. (%) for C$_9$H$_{11}$NO$_3$: C, 59.66; H, 6.12; N, 7.73, Found (%): C, 59.62; H, 6.11; N, 7.77.

(3)  Exo-2-cyanomethyl-endo-3-(tert-butoxycarbonylamino)-7-oxabicyclo[2.2.1]heptane 12a In the same manner as in Example 47 (2), 4,6 g of the above carboxylic acid 11 is treated with tert-butanol in the place of benzyl alcohol to give 3.45 g of the titled compound 12a in 53.9% yield. The physical constants are as follows.

IR(Film): $\nu$max 3345, 2250, 1703 cm$^{-1}$.

$^1$H-NMR(CDCl$_3$): $\delta$ppm 1.43 (9H, s), 1.5~2.0 (5H, m), 2.4~2.8 (2H, m), 3.50 (1H, m), 4.37 (1H, d, J=5 Hz), 4.63 (1H, t, J=4 Hz), 4.80 (1H, s).

(4)  Exo-2-formylmethyl-endo-3-(tert-butoxycarbonylamino)-7-oxabicyclo[2.2.1]heptane 13a To a solution of 2.94 g of the above cyano derivative 12a in dry toluene is dropwise added 13 ml of 1M aluminum diisobutyl hydrid/hexane solution at 20° C. in a stream of nitrogen. After the mixture is stirred at −20° C. for 6 hours, the reaction is stopped by the addition of saturated aqueous solution of ammonium chloride. The solid is dissolved with diluted hydrochloric acid and the two layers are separated. The aqueous layer is extracted with ethyl acetate and then the combined organic layers are washed with water, dried over sodium sulfate, and evaporated under reduced pressure. It is realized from the thin layer chromatogram and NMR spectrum that the 2.05 g of the residue is contaminated with the starting material. A small amount of oily residue is purified by chromatography and eluted with hexane-ethyl acetate (2:1) to give the titled compound 12a, of which the physical constants are as follows.

IR(Film): $\nu$max 3330, 1705, 1515 cm$^{-1}$.

$^1$H-NMR(CDCl$_3$): $\delta$ppm 1.40 (9H, s), 1.5~2.0 (5H, m), 2.71 (2H, d, J=7 Hz), 3.46 (1H, m), 4.10 (1H, d, J=4 Hz), 4.63 (1H, t, J=4 Hz), 4.96 (1H, s), 9.76 (1H, s).

The remaining residue is used in the next reaction without purification.

(5)  Methyl 5(Z)-7-[endo-3-(tert-butoxycarbonylamino)-7-oxabicyclo[2.2.1]hept-exo-2-yl]-5-heptenoate II b-ab(2R*-t)

In the same manner as in Example 47 (6), 813 mg of the above crude aldehyde 13a is treated to give 300 mg of the carboxylic acid II b-bb(2R*-t), of which the physical constant is as follows.

$^1$H-NMR(CDCl$_3$): $\delta$ppm 1.45 (9H, s), 1.2~1.9 (7H, m), 1.9~2.5 (6H, m), 3.49 (1H, m), 4.14 (1H, d, J=5 Hz), 4.61 (1H, t, J=3 Hz), 5.39 (2H, m), 8.35 (1H, s).

In the same manner as in Example 47 (6), 1.05 g of the carboxylic acid II b-bb(2R*-t) is esterified to give 0.95 g of the titled compound II b-ab(2R*-t), of which the physical constants are as follows.

IR: $\nu$max (Film) 3340, 1740, 1713, 1170 cm$^{-1}$.

$^1$H-NMR(CDCl$_3$): $\delta$ppm 1.42 (9H, s), 1.1~1.9 (6H, m), 1.9~2.4 (7H, m), 3.47 (1H, m), 4.11 (1H, d, J=5 Hz), 4.61 (1H, t, J=3 Hz), 4.82 (1H, d, J=6 Hz), 5.37 (2H, m).

(6) Methyl 5(Z)-7-[endo-3-benzenesulfonamido-7-oxabicyclo[2.2.1]hept-exo-2-yl]-5-heptenoate I b-aa(2R*-t)

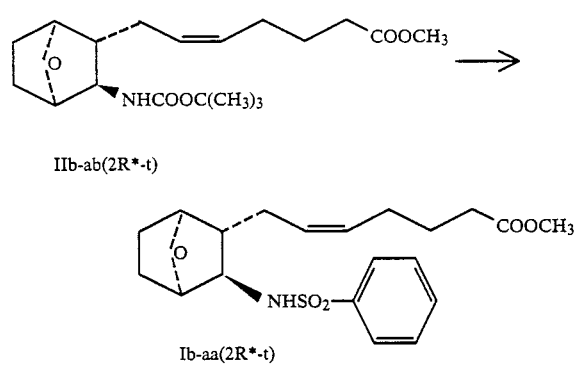

IIb-ab(2R*-t)

Ib-aa(2R*-t)

In the same manner as in Example 48 (1), 0.90 g of the above BOC derivative II b-ab(2R*-t) is treated to give the trifluoroacetate salt, quantitatively. In the same manner as in Example 48 (1), 601 mg of the salt is allowed to react to give 361 mg of the titled compound I b-aa(2R*-t), of which the physical constants are as follows. (Yield 67.9%: from the BOC derivative).
IR(Film): $\nu$max 3270, 1735, 1160 cm$^{-1}$.
$^1$H-NMR(CDCl$_3$): $\delta$ppm 1.0~2.4 (13H, m), 3.02 (1H, m), 3.69 (3H, s), 4.09 (1H, d, J=4 Hz), 4.46 (1H, t, J=3 Hz), 5.17 (2H, m), 5.64 (1H, d, J=5 Hz), 7.60 (3H, m), 7.93 (2H, m).

(7) 5(Z)-7-[Endo-3-benzenesulfonamido-7-oxabicyclo[2.2.1]hept-exo-2-yl]-5-heptenoic acid I b-ba(2R*-t) and its sodium salt I b-ca(2R*-t)

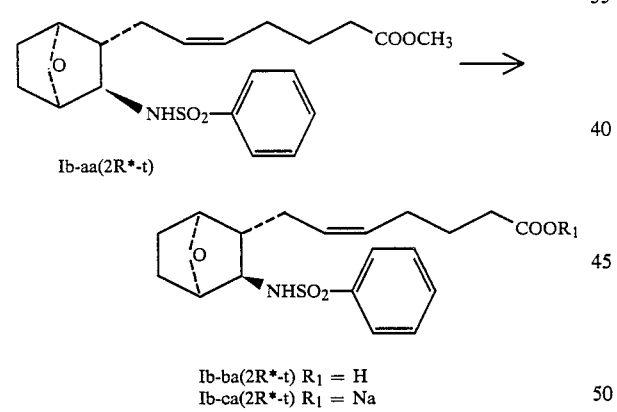

Ib-aa(2R*-t)

Ib-ba(2R*-t) R$_1$ = H
Ib-ca(2R*-t) R$_1$ = Na

① Carboxylic acid I b-ba(2R*-t)
In the same manner as in Example 47 (8), 335 mg of the above ester I b-aa(2R*-t) is treated to give 310 mg of the titled compound I b-ba(2R*-t), of which the physical constants are as follows.
IR(Film): $\nu$max 3260, 1706, 1157 cm$^{-1}$.
$^1$H-NMR(CDCl$_3$): $\delta$ppm 1.2~2.4 (13H, m), 3.01 (1H, m), 4.07 (1H, d, J=4 Hz), 4.41 (1H, t, J=5 Hz), 5.16 (2H, m), 5.64 (1H, d, J=6 Hz), 7.55 (3H, m), 7.88 (2H, m).

② Sodium salt I b-ca(2R*-t)
To a solution of 255 mg of the above carboxylic acid I b-ba(2R*-t) in 2 ml of methanol is added 3.0 ml of 0.21M solution of sodium methoxide in methanol and the mixture is evaporated under reduced pdressure. The residue is dissolved in water, to which active carbon is added, and the mixture is filtered. The filtrate is freeze-dried to give 240 mg of the titled compound I b-ca(2R*-t), of which the physical constant is as follows.
IR (KBr): $\nu$max 3410, 3260, 1560, 1320, 1155 cm$^{-1}$.

I-9
EXAMPLE 50

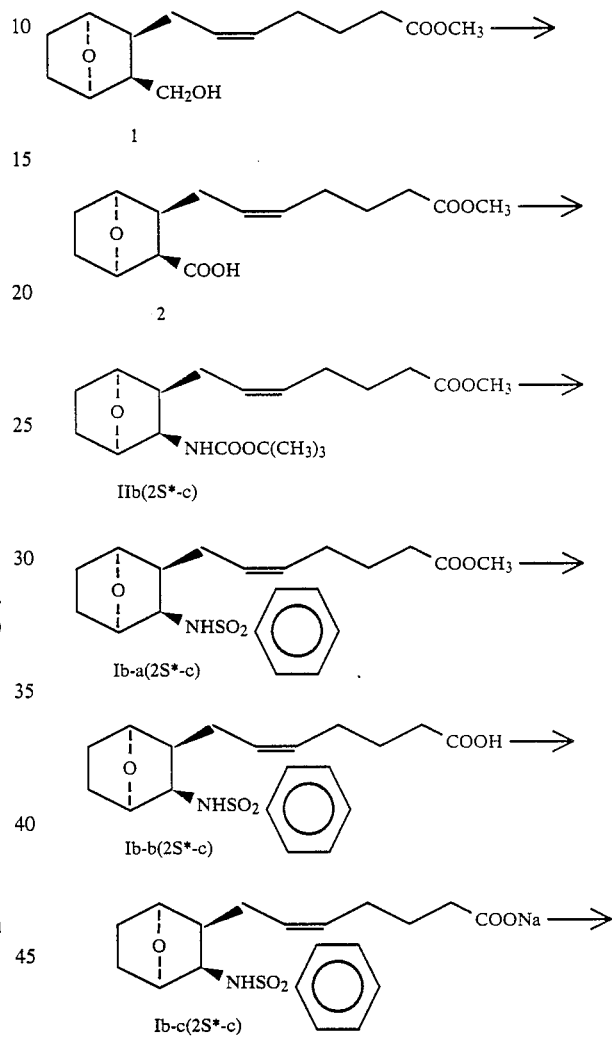

5(Z)-Methyl 7-[endo-3-carboxy-7-oxabicyclo[2.2.1]hept-endo-2-yl]-5-heptenoate 2

Jones' reagent was added dropwise to a solution of 1.47 g of 5(Z)-methyl 7-[endo-3-(hydroxymethyl)-7-oxabicyclo[2.2.1]hept-endo-2-yl]-5-heptenoate 1 [P. W. Sprauge, etal., J. Med. Chem., 28, 1580, (1985)] in acetone (15 ml) with cooling in ice until the brown color persisted. Ice-water was acced. The mixture was extracted with ethyl acetate. The extracts were washed with water, dried over anhydrous sodium sulfate and concentrated under reduced pressure. The residue was chromatographed on silica gel (50 g) in hexane-ethyl acetate (1:3). 0.877 g (56.7%). NMR: $\delta$ppm (CDCl$_3$); 1.4–2.6 (13H), 3.09 (1H, dd, J+5, 11 Hz), 3.68 (3H, s), 4.52 (1H, t, J=3 Hz), 5.35 (2H, m), 8.1 (1H, br. s).

5(Z)-7-[endo-3-(tert-butoxycarbonylamino)-7-oxabicyclo[2.2.1]hept-endo-2-yl]-5-heptenoic acid methyl ester II b(2S*-c)

Yield 49.6%. IR: νmax (Film) 3370, 1739, 1716, 1698 cm⁻¹. NMR: δppm (CDCl₃); 1.44 (9H, s), 1.5–2.5 (13H), 3.67 (3H, s), 4.05 (1H, m), 4.47 (1H, m), 4.55 (1H, m), 4.57 (1H, m, NH), 5.34 (2H, m).

5(Z)-7-[endo-3-benzenesulfonamido-7-oxabicyclo[2.2.1-]hept-endo-2-yl]-5-heptenoic acid methyl ester I b-aa(2S*-c)

Yield 56.4%. IR νmax(Film) 3300, 1737, 1343, 1163 cm⁻¹. NMR: δppm(CDCl₃) 1.4–2.4 (13H), 3.60 (1H, m), 3.69 (3H, s), 4.33 (2H, m), 5.25 (2H, m), 5.35 (1H, m), 7.55 (3H, m), 7.88 (2H, m).

5(Z)-7-[endo-3-benzenesulfonamido-7-oxabicyclo[2.2.1-]hept-endo-2-yl]-5-heptenoic acid I b-ba(2S*-c) and its salt I b-ca(2S*-c)

Free carboxylic acid: Yield 94.0% IR νmax (film) 3290, 1709, 1340, 1162 cm⁻¹. NMR: δppm(CDCl₃) 1.4–2.5 (13H, m), 3.66 (1H, m), 4.27 (1H, m), 4.38 (1H, m), 5.27 (2H, m), 5.65 (1H, d, J=9 Hz), 7.58 (3H, m), 7.90 (2H, m), 8.14 (1H, br, s), Na-salt IR νmax (KBr) 3430, 1558, 1339, 1158 cm⁻¹.

II

EXAMPLE 1

(1) Preparation of 2-allyl-3-hydroxyiminobicyclo[2.2.2]octane 10

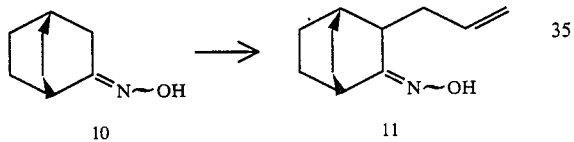

To a solution of 3.48 g (25 mM) of the starting bicyclo[2.2.2]octan-2-one oxime 10 [H. K. Hall, Jr. etal., J. Am. Chem. Soc., 82, 1209, (1960)] in 63 ml of tetrahydrofuran (hereinafter abbrevaited to THF) is added 40 ml (60 mM) of n-butyl lithium (1.5M in hexane) directly at −70° C. Large amount of white precipitate is deposited and the mixture is stirred at the same temperature for about 10 minutes, and then the temperature is gradually raised up to room temperature. The white precipitate is dissolved within an hour at room temperature and then 2.58 ml (30 mM) of allyl bromide is added thereto. After stirring for about an hour, the mixture is poured into aqueous ammonium chloride, salted-out and extracted with ether. Then ether extract is dried over magnesium sulfate (hereinafter referred to as "dried"), and evaporated to give the compound 11 as crude white crystals. Thin layer chromatogram of this product shows only one spot of the aimed compound (Yield 90%). This is recrystallized from a mixture of hexane and ether to give the pure product 11 (a mixture of E and Z-forms), mp. 124°–125° C. (a portion melts and is isomerized at 103° C.).

Anal. Calcd. (%) for C₁₁H₁₇NO: : C, 73.70; H, 9.56; N, 7.81; Found (%): C, 73.64; H, 9.63; N, 7.89.

NMR: δ(CDCl₃)1.0∼3.83(m, 14H), 4.90∼5.20(m, 2H), 5.60∼6.10(m, 1H).

IR: νmax(CHCl₃) 3590, 3250, 2935, 2860, 1640, 1460, 1440, 1395∼1300, 1120, 1090, 990, 915, 850 cm⁻¹.

(2) Preparation of 2-allyl-3-aminobicyclo[2.2.2]octane 12

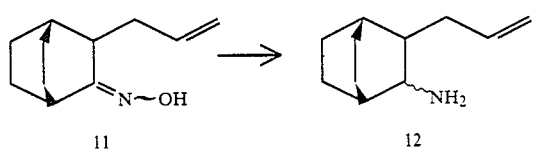

To a solution of 1.79 g (10 mM) of the above-prepared allyl oxime 11 in 20 ml of THF is added 836 mg of lithium aluminium hydride and the mixture is refluxed with heating for 4 hours. Aqueous ether is added to the mixture under ice-cooling to decompose lithium aluminum hydride remaining unchanged. Then the precipitate of aluminum hydroxide is removed by filtration and washed with ether. The organic layer is dried and evaporated to give 1.352 g of the compound 12 as white crude crystals. This product is converted into the sulfonamide derivative in the next step without isolation and purification.

(3) Preparation of 2-allyl-3-benzenesulfonamidobicyclo[2.2.2]octane 13a

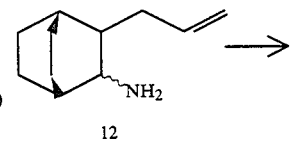

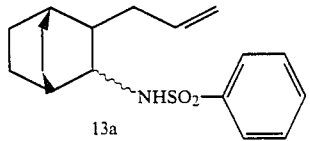

To a solution of 1.352 g (8.2 mM) of the compound 12 prepared above in 15 ml of dichloromethane are added 1.37 ml (9.83 mM) of triethylamine and then 1.25 ml (9.80 mM) of benzenesulfonyl chloride under stirring and ice-cooling. The mixture is allowed to react at room temperature for about an hour, poured into ice-water, and extracted with ethyl acetate. The organic layer is washed with a cold diluted aqueous hydrochloric acid, a cold sodium hydrogencarbonate aqueous solution and water, dried, and evaporated to give an oily material (partially crystals are formed). The NMR spectra show the characteristic absorptions spectrum of trans form (δ; 2.90, t) and cis form (δ; 3.86–4.30, m), of which the ratio is about 2:1. This mixture is chromatographed on a silica gel column [Lobar (Merck)] and the resulting crystals are recrystallized from a mixture of n-hexane and ether to give 850 mg of the trans sulfonamide derivative in 51.1% yield.

Mp. 114°–115° C.

Anal. Calcd. (%) for C₁₇H₂₃NSO₂: : C, 66.85; H, 7.59; N, 4.59; S, 10.50; Found (%): C, 66.84; H, 7.55; N, 4.69; S, 10.50.

IR; νmax(CHCl₃) 3390, 2940, 2855, 1640, 1445, 1330, 1160, 1095, 1000, 960, 915 cm⁻¹.

NMR: δ(CDCl₃)1.0∼2.2(m, 12H), 2.90(t-type m, 1H), 4.70∼5.10(m, 3H), 5.30∼5.80(m, 1H), 7.47∼8.06 (m, 5H).

(4) Preparation of 2α, 3β-2-(2,3-epoxypropyl)-3-benzenesulfonamidobicyclo[2.2.2]octane 14a and 2α,3β-3- benzenesulfonamidobicyclo[2.2.2]octan-2-acetaldehyde II e-a

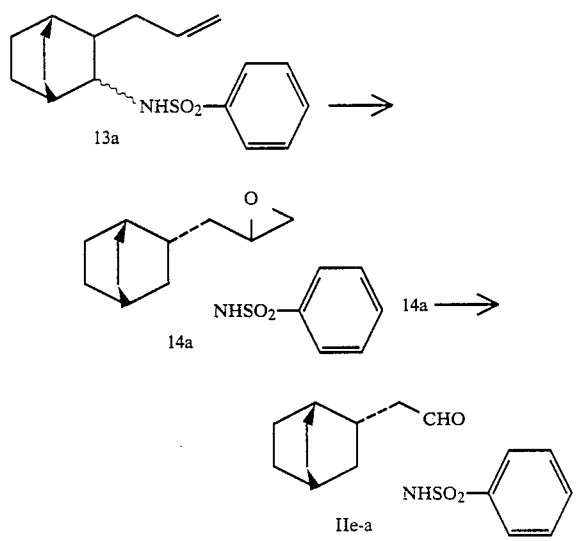

To a solution of 597 mg (1.95 mM) of the above prepared allylsulfonamide 13a in 6 ml of chloroform is added 516 mg (3 mM) of m-chloroperbenzoic acid under ice-cooling and the mixture is allowed to react at room temperature for several hours. Then, the reaction mixture is poured into a cold sodium hydrogensulfate aqueous solution and extracted with ethyl acetate. The organic layer is washed with a sodium hydrogencarbonate aqueous solution and water, dried, and evaporated to give 670 mg of the epoxide 14a as an oily crude product.

NMR: $\delta$(CDCl$_3$) 1.20~200(m, 13H), 2.26~3.10(m, 4H), 5.10~5.35(m, 1H), 7.40~8.00(m, 5H).

To a solution of 625 mg (1.95 mM) of the epoxide 14a in 11 ml of a mixture of dioxane and water (10:3) is added 827 mg (3.9 mM) of periodic acid (HIO$_4$·2H$_2$O) is added under ice-cooling and the mixture is allowed to react at room temperature for about 3 hours. The reaction mixture is poured into a saturated sodium chloride aqueous solution and extracted with ether. The organic layer is dried and evaporated to give 598 mg of the crude aldehyde II e-a.

NMR: $\delta$(CDCl$_3$) 1.13~2.00(m, 12H), 2.40(dd, 2H, J=6.0 Hz), 2.82(m, 1H), 5.47(d, 1H, J=6.7 Hz), 6.40~8.00(m, 5H), 9.57(m, 1H).

This product is used directly in the next reaction without isolation and purification.

(5) ① Preparation of methyl 2α,3β-7-(3-benzenesulfonamidobicyclo[2.2.2]oct-2-yl)-5(Z)-heptenoate I e-aa(2S*-t)

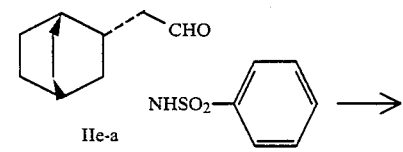

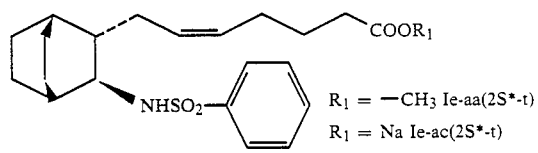

Wittig reagent which is used for the coupling reaction is prepared in accordance with the Corey's method as follows. Sodium hydride is added to a solution of 2.75 g (6.2 mM) of 4-carboxybutyl triphenylphosphonium bromide in 11.7 ml of dimethylsulfoxide (hereinafter abbreviated to DMSO) in an atmosphere of nitrogen and heated at about 70° C. for an hour in order to dissolve the sodium hydride. The reaction mixture is cooled to 10° C. (so as to give no solid) and a solution of 598 mg (1.95 mM) of the aldehyde II e-a prepared above in 11 ml of DMSO is dropwise added thereto. The reaction temperature rises to about 25°–30° C. and the reaction rapidly proceeds to completion. After stirred at room temperature for an hour, the reaction mixture is poured into a saturated sodium chloride aqueous solution and extracted with ethyl acetate. DMSO is thoroughly removed by washing with water and the organic layer is dried and evaporated to give the crude oily substance, which is dissolved in THF to esterify with diazomethane. The product is chromatographed on a silica gel column [Lobar(Merck)] to give 459 mg of the compound I e-aa(2S*-t) as pure specimen in 58.2% yield and additional 86 mg of the same compound with a small amount of contaminants in 10.9% yield. The NMR and IR data of the former compound are as follows.

NMR: $\delta$(CDCl$_3$) 1.0~2.10(m, 17H), 2.27(t, 2H, J=7.5 Hz), 2.83(m, 1H), 3.66(s, 3H), 4.93~5.40(m, 3H)7.40~8.03(m, 5H).

IR: $\nu$max(CHCl$_3$) 3370, 2925, 2850, 1720, 1440, 1320, 1150, 1090, 960, 905, 860 cm$^{-1}$.

② Preparation of the sodium salt I e-ac(2S*-t)

To a solution of 600 mg (1.48 mM) of the above prepared ester I e-aa(2S*-t) in 7.1 ml of ethanol is added 2.96 ml of 1N potassium hydroxide aqueous solution under cooling, and the mixture is allowed to stand at room temperature overnight until the reaction is completed. Then, the reaction mixture is poured into cold water and the aqueous layer is washed with ethyl acetate to remove the starting material remaining unchanged, acidified with hydrochloric acid, salted-out, and extracted with ethyl acetate. The organic layer is washed with water, dried, and evaporated with a high performance vacuum pump. The residue, of which the purity is estimated 95% (the remaining is solvent), is treated with 1N sodium hydroxide to give the sodium salt. This is freeze-dried to give an authentic specimen for analyses.

Anal. Calcd. (%) for C$_{21}$H$_{28}$NSO$_4$Na·0.2H$_2$O: : C, 60.47; H, 6.86; N, 3.36; S, 7.69; Na, 5.51; Found (%): C, 60.33; H, 7.11; N, 3.33; S, 7.67; Na, 60.4.

IR: $\nu$max(KBr) 3440, 3290, 2950, 2880, 1565, 1450, 1410, 1320~1310, 1160, 1095, 968, 920, 875 cm$^{-1}$.

NMR: $\delta$ext. TMS(D$_2$O) 1.30~2.47(m, 17H), 2.58(t, J=7.5 Hz, 2H), 3.25(m, 1H), 5.40~5.95(m, 2H), 7.80~8.50(m, 5H).

III-1

EXAMPLE 1

(1) (dl)-1β, 2α,3α,5β)-2-Hydroxyethyl-3-hydroxybicyclo[3.1.0]hexane 2b-a 13.1 g (0.2 gram atom) of zinc dust is added to a hot solution of 80 mg of silver acetate in 200 ml of acetic acid; acetic acid is then removed and the residue is washed with ether to give a zinc-silver couple. To a suspension of the zinc-silver couple thus prepared in 120 ml of ether is added 26.8 g (0.1 mole) of methylene iodide at such a rate that gentle refluxing is kept. The mixture is heated for an hour and then, a solution of 6.4 g (53.3 mmole) of (dl)-2-hydroxycyclopent-4-enylethanol 1a(2R*) [M. R. Vskokovic, J. Am. Chem. Soc., 95, 7171, (1973)] in 10 ml of ether is dropwise added thereto. The reaction mixture is allowed to react under refluxing and stirring for additional 4 hours. After cooled, the reaction mixture is poured into a saturated ammonium chloride aqueous solution and the product is extracted with ethyl acetate. The ethyl acetate layer is washed with a saturated sodium chloride aqueous solution, dried over anhydrous magnesium sulfate and evaporated. The residue is purified by column chromatography on slica gel with a mixture of benzene and ethyl acetate (1:1) to give 3.98 g of the titled compound 2b-a as an eluate in 56% yield.

$^1$H-NMR: δ(CDCl$_3$); 0.0–0.5(m, 1H), 0.5–0.8(m, 1H), 1.1–1.14(m, 2H), 1.5–2.0(m, 3H), 2.0–2.8(m, 4H), 3.55–4.1(m, 2H), 4.1–4.35(m, 1H) ppm. IR: νmax(CHCl$_3$); 3450 cm$^{-1}$.

(2) (dl)-(1β,2α, 3α, 5β)-3-Hydroxy-2-triphenylmethoxyethylbicyclo[3.1.0]hexane 2a-a(3R*-β)

A solution of 2.1 g (14.8 mmole) of (dl)-(1β, 2α,3α, 5β)-2-hydroxyethyl-3-hydroxybicyclo[3.1.0]hexane 2b-a and 4.36 g (15.6 mmole) of triphenylmethyl chloride in 50 ml of dichloromethane are added 2.5 ml (17.8 mmole) of triethylamine and then 100 mg of 4-dimethylaminopyridine under ice-cooling, and the mixture is allowed to react under ice-cooling for 30 minutes, and then at room temperature for additional 20 hours. The product is extracted with dichloromethane. The dichloromethane layer is washed with a saturated sodium chloride aqueous solution, dried over anhydrous magnesium sulfate and evaporated. The residue is purified by column chromatography on silica gel with a mixture of benzene and ethyl acetate (2:1) to give 5.46 g of the titled compound 2a-a(2R*-β) as an eluate in 95.7% yield.

$^1$H-NMR: δ(CDCl$_3$); 0.1–0.4(m, 1H), 0.5–0.8(m, 1H), 1.0–1.35(m, 2H), 1.4–2.5(m, 6H), 2.95–3.28(m, 1H), 3.28–3.55(m, 1H), 4.10(t, J=6 Hz, 1H), 7.0–7.6(m, 15H) ppm.

IR: νmax(CHCl$_3$); 3450 cm$^{-1}$.

(3) (dl)-(cis)-2-Hydroxycyclopent-4-enylethanol triphenylmethyl ether 1b-a(2R*)

To a solution of 14 g (109 mmole) of (dl)-2-hydroxycyclopent-4-enylethanol 1a(2R*) in 500 ml of dichloromethane is added a solution of 32 g (144 mmole) of triphenylmethyl chloride in 100 ml of dichloromethane and then 19.8 ml (142 mmole) of triethylamine and 300 mg of 4-dimethylaminopyridine are added, and the mixture is allowed to react at room temperature for 20 hours. The product is extracted with dichloromethane. The dichloromethane layer is washed with diluted hydrochloric acid, a saturated sodium hydrogencarbonate aqueous solution and a saturated sodium chloride aqueous solution, dried over anhydrous magnesium sulfate, and evaporated. The residue is purified by column chromatography on silica gel with a mixture of n-hexane and ethyl acetate (4:1) to give 38.63 g of the titled compound 1b-a(2R*) as an eluate in 96% yield.

$^1$H-NMR; δ(CDCl$_3$); 1.5–2.0(m, 2H), 2.15–2.85(m, 3H), 3.02–3.5(m, 2H), 4.2–4.5(m, 1H), 5.4–5.6(m, 1H), 5.6–5.7(m, 1H), 7.15–7.65(m, 15H) ppm.

IR: νmax(CHCl$_3$); 3450 cm$^{-1}$.

(4) (dl)-(trans)-2-Benzoyloxycyclopent-4-enylethanol triphenylmethyl ether 1-a(2S*)

To a cooled solution with ice-bath of 1.86 g (5 mmole) of (dl)-(cis)-2-hydroxycyclopent-4-enylethanol triphenylmethyl ether 1b-a(2R*), 2.62 g (10 mmole) of triphenylphosphine and 1.22 g (10 mmole) of benzoic acid in 100 ml of tetrahyrofuran is added 1.74 g (10 mmole) of diethyl azodicarboxylate and the mixture is allowed to react at room temperature for 15 minutes. Then is added 1 ml of methanol and the mixture is evaporated. Ether is added to the residue and resulting insoluble substance is removed by filtration. The ether soluble product is purified by column chromatography on silica gel with a mixture of n-hexane and ethyl acetate (9:1) to give 1.32 g of the titled compound 1a(2S*) as an eluate in 55.6% yield. Further, as a nonpolar product, 0.72 g of (dl)-cyclopenta-1,4-dienylethanol triphenylmethyl ether is obtained in 40.9% yield.

$^1$H-NMR: δ(CDCl$_3$); 1.55–1.95(m, 2H), 2.33(d,d, J=12, 2 Hz, 1H), 2.81(d,d, J=12, 5 Hz, 1H), 2.9–3.4(m, 3H), 5.13–5.36(m, 1H), 5.45–5.70(m, 2H), 6.95–8.15(m, 20H) ppm.

IR: νmax(CHCl$_3$); 1710 cm$^{-1}$.

(5) (dl)-(trans)-2-Hydroxycyclopent-4-enylethanol triphenylmethyl ether 1b-a(2S*)

A solution of 1.32 g (2.8 mmole) of (dl)-(trans)-2-benzoyloxy-cyclopent-4-enylethanol triphenylmethyl ether 1-a(2S*) and 0.8 g (5.79 mmole) of potassium carbonate in a mixture of 16 ml of methanol, 4 ml of water and 10 ml tetrahydrofuran is refluxed with heating for 5 hours. After cooled, the product is extracted with dichloromethane. The dichloromethane layer is washed with a saturated sodium chloride aqueous solution and dried over anhydrous magnesium sulfate, and evaporated. The residue is purified by column chromatography on silica gel with a mixture of benzene and ethyl acetate (2:1) to give 0.98 g of the titled compound 1b-a(2S*) as an eluate.

$^1$H-NMR: δ(CDCl$_3$); 1.83–1.50(m, 3H), 2.06–2.40(m, 1H), 2.47–2.83(m, 2H), 3.05–3.40(m, 2H), 4.0–4.23(m, 1H), 5.43–5.7(m, 2H), 7.10–7.65(m, 15H) ppm.

IR: νmax(CHCl$_3$); 3450 cm$^{-1}$.

(6) (dl)-(1α,2α, 3β,5α)-3-Hydroxy-2-triphenylmethoxyethylbicyclo[3.1.0]hexane 2a-a(3S*-α)

11.5 g (176 milli gram atom) of zinc dust is added to a hot solution of 100 mg of silver acetate in 80 ml of acetic acid; acetic acid is then removed and the residue is washed with ether to give a zinc-silver couple. To a solution of the zinc-silver couple thus prepared in 60 ml of ether is added 23.57 g (88 mmole) of methylene iodide at such a rate that gentle refluxing is kept. After the mixture is heated for an hour, a solution of 8.2 g (22 mmole) of (dl)-trans-2-hydroxycyclopent-4-enylethanol triphenylmethyl ether 1b-a(2S*) in 10 ml of ether is dropwise added thereto. The reaction mixture is refluxed with heating and stirring for additional 4 hours. After cooled, the reaction mixture is poured into a saturated ammonium chloride aqueous solution and the product is extracted with ethyl acetate. The ethyl acetate layer is washed with a saturated sodium chloride aqueous solution, dried over anhydrous magnesium sulfate and evaporated. The residue is purified by column chromatography on silica gel with a mixture of n-hexane and ethyl acetate (9:1→4:1) to give 7.5 g of the titled compound 2a-a(3S*-α) as an eluate in 87% yield.

$^1$H-NMR: δ(CDCl$_3$); 0.33–0.66(m, 2H), 0.86–1.30(m, 2H), 1.34–(s, 3H), 1.43–1.77(m, 3H), 1.81–2.27(m, 2H), 3.28(t, J=6 Hz, 2H), 3.95(d, J=6 Hz, 1H), 7.2–7.63(m, 15H) ppm.

IR: νmax(CHCl$_3$); 3450 cm$^{-1}$.

(7) (dl)-cis-2-Acetoxycyclopent-4-enylethanol triphenylmethyl ether 1-a(2R*)

To a solution of 15.3 g (41.3 mmole) of (dl)-cis-2-hydroxycyclopent-4-enylethanol triphenylmethyl ether 1b-a(2R*) in 60 ml of pyridine are added 40 ml of acetic anhydride and 0.1 g of 4-dimethylaminopyridine and the mixture is allowed to react at room temperature for 2 hours. Solvent and excess reagent are evaporated under reduced pressure and then the product is extracted with ethyl acetate. The ethyl acetate layer is washed with a diluted sodium hydrogensulfate aqueous solution, a saturated sodium hydrogencarbonate aqueous solution and a saturated sodium chloride aqueous solution, dried over anhydrous magnesium sulfate, and evaporated. The residue is purified by column chromatography on silica gel with a mixture of n-hexane and ethyl acetate (9:1) to give 16.87 g of the titled compound 1-a(2R*) as a eluate in 99.0% yield.

$^1$H-NMR: δ(CDCl$_3$); 1.5–3.05(m, 5H), 1.9(s, 3H), 3.14(t, J=6 Hz, 2H), 5.2–5.45(m, 1H), 5.6(s, 2H), 7.05–7.9(m, 15H) ppm.

IR: νmax(CHCl$_3$); 1720 cm$^{-1}$.

(8) (dl)-(1α,2α,3α,5α)-6,6-Dibromo-3-acetoxy-2-triphenylmethoxyethylbicyclo[3.1.0]hexane 2-c(3R*-α)

To a solution of 16.5 g (40 mmole) of cis-2-acetoxycyclopent-3-enylethanol triphenylmethyl ether 1-a(2R*) in 80 ml of dichloromethane are added 14 ml (160 mmole) of bromoform, 1 g of triethylbenzylammonium chloride and 50 ml of 40% sodium hydroxide aqueous solution. The mixture is stirred well and allowed to react at 50° C. for 20 hours. After cooled, the mixture is diluted with 200 ml of dichloromethane and insoluble material is filtrated off through celite. The filtrate is washed with water and a saturated sodium chloride aqueous solution, dried over anhydrous magnesium sulfate, and evaporated. The residue is purified by column chromatography on silica gel with a mixture of n-hexane and ethyl acetate (9:1) to give 19.6 g of the titled compound 2-c (3R*-α) as an eluate in 84% yield.

$^1$H-NMR: δ (CDCl$_3$); 1.5–2.55(m, 7H), 1.92(s, 3H), 3.16(t, J=6 Hz, 2H), 5.06–5.3(m, 1H), 7.1–7.7(m, 15H) ppm.

IR: νmax(CHCl$_3$): 1735 cm$^{-1}$.

(9) (dl)-(1α, 2α, 3α, 5α)-3-Acetoxy-6,6-dimethyl-2-triphenylmethoxyethylbicyclo[3.1.0]hexane 2-b(3R*-α)

To a suspension of 26.3 g (216 mmole) of copper(I) thiocyanate in 250 ml of either cooled at a temperature of −50° to −60° C. is dropwise added 283 ml (396 mmole) of 1.4N solution of methyl lithium in either while keeping the reaction temperature below −50° C. The reaction temperature is raised to 0° C. over a period of 30 minutes and then lowered to −20° C. To the mixture are added a solution of 11.5 g (19 mmole) of (dl)-(1α, 2α, 3α, 5α)-3-acetoxy-6,6-dibromo-2-triphenylmethoxyethylbicyclo[3.1.0]hexane 2-c(3R*-α) in 50 ml of ether and 8.56 ml (47.5 mmole) of hexamethylphosphoramide and the mixture is allowed to react at −20° C. for an hour. After the above mixture is cooled to −50° C. again, excess methyl iodide is added, and then the mixture is stirred for 10 minutes. To the mixture, which is cooled to −70° C., is added a saturated ammonium chloride aqueous solution and the resulting insoluble material is filtered off through celite. The filtrate is washed with a diluted ammonia water and a saturated sodium chloride aqueous solution, dried over anhydrous magnesium suflate, and evaporated to give a titled compound 2-b(3R*-α), which is used in the following reaction without purification.

$^1$H-NMR: δ (CDCl$_3$); 0.93(s, 6H), 0.8–1.4(m, 3H), 1.4–2.2(m, 4H), 1.92(s, 3H), 3.12(t, J=6 Hz, 2H), 4.95–5.2(m, 1H), 7.05–7.7(m, 15H) ppm.

IR: νmax(CHCl$_3$); 1725 cm$^{-1}$.

(10) (dl)-(1α, 2α, 3α, 5α)-6,6-Dimethyl-3-hydroxy-2-triphenylmethoxyethylbicyclo[3.1.0]hexane 2a-b(3R*-α)

To a solution of the above perpared crude product of (dl)-(1α, 2α, 3α, 5α)-3-acetoxy-6,6-dimethyl-2-triphenylmethoxyethylbicyclo[3.1.0]hexane 2-b(3R*-α) in a mixture of 60 ml of methanol and 60 ml of tetrahydrofuran is added 29 ml (58 mole) of 2N sodium hydroxide aqueous solution and the mixture is refluxed with heating for 3 hours, and evaporated under reduced pressure. The residue is extracted with ethyl acetate and the ethyl acetate layer is washed with a saturated sodium chloride aqueous solution, dried over anhydrous magnesium sulfate, and evaporated. The residue is purified by column chromatography on silica gel with a mixture of n-hexane and ethyl acetate (5:1) containing 2% triethylamine to give 7.41 g of the titled compound 2a-b(3R*-α) as an eluate. (in 95% yield from the compound 2-c(3R*-α))

$^1$H-NMR δ (CDCl$_3$); 0.87(s, 3H), 0.93(s, 3H), 0.75–1.1(m, 1H), 1.1–1.4(m, 1h), 1.5–2.1(m, 1H), 2.44(br.s, 1H), 3.0–3.43 (m, 2H), 4.12(m, 1H), 7.0–7.8(m, 15H), ppm.

IR: νmax(CHCl$_3$): 3420 cm$^{-1}$.

(11) (dl)-(1α, 2α, 5α)-6,6-Dimethyl-2-triphenylmethoxyethylbicyclo[3.1.0]hexan-3-one 4-b(α)

A solution of 0.74 ml (8.3 mmole) of oxalyl chloride in 20 ml of dichloromethane, cooled to −78° C., is added to a solution of 1.2 ml (16.9 mmol) of dimethylsulfoxide in 1 ml of dichloromethane and the mixture is stirred for 5 minutes. To the mixture is added a solution of 2.9 g (7.03 mmole) of (dl)-(1α, 2α, 3α, 5α)-6,6-dimethyl-3-hydroxy-2-triphenylmethoxyethylbicyclo[3.1.0]hexane 2a-b)3R*-α) in 5 ml of dichloromethane and the resulting mixture is allowed to react at −60° C. for 20 minutes and 6.86 ml (49.2 mmole) of triethylamine is added thereto. The temperature of the reaction mixture is gradually raised up to room temperature and then the product is extracted with dichloromethane. The dichloromethane layer is washed with 1N hydrochloric acid, a saturated sodium hydrogencarbonate aqueous solution and a saturated sodium chloride aqueous solution, dried over anhydrous magnesium sulfate, and evaporated. The residue is purified by column chromatography on silica gel with a mixture of n-hexane and ethyl acetate (2:1) to give 2.86 g of the titled compound 4-b(α) in 99% yield.

$^1$H-NMR δ (CDCl$_3$); 0.82(s, 3H), 1.00(s, 3H), 0.8–1.3(m, 2H), 1.4–2.3(m, 4H), 2.48(d.d, J=20, 6 Hz, 1H), 3.2(t, J=6 Hz,2H), 7.1–7.6(m, 15H) ppm.

IR: νmax(CHCl$_3$): 1725 cm$^{-1}$.

(12) (dl)-1β, 2α, 5β)-6,6-Dimethyl-2-triphenylmethoxyethylbicyclo[3.1.0]hexan-3-one 4-b(β)

A solution of 4.5 g (11 mmole) of (d1)-(1α,2α,5α)-6,6-dimethyl-2-triphenylmethoxyethylbicyclo[3.1.0]-hexan-3-one 4-b(α) and 10.86 g (96.8 mmole) of potassium tert-butoxide in 110 ml of dimethylsulfoxide is allowed to react at room temperature for 8 hours. The reaction mixture is poured into a solution of 12 g (0.2 mmole) of acetic acid in 200 ml of dichloromethane cooled to −20° C. and then the product is extracted with ethyl acetate. The ethyl acetate layer is washed with a saturated sodium hydrogencabonate aqueous solution and a saturated sodium chloride aqueous solution, dried over anhydrous magnesium sulfate, and evaporated. The residue is purified by column chromatography on silica gel with a mixture of benzene and ethylene acetate (9:1) to give 3.37 g of the titled compound 4-b(β) as an elute in 75% yield.

$^1$H-NMR: δ (CDCl$_3$): 0.80(s, 3H), 0.93(s, 3H), 1.0–1.68(m, 3H), 2.0–2.93(m, 4H), 3.03–3.48(m, 2H), 7.10–7.60(m, 15H) ppm.

IR: νmax(CHCl$_3$); 1725 cm$^{-1}$.

(13) (d1)-(1β, 2α, 3α, 5β)-6,6-Dimethyl-3-hydroxy-2-triphenylmethoxyethylbicyclo[3.1.0]hexane 2a-b(3R*-β)

To a solution of 1.64 g (4 mmole) of (d1)-(1β, 2α, 5β)-6,6-dimethyl-2-triphenylmethoxyethylbicyclo[3.1.0]hexan-3-one 4-b(β) in 164 ml of tetrahydrofuran is added 2.03 g (8 mmole) of lithium tri-tert-butoxyaluminohydride and the mixture is allowed to react at room temperature for 2.5 hours. The excess reagent is decomposed with addition of water and then the product is extracted with ethyl acetate. The ethyl acetate layer is washed with a saturated sodium chloride aqueous solution, dried over anhydrous magnesium sulfate, and evaporated. The residue is purified by column chromatography on silica gel with benzene eluent containing 1% triethylamine to give 988 mg of the titled compound 2a-b(3R*-β) as an eluate in 60% yield.

$^1$H-NMR: δ (CDCl$_3$); 0.77–1.13(m, 2H), 0.88(s, 3H), 1.30(s, 3H), 1.44–1.80(m, 2H), 1.80–2.22(m, 1H), 2.23–2.6(m, 2H), 3.23–3.52(m, 1H), 4.55(t, J=9 Hz, 1H), 7.1–7.6(m, 15H) ppm.

IR: νmax(CHCl$_3$); 3430 cm$^{-1}$.

(14) (d1)-(1β, 2α, 3β, 5β)-3-Azido-6,6-dimethyl-2-triphenylmethoxyethylbicyclo[3.1.0]hexane 6-b(β)

To a solution of 988 mg (2.39 mmole) of (d1)-1β, 2α, 3α, 5β)-6,6-dimethyl-3-hydroxy-2-triphenyloxyethylbicyclo[3.1.0]hexane 2a-b(3R*-β) in 10 ml of dichloromethane are added 0.2 ml) 2.6 mmole) of methanesulfonyl chloride and 0.43 ml (3.12 mmole) of triethylamine under ice-cooling, and the mixture is allowed to react at room temperature for 30 minutes, and then the product is extracted with dichloromethane. The dichloromethane layer is washed with a saturated sodium chloride aqueous solution and evaporated. To a solution of the above prepared crude (d1)-(1β, 2α, 3α, 5β)-6,6-dimethyl-3-methanesufonyloxy-2-triphenylmethoxyethylbicyclo[3.1.0]hexane in 20 ml of dimethylformamide is added 932 mg (14.4 mmole) of sodium azide and the mixture is allowed to react at 75° C. for 7 hours. After cooled the product is extracted with ethyl acetate. The ethyl acetate layer is washed with a saturated sodium chloride aqueous solution, dried over magnesium sulfate, and evaporated.

The residue is purified by column chromatography on silica gel with a mixture of benzene and n-hexane eluent containing 1% triethylamine to give 835 mg of the titled compund 6-b(β) as an eluate in 80% yield.

$^1$H-NMR δ (CDCl$_3$); 0.73–1.2(m, 2H), 0.80(s, 3H), 0.97(s, 3H, 1.4–2.6(m, 5H), 2.98–3.43(m, 3H), 7.1–7.63(m, 15H) ppm.

IR: νmax(CHCl$_3$): 2080 cm$^{-1}$.

(15) (d1)-(1β, 2α, 3β, 5β)-3-Amino-6,6-dimethyl-2-triphenylmethoxyethylbicyclo[3.1.0]hexane 7-b(3S*-β)

To a solution of 830 mg (1.9 mmole) of the above prepared (d1)-(1β, 2α, 3β, 5β)-3-azido-6,6-dimethyl-2-triphenylmethoxyethylbicyclo[3.1.0]hexane 6-b(β) in 8 ml of tetrahydrofuran is added 748 mg (2.85 mmole) of triphenylphosphine and the mixture is allowed to react at 45° C. for 6 hours.

To the reaction mixture is added 0.8 ml of water and the resulting mixture is allowed to react at 45° C. for additional 2 hours, and then the product is extracted with ethyl acetate. The ethyl acetate layer is washed with a saturated sodium chloride aqueous solution, dried over anhydrous magnesium sulfate, and evaporated. The residue is purified by column chromotography on silica gel with a mixture of benzene and ethyl acetate (1:1) to give 873 mg of the titled compound 7-b(3S*-β) as an eluate. The product is used in the following reaction without further purification.

(16) (d1)-(1β,2α, 3β, 5β)-6,6-Dimethyl-3-phenylsulfonylamino-2-triphenylmethoxyethylbicyclo[3.1.0]hexane 8-b(3S*-β)

To a solution of 873 mg of the above prepared crude (d1)-(1β, 2α, 3β, 5β)-3-amino-6,6-dimethyl-2-triphenylmethoxyethylbicyclo[3.1.0]hexane 7-b(3S*-β) in 10 ml of dichloromethane are added 0.36 ml (2.6 mmole) of triethylamine and 0.28 ml (2.2 mmole) of benzenesulfonyl chloride and the mixture allowed to react at room temperature for 15 hours. The reaction mixture is cooled with ice again and diluted aqueous ammonia is added thereto in order to decompose excess reagent and then the product is extracted with dichloromethane. The dichloromethane layer is washed with a saturated sodium chloride aqueous solution, dried over anhydrous magnesium sulfate, and evaporated. The residue is purified by column chromatography on silica gel with benzene eluent containing 2% triethylamine to give 574 mg of the titled compound 8-b(3S*-β) as an eluate (in 55% yield from the compound 6-b(β)).

$^1$H-NMR: δ (CDCl$_3$); 0.63–1.07(m, 2H), 0.84(s, 3H), 0.89(s, 3H, 1.1–2.4(m, 5H), 2.85–3.4(m, 3H), 4.65(d, J=9 Hz), 7.1–7.62(m, 18H), 7.78–7.98(m, 2H) ppm.

IR: νmax(CHCl$_3$): 3360, 1320, 1155 cm$^{-1}$.

(17) (d1)-(1β, 2α, 5β)-2-Triphenylmethoxyethylbicyclo[3.1.0]hexan-3-one 4-a(β)

To a solution of 5.62 g of (d1)-(1β, 2α, 3α, 5β)-3-hydroxy-2-triphenylmethoxyethylbicyclo[3.1.0]hexane 2a-a(3R*-β) in 30 ml of dimethylformamide is added 11.1 g (25.5 mmole) of pyridinium dichromate and the mixture is allowed to react under ice-cooling at room temperature for 3 hours. The reaction mixture is poured into ice-water and the product is extracted with ethyl acetate. The ethyl acetate layer is washed with a saturated sodium chloride aqueous solution, dried over anhydrous magnesium sulfate, and evaporated. The residue is purified by chromatography on silica gel with a mixture of benzene and ethyl acetate (9:1) to give 3.21 g of the titled compound 4-a(β) as an eluate in 56.8% yield.

$^1$H-NMR δ (CDCl$_3$); -0.35–0.0(m, 1H), 0.45–0.80(m, 1H), 0.9–1.8(m, 3H), 1.95–2.4(m, 2H), 2.47–3.0(m, 2H), 3.0–3.4(m, 2H), 7.1–7.6(m, 15H) ppm.

IR: νmax(CHCl$_3$); 1725 cm$^{-1}$.

(18) (dl)-(1β, 2α, 5β)-3-Hydroxyimino-2-triphenyl-methoxyethylbicyclo[3.1.0]hexane 5-a(β)

To a solution of 1.11 g (16.8 mmole) of potassium hydroxide in 65 ml of methanol is added 1.17 g (16.8 mmole) of hydroxylamine hydrochloride. To the mixture is added 3.21 g (8.4 mmol) of (dl)-(1β, 2α, 5β)-2-triphenylmethoxymethylbicyclo[3.1.0]hexan-3-one 4-a(β) and the resulting mixture is allowed to react at room temperature for 3 hours. Water is added to the reaction mixture, which is extracted with ethyl acetate. The ethyl acetate layer is washed with a saturated sodium chloride aqueous solution, dried over magnesiun sulfate, and evaporated. The residue is purified by column chromatography on silica gel with a mixture of benzene and ethyl acetate (9:1) followed by recrystallization from a mixture of benzene and n-hexane to give 3.30 g of the titled compound 5-a(β) in 99% yield.

Mp. 58°–60° C.

$^1$H-NMR: δ (CDCl$_3$); -0.4–0.2(m, 1H), 1.23–1.60(m, 1H), 1.13–1.67(m, 4H), 1.95–2.30(m, 1H), 2.4(d, J=18 Hz, 1H), 2.8(d, J=18 Hz, 1H), 3.0–3.4(m, 2H), 7.2–7.64(m, 15H), 8.08(s, 1H) ppm.

IR: νmax(CHCl$_3$); 3560 cm$^{-1}$.

(19) (dl)-(1β, 2α, 3β, 5β)-3-Phenylsulfonylamino-2-triphenylmethoxyethylbicyclo[3.1.0]hexane 8-a(3S*-β) and (dl)-(1β, 2α, 3α, 5β)-3-phenylsulfonylamino-2-triphenylmethoxyethylbicyclo[3.1.0]hexane 8-a(3R*-β)

To a solution of 2.91 g (7.31 mmole) of (dl)-(1β, 2α, 5β)-3-hydroxyimino-2-triphenylmethoxymethylbicyclo[3.1.0]hexane 5-a(β) in 20 ml of tetrahydrofuran are added 1.92 g (8.77 mmole) of diphenyldisulfide and 3.27 ml (13.16 mmole) of n-tributylphosphine under ice-cooling and the mixture is allowed to react at room temperature for an hour. After the reaction mixture is cooled to −70° C., 10 ml of acetic acid and 1.65 g (26.32 mmole) of sodium cyanoborohydride is added thereto. The resulting mixture is allowed to react at −78° C. for 10 minutes and then the temperature is gradually raised up to room temperature. Sodium hydrogencarbonate is added to the reaction mixture and then added water, and the product is extracted with ethyl acetate. The ethyl acetate layer is washed with a saturated sodium chloride aqueous solution, dried over anhydrous magnesium sulfate, and evaporated. The residue is dissolved in 30 ml of dichloromethane, and 4.2 ml (32.9 ml) of benzenesufonyl chloride and 9.13 ml (65.8 ml) of triethylamine are added to the solution under ice cooling and the mixture is allowed to react at room temperature for 3 hours. The product is extracted with ethyl acetate and the ethyl acetate layer is washed with a saturated sodium chloride aqueous solution, dried over anhydrous magnesium sulfate, and evaporated. The residue is purified by column chromatography on silica gel with a mixture of benzene and ethyl acetate (19:1) to give 2.18 g of the titled compounds 8-a(3S*-β) and 8-a(3R*-β) as a mixture.

(20) (dl)-(1β, 2α, 3β, 5β) and (1β, 2α, 3α, 5β)-2-Hydroxyethyl-3-phenylsulfonylaminobicyclo[3.1.0]hexane 9-a(3S*-β) and 9-a(3R*-β)

A solution of 1.77 g (3.38 mmole) of a mixture of (dl)-(1β, 2α, 3β, 5β)-3-phenylsulfonylamino-2-triphenylmethoxyethylbicyclo[3.1.0]hexane 8-a(3S*-β) and (dl)-(1β, 2α, 3α, 5β)-3-phenylsulfonylamino-2-triphenylmethoxyethylbicyclo[3.1.0]hexane 8-a(3R*-β) in 50 ml of 80% aqueous acetic acid is refluxed with heating for 15 hours. After the solvent is evaporated, the product is extracted with ethyl acetate. The ethyl acetate layer is washed with a saturated sodium hydrogencarbonate aqueous solution and then a saturated sodium chloride aqueous solution, dried over anhydrous magnesium sulfate, and evaporated to give the product consisting of (dl)-(1β, 2α, 3β, 5β) and (1β, 2α, 3α, 5β)-2-hydroxyethyl-3-phenylsulfonylaminobicyclo[3.1.0]hexane, and (dl)-(1β, 2α, 3β, 5β) and (1β, 2α, 3α, 5β)-2-acetoxyethyl-3-phenylsulfonylaminobicyclo[3.1.0]hexane. This product is dissolved in a solution of 716 mg of sodium carbonate in a mixture of 60 ml of methanol and 30 ml of water and the mixture is refluxed with heating for 5 hours. After cooled, the reaction mixture is poured into water and extracted with ethyl acetate. The ethyl acetate layer is washed with a saturated sodium chloride aqueous solution, dried over anhydrous magnesium sulfate, and evaporated. The residue is purified by column chromatography on silica gel with a mixture of benzene and ethyl acetate (2:1) to give 593 mg of the titled compounds of (dl)-(1β, 2α, 3β, 5β)-2-hydroxyethyl-3-phenylsulfonylaminobicyclo[3.1.0]hexane 9-a(3S*-β) in 63% yield.

$^1$H-NMR: δ (CDCl$_3$), -0.14–0.34(m, 2H), 0.94–2.34(m, 8H), 2.54–2.99(m, 1H), 3.69(t, J=6 Hz, 2H), 5.39(d, J=8 Hz, 1H), 7.29–7.69(m, 3H), 7.77–8.04(m, 2H) ppm.

IR: νmax(CHCl$_3$); 3650–3100, 3360, 1325, 1160 cm$^{-1}$. and 154 mg of (dl)-(1β, 2α, 3α, 5β)-2-hydroxyethyl-3-phenylsulfonylaminobicyclo[3.1.0]hexane 9-a(3R*-β) in 16% yield.

$^1$H-NMR: δ (CDCl$_3$); -0.98–0.5(m, 2H), 0.94–2.22(m, 8H), 2.3–2.67(m, 1H), 3.44–3.92(m, 3H), 5.08(d, J=8 Hz, 1H), 7.32–7.6(m, 3H), 7.67–8.00(m, 2H) ppm.

IR: νmax(CHCl$_3$); 3650–3100, 3360, 1335, 1150 cm$^{-1}$.

(21) (dl)-(1β, 2α, 3β, 5β)-2-Formylmethyl-3-phenylsulfonylaminobicyclo[3.1.0]hexane II f-a(3S*-β)

To a solution of 0.2 ml (2.24 mmole) of oxalyl chloride in 10 ml of dichloromethane, cooled to −78° C., is added 0.34 ml (4.8 mmole) of dimethylsulfoxide and the mixture is stirred for 5 minutes. A solution of 561 mg (1.99 mmol) of (dl)-(1β, 2α, 3β, 5β)-2-hydroxyethyl-3-phenylsulfonylaminobicyclo[3.1.0]hexane 9-a(3S*-β) in 10 ml of dichloromethane is added to the above mixture and the resulting mixture is allowed to react at −60° C. for 15 minutes, and then 3.34 ml (24 mmole) of triethylamine is added thereto. The reaction temperature is gradually raised up to room temperature and the product is extracted with ethyl acetate. The ethyl acetate layer is washed with water, 2N hydrochloric acid and a saturated sodium chloride aqueous solution, dried over anhydrous magnesium sulfate, and evaporated to give the titled compound II f-a(3S*-β), which is used in the following reaction without further purification.

$^1$H-NMR: δ (CDCl$_3$); -0.13–0.39(m, 2h), 0.98–1.98(m, 5H), 2.08 -2.98(m, 3H), 4.78–5.38(br.s, 1H), 7.33–7.65(m, 3H), 7.68–8.10(m, 2H), 9.80(s, 1H) ppm.

IR: νmax(CHCl$_3$); 1720, 1340, 1320, 1160 cm$^{-1}$.

(22) (dl)-(1α, 2α, 5α)-2-Triphenylmethoxyethylbicyclo[3.1.0]hexan-3-one 4-a(α)

The compound 4-a(α) is prepared in accordance with the manner of III-1, Example 1, (17).

NMR: δ (CDCl$_3$); 0.67–1.0(m, 1H), 1.07–2.09(m, 5H), 2.14–2.37(m, 2H), 2.39–2.77(m, 1H), 3.21(t, J=6 Hz, 2H), 7.17–7.67(m, 15H) ppm.

IR: νmax(CHCl$_3$); 1730 cm$^{-1}$.

(23) The following compounds are prepared in accordance with the manner of III-1, Example 1, (18).

① (dl)-(1α, 2α, 5α)-3-Hydroxyimino-2-triphenylmethoxyethylbicyclo[3.1.0]hexane 5-a(α)

NMR: δ (CDCl₃); (a mixture of syn and anti-form) 0.40–0.77(m, 1H), 0.90–3.40(m, 8H), 3.23(t, J=6 Hz, 2H), 7.1–7.7(m, 16H) ppm.

IR: νmax(CHCl₃); 3580 cm⁻¹.

② (dl)-(1α, 2α, 5α)-6,6-Dimethyl-3-hydroxyimino-2-triphenylmethoxyethylbicyclo[3.1.0]hexane 5-b(α)

NMR: δ (CDCl₃); (a mixture of syn and anti-form) 0.83(s, 3H), 0.93(s, 3H), 0.9–1.4(m, 2H), 1.6–2.1(m, 2H), 2.4–2.8(m, 3H), 3.21 (m, 3H), 7.0–7.6(m, 15H), 8.38(br.s., 1H) ppm.

NMR: δ (CDCl₃); 0.83(s, 3H), 0.9(s, 3H), 0.95–2.25(m, 4H), 2.27(d, J=18 Hz, 1H), 2.58(d,d, J=18, 5 Hz, 1H), 3.03(m, 1H), 3.2 (t, J=6 Hz, 2H), 7.07–7.7(m, 16H) ppm.

IR: νmax(CHCl₃); 3490, 3325 cm⁻¹.

(24) The following compounds are prepared in accordance with the manner of III-1, Example 1, (19).

① (dl)-(1α, 2α, 3β, 5α)-3-Phenylsulfonylamino-2-triphenylmethoxyethylbicyclo[3.1.0]hexane 8-a(3S*-α)

NMR: δ (CDCl₃); 0.0–0.3(m, 1H), 0.4–0.7(m, 1H), 0.7–2.27(m, 7H), 3.0(t, J=6. Hz, 2H), 3.2–3.5(m, 1h), 4.43(d, J=6 Hz, 1H), 7.17–7.65(m, 19H), 7.7–7.9(m, 2H) ppm.

IR: νmax(CHCl₃); 3360, 1330, 1160 cm⁻¹.

② (dl)-(1α, 2α, 3β, 5α)-6,6-Dimethyl-3-phenylsulfonylamino-2-triphenylmethoxyethylbicyclo[3.1.0]hexane 8-b(3S*-α)

NMR: δ (CDCl₃); 0.87(s, 3H), 0.93(s, 3H), 0.6–1.2(m, 5H), 1.2–2.2(m, 5H), 2.9–3.2(m, 2H), 3.2–3.6(m, 1H), 4.98(d, J=8 Hz, 1H), 7.1–7.95(m, 18H), 7.7–7.95(m, 19H) ppm.

IR: νmax(CHCl₃); 3360, 1320, 1160 cm⁻¹.

(25) The following compounds are prepared in accordance with the manner of III-1, Example 1, (20).

① (dl)-(1α, 2α, 3β, 5α)-2-Hydroxyethyl-3-phenylsulfonylaminobicyclo[3.1.0]hexane 9-a(3S*-α)

NMR: δ (CDCl₃); 0.12–0.33(m, 1H), 0.43–0.77(m, 1H), 0.86–2.33(m, 9H), 3.27–3.63(m, 1H), 4.8–5.05(d, J=6 Hz, 1H), 7.43–7.67 (m, 3H), 7.8–8.0(m, 2H) ppm.

IR: νmax(CHCl₃); 3360, 3250, 1330, 1160 cm⁻¹.

② (dl)-(1β, 2α, 3β, 5β)-6,6-Dimethyl-2-hydroxyethyl-3-phenylsulfonylaminobicyclo[3.1.0]hexane 9-b(3S*-β)

NMR: δ (CDCl₃); 0.63–1.3(m, 2H), 0.88(s, 3H), 0.95(s, 3H), 1.3–2.7(m, 6H), 3.0–3.38(m, 1H), 3.68(t, J=6 Hz, 2H), 5.33–5.9 (m, 1H), 7.32–7.67(m, 3H), 7.79–8.0(m, 2H) ppm.

IR: νmax(CHCl₃); 3100, 1325, 1155 cm⁻¹.

③ (dl)-(1α, 2α, 3β, 5α)-6,6-Dimethyl-2-hydroxyethyl-3-phenylsulfonylaminobicyclo[3.1.0]hexane 9-b(3S*-α)

NMR: δ (CDCl₃); 0.9(s, 3H), 0.94(s, 3H), 0.6–1.3(m, 3H), 1.4–2.15(m, 5H), 2.35(br.s, 1H), 3.43(br.s, 1H), 3.62(t, J=6 Hz, 2H), 5.7–6.0(d, J=7 Hz, 1H), 7.4–7.7(m, 3H), 7.8–8.1(m, 2H) ppm.

IR: νmax(CHCl₃); 3500, 3370, 1325, 1165 cm⁻¹.

(26) The following compounds are prepared in accordance with the manner of III-1, Example 1, (21).

① (dl)-(1β, 2α, 3α, 5β)-2-Formylmethyl-3-phenylsulfonylaminobicyclo[3.1.0]hexane II f-a(3R*-β)

NMR: δ (CDCl₃+CD₃OD); -0.1–0.5(m, 2H), 0.80–2.40(m, 7H), 2.9–4.1(m, 1H), 5.17–5.33(d,d, J=7.0, 3 Hz, 0.6H), 5.47–5.6(m, 0.4H), 7.3–7.57(m, 3H), 7.57–7.88(m, 2H) ppm.

IR: νmax(CHCl₃); 3520, 3360, 1155 cm⁻¹.

② (dl)-(1α, 2α, 3β, 5α)-2-Formylmethyl-3-phenylsulfonylaminobicyclo[3.1.0]hexane II f-a(3S*-α)

NMR: δ (CDCl₃); 0.24–0.47(m, 1H), 0.53–0.84(m, 1H), 0.87–1.90(m, 3H) 1.95–2.57(m, 4H), 3.23–3.6(m, 1H), 4.85(d, J=6 Hz, 1H), 7.4–7.8(m, 3H), 7.89–8.0(m, 2H), 9.68(s, 1H) ppm.

IR: νmax(CHCl₃); 3350, 1715, 1338, 1155 cm⁻¹.

③ (dl)-(1β, 2α, 3β, 5β)-6,6-Dimethyl-2-formylmethyl-3-phenylsulfonylaminobicyclo[3.1.0]hexane II f-b(3S*-β)

NMR: δ (CDCl₃); 0.85–1.2(m, 2H), 0.86(s, 3H), 0.96(s, 3H), 1.2–2.3(m, 3H), 2.53–2.7(m, 2H), 3.05–3.4(m, 1H), 5.25–5.5(m, 1H), 7.47–7.7(m, 3H), 7.8–8.0(m, 2H) ppm.

IR: νmax(CHCl₃); 3360, 2825, 2725, 1725, 1330, 1160 cm⁻¹.

④ (dl)-(1α, 2α, 3β, 5α)-6,6-Dimethyl-2-formylmethyl-3-phenylsulfonylaminobicyclo[3.1.0]hexane II f-b(3S*-α)

NMR: δ (CDCl₃): 0.9(s, 3H), 0.99(s, 3H), 0.55–1.45(s, 3H), 1.7–2.2(m, 2H), 2.4–2.9(m, 2H), 3.2–3.7(m, 1H), 5.67(br.s, 1H), 7.35–7.7(m, 3H), 7.75–8.0(m, 2H), 9.65(s, 1H) ppm.

(27) ① (dl)-(1β,2α,3β,5β)-7-[3-Phenylsulfonylaminobicyclo[3.1.0]hexan-2-yl]-(5Z)-5-heptenoic acid If-ab (3S*-β)

[Chemical structure diagram showing bicyclic compound with CHO and NHSO₂-phenyl groups (IIf-a(3S*-β)), converted to a compound with COOR₁ chain and NHSO₂-phenyl group]

R₁ = —CH₃ If-aa(3S*-β)

R₁ = H If-ab(3S*-β)

R₁ = Na If-ac(3S*-β)

A mixture of 430 mg (10.8 mmole) of 60% oily sodium hydride in 10 ml of dimethylsulfoxide is allowed to react at 75° C. for 1.5 hours. The resulting solution of sodium methylsulfinylmethide is kept at 12° C., to which 2.71 g (6 mmole) of (4-carboxybutyl)triphenylphosphonium bromide is added, and the mixture is allowed to react at room temperature for 20 minutes. To this mixture is added a solution of the above prepared crude (dl)-(1β,2α,3β,5β)-2-formylmethyl-3-phenylsulfonylaminobicyclo[3.1.0]hexane IIf-a(3S*-β) (1.99 mmole) in 10 ml of dimethylsulfoxide and the mixture is allowed to stand at room temperature for 2 hours. The reaction mixture is poured into a mixture of ethyl acetate and water, and the aqueous layer is acidified with 2N hydrochloric acid and extracted with ethyl acetate. The ethyl acetate layer is washed with a saturated sodium chloride aqueous solution, dried over anhydrous magnesium sulfate, and evaporated. The residue is purified by column chromatography on silica gel with a mixture of benzene-ethyl acetate (4:1) to give 634 mg of the title compound If-ab(3S*-β) as a crude product in 88.6% yield.

NMR: δ (CDCl₃): −0.07–0.37 (m, 2H), 1.00–2.50 (m, 13H), 2.60–3.03 (m, 1H), 5.10 (d, J=9 Hz, 1H), 5.20–5.70 (m, 2H), 7.47–7.68 (m, 3H), 7.83–8.05 (m, 2H), 8.00–9.00 (br.s, 1H) ppm.

IR: νmax (CHCl₃); 3360, 3250, 1705, 1320, 1155 cm⁻¹.

② Methyl (dl)-(1β,2α,3β,5β)-7-[3-phenylsulfonylaminobicyclo[3.1.0]hexan-2-yl]-(5Z)-heptenoate If-aa(3S*-β)

A solution of diazomethane in ether is added to a solution of 634 mg (1.76 mmole) of (dl)-(1β,2α,3β,5β)-7-[3-phenylsulfonylaminobicyclo[3.1.0]hexane-2-yl]-(5Z)-5-heptenoic acid If-ab(3S*-β) in 10 ml of dichloromethane under ice-cooling. The mixture is evaporated and the product is purified by column chromatography on silica gel with a mixture of benzene and ethyl acetate (4:1) to give 548 mg of the titled compound If-aa(3S*-β) in 73.0% yield (calcd. from the compound IIf-a(3S*-β)).

NMR: δ (CDCl₃); −0.14–0.3 (m, 2H), 0.93–2.36 (m, 13H), 2.43–2.96 (m, 1H), 3.61 (s, 3H), 4.46–4.73 (d, J=9 Hz, 1H), 5.2–5.3 (m, 2H), 7.36–7.6 (m, 3H), 7.73–7.93 (m, 2H), ppm.

Ir; νmax (CHCl₃); 3360, 1725, 1325, 1155 cm⁻¹.

[2] Sodium (dl)-(1β,2α,3β,5β)-7-[3-phenylsulfonylaminobicyclo[3.1.0]hexan-2-yl]-(5Z)-5-heptenaoate If-ac(3S*-β)

A solution of 290 mg (0.8 mmole) of (dl)-(1β,2α,3β,5β)-7-[3-phenylsulfonylaminobicyclo[3.1.0]hexan-2-yl]-(5Z)-5-heptenoic acid If-ab(3S*-β) in 8 ml of 0.1N sodium hydroxide aqueous solution is freeze-dried to give 298.8 mg of the titled compound If-ac(3S*-β).

Anal. Calcd. (%) for C₁₉H₂₄O₄NSNa¼H₂O: C, 58.50, H 6.27, N 3.59, S 8.22, Na 5.90, Found (%): C 58.60, H 6.33, N 3.77, S 8.11, Na 5.91.

Examples 2 to 5 are carried out in accordance with the manner of III-1, Example 1 (27).

The results are shown in the Tables 3 to 6, respectively.

TABLE 3

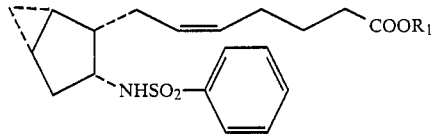

| Compound Number | R₁ | Physical Constants | |
|---|---|---|---|
| I f-aa (3R*-β) | —CH₃ | NMR: δ(CDCl₃): −0.07–0.5(m, 2H), 0.93–1.37(m, 2H), 1.37–2.6(m, 11H), 3.60 (s, 3H), 3.47–3.83(m, 1H), 4.68(d, J = 9 Hz, 1H), 5.1–5.6(m, 2H), 7.4–7.63(m, 3H). 7.7–8.0(m, 2H) ppm, | IR: νmax(CHCl₃): 3360, 1720, 1340, 1155 cm⁻¹. |
| I f-ab (3R*-β) | —H | NMR: δ(CDCl₃); −0.11–0.52(m, 2H), 0.92–2.82(m, 13H), 3.42–3.85(m, 1H), 4.90 (d, J = 8 Hz, 1H), 5.07–5.62(m, 2H), 7.30–7.67(m, 3H), 7.67–8.02(m, 2H) ppm. | IR: νmax(CHCl₃); 3360, 3250, 1750, 1320, 1155 cm⁻¹. |
| I f-ac (3R*-β) | Na | Anal. Calcd. (%) for C₁₉H₂₄O₄NSNa,5/3H₂O; C 54.93; H 6.23; N 3.37; S 7.72; Found (%):C 54.59; H 6.04; N 3.39; S 7.80. | |

TABLE 4

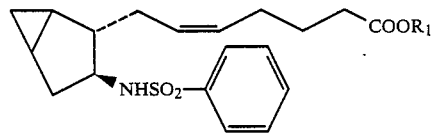

| Compound Number | R₁ | Physical Constants | |
|---|---|---|---|
| I f-aa (3S*-α) | —CH₃ | NMR: δ(CDCl₃); 0.08–0.34(m, 1H), 0.39–0.71(m, 1H), 0.86–1.29(m, 2H), 1.45–2.39(m, 11H), 3.16–3.46(m, 1H), 3.63(s, 3H), 4.64(d, J = 6 Hz, 1H), 5.03–5.49(m, 2H), 7.43–7.66(m, 3H), 7.76–7.99(m, 2H) ppm. | IR: νmax(CHCl₃); 3350, 1720, 1350, 1155 cm⁻¹. |
| I f-ab (3S*-α) | —H | NMR: δ(CDCl₃); 0.08–0.33(m, 1H), 0.36–0.73(m, 1H), 0.74–1.3(m, 2H), 1.3–2.43(m, 11H), 3.13–3.53(m, 1H), 4.92(d, J = 6 Hz, 1H), 5.06–5.50(m, 2H), 7.43–7.66(m, 3H), 7.76–8.01(m, 2H), 8.53–9.66(m, 1H) ppm. | IR: νmax(CHCl₃); 3360, 3250, 1705, 1320, 1160 cm⁻¹. |
| I f-ac (3S*-α) | Na | Anal. Calcd. (%) for C₁₉H₂₄O₄NSNa, 1/4H₂O C 58.50; H 6.27; N 3.59; S 8.22; Na 5.90; Found (%):C 58.40; H 6.32; N 3.81; S 8.21; Na 6.04. | |

TABLE 5

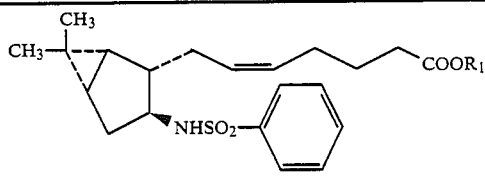

| Compound Number | $R_1$ | Physical Constants | |
|---|---|---|---|
| I f-ba (3S*-β) | —CH₃ | NMR: δ(CDCl₃); 0.85–1.15(m, 2H), 0.88(s, 3H), 1.00(s, 3H), 1.37–2.50(m, 11H), 3.0–3.45(m, 1H), 4.77(d, J = 9 Hz, 1H), 5.2–5.6(m, 2H), 7.43–7.7(m, 3H), 7.8–8.03(m, 2H) ppm. | IR: δmax(CHCl₃); 3350, 1720, 1320, 1155 cm⁻¹. |
| I f-bb (3S*-β) | —H | NMR: δ(CDCl₃); 0.73–1.10(m, 2H), 0.87(s, 3H), 0.99(s, 3H), 1.3–2.3(m, 9H), 2.35(t, J = 6 Hz, 2H), 2.95–3.4(m, 1H), 5.07(d, J = 9 Hz, 1H), 5.2–5.55(m, 2H), 7.39–7.68(m, 3H), 7.77–7.97(m, 2H), 7.9–8.9(m, 1H) ppm. | IR: νmax(CHCl₃); 3350, 3240, 1700, 1315, 1150 cm⁻¹. |
| I f-bc (3S*-β) | Na | Anal. Calcd. (%) for C₂₁H₂₈O₄NSNa, H₂O C 58.45; H 7.01; N 3.25; S 7.43; Na 5.33. Found (%):C 58.74; H 6.93; N 3.45; S 7.80; Na 5.18. | |

TABLE 6

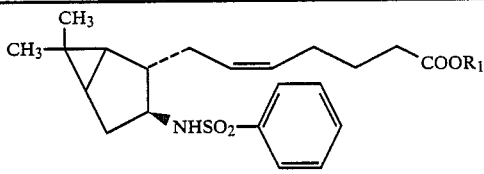

| Compound Number | $R_1$ | Physical Constants | |
|---|---|---|---|
| I f-bb (3S*-α) | —H | NMR: δ(CDCl₃); 0.9(s, 3H), 0.92(s, 3H), 0.6–2.25(m, 11H), 2.34(t, J = 6 Hz, 2H), 3.47(m, 1H), 5.2–5.5(m, 1H), 5.65(d, J = 9 Hz, 1H), 7.35–7.7(m, 3H), 7.8–8.0(m, 2H), 9.09(br.s, 1H) ppm. | IR: νmax(CHCl₃); 3360, 3250, 1705, 1320, 1160 cm⁻¹. |
| I f-bc (3S*-α) | Na | Anal. Calcd. (%) for C₂₁H₂₈O₄NSNa, H₂O C 58.45; H 7.01; N 3.25; S 7.43; Na 5.33; Found (%):C 58.13; H 6.79; N 3.30; S 7.54; Na 5.22. | IR: νmax(CHCl₃); 3250, 1565, 1320, 1160 cm⁻¹. |

III-2

EXAMPLE 6

(1) (dl)-(trans)-2-Azidocyclopent-4-enylethanol triphenylmethyl ether 2(β).

To a cooled solution of 3.83 g (10.3 mmol) of (dl)-(cis)-2-hydroxycyclopent-4-enylethanol triphenylmethyl ether 1b(2R*), prepared in III-1 Example 1, in 50 ml of dichloromethane with ice bath, was added 0.88 ml (11.3 mmol) of methanesulfonyl chloride and 1.72 ml (12.36 mmol) of triethylamine, and the mixture was reacted with ice cooling for 30 min. The product was isolated by dichloromethane extraction. The dichloromethane layer was washed with 2N aqueous hydrochloric acid, saturated aqueous sodium bicarbonate and saturated brine, dried with magnesium sulfate and evaporated. The sample of crude (dl)-(cis)-2-methanesulfonyloxycyclopent-4-enylethanol triphenylmethyl ether thus obtained, was dissolved in 50 ml of N,N-dimethylformamide and 12.05 g (185.4 mmol) of sodium azide, and the mixture was reacted at 75° C. for 5 hr. After cooling, the product was isolated by ethyl acetate extraction. The ethyl acetate layer was washed with saturated brine, dried with magnesium sulfate and evaporated. The product was purified by column silica gel chromatography using benzene-ethyl acetate (9:1) mixture containing 1% triethylamine as an eluent and 3.99 g (98%) of the titled compound 2(β) was obtained.

NMR: δ (CDCl₃); 1.50–1.85 (m, 2H), 2.20–3.00 (m, 3H), 3.15 (t, J=6 Hz), 3.50–3.80 (m, 1H), 5.59 (s, 2H), 7.20–7.60 (m, 15H) ppm.

Ir: $ν_{max}$ (CHCl₃); 2.80 cm⁻¹.

(2) (dl)-(trans)-2-Aminocyclopent-4-Aminocyclopent-4-enylethanol triphenylmethyl ether 3(β).

A solution of 3.99 g (10.1 mmol) of (dl)-(trans)-2-azidocyclopent-4-enylethanol triphenylmethyl ether and 3.54 g (13.5 mmol) of triphenylphosphine and 10 ml of tetrahydrofuran was reacted at room temperature for 15 h. To this solution was added 1 ml of water and the mixture was reacted at 45° C. for 2 hr and then under reflux for 1 hr. After cooling, the product was isolated by ethyl acetate extraction. The ethyl acetate layer was washed with saturated brine, dried with magnesium sulfate and evaporated. The residue was separated by column silica gel chromatography using benzene-ethyl acetate (4:1) mixture as an eluent and 4.67 g of the titled compound 3(β) was obtained. The product was subjected for the next reaction without further purification.

NMR: δ (CDCl₃); 1.31 (s, 2H), 1.57-1.82 (m, 2H), 1.83-2.17 (m, 1H), 2.23-2.80 (m, 2H), 3.00-3.27 (m, 1H), 3.15 (t, J=6 Hz, 2H), 5.55 (s, 2H), 7.03-7.56 (m, 15H) ppm.

IR: ν$_{max}$ (CHCl₃); 2080 cm⁻¹.

(3) (dl)-(trans)-2-Phenylsulfonylaminocyclopent-4-enylethanol triphenylmethyl ether 4(β)

A 3.60 g sample of the crude (dl)-(trans)-2-aminocyclopent-4-enylethanol triphenylmethyl ether 3(β) was dissolved in 15 ml of dichloromethane and cooled with ice-bath, and 1.52 ml (10.97 mmol) of triethylamine and 1.12 ml (8.77 mmol) of benzenesulfonyl chloride was added. After reacting at 0° C. for 30 min, the excess reagent was decomposed by adding diluted aqueous ammonium hydroxide and the product was isolated by dichloromethane extraction. The dichloromethane layer was washed with saturated brine, dried with magnesium sulfate and evaporated. The product was purified by column silica gel chromatography using benzeneethyl acetate (4:1) mixture as an eluent, and 2.16 g (55.2%) of the titled compound 4(β) was obtained.

NMR: δ (CDCl₃); 1.33-1.83 (m, 2H), 1.85-2.20 (m, 1H), 2.33-2.82 (m, 2H), 3.03 (t, J=6 Hz), 3.32-3.67 (m, 1H), 4.76 (d, J=8 Hz, 1H), 5.49 (s, 2H), 7.17-7.57 (m, 18H), 7.70-7.90 (m, 2H) ppm.

IR: ν$_{max}$ (CHCl₃); 3360, 1335, 1320, 1155 cm⁻¹.

(4) (dl)-(trans)-2-phenylsulfonylaminocyclopent-4-enylethanol 5a(β)

A solution of 1.37 g (2.69 mmol) of (dl)-(trans)-2-phenylsulfonylaminocyclopent-4-enylethanol triphenylmethyl ether 4(β) in a mixture of 5 ml of 1N aqueous hydrochloric acid, 10 ml of tetrahydrofuran and 10 ml methanol was reacted at 45° C. for 2 hrs. The solvents were evaporated and the product was isolated by ethyl acetate extraction. The ethyl acetate layer was washed with saturated aqueous sodium bicarbonate and saturated brine, dried with magnesium sulfate and evaporated. The product was purified by column silica gel chromatography using benzene-ethyl acetate (4:1) mixture, and 2.16 g (55.2% from 2(β) of the titled compound 5a(β) was obtained.

NMR: δ (CDCl₃+CD₃OD); 1.40-1.70 (m, 2H), 1.90-2.23 (m, 1H), 2.30-2.80 (m, 2H), 3.50-3.70 (m, 1H), 3.60 (t, J=6 Hz, 2H), 5.59 (s, 2H), 7.43-7.67 (m, 3H), 7.8-8.0 (m, 2H) ppm.

IR: ν$_{max}$ (CHCl₃); 3650-3100, 1340, 1 320, 1155 cm⁻¹.

(5) (dl)-(1α,2α,3β,5α) and (1β,2α,3β,5β)-2-Hydroxyethyl-3-phenylsulfonylamino-6-oxabicyclo[3.1.0]hexane 6(3S*-α) and 6(3S*-β).

A solution of 732 mg (2.74 mmol) of (dl)-trans)-2-phenylsulfonylaminocyclopent-4-enylethanol 5a(β) and 650 mg (3.0 mmol) of 80% 3-chloroperoxybenzoic acid in 10 ml of dichloromethane was reacted at 0° C. for 15 h. The excess reagent was decomposed by addition of 5% aqueous sodium thiosulfate and stirring of the mixture, and the product was isolated by dichloromethane extraction. The dichloromethane layer was washed with saturated aqueous sodium bicarbonate and saturated brine, dried with magnesium sulfate and evaporated. The products were separated by column silica gel chromatography using benzene-ethyl acetate (1:1) mixture as an eluent. From the less polar fraction, 335 mg (43.4%) of (dl)-(1α,2α,3β,5α)-2-hydroxyethyl-3-phenylsulfonylamino-6-oxabicyclo[3.1.0]hexane 6(3S*-α) was obtained. NMR: δ (CDCl₃); 1.00-1.53 (m, 2H), 1.62 (s, 1H), 1.77-2.06 (m, 2H), 2.10-2.43 (m, 1H), 3.30-3.80 (m, 5H), 5.08 (d, J=10 Hz, 1H), 7.43-7.63 (m, 3H), 7.72-7.95 (m, 2H) ppm.

IR: ν$_{max}$ (CHCl₃); 3100-3650, 1345, 11 55 cm⁻¹.

and from the polar fraction 174 mg (22.6%) of (dl)-(1β,2α,3β,5β)-2-hydroxyethyl-3-phenylsulfonylamino-6-oxabicyclo[3,1,0]hexane 6(3S*-β) was obtained. NMR: δ (CDCl₃); 1.23-2.35 (m, 5H), 2.42 (broad s, 1H), 2.80-3.20 (m, 1H), 3.33-3.48 (m, 2H), 3.69 (t, J=6 Hz, 2H), 5.68 (d, J=8 Hz, 1H), 7.47-7.63 (m, 3H), 7.80-7.95 (m, 2H) ppm.

IR: ν$_{max}$ (CHCl₃); 3400-3200, 3360, 13 20, 1155 cm⁻¹.

(6) (dl)-(1α,2α,3β,5α)-2-Formylmethyl-3-phenylsulfonylamino-6-oxabicyclo[3.1.0]hexane IIg-a(3S*-α).

To a cooled solution of 0.105 ml (1.2 mmol) of oxalyl chloride in 20 ml of dichloromethane with dry ice-acetone bath at −78° C., was added 0.19 ml (2.4 mmol) of dimethylsulfoxide, and the mixture was stirred at this temperature for 5 min. To this mixture was added a solution of 271 mg (0.96 mmol) of (dl)-(1α,2α,3β,5α)-2-hydroxyethyl-3-phenylsulfonylamino-6-oxabicyclo[3.1.0]hexane in dichloromethane dropwise. After reacting the mixture at −60° C. for 15 min, 1.67 ml (12 mmol) of triethylamine was added and the temperature of the reaction mixture was allowed to rise to room temperature and reacted at room temperature for additional 1 h. The product was isolated by ethyl acetate extraction. The ethyl acetate layer was washed with water, 2N aqueous hydrochloric acid, saturated aqueous sodium bicarbonate and saturated brine, dried with magnesium sulfate and evaporated. The crude titled compound IIg-a(3S*-α) thus obtained was subjected to the next reaction without further purification.

NMR: δ (CDCl₃); 1.67-2.17 (m, 2H), 2.20-2.67 (m, 3H), 3.30-3.63 (m, 3H), 4.97-5.35 (m, 1H), 7.40-7.67 (m, 3H), 9.62 (s, 1H) ppm.

IR: ν$_{max}$ (CHCl₃); 3360, 2820, 2720, 1 725, 1345, 1160 cm⁻¹.

(7) Preparation of Ig-a(3S*-α)

① (dl)-(1α,2α,3β,5α)-7-[3-Phenylsulfonylamino-6-oxabicyclo[3.1.0]hexan-2-yl]-(5Z)-heptenoic acid Ig-ab(3S*-α)

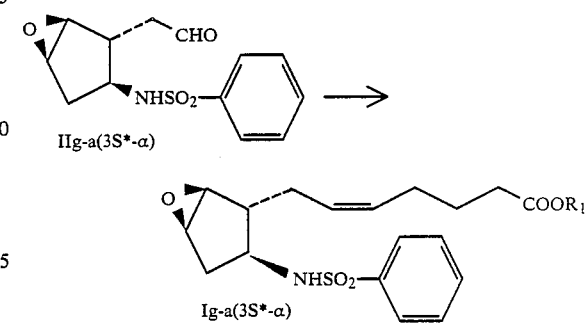

R₁ = H; Ig-ab(3S*-α)

R₁ = CH₃; Ig-aa(3S*-α)

R₁ = Na; Ig-ac(3S*-α)

A suspension of 216 mg (5.6 mmol) of 60% sodium hydride in mineral oil, in 10 ml of dimethylsulfoxide was heated at 70° C. for 2.5 hr. To the solution of sodium methylsulfinylmethide in dimethylsulfoxide at 12° C., was added 1.36 g (3 mmol) of (4-carboxybutyl)triphenylsulfonium bromide and the mixture was stirred at room temperature for 20 min. A solution of 293 mg of the crude (dl)-(1α,2α,3β,5α)-2-formylmethyl-3-phenylsulfonylamino-6-oxabicyclo[3.1.0]hexane in 3 ml of dimethylsulfoxide was added to the reagent solution obtained above, and this mixture was reacted at room temperature for 2 h. Ethyl acetate and water was added to the reaction mixture, and after acidifying the aqueous layer by adding 2N aqueous hydrochloric acid, the product was isolated by ethyl acetate extraction. The ethyl acetate layer was washed with 2N aqueous hydrochloric acid and saturated brine, dried with magnesium sulfate and evaporated. The product was purified by column silica gel chromatography using benzene/ethyl acetate (2:1) mixture as an eluent and 153 mg (42.0%) of the titled compound Ig-ab(3S*-α) was obtained.

NMR: δ (CDCl$_3$); 1.50–2.20 (m, 9H), 2.33 (t, J=6 Hz, 2H), 3.27–3.63 (m, 2H), 4.90–5.60 (m, 3H), 7.40–7.65 (m, 3H), 7.78–7.97 (m, 2H) ppm.

IR: $\nu_{max}$ (CHCl$_3$); 3360, 1705, 1345, 1160 cm$^{-1}$.

② (dl)-(1α,2α,3β,5α)-7-[3-Phenylsulfonylamino-6-oxabicyclo[3.1.0]hexan-2-yl]-(5Z)-5-heptenoic acid methyl ester Ig-aa(3S*-α).

A solution of diazomethane in ether was added to a solution of 153 mg of the crude (dl)-(1α,2α,3β,5α)-7-[3-phenylsulfonylamino-6-oxabicyclo[3.1.0]hexan-2-yl]-(5Z)-5-heptenoic acid in 5 ml of dichloromethane cooled with ice bath. After evaporating the solvents, the product was purified by column silica gel chromatography using benzene-ethyl acetate (2:1) mixture as an eluent and 153 mg (42% from 6(3S*-α)) of the titled compound Ig-aa(3S*-α) was obtained.

NMR: δ (CDCl$_3$); 1.50–2.16 (m, 9H), 2.28 (t, J=6 Hz, 2H), 3.27–3.60 (m, 3H), 3.66 (s, 3H), 5.00–5.60 (m, 3H), 7.47–7.66 (m, 3H), 7.80–7.97 (m, 2H) ppm.

IR: $\nu_{max}$ (CHCl$_3$); 3350, 1720, 1335, 1155, 1088 cm$^{-1}$.

③ (dl)-Sodium (1α,2α,3β,5α)-7-[3-phenylsulfonylamino-6-oxabicyclo[3.1.0]hexan-2-yl]-(5Z)-5-heptenoate Ig-ac(3S*-α).

A sample of 67 mg (0.18 mmol) of (dl)-(1α,2α,3β,5α)-7-[3-benzenesulfonylamino-6-oxabicyclo[3.1.0]hexan-2-yl]-(5Z)-5-heptenoic acid was dissolved in 8 ml of 0.1N aqueous sodium hydroxide and the solution was lyophilized to obtain 69 mg of the titled compound Ig-ac(3S*-α).

Anal. Calcd. (%) for C$_{18}$H$_{22}$O$_4$SNSNa: C, 55.80; H, 5.72; N, 3.62; S, 8.28; Na, 5.93, Found (%): C, 55.63; H, 6.05; N, 3.72; S, 8.50; Na, 5.72.

EXAMPLE 7

The compound 6(3S*-β), prepared in Example 6(5), is treated in accordance with a manner of Example 6(6) and (7) to give the following compounds.

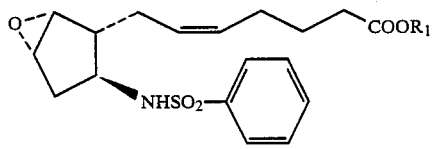

R$_1$; H Ig-ab(3S*-β)
NMR: δ (CDCl$_3$); 1.20–2.40 (m, 9H), 2.33 (t, J=6 Hz, 2H), 2.77–3.18 (m, 1H), 3.34 (s, 2H), 5.25–5.67 (m, 3H), 7.40–7.63 (m, 3H), 7.77–7.95 (m, 2H), 7.60–8.40 (m, 1H) ppm.

IR: $\nu_{max}$ (CHCl$_3$); 3350, 1705, 1325, 1155 cm$^{-1}$.

R$_1$; CH$_3$ Ig-aa(3S*-β).
NMR: δ (CDCl$_3$); 1.23–2.45 (m, 9H), 2.30 (t, J=6 Hz, 2H), 2.80–3.23 (m, 1H), 3.35 (s, 2H), 3.69 (s, 3H), 5.10–5.65 (m, 3H), 7.43–7.70 (m, 3H), 7.80–8.00 (m, 2H) ppm.

IR: $\nu_{max}$ (CHCl$_3$); 3360, 1720, 1320, 1155 cm$^{-1}$.

R$_1$; Na Ig-aa(3S*-β)
Anal. Calcd. (%) for C$_{18}$H$_{22}$O$_4$SNSNa·½H$_2$O: C, 54.50; H, 5.88; N, 5.53; S, 8.09; Na, 5.80. Found (%): C, 54.84; H, 5.91; N, 3.70; S, 7.74; Na, 5.59.

EXAMPLES 8 AND 9

(1) In the same manner as above, the following compounds Ig-a(3R*) are prepared from the compound Ib-a(2S*) [III-1, Example 1, (5)] through the intermediates mentioned below.

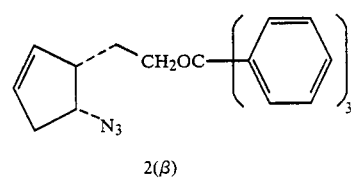

2(β)

NMR: δ (CDCl$_3$); 1.55–2.10 (m, 2H), 2.27–3.40 (m, 3H), 3.18 (t, J=6 Hz, 2H), 3.73–4.10 (m, 1H), 5.40–5.80 (m, 2H), 7.10–7.60 (m, 15H) ppm.

IR: $\nu_{max}$ (CHCl$_3$); 2080 cm$^{-1}$.

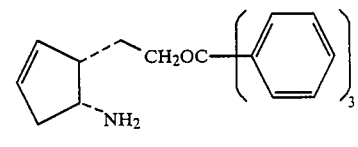

3(α)

NMR: δ (CDCl$_3$); 1.40–2.00 (m, 2H), 2.08–2.20 (m, 1H), 2.40–2.85 (m, 2H), 3.05–3.35 (m, 2H), 3.37–3.70 (m, 1H), 5.40–5.80 (m, 2H), 7.17–7.63 (m, 15H) ppm.

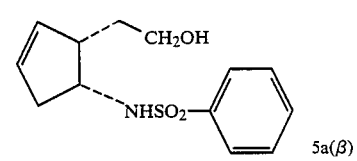

5a(β)

NMR: δ (CDCl$_3$); 1.45–1.90 (m, 2H), 1.92–2.57 (m, 3H), 2.65–3.00 (m, 1H), 3.65 (t, J=6 Hz, 2H), 3.80–4.23 (m, 1H), 5.64 (s, 2H), 5.97 (d, J=9 Hz, 1H), 7.43–7.70 (m, 3H), 7.85–8.10 (m, 2H) ppm.

IR: $\nu_{max}$ (CHCl$_3$); 3650–3100; 3360, 1325, 1155 cm$^{-1}$.

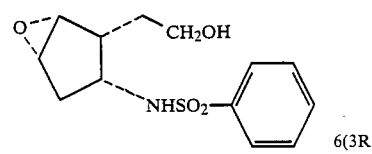

6(3R*-β)

NMR: δ (CDCl$_3$); 1.58–2.05 (m, 5H), 2.20–2.50 (m, 1H), 3.30–3.53 (m, 2H), 3.55–3.0 (m, 1H), 3.75 (s, 3H), 4.92 (d, J=11 Hz, 1H), 7.40–7.63 (m, 3H), 7.83–7.93 (m, 2H) ppm.

IR: νmax (CHCl₃); 3650–3100, 3350, 1330, 1150 cm⁻¹.

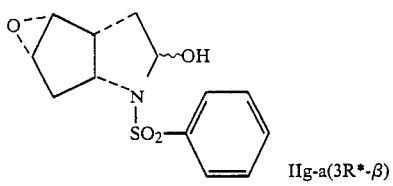

IIg-a(3R*-β)

NMR: δ (CDCl₃); 1.55–2.45 (m, 4H), 2.85–3.15 (m, 1H), 3.30–3.85 (m, 2H), 4.23–4.50 (m, 1H), 4.99 (d, J=12 Hz, 1H), 5.38–5.67 (m, 1H), 7.36–7.65 (m, 3H), 7.75–8.05 (m, 2H) ppm.

IR: νmax (CHCl₃); 3600–3150, 3360, 1325, 1155 cm⁻¹.

(6) (dl)-(1α,5α)-2-Phenylsulfonyl-3-hydroxy-2-azabicyclo[3.3.0]octane 7(α).

A cooled solution of 0.28 ml (3.2 mmol) of oxalyl chloride in 35 ml of dichloromethane with dry ice-actone bath at −78° C. was added 0.45 ml of dimethylsulfoxide and the mixture was stirred at −78° C. for 5 min. To this reagent solution was added a solution of 672 mg (2.51 mmol) of (dl)-cis-3-phenylsulfonylaminocyclopent-4-enylethanol 5a(α) in 5 ml of dichloromethane and the mixture was reacted at −60° C. for 15 min. Triethylamine, 4.2 ml (30 mmol) was added to the reaction mixture and the temperature of the mixture was allowed to rise to room temperature. After stirring the reaction mixture at room temperature for another 1 h, the product was isolated by ethyl acetate extraction.. The ethyl acetate layer was washed with water, 2N aqueous hydrochloric acid, saturated aqueous sodium bicarbonate and saturated brine, dried with magnesium sulfate and evaporated. The product was purified by column silica gel chromatography using benzene-ethyl acetate (2:1) mixture as an eluent and 456 mg (64.0%) of the titled compound 7(α) was obtained.

NMR: δ (CDCl₃); 1.50–2.20 (m, 2H), 2.50–3.00 (m, 2H), 3.15–3.65 (m, 1H), 4.10–4.45 (m, 2H), 5.10–6.40 (m, 3H), 7.35–7.70 (m, 3H), 7.75 8.05 (m, 2H) ppm.

IR: νmax (CHCl₃); 3550, 3200–3450, 13 45, 1155 cm⁻¹.

(7) (dl)-(1α,5α)-2-Phenylsulfonyl-3-hydroxy-6α,7α-epoxy-2-azabicyclo[3.3.0]octane II g-a(3R*-α).

A mixture of 265 mg (1.0 mmol) of (dl)-(1α,5α)-2-phenylsulfonyl-3-hydroxy-2-azabicyclo[3.3.0]octane 7(α) and 258 mg (1.2 mmol) of 80% 4-chloroperoxybenzoic acid in 10 ml of dichloromethane was stirred at room temperature for 5 h. The product was isolated by dichloromethane extraction. The dischloromethane layer was washed with saturated aqueous thiosulfate, 2N aqueous sodium carbonate and saturated brine, dried with magnesium sulfate and evaporated. The product was purified by column silica gel chromatography using benzene-ethyl acetate (2:1) mixture as an eluent and 76 mg (27%) of the titled compound IIg-a(3R*-α) was obtained.

NMR: δ (CDCl₃); 1.5–3.0 (m, 3H), 3.2–3.65 (m, 2H), 3.65–4.0 (m, 1H), 4.5–4.9 (m, 1H), 5.4–5.75 (m, 1H), 7.3–7.65 (m, 3H), 7.75–8.2 (m, 2H) ppm.

IR: νmax (CHCl₃); 3580, 3360, 1350, 1160 cm⁻¹.

(8) Methyl (dl)-(1α,2α,3α,5α)-7-[3-phenylsulfonylamino-6-oxabicyclo[3.1.0.]hexan-2-yl]-(5Z)-5-heptenoate I g-a(3R*-α)

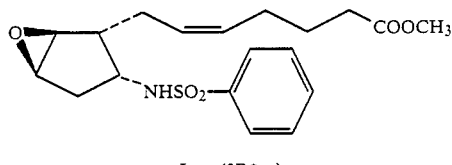

Ig-aa(3R*-α)

NMR: δ (CDCl₃); 1.5–1.9 (m, 4H), 1.9–2.5 (m, 7H), 3.33 (s, 2H), 3.45 –3.8 (m, 1H), 3.67 (s, 3H), 4.82 (d, J=9 Hz, 1H), 5.30–5.56 (m, 2H), 7.35–7.65 (m, 3H), 7.75–8.0 (m, 2H) ppm.

IR: νmax (CHCl₃); 3375, 1728, 1150, 1 095 cm⁻¹.

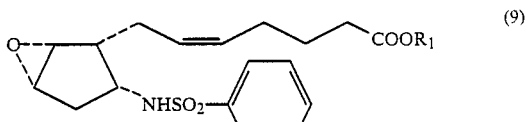

Ig-ab(3R*-β)

R₁; H I g-ab(3R*-β)

NMR: δ (CDCl₃); 1.50–1.90 (m, 4H), 1.93–2.50 (m, 7H), 3.41 (s 2H), 3.55–3.90 (m, 1H), 4.94 (d, J=11 Hz, 1H), 5.35–5.57 (m, 2H), 7.40–7.63 (m, 3H), 7.73–7.97 (m, 2H), 8.80–9.60 (m, 1H) ppm.

IR: νmax (CHCl₃); 3350, 1700, 1340, 1155 cm⁻¹.

R₁; CH₃ I g-aa(3R*-β)

NMR: δ (CDCl₃); 1.50–1.87 (m, 4H), 1.92–2.45 (m, 7H), 3.39 (s, 2H), 3.50–3.87 (m, 1H), 3.66 (s, 3H), 4.70–4.98 (m, 1H), 5.33–5.52 (m, 23H), 7.40–7.60 (m, 3H), 7.75–7.93 (m, 2H) ppm.

IR: νmax (CHCl₃); 3350, 1720, 1335, 1155 cm⁻¹.

R₁; Na I g-ac(3R*-β)

Anal. Calcd. (%) for C₁₈H₂₂O₄₅NSNa.½H₂O: C, 54.50; H, 5.88; N, 3.53; S, 8.09; Na, 5.80. Found (%): C, 54.29; H, 5.87; N, 3.60; S, 8.23; Na, 5.43.

EXAMPLE 10

(dl)-(1β,2α,3β,5β)-7-[Phenylsulfonylamino-6-thiabicyclo[3.1.0]hexan-2-yl]-(5Z)-5-heptanoic acid methyl ester I g-ba(3S*-β).

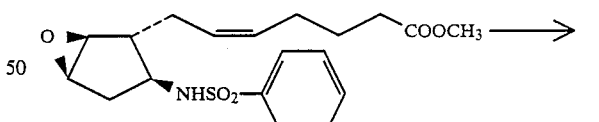

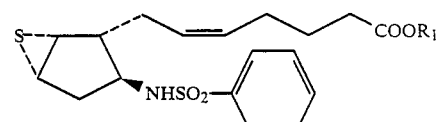

R₁:H Ig-bb(3S*-β)

R₁: CH₃ (Ig-ba(3S*-β)

A two layer mixture of 4.5 g (0.6 mmol) of potassium thiocyanate in 5 ml of water, 6.75 g of phosphoric acid and 15 ml of ether was stirred vigorously and the ether layer was separated. The thiocyanic acid solution in ether thus obtained was cooled with ice bath and a solution of 568.5 mg (1.5 mmol) of (dl)-(1α,2α,3β,5α)-7-[3-phenylsulfonylamino-6-oxabicyclo[3.1.0]hexan-2-yl]-(5Z)-5-heptenoic acid methyl ester I g-aa(3S*-β) was added. After the temperature of the reaction mixture was allowed to rise to room temperature, the mixture was stirred for another 2 h, and the product was isolated by ether extraction. The ether layer was washed with 2N aqueous sodium carbonate and saturated brine, dried with magnesium sulfate and evaporated to obtain the product mixture containing (dl)-[1β(or 2β)-hydroxy-2α(or -1α)-thiocyano-4β-phenylsulfonylaminocyclohexan-3α-yl]-(5Z)-5-heptenoic acid methyl ester. This product was dissolved in 10 ml of dichloromethane and cooled with ice bath and 0.128 ml (1.65 mmol) of methanesulfonyl chloride and 0.314 ml (82.25 mmol) of triethylamine was added to the solution and the mixture was reacted at 0° C. for 30 min. The product was isolated by dichloromethane extraction. The dichloromethane layer was washed with 2N aqueous hydrochloride acid, saturated aqueous sodium bicarbonate and saturated brine, dried with magnesium sulfate and evaporated to obtain the product mixture containing (dl)-7-[1β(or 2β)-methanesulfonyloxy-2α(or -1α)-thiocyano-4β-phenysulfonylaminocyclohexan-3α-yl]-(5Z)-5-heptenoic acid methyl ester. This product mixture was dissolved in 25 ml of dioxane and 5% potassium hydroxide solution in methanol, and the mixture was stirred at room temperature for 12 hr. After evaporating the solvents, ethyl acetate and water was added to the residue and the aqueous layer was acidified with 2N aqueous hydrochloric acid. The product was isolate by ethyl acetate extraction. The ethyl acetate layer was washed with 2N aqueous hydrochloric acid and saturated brine, dried with magnesium sulfate and evporated.

Crystallization of the residue from ether-n-hexane gave 444 mg of the crude (dl)-(1β,2α,3β,5β)-7-[3-phenylsulfonylamino-6-thiabicyclo[3.1.0]hexan-2-yl]-(5Z)-5-heptanoic acid Ig-bb(3S*-β).

NMR: δ (CDCl₃); 2.50–1.30 (m, 11H), 2.90–3,40 (m, 3H), 5,20–5,70 (m, 3H), 7.37–7.70 (m, 3H), 7,60–8,30 (m, 1H), 7,76–8.00 (m, 2H) ppm.

IR: $\nu_{max}$ (CHCl₃); 3360, 3350–3100, 1700, 1320, 1155, 1085 cm⁻¹.

A 370 mg portion of the crude product of the compound I g-bb (3S*-β) was dissolved in dichloromethane and a solution of diazomethane in ether was added with cooling by ice bath. The solvents were evaporated and the product was purified by column silica gel chromatography using benzene-ethyl acetate (2:1) mixture as an eluant to obtain 349 mg (88.3% from I g-aa(3S*-β) of the titled compound I g-ba(3S*-β).

NMR* δ (CDCl₃); 1.50–2.50 (m, 11H), 3.07–3.46 (m, 3H), 3.70 (s, 3H), 506 (d, J=10 Hz, 1H), 5,36–5,57 (m, 2H), 7,43–7.70 (m, 3H), 7.80–7.97 (m, 2H) ppm.

IR: $\nu_{max}$ (CHCl₃); 3360, 1720, 1325, 1155, 1088 cm⁻¹.

EXAMPLE 11

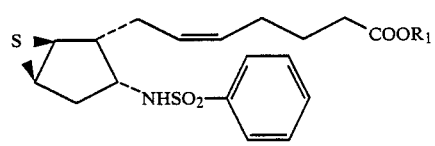

R₁; H I g-bb(3R*-α)

NMR: δ (CDCl₃); 1.5–1.9 (m, 4H), 1.9–2.6 (m, 7H), 3.15 (m, 2H), 3.63–4.05 (m, 1H), 5.25 (d, J=10 Hz), 5.25–5.60 (m, 1H), 7.4–7.7 (m, 3H), 7.8–8.0 (m, 3H) ppm.

IR: $\nu$max (CHCl₃); 3370, 3100–3350, 1700, 1155, 1083 cm⁻¹.

R₁; CH₃ I g-ba(3R*-α)

NMR: δ (CDCl₃); 1.50–2.50 (m, 11H), 3.14 (m, 2H), 3.66 (s, 3H), 3.73–4.10 (m, 1H), 5.14 (d, J=10 Hz), 5.25–5.65 (m, 2H), 7.35–7.63 (m, 3H), 7.77–7.97 (m, 2H) ppm.

IR: $\nu$max (CHCl₃); 3370, 1720, 1155, 1088 cm⁻¹.

EXAMPLE 12

(dl)-(1α,2α,3β,5α)-7-[3-Phenylsulfonylamino-6-thiabicyclo[3.1.0]hexan-2-yl]-(5Z)-5-heptenoic acid methyl ester I g-ba(3S*-α)

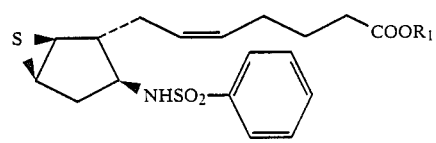

R₁; CH₃

NMR: δ (CDCl₃); 1.50–2.60 (m, 11H), 3.07–3.22 (m, 1H), 3.23–3.40 (m, 1H), 3.45–3.77 (m, 1H), 3.67 (s, 3H), 5.00–5.60 (m, 3H), 7.43–7.65 (m, 3H), 7.77–7.93 (m, 2H), ppm.

IR: $\nu$max (CHCl₃); 3300, 1723, 1155, 1088 cm⁻¹.

IV-1

EXAMPLE 1-1

(1) Methyl 5(Z)-7-[(1S,2S,3S,5R)-3-benzenesulfonamido-6,6-dimethyl-bicyclo[2.1.1]hept-2-yl]-5-heptenoate I h-aa(2S-t-5Z)

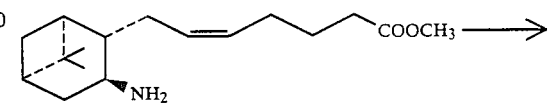

II h-a(2S-t-5Z)

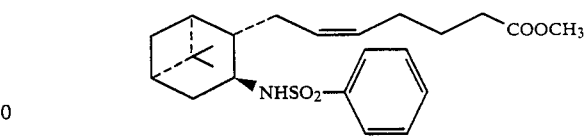

I h-aa(2S-t-5Z)

To a solution of 107 mg of methyl 5(Z)-7-[(1S,2S,3S,5R)-3-amino-6,6-dimethylbicyclo[3.1.1]hept-2-yl]-5-heptenoate II h-a(2S-t-5Z) [Japan Unexamin. Pat. Pub. No. 13551/1983] in 10 ml of dichloromethane is added 1 ml of triethylamine and then 126 mg of benzenesulfonyl chloride added, and the mixture is stirred at room temperature for 1 hour. The reaction mixture is successively washed with 5 ml of 10% hydrochloric acid, 10 ml of 5% sodium carbonate aqueous solution and 10 ml of a saturated sodium chloride aqueous solution, dried over anhydrous sodium sulfate, and evaporated under reduced pressure. The residue is purified by chromatography on a silica gel column and eluted with n-hexaneethyl acetate (10:1→4:1) to give 85 mg of the titled compound I h-aa(2S-t-5Z), of which the physical constants are as follows.

[α]$_D$ 10.5° (21° C., c=1.609, Methanol).

CD(CH$_3$OH): λnm (Δε) 268.5 (0.061), 260 (0.115), 225 (4.48).

$^1$H-NMR (CDCl$_3$): δppm 0.78 (1H, d, J=9 Hz), 0.93 (3H, s), 1.15 (3H, s), 1.43–2.50 (14H), 3.57 (1H, m), 3.67 (3H, s), 4.82 (1H, d, J=8 Hz), 5.26 (2H, m), 7.36~7.63 (3H, m), 7.86~7.97 (2H, m).

IR (Film): νmax 3280, 1737, 1330, 1159 cm$^{-1}$.

MS: m/z 419 (M+).

(2) 5(Z)-7-[(1S,2S,3S,5R)-3-benzenesulfonamido-6,6-dimethylbicyclo[3.1.1]hept-2-yl]-5-heptenoic acid I h-ba(2S-t-5Z) and its salts I h-ca(2S-t-5Z) and I h-da(2S-t-5Z)

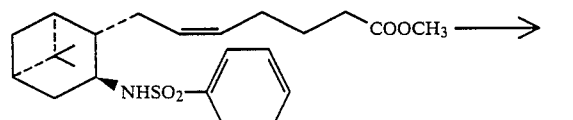

I h-aa(2S-t-5Z)

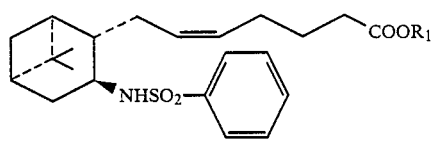

I h-ba(2S-t-5Z) R$_1$ = H
I h-ca(2S-t-5Z) R$_1$ = Na
I h-da(2S-t-5Z) R$_1$ = NH$_2$(C$_6$H$_{10}$)$_2$

① Carboxylic acid I h-ba(2S-t-5Z)

To a solution of 120 mg of the methyl ester I h-aa(2S-t-5Z) (prepared in Example 7) in 15 ml of methanol is added 7 ml of 5% potassium hydroxide aqueous solution and the mixture is stirred at room temperature for 20 hours. The reaction mixture is acidified with 10% hydrochloric acid and extracted with 25 ml of ethyl acetate twice. The extract is washed with 5 ml of saturated sodium chloride aqueous solution twice, dried over anhydrous sodium sulfate, and evaporated under reduced pressure. The residue is purified by chromatography on silica gel and eluted with mixed solvent of n-hexane-ethyl acetate (2:1) to give 109 mg of the titled carboxylic acid I h-ba(2S-t-5Z), of which the physical constants are as follows:

$^1$H-NMR (CDCl$_3$); δppm 0.79 (1H, d, J=10 Hz), 0.92 (3H, s), 1.14 (3H, s), 1.40~2.53 (14H), 3.60 (1H, m), 5.10~5.50 (3H), 7.37~7.70 (3H, m), 7.89~8.00 (2H, m), 8.86 (1H, br.s).

IR (Film): νmax 3270, 1709, 1325, 1156 cm$^{-1}$.

MS: m/z 406 (MH).

② Sodium salt I h-ca(2S-t-5Z)

To a solution of 90 mg of the resulting carboxylic acid I H-ba(2S-t-5Z) in 6 ml of methanol is added 1 ml of 0.21M solution of sodium methoxide in methanol and the mixture is evaporated under reduced pressure. The resulting residue is dissolved in 5 ml of water, to which and active carbon is added, and then the mixture is filtered. The resulting aqueous solution is freezed-dried to give 86 mg of the sodium salt I h-ca(2S-t-5Z), of which the physical constants are as follows.

IR (KBr): νmax 3420, 3275, 1565, 1324, 1157 cm$^{-1}$.

Anal. Calcd. (%) for C$_{22}$H$_{30}$NO$_4$SNa: C 61.81; H 7.07; N, 3.28; S, 7.50; Found (%): C 61.52; H 7.04; N, 3.31; S, 7.43.

③ Dicyclohexylammonium salt I h-da(2S-t-5Z)

To a solution of 6.83 g of the carboxylic acid I h-ba(2S-t-5Z) in 180 ml of ether is dropwise added a solution of 3.06 g of dicyclohexylamine in 20 ml of ether. The resulting colorless crystals are collected by filtration to give 9.8 g of the salt I h-da(2S-t-5Z), of which the physical constants are as follows.

mp 129°–131° C.

$^1$H-NMR (CDCl$_3$): δppm 0.83 (1H, d, J=6 Hz), 0.90 (3H, s), 1.13 (3H, s) 1.00~2.60 (34H), 2.92 (2H, m), 3.47 (1H, m), 5.10~5.50 (2H), 7.18 (1H, br.s), 7.35~7.66 (3H), 7.85~8.11 (2H), 8.71 (2H, br.s).

IR (Kbr): νmax 3435, 1618, 1555, 1324, 1165, 1155 cm$^{-1}$.

Anal. Calcd. (%) for C$_{34}$H$_{54}$N$_2$O$_4$S: C 69.58; H 9.27; N, 4.77; S, 5.46; Found (%): C 69.40; H 9.34; N, 4.66; S, 5.53.

EXAMPLE 1-2

(1) 5(Z)-7-[(1S,2S,3S,5R)-3-benzenesulfonamido-6,6-dimethylbicyclo[3.1.1]hept-2-yl-5-heptenoic acid I h-ba(1S-t-5Z) and its sodium salt I h-ca(2S-t-5Z) and 5(E)-7-[(1S,2S,3S,5R)-3-benzenesulfonamido-6,6-dimethylbicyclo[3.1.1]-hept-2-yl]-5-heptenoic acid I h-ba(2S-t-5E) and its sodium salt I h-ca(2S-t-5E)

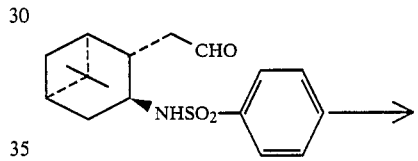

III h-a(2S-t)

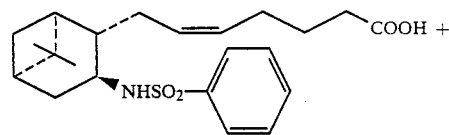

Ih-ba(2S-t-5Z)

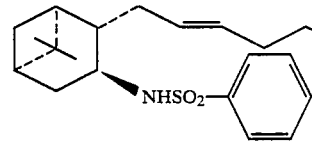

Ih-ba(2S-t-5E)

The starting compound, (1S,2S,3S,5R)-2-formyl-methyl-3-benzenesulfonamido-6,6-dimethylbicyclo[3.1.1]heptane III h-a(2S-t) can be prepared from (1S,2S,3S,5R)-2-[2-tetrahydropyran-2-yloxy)ethyl]-3-amino-6,6-dimethylbicyclo[3.1.1]heptane [The compound described in Jap. Unexamined Pat. Pub. 13551/1983] as a starting material by the following method. The starting amine which is the starting compound of this reaction is first sulfonylated with benzenesulfonyl chloride in the same manner as in IV-1, Example 1-1, (1) to give the sulfonamide derivatives Removal of 2-tetrahydropyranyl gives the hydroxyl compound, which is further oxidized with an oxidizing agent such as dimethyl sulfoxide-oxalyl chloride to give the anhydride III h-a(2S-t) as the starting compound. The titled compound I h-ba(2S-t) is prepared from the above-mentioned aldehyde III h-a(2S-t) as follows.

In 250 ml of tetrahydrofuran is suspended 36 g of 4-carboxybutyltriphenylphosphonium bromide in a stream of nitrogen and 22 g of potassium tert-butoxide is added thereto at room temperature. The mixture is stirred for 1 hour, to which a solution of 9.76 g of the above-mentioned aldehyde III h-a(2S-t) in 130 ml of tetrahydrofuran is dropwise added at room temperature, and then the resulting mixture is stirred for 1 hour. 300 ml of water is added and the reaction mixture is washed with 200 ml of ether. The aqueous layer is acidified with 10% hydrochloric acid and extracted with ether. The extract is washed with a saturated sodium chloride aqueous solution, dried over sodium salfate, and evaporated under reduced pressure. The obtained residue is purified by chromatography on a silica gel column and eluted with ethyl acetate-n-hexane (1:2) to give 8.46 g of the 5Z-olefin I h-ba(2S-t-5Z) as polar fraction and 1.91 g of the titled 5E-olefin I h-ba(2S-t-5E), of which the physical constants are as follows.

$[\alpha]_D$ 5.0° (26° C., c=1.562, Methanol)
IR (Film); $\nu$max 3275, 1709, 1328, 1155, 970 cm$^{-1}$.
NMR (CDCl$_3$): $\delta$ ppm 0.81 (1H, d, J=10 Hz), 0.88 (3H, s), 1.13 (3H, s), 1.41~2.53 (14H), 3.55 (1H, m), 5.02~5.44(3H), 7.35~7.70(3H), 7.86~7.96(2H), 9.20 (1H, br.s).

In the same manner as in Example 3, 600 mg of the abovementioned carboxylic acid I h-ba(2S-t-5E) is treated to give 600 mg of the sodium salt I h-ca(2S-t-5E), of which the physical constant is as follows.

IR (KBr): $\nu$max 3420, 3280, 1562, 1326, 1153, 968 cm$^{-1}$.

IV-2

EXAMPLE 2

(1) ① (1S,2S,3S,5R)-2-[2-(Tetrahydropyran-2-yloxy)-ethyl]-3-methanesulfonyloxy)-6,6-dimethylbicyclo[3.1.1]heptane 14a

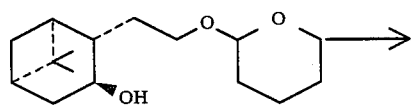

14

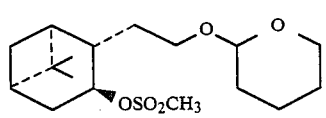

14a

To a solution of 13 g of (1S,2S,3S,5R)-3-hydroxy-6,6-dimethyl-2-[2-(tetrahydrofuran-2-yloxy)-ethyl]bicyclo[3.1.1]heptane 14 [Jap. Unexamined Pat. Pub. No. 13551/1983] in 130 ml of dichloromethane is added 9.9 ml of triethylamine in a stream of nitrogen and then 6.16 g of methanesulfonyl chloride is dropwise added at −20° C., and the resulting mixture is stirred at the same temperature for 15 minutes. The reaction mixture is diluted with ether, washed with water, a saturated aqueous solution of ammonium chloride and a saturated sodium chloride aqueous solution successively, dried over sodium sulfate, and evaporated under reduced pressure to give 16 g of the titled compound 14a, of which the physical constant is as follows.

$^1$H-NMR (CDCl$_3$) $\delta$ ppm 0.92 (3H, s), 1.12 (1H, d, J=10 Hz), 1.22 (3H, s), 1.36~2.86 (14H), 3.03 (3H, s), 3.30~3.63 (2H, m), 3.67~3.83 (2H, m), 4.57 (1H, m), 5.06 (1H, m).

② (1S,2S,3R,5R)-2-[2-(Tetrahydropryan-2-yloxy)ethyl]-3-azido-6,6-dimethylbicyclo[3.1.1]heptane 15

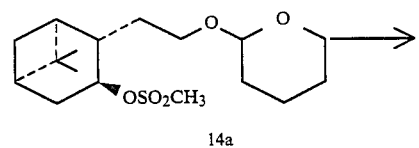

14a

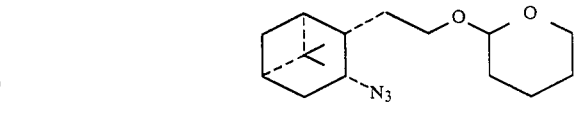

15

To a solution of 16 g of the above-mentioned methanesulfonyl compound 14a in 60 ml of hexamethylphosphoramide is added 4.73 g of sodiium azide in stream of nitrogen and the mixture is stirred at 50° C. for 2 hours. 200 ml of ether is added and the reaction mixture is washed with water and a saturated sodium chloride aqueous solution, dried over sodium sulfate, and evaporated under reduced pressure. The residue is purified by chromatography on a silica gel column and eluted with n-hexane-ethyl acetate (20:1) to give 8.64 g of the titled compound 15, of which the physical constant is as follows.

$^1$H-NMR (CDCl$_3$): $\delta$ ppm 0.96 (3H, s), 1.12 (1H, d, J=10 Hz), 1.16 (3H, s), 1.36~2.68 (11H), 3.21~3.97 (4H), 4.22 (1H, td, J=10, 6 Hz), 4.54 (1H, m).

③ (1S,2S,3R,5R)-2-[2-(Tetrahydropyran-2-yloxy)-ethyl]-3-amino-6,6-dimethylbicyclo[3.1.1]heptane 16

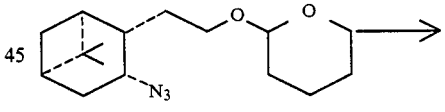

15

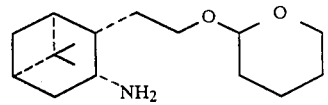

16

To a solution of 8.64 g of the above-mentioned azide compound 15 in 300 ml of ether is portionwise added 1.2 g of lithium aluminium hydride and the mixture is refluxed under heating for 1 hour. To the reaction mixture is added 10 g of ice and then added 300 ml of 10% aqueous solution of sodium hydroxide. The resulting mixture is shaken well and then the ether layer is collected. The aqueous layer is extracted with ether again. The combined ether layers are washed with water, dried over sodium sulfate, and evaporated under reduced pressure to give 7.56 g of the titled compound 16, of which the physical constant is as follows.

¹H-NMR (CDCl₃): δ ppm 0.93 (3H, s), 1.16 (3H, s), 1.28 (1H, d, J=9 Hz), 1.30~2.47 (16H), 3.16~3.97 (5H), 4.56 (1H, m).

(2) ① (+)-(1S,2S,3R,5R)-2-[2-(Tetrahydropyran-2-yloxy)ethyl]-3-(trifluoroacetylamino)-6,6-dimethylbicyclo[3.1.1]heptane 17a

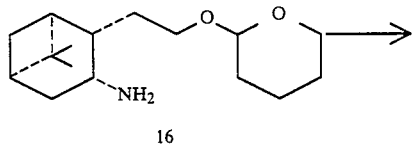

16

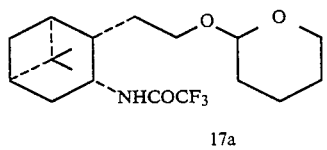

17a

In an atmoshere of nitrogen, 23 ml of pyridine is added to a solution of 7.56 g of the above-mentioned amino compound 16 in 200 ml of dichloromethane at 0° C. and then 7.44 g of trifluoroacetic anhydride is dropwise added slowly. The mixture is stirred for 15 minutes. Ether is added and the resulting mixture is washed with water and a saturated sodium chloride aqueous solution, dried over sodium sulfate, and evaporated under reduced pressure. The residue is purified by chromatography on a silica gel column and eluted with n-hexane-ethyl acetate (9:1) to give 9.9 g of the titled compound 17a of which the physical constants are as follows.

[α]_D +63.8° (25° C., c=2.241, Methanol).
¹H-NMR (CDCl₃): δ ppm 0.97 (3H, s), 1.21 (3H, s), 1.38 (1H, d, J=9 Hz), 1.40~2.78 (14H), 3.13~4.00 (4H), 4.45~4.93 (2H), 6.62 (1H, br.s).
IR (Film): νmax 3310, 1697, 1554 cm⁻¹.
MS: m/z 364 (MH).
Anal. Calcd. (%) for C₁₈H₂₈NO₃F₃: C, 59.49; H, 7.77; N, 3.85; F, 15.68; Found (%): C, 59.30; H, 7.84; N, 3.60; F, 15.59.

② (+)-1S,2S,3R,5R)-2-(2-Hydroxy)ethyl-3-(trifluoroacetylamino-6,6-dimethylbicyclo[3.1.1]heptane 18a

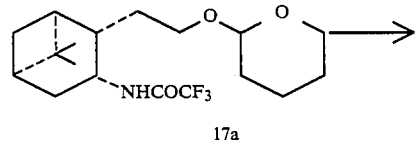

17a

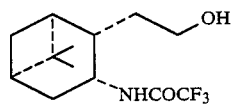

18a

To a solution of 9.7 g of the above-mentioned tetrahydropyran-2-yloxy compound 17a in 270 ml of methanol is added 115 mg of p-toluensulfonic acid and the mixture is stirred at room temperature for 2 hours, and then 0.5 ml of triethylamine is added thereto. The resulting mixture is evaporated under reduced pressure, the residue is dissolved in chloroform washed with water and a saturated sodium chloride aqueous solution, dried over sodium sulfate, and evaporated under reduced pressure.

The residue is crystallized from chloroform-hexane to give 6.62 g of the titled compound 18a as needles, of which the physical constants are as follows. Mp 143°-144° C.

[α]_D +69.3° (25° C., c=2.639, Methanol).
¹H-NMR (CDCl₃): δ ppm 1.95 (3H, s), 2.21 (3H, s), 1.38 (1H, d, J=10 Hz), 1.50-2.85 (9H), 3.61 (2H, m), 4.67 (1H, m), 6.25 (1H, br.s)
IR (KBr): νmax 3450, 3220, 3080, 1695, 1566 cm⁻¹.
M m/z: 280 (MH).
Anal. Calcd. (%) for C₁₃H₂₀NO₂F₃: C, 55.90; H, 7.22; N, 5.02; F, 20.41; Found (%): C, 56.22; H, 7.29; N, 4.99; F, 20.34.

(3) (−)-(2RS,3aS,4S,6R,7aR)-2-Hydroxy-5,5-dimethyl-1-trifluoroacetyl-4,6-methano-octahydroindole 19a

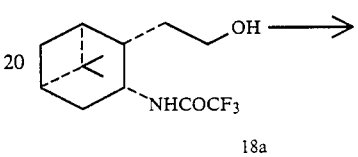

18a

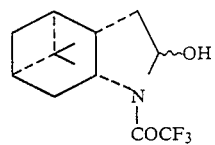

19a

In an atmosphere of nitrogen, 3.4 ml of dimethylsulfoxide in 5 ml of dichloromethane is dropwise slowly added to a solution of 2 ml of oxalyl chloride in 25 ml of dichloromethane at −50° C. and the mixture is stirred at the same temperature for 2 minutes. To the above mixture is added 2.79 g of the above-mentioned alcohol 18a in a mixture of 20 ml of dichloromethane and 2 ml of dimethylsulfoxide at −50° C. and the resulting mixture is stirred at −15° C. for 20 minutes, then cooled to −50° C. again, and 10 ml of triethylamine is added thereto. After stirred for 5 minutes, the mixture is warmed up to room temperature, then added 50 ml of water thereto. This is extracted with a mixture of ether and ethyl acetate (1:1) and the extract is washed with water, dried over sodium sulfate, and evaporated under reduced pressure. The extract is washed with water, dried over sodium sulfate, evaporated under reduced pressure. The residue is purified by chromatography on a silica gel column and eluted with dichloromethane-hexane (10:1→5:1). The eluate is recrystallized from dichloromethane and hexane to give 1.9 g of the titled compound 19a, of which the physical contents are as follows.

Mp. 90°-91° C.
[α]_D 63.8° (25° C., c=1.208, Methanol) (with mutarotation; the data one hour after the dissolution).
¹H-NMR (CDCl₃): δ ppm (0.89 (3H, s), 1.15 (1H, d, J=10 Hz), 1.21 (3H, s), 1.60~3.60 (9H), 4.23~4.80 (1H, m), 5.75~6.10 (1H, m).
IR (KBr): νmax 3520, 1672 cm⁻¹.
MS: m/z 277 (M+).
Anal. Calcd. (%) for C₁₃H₁₈NO₂F₃: C, 56.31; H, 6.54; N, 5.05; F, 20.55; Found (%): C, 56.25; H, 6.53; N, 5.14; F, 20.73.

(4) ① (+)-7-[(1S,2S,3R,5S)-3-(Tri-fluoroacetylamino)-6,6-dimethylbicyclo[3.1.1]hept-2-yl]-5-heptenoic acid II h-b(2S-c)

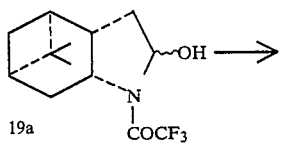

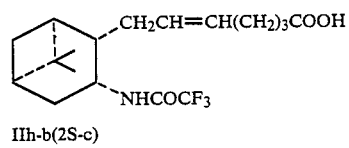

Procedure A

To a suspension of 6.785 g of 4-carboxylbutyltri-phenylphosphonium bromide in 60 ml of tetrahydrofuran is added 4.117 g of potassium tert-butoxide at room temperature and the mixture is stirred for 30 minutes, and then 1.697 g of the above aldehyde equivalent 19a in 50 ml of tetrahydrofuran is dropwise added thereto at room temperature. The resulting mixture is stirred at the same temperature for 1 hour, to which then 100 ml of water is added, and washed with ether. The ether layer is extracted with 10% aqueous solution of sodium carbonate and the combined aqueous layers are acidified with 10% hydrochloric acid and extracted with ether. The organic layer is washed with water, dried over sodium sulfate, and evaporated under reduced pressure. The residue is purified by chromatography on a silica gel column using n-hexane-ethyl acetate (4:1→2:1) as eluent to give 2.045 g of the titled compound II h-b(2S-c) as a mixture of the Z-isomer and the E-isomer. The physical constants are as follows.

$[\alpha]_D$ +92.0° (25° C., c=1.876, Methanol).

NMR (CDCl$_3$): δ ppm 0.97 (3H, s), 1.20 (3H, s), 1.32 (1H, d, J=10 Hz), 1.47~2.80 (14H), 4.72 (1H, m), 5.33 (2H, m), 6.38 (1H, br.d, J=9 Hz), 9.67 (1H, br.s).

IR (Film): νmax 3300, 3100, 1705, 1558 cm$^{-1}$.

MS: m/z 361 (M+).

Procedure B

A suspension of 2.4 g of sodium hydride (content 50%) in 50 ml of dimethylsulfoxide is stirred at 70° C. for 1.5 hours and then a solution of 11.08 g of 4-carboxybutyltriphenylphosphonium bromide in 25 ml of methylsulfoxide is dropwise added thereto at room temperature. The mixture is stirred at the same temperature for 15 minutes, to which a solution of 1.664 g of the aldehyde equivalent 19a in 20 ml of dimethylsulfoxide is dropwise added, and then the resulting mixture is stirred at room temperature for 1 hour. 10 g of ice is added and further 100 ml of water added, and the mixture is washed with ether. The aqueous layer is acidified with 10% hydrochloric acid and extracted with 50 ml ether twice. The extract is washed with a saturated sodium chloride aqueous solution, dried over sodium sulfate, and evaporated under reduced pressure. The residue is purified by chromatography on a silica gel column using n-hexane-ethyl acetate (4:1) as an eluent to give 2.107 g of the titled compound, the Z-isomer II h-b(2S-c-5Z), of which the physical constants are as follows.

$[\alpha]_D$ +94.0° (25° C., c=0.957, Methanol).

$^1$H-NMR (CDCl$_3$): δ ppm 0.97 (3H, s), 1.20 (3H, s), 1.32 (1H, d, J=10 Hz), 1.46~2.75 (14H), 4.70 (1H, m), 5.30 (2H, m), 6.31 (1H, br.d, J=7 Hz), 7.20 (1H, br.s).

IR (Film): νmax 3300, 3100, 1705, 1558 cm$^{-1}$.

② Methyl (+)-7-[(1S,2S,3R,5R)-3-amino-6,6-dimethylbicyclo[3.1.1]hept-2-yl]-5-heptenoate II h-a(2S-c)

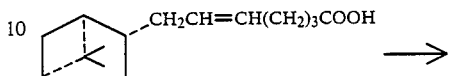

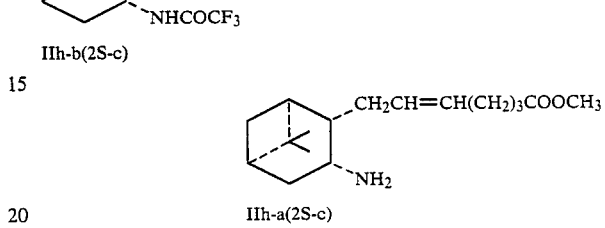

To 1.995 g of the carboxylic acid prepared in the procedure A is added 10% aqueous solution of potassium hydroxide and the mixture is heated under refluxing for 2 hours. The reaction mixture is cooled to room temperature, neutralized with acetic acid, and evaporated under reduced pressure. The residue is dissolved in 40 ml of methanol, then the insoluble material is removed by filtration, and the filtrate is evaporated under reduced pressure again. The residue is dissolved in 40 ml of methanol again and the insoluble material is removed by filtration. An excess of diazomethane/ether solution is added to the filtrate at 0° C. The reaction mixture is evaporated under reduced pressure and the resulting residue is purified by chromatography on a silical gel column using chloroform/methanol (10:1) as an eluent to give 1.06 g of the titled compound II h-a(2S-c) as a mixture of the Z-isomer and E-isomer, of which the physcal constant is as follows.

$^1$H-NMR (CDCl$_3$): δ ppm 0.96 (3/2H, s), 1.0 (3/2H, s), 1.15 (3H, s), 1.23 (1H, d, J=10 Hz), 1.40~2.62 (16H), 3.66 (3H, s), 3.40~3.90 (1H, m), 5.38 (2H, m).

The compound II h-b(2S-s-5Z) is treated in the same manner as to give the titled compound of the Z-form II h-a(2S-c-5Z).

$^1$H-NMR (CDCl$_3$): δ ppm 0.99 (3H, s), 1.16 (3H, s), 1.22 (1H, d, J=10 Hz), 1.40~2.65 (16H), 3.5~3.9 (1H), 3.66 (3H, s), 5.36 (2H, m).

(5) ① Methyl (+)-7-[(1S,2S,3R,5R)-3-benzenesulfonamido-6,6-dimethylbicyclo[3.1.1]hept-2-yl]-5-heptenoate I h-aa(2S-c)

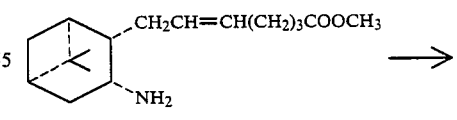

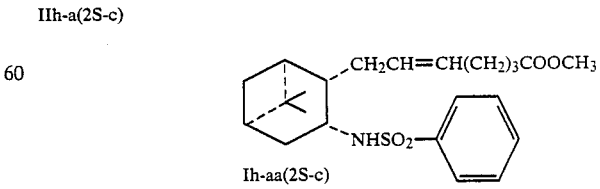

In the same manner as in Example 7, 1.06 g of the amino compound II h-a(2S-c) is treated to give 1.36 g of the titled compound I h-aa(2S-c) as a mixture of the Z-isomer and E-isomer, of the which the physical constants are as follows.

[α]$_D$ +52.0° (25° C., c=2.521, Methanol).

$^1$H-NMR (CDCl$_3$): δ ppm 0.90 (3/2H, s), 0.92 (3/2H, s), 1.12 (3H, s), 1.15 (1H, d, J=10 Hz), 1.45~2.53 (14H), 3.67 (3H, s), 4.05 (1H, m), 4.80 (1H, m), 5.27 (2H, m), 7.40~7.70 (3H, m), 7.87~7.97 (2H, m).

IR (Film): νmax 3285, 1737, 1322 cm$^{-1}$.

MS: m/z 419 (M$^+$)

CD(Methanol): λnm(Δε)269(+0.300), 262(+0.390), 257(+0.358), 221(+4.63).

Anal. Calcd. (%) for C$_{23}$H$_{33}$NO$_4$S: C, 65.84; H, 7.93; N, 3.34; S, 7.64; Found (%): C, 65.42; H, 7.91; N, 3.36; S, 7.52.

The compound II h-a(2S-c-5Z) is treated in the same manner to give the titled compound of the Z-form I h-aa(2S-c-5Z).

[α]$_D$ +48.2° (25° C., c=1.826, Methanol).

NMR (CDCl$_3$): δ ppm 0.93 (3H, s), 1.13 (3H, s), 1.15 (1H, d, J=10 Hz), 1.43~2.53 (14H), 3.66 (3H, s), 4.02 (1H, m), 4.92 (1H, d, J=9 Hz), 5.26 (2H, m), 7.37~7.68(3H), 7.85~7.96, (2H).

② (+)-7-[(1S,2S,3R,5R)-3-Benzenesulfonamido-6,6-dimethylbicyclo[3.1.1]hept-2-yl]-5-heptenoic acid I h-ba(2S-c) and its sodium salt I h-ca(2S-c)

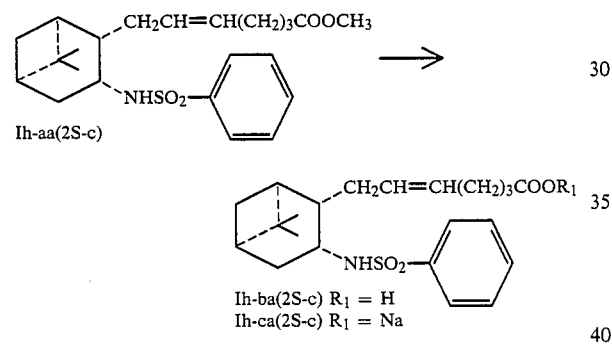

In the same manner as in IV-1 Example 1-1(2), 1.237 g of the methyl ester I h-aa(2S-c) is treated to give the titled carboxylic acid I h-ba(2S-c) as a mixture of the Z-isomer and E-isomer, of which the physical constants are as follows.

[α]$_D$ +51.0° (25° C., c=2.524, Methanol).

$^1$H-NMR (CDCl$_3$): δ ppm 0.92 (3H, s), 1.12 (3H, s), 1.15 (1H, d, J=10 Hz), 1.45~2.57 (14H), 4.02 (1H, m), 5.00~5.40 (3H, m), 7.34~7.96 (3H, m), 7.84~7.95 (2H, m), 8.36 (1H, br.s)

IR(Film): ν max 3285, 1708, 1320, 1160 cm$^{-1}$.

The compound I h-aa(2S-c-5Z) is treated in the same manner to give the titled compound of the Z-form I h-ba(2S-c-5Z).

[α]$_D$ +46.0° (25° C., c=1.620, Methanol).

$^1$H-NMR (CDCl$_3$): δ ppm 0.92 (3H, s), 1.11 (3H, s), 1.15 (1H, d, J=10 Hz), 1.43~2.53 (14H), 4.03 (1H, m), 5.06~5.48(3H, m), 7.35~7.67(3H), 7.84~7.96(2H, m), 8.50 (1H, br.s).

MS: m/z 4.05(M$^+$).

IR (Film): ν max 3285, 1708, 1320, 1160 cm$^{-1}$.

The above carboxylic acid I h-ba(2S-c) or I h-ba(2S-c-5Z) is treated in the manner of IV-1, Example 1-1 (2), to give the sodium salt I h-ca(2S-c) or the sodium salt I h-ca(2S-c-5Z), of which the physical constants are as follows, respectively.

IR (KBr): ν max 3420, 3280, 1560, 1320, 1160 cm$^{-1}$.

Anal. Calcd. (%) for C$_{22}$H$_{30}$NO$_4$SNa: C, 61.81; H, 7.07; N, 3.28; S, 7.50; Found (%): C, 61.17; H, 6.89; N, 3.33; S, 7.49.

IV-3

EXAMPLE 3

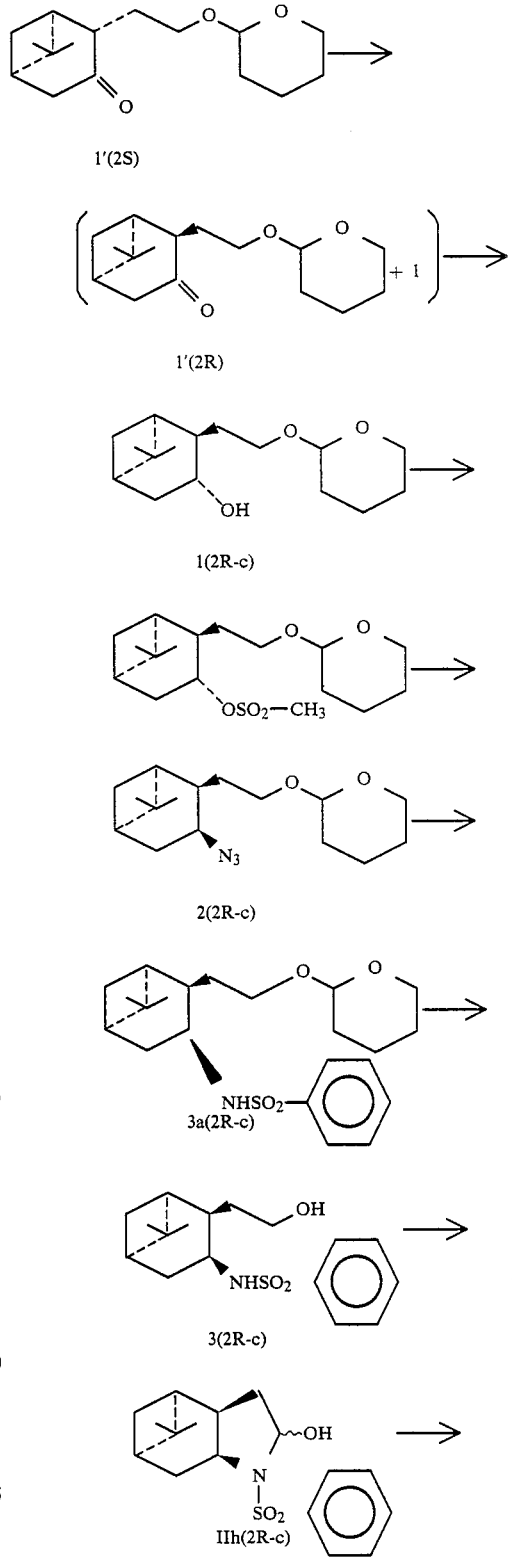

-continued

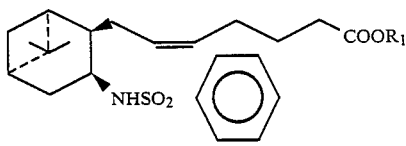

Ih(2R-c)
Ih-aa(2R-c); R₁ = CH₃
Ih-ab(2R-c); R₁ = H
Ih-ac(2R-c); R₁ = Na (1S,2R,3S,5R)-3-Hydroxy-6,6-dimethyl-2-2-[2-tetrahydropyran-2-yloxy)-ethyl]-bicyclo[3.1.1]heptane 1(2R-c)

(1S,2R,5R)-6,6-Dimethyl-3-keto-2-[2-(tetrahydropyran-2-yloxy)ethyl]-bicyclo[3.1.1]heptane [Japan Unexamin. Pat. Pub. No. 13551/1983] (15.4 g) was dissolved in a solution of sodium methoxide (1.11M, 160 ml) at room temperature. The solution was stirred at room temperature for 2 h. The nmr spectrum showed to be a (ca 11:1) mixture of the epimerized ketone 1'(2R) and 1'(2S). The reduction of the mixture was carried out with sodium borohydride according to the method used to the reduction of the ketone 1. The residue was chromatographed on silica gel in hexaneethyl acetate (10:1), 90.3% Yield. nmr δ ppm(CDCl₃) 0.92 (3H, s), 1.19 (3H, s), 1.25 (1H, d, J=10 Hz), 1.35-2.53 (14H), 3.35-4.15 (6H), 4.63 (1H, m).

In the same manner as mentioned in IV-2 Example 2, the following compound Ih(2R-c) is prepared through the intermediates mentioned below.

(1S,2R,3R,5R)-2-[2-(Tetrahydropyran-2-yl-oxy)ethyl]-3-(methanesulfonyloxy)-6,6-dimethylbicyclo[3.1.1]heptane:

Yield 97.7%. nmr δ ppm(CDCl₃) 0.91 (3H, s), 1.22 (3H,s), 1.27 (1H, d, J=10 Hz), 1.37-2.73 (14H), 3.03 (3H, s), 3.25-4.00 (4H), 4.48-4.88 (2H).

(1S,2R,3S,5R)-2-[2-(Tetrahydropyran-2-yloxy)ethyl]-3-azido-6,6-dimethylbicyclo[3.1.1]-heptane:

Yield 83.2%, nmr δ ppm (CDCl₃) 0.79 (3H, s), 1.21 (3H, s), 1.34-2.60 (15H), 3.24-4.05 (3H), 4.55 (1H, m). ir $\nu_{max}$ (film) 2200 cm⁻¹.

(1S,2R,3S,5R)-2-[2-(Tetrahydropyran-2-yloxy)ethyl]-3-benzenesulfonamido-6,6-dimethylbicyclo[3.1.1]heptane:

Yield 76.3%. mp 152°-4° C. $[\alpha]_D^{25}$ −48.9 (c 0.791, Methanol), nmr δ ppm(CDCl₃) 0.76 (3H, s), 1.01 and 1.04 (each ½H, d, J=10 Hz), 1.30-2.70 (14H), 3.15-4.03 (5H), 4.51 (1H, br.s), 5.14 and 5.28 (each ½H, d, J=9 Hz), 7.34-7.68 (3H), 7.80-8.00 (2H). IR νmax (KBr) 3275, 1325, 1312, 1168 cm⁻¹.

Anal. calcd. for C₂₂H₃₃NO₄S: C, 64.83; H, 8.16; N, 3.44; S, 7.87.

(1S,2R,3S,5R)-2-(2-Hydroxy)ethyl-3-benzenesulfonamido-6,6-dimethylbicyclo[3.1.1]heptane Yield 89.3%. mp 129°-131° C., $[\alpha]_D^{25}$ (c 1.041, Methanol), nmr δ ppm (CDCl₃) 0.76 (3H, s), 1.07 (1H, d, J=10 Hz), 2.15 (3H, s), 1.30-2.66 (9H), 3.45-3.96 (3H), 5.68 (1H, d, J=9 Hz), 7.35-7.67 (3H), 7.86-7.97 (2H). IR ν max (KBr) 3460, 3110, 1324, 1306, 1156 cm⁻¹.

Anal. calcd. for C₁₇H₂₅NO₃S: C, 63.13; H, 7.79; N, 4.33; S, 9.91 Found: C, 62.97; H, 7.69; N, 4.22; S, 9.78.

(+)-(2RS,3aR,4S,6R,7aS)-2-Hydroxy-5,5-dimethyl-1-benzenesulfonyl-4,6-methanoocta-hydroindole:

Yield 78.1%. $[\alpha]_D^{24}$ +51.4 (c 3.371, Methanol), nmr δ ppm(CDCl₃) 0.77 and 0.83 (3H, eachs), 1.06 (1H, d, J=9 Hz), 1.18 (3H, s), 1.50-4.30 4.30 (10H), 5.30 and 5.59 (1H, each m), 7.38-7.70 (3H), 7.77-8.00 (2H). ir: ν max (CHCl₃) 3570, 1348, 1329, 1318, 1310, 1160, 1152 cm⁻¹.

(−)-5(Z)-7-[(1S,2R,3S,5R)-3-benzenesulfonamido-6,6-dimethylbicyclo[3.1.1]hept-2-yl]-5-heptenoic acid and its salt:

Yield 82.0%. $[\alpha]_D^{23}$ −31.3 (C 3.452, Methanol). CD(Methanol); λ nm (Δε): 269 (−0.236), 262.5 (−0.312), 255.5 (−0.321), 223 (−4.24). nmr: δ ppm(CDCl₃) 0.73 (3H, s), 1.02 (1H, d, J=10 Hz), 1.14 (3H, s), 1.33-2.60 (14H), 3.83 (1H, m), 3.12-3.51 (3H), 7.37-7.73 (3H), 7.87-7.98 (2H), 8.86 (1H, br.s). IR: νmax (CHCl₃); 3525, 3400, 3280, 1721, 1352, 1330, 1310, 1161, 1095 cm⁻¹.

Dicyclohexylamine salt: mp 122-124, $[\alpha]_D^{25}$ −17.6 (C 1.051, Methanol). nmr; δ ppm (CDCl₃); 0.73 (3H, s), 1.14 (3H, s), 0.88-2.43 (36H), 2.70-3.13 (2H), 3.78 (1H, br.s), 5.03-5.56 (2H), 5.85 (1H, br.d, J=6 Hz), 7.36-7.67 (3H), 7.77-8.03 (2H), 8.24 (1H, br.s). ir νmax (KBr) 3440, 3180, 3080, 1624, 1553, 1310, 1154, 1096 cm⁻¹.

Anal. Calcd. for C₃₄H₅₄N₂O₄: C, 69.58; H, 9.27; N, 4.77; S, 5.46 Found: C, 69.55; H, 9.21; N, 4.63; S, 5.29.

Sodium salt: IR ν max (KBr) 1560, 1327, 1309, 1160, 1093 cm⁻¹.

Anal. Calcd. for C₂₂H₃₀NO₄SNa: C, 61.81; H, 7.07; N, 3.28; S, 7.50. Found: C, 61.50; H, 7.03; N, 3.37; S, 7.47.

EXAMPLE 4

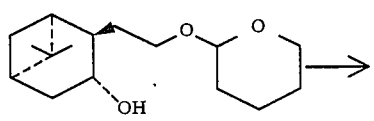

1(2R-c)

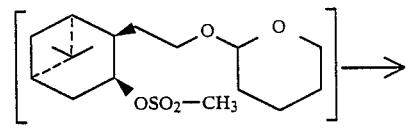

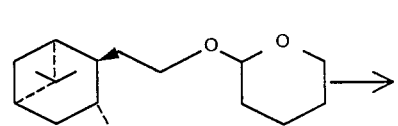

3a(2R-t)

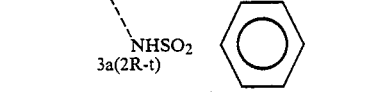

3(2R-t)

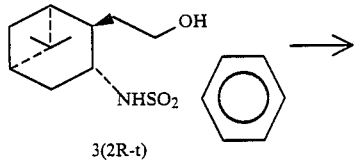

3(2R-t)

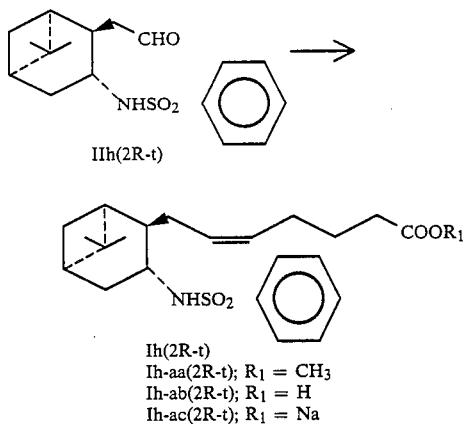

Ih(2R-t)
Ih-aa(2R-t); $R_1 = CH_3$
Ih-ab(2R-t); $R_1 = H$
Ih-ac(2R-t); $R_1 = Na$ (1S,2R,3R,5R)-2-(2-(Tetrahydropyran-2-yloxy)-ethyl)-3-azido-6,6-dimethylbicyclo[3.1.1]heptane 2(2R-t)

Diethyl azadicarboxylate (20 g) was added dropwise to a suspension of the alcohol 1(2R-c) (6.11 g), triphenylphosphin (30 g) and zinc dimethanesulfonate (5.83 g) in benzene (350 ml) at room temperature under nitrogen. The mixture was stirred at room temperature for 3 h, washed with water, dried over anhydrous sodium sulfate and concentrated under reduced pressure. The residue was purified by flash chromatography on silica gel in hexane ethyl acetate (5:1) to give the crude mesylate (6.7 g). The mesylate was treated with sodium azide by the same procedure cited for the preparation of 15 (IV-2, Example 2 (2)), 2.05 g, 31.3%. nmr δ (CDCl$_3$) 0.86 (3H, s), 1.21 (3H, s), 1.28 (1H, d, J=10 Hz), 1.40–2.50 (14H), 3.22–4.00 (5H), 4.57 (1H, m).

In the same manner as mentioned in IV-2, Example 2, the compound Ih(2R-t) is prepared through the intermediates mentioned below:

(−)-(1S,2R,3R,5R)-2-[2-(Tetrahydropyran-2-yloxy)ethyl]-3-benzenesulfonamido-6,6-dimethylbicyclo[3.1.1]heptane:

Yield 85.6%. mp 119-121. $[\alpha]_D^{25}$ −26.3 (c 0.883, Methanol). nmr δ ppm (CDCl$_3$) 0.80 (3H, s), 1.13 (3H, s), 1.20 (1H, d, J=10 Hz), 1.35–2.30 (14H), 2.90–4.10 (5H), 4.40–4.60 (1H), 5.03 and 5.21 (each ½H, d, J=6 Hz), 7.35–7.68 (3H), 7.86–7.97 (2H). IR ν max (KBr) 3270, 1322, 1168 cm$^{-1}$.

Anal. Calcd. for C$_{22}$H$_{33}$NO$_4$S: C, 64.83; H, 8.16; N, 3.44; S, 7.87 Found: C, 64.89; H, 8.12; N, 3.42; S, 7.77.

(−)-(1S,2R,3R,5R)-2-(2-Hydroxy)ethyl-3-benzenesulfonamido-6,6-dimethylbicyclo[3.1.1]-heptane:

Yield 90.6%. $[\alpha]_D^{23}$ −31.6 (c 1.094, Methanol). nmr δ ppm(CDCl$_3$) 0.80 (3H, s), 1.14 (3H, s), 1.21 (1H, d, J=10 Hz), 1.35–2.18 (8H), 2.30 (1H, br.s), 3.20 (1H, q, J=9 Hz), 3.57 (2H, t, J=6 Hz), 5.65 (1H, d, J=7 Hz), 7.36–7.63 (3H), 7.88–7.99 (2H). IR ν max (CHCl$_3$) 3025, 3530, 3385, 3275, 1327, 1310, 1160, 1091 cm$^{-1}$.

(−)-(1S,2R,3R,5R)-2-Formylmethyl-3-benzenesulfonamido-6,6-dimethylbicyclo[3.1.1]-heptane:

Yield 95.9%. $[\alpha]_D^{24}$ −19.3 (c 2.754, Methanol), nmr δ ppm (CDCl$_3$) 0.82 (3H, s), 1.13 (3H, s), 1.22 (1H, d, J=10 Hz), 1.49–2.78 (8H), 3.24 (1H, m), 5.51 (1H, d, J=9 Hz), 7.38–7.73 (3H), 7.88–7.99 (2H), 9.65 (1H, d, J=2 Hz). Ir, ν max (CHCl$_3$) 3390, 3280, 1723, 1330, 1161 cm$^{-1}$.

(−)-5(Z)-7-[(1S,2R,3R,5R)-3-Benzenesulfonamido-6,6-dimethylbicyclo[3.1.1]hept-2-yl]-5-heptenoic acid (Ih(2R-t))

Yield 95.1%. $[\alpha]_D^{23}$ −2.4, $[\alpha]_{365}^{23}$ +17.6 (c 2.154, Methanol). nmr δ ppm (CDCl$_3$) 0.76 (3H, s), 1.13 (3H, s), 1.22 (1H, d, J=10 Hz), 1.35–2.50 (14H), 3.20 (1H, m), 5.30 (2H, m), 5.42 (1H, d, J=9 Hz), 7.35–7.63 (3H), 7.63 (1H, br.s), 7.86–7.97 (2H). IR ν max (film) 3280, 1710, 1325, 1310, 1160, 1093 cm$^{-1}$.

(−)-5(Z)-7-[(1S,2R,3R,5R)-3-benzenesulfonamido-6,6-dimethylbicyclo[3.1.1]hept-2-yl]-5-heptenoic acid methyl ester:

$[\alpha]_D^{23}$ −1.6, $[\alpha]_{365}^{23}$ 24.8 (c 2.498, Methanol), CD (Methanol) λ nm (Δε): 268.5 (+0.085), 2.61 (+0.112), 258 sh (+0.155), 225 (+2.52). nmr δ (CDCl$_3$) 0.76 (3H, s), 1.13 (3H, s), 1.23 (1H, d, J=10 Hz), 1.40–2.43 (14H), 3.23 (1H, m), 3.69 (3H, s), 5.30 (2H, m), 5.62 (1H, d, J=9 Hz), 7.36–7.70 (3H), 7.92–8.03 (2H). IR ν max (film) 3290, 1740, 1329, 1161, 1096 cm$^{-1}$.

Anal. Calcd. for C$_{23}$H$_{33}$NO$_4$S: C, 65.84; H, 7.93; N, 3.34; S, 7.64 Found: C, 65.78; H, 7.98; N, 3.42; S, 7.49.

Sodium salt of Ih(2R-t); IR ν max (KBr) 1560, 1323, 1308, 1160, 1093 cm$^{-1}$.

Effects of the Invention

The objective compounds of this invention have potent antagonistic action to thromboxane A$_2$ at the receptor, and strongly inhibit platelet agglutination caused by thromboxane A$_2$. This means that the compounds of this invention are expected to be useful antithrombotic and antivasoconstricting drugs. Representative of the compounds of the present invention inhibit platelet-agglutinating actions as shown in the following in vitro test.

[Material tested and Method]

From the carotid artery of a male rabbit (NIBS-JW, body weight 2.2–2.7 kg), the technically obtainable whole blood, 7.2 ml each was collected consecutively with a plastic syringe containing 0.8 ml of 3.8% sodium citrate to make the volumn of each syringe 8.0 ml. The blood was placed in a plastic test tube, mixed by moderate turning and centrifuged for 10 minutes at 210 g at 20° C. to give platelet rich plasma (PRP). The remaining blood was further centrifuged at 3,000 rpm (about 1,900 g) for 10 minutes at 20° C. to give platelet-poor plasma (PPP).

PRP was diluted with PPP to prepare a sample whose platelet number was 5–50×10$^4$/μl. The sample was then subjected to a platelet agglutination test.

The platelet agglutination test was performed according to Born's method [Born, G. V. R., Nature, 194, 927–929 (1962)], and the measurement was made by an aggregometer (Model AUTO RAM-61, Rika Denki Kogyo CO., Ltd.). 400 μl of PRP, whose platelet number was prepared to count 50–55×10$^4$/μl, was placed in a measuring cuvette and set in the aggregometer. PRP was stirred for 1 minute (at 1,200 rpm) at 37° C. and preliminarily warmed. Two minutes after adding the solution of the test compound (50 μl saline solution of the compound, or 2 μl dimethylsulfoxide solution of the compound +48 μl saline) to the cuvette, 50 μl of adenosine 5-diphosphate (ADP: PL-Biochemical Inc.), collagen (Hormon-Chemie, München), or arachidonic acid (sodium salt, Sigma) was added as a platelet agglutinating agent, and the change in light transmittance caused by platelet agglutination was recorded against time elapsed.

Setting the light transmittance for PRP at 0% of platelet agglutination rate, and that for PPP at 100%, the maximum light transmittance for the sample PRP after the addition of the platelet agglutinating agent was regarded as the maximum platelet agglutination rate.

The agglutination inhibition rate (%) was calculated from the ratio of the maximum agglutination rate in the test-compound-added group to that in the control group (carrier-added group).

[Results]

The results of the test are shown in Table 7.

Prostaglandin (PG) $E_1$ served as a standard substance.

TABLE 7
(No. 1)
The results of the compounds (sodim salt) prepared in Example I - 1

| Platelet agglutinating agent and final concentration | * Compound number | Final concentration (μM) | Agglutination inhibition rate (%) |
|---|---|---|---|
| Arachidonic acid 500 μM | | 0.5 | 9.2 |
| | 12 (Example 8) | 1 | 72.5 |
| | | 2 | 96.7 |
| | | 5 | 13.9 |
| | | 10 | 31.0 |
| | 14 (Example 8) | 20 | 69.9 |
| | | 40 | 94.0 |
| | 19 (Example 13) | 1 | 12.3 |
| | | 2 | 78.8 |
| | | 4 | 90.0 |
| | 20 (Example 14) | 1 | 26.6 |
| | | 2 | 83.0 |
| | | 4 | 87.2 |
| ADP 30 μM | 12 | 800 | 3.6 |
| | 14 | 800 | −0.2 |
| | 19 | 800 | −2.3 |
| | 20 | 800 | 4.5 |
| | PG $E_1$ | 0.2 | 91.1 |
| Collagen 20 μG/HL | 12 | 800 | 41.8 |
| | 14 | 800 | 29.7 |
| | 19 | 800 | 36.5 |
| | 20 | 800 | 26.3 |
| | PG $E_1$ | 0.1 | 100.0 |

TABLE 7
(No. 2)
The results of the compounds described in Example I - 1, Table 1.

| Platelet agglutinating agent and final concentration | * Compound number | Final concentration (μM) | Agglutination inhibition rate (%) |
|---|---|---|---|
| | 23 (No. 1) | 2.5 | 2.2 |
| | | 5 | 16.5 |
| | | 10 | 79.1 |
| | 26 (No. 1) | 0.25 | 2.1 |
| | | 0.5 | 60.0 |
| | | 1 | 92.4 |
| | 29 (No. 2) | 1.25 | 0.4 |
| | | 2.5 | 10.8 |
| | | 5 | 29.1 |
| | | 10 | 78.5 |
| | 32 (No. 2) | 1.25 | 10.4 |
| | | 2.5 | 27.9 |
| | | 5 | 43.8 |
| | | 10 | 83.2 |
| | 35 (No. 3) | 200 | 6.2 |
| | | 400 | 18.4 |
| | 38 (No. 3) | 400 | 6.7 |
| | | 800 | 23.8 |
| | PG $E_1$ | 0.1 | 13.4 |
| | | 0.2 | 34.9 |
| | | 0.4 | 72.0 |
| | | 0.8 | 99.1 |

TABLE 7
(No. 3)
The results of the compounds prepared in Example I - 5

| Platelet agglutinating agent and final concentration | * Compound number | Final concentration (μM) | Agglutination inhibition rate (%) |
|---|---|---|---|
| Arachidonic acid 500 μM | 9 (Example 44) | 10 | 6.1 |
| | | 20 | 12.7 |
| | | 40 | 34.5 |
| | | 80 | 89.5 |
| | 17 (Example 45) | 2.5 | 4.1 |
| | | 5 | 19.6 |
| | | 10 | 65.7 |
| | | 20 | 78.7 |
| | PG $E_1$ | 0.1 | 13.4 |
| | | 0.2 | 34.9 |
| | | 0.4 | 72.0 |
| | | 0.8 | 99.1 |

TABLE 7
(No. 4)
The results of the compound prepared in Example I - 6.

| Platelet agglutinating agent and final concentration | * Compound number | Final concentration (μM) | Agglutination inhibition rate (%) |
|---|---|---|---|
| Arachidonic acid 500 μM | I a-ca (2S*-c) (Example 46) | 5 | 10.0 |
| | | 10 | 22.1 |
| | | 20 | 51.9 |
| | | 40 | 87.3 |
| | PG $E_1$ | 0.1 | 13.4 |
| | | 0.2 | 34.9 |
| | | 0.4 | 72.0 |
| | | 0.8 | 99.1 |

TABLE 7
(No. 5)
The results of the compounds prepared in Examples I - 7 and I - 8.

| Platelet agglutinating agent and final concentration | * Compound number | Final concentration (μM) | Agglutination inhibition rate (%) |
|---|---|---|---|
| Arachidonic acid 500 μM | I b-ca (2S*-t) Example 47) | 25 | 18.3 |
| | | 50 | 65.8 |
| | | 100 | 93.3 |
| | I b-ca (2R*-c) (Example 48) | 5 | 0.5 |
| | | 10 | 18.7 |
| | | 20 | 38.8 |
| | | 40 | 77.5 |
| | I b-ca (2R*-t) (Example 49) | 0.5 | 11.0 |
| | | 1 | 53.5 |
| | | 2 | 84.5 |
| | PG $E_1$ | 0.1 | 13.4 |
| | | 0.2 | 34.9 |
| | | 0.4 | 72.0 |
| | | 0.8 | 99.1 |

TABLE 7
(No. 6)
The results of the compounds prepared in Example II.

| Platelet agglutinating agent and final concentration | * Compound number | Final concentration (μM) | Agglutination inhibition rate (%) |
|---|---|---|---|
| Arachidonic acid 500 μM | I e-ac (2S*-t) (Example 1) | 2 | 10.1 |
| | | 4 | 26.0 |
| | | 8 | 73.9 |
| | PG $E_1$ | 0.1 | 13.4 |
| | | 0.2 | 34.9 |
| | | 0.4 | 72.0 |
| | | 0.8 | 99.1 |

TABLE 7

(No. 7)
The results of the compounds prepared in Example III.

| Platelet agglutinating agent and final concentration | * Compound number | Final concentration (μM) | Agglutination inhibition rate (%) |
|---|---|---|---|
| Arachidonic acid 500 μM | I f-ac (3S*-β) (Example 1) | 2 | 1.3 |
| | | 4 | 30.1 |
| | | 8 | 74.5 |
| | | 10 | 0.9 |
| | I f-ac (3R*-β) (Table 3) | 20 | 29.2 |
| | | 40 | 51.7 |
| | | 80 | 74.8 |
| | I f-ac (3S*-α) (Table 4) | 5 | 14.2 |
| | | 10 | 36.3 |
| | | 20 | 82.2 |
| | I f-bc (3S*-β) (Table 5) | 200 | 6.2 |
| | | 400 | 30.2 |
| | | 800 | 95.8 |
| | I f-bc (3S*-α) (Table 6) | 20 | 9.0 |
| | | 40 | 36.0 |
| | | 80 | 88.4 |
| | PG E₁ | 0.1 | 13.4 |
| | | 0.2 | 34.9 |
| | | 0.4 | 72.0 |
| | | 0.8 | 99.1 |

TABLE 7

(No. 8)
The results of the compound prepared in Example IV.

| Platelet agglutinating agent and final concentration | * Compound number | Final concentration (μM) | Agglutination inhibition rate (%) |
|---|---|---|---|
| | I h-ca (2S-t-5Z) (Example 1) | 50 | 12.7 |
| | | 100 | 31.2 |
| | | 200 | 88.9 |
| | I h-ca (2S-c) (Example 2) | 400 | 8.7 |
| | | 800 | 30.3 |
| | PG E₁ | 0.1 | 13.4 |
| | | 0.2 | 34.9 |
| | | 0.4 | 72.0 |
| | | 0.8 | 99.1 |

*Compound number corresponds to that used in Example.

The objective compounds of this invention show potent inhibitory action against platelet agglutination caused by thromboxane.

The objective compounds of this invention strongly inhibit thromboxane induced platelet agglutination, vasoconstriction, and bronchoconstriction. Therefore, clinical application of such pharmacological action of the compound can be expected, that is, the compounds can be used for treatment or improvement of such symptoms as arteriosclerosis, myocardial infarction, acute ischemic angina pectoris, circulatory shock, sudden death and so forth. The objective compounds of this invention can be administered oral by or parenterally. For example, tablets, capsules, pills, granules, fine subtilaes, solutions, emulsions, suppositories, and injections for intravenous, intramuscular, and subcutaneous administration can be prepared for the compound. When the pharmaceutical preparations of the compounds are prepared, adequate carriers and fillers are selected from conventionally used carriers and fillers.

The objective compounds of this invention are to be administered to an adult in a daily dose of 10-800 mg.

What we claim is:

1. A compound represented by the formula:

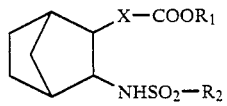

wherein $R_1$ is a hydrogen or $C_1$-$C_5$ alkyl; $R_2$ is an $C_1$-$C_{10}$ alkyl, aryl, aralkyl, or pyridyl, where the aryl, aralkyl, or pyridyl are unsubstituted or are substituted by $C_1$-$C_5$ alkyl, $C_1$-$C_5$ alkoxy, nitro, hydroxy, carboxy, amino, $C_1$-$C_5$ alkylamino, $C_1$-$C_5$ dialkylamino whose two alkyl groups may be different from each other, $C_1$-$C_3$ alkanoylamino, or halogen and X is an $C_1$-$C_7$ alkylene, $C_2$-$C_7$ alkenylene, 1-fluoro-2-hexenylene, trimethylenethioethylene, ethylenethiotrimethylene, phenyleneoxymethylene, or 2-propylene-m-phenylene, or its pharmaceutically acceptable salt.

2. A compound represented by the formula:

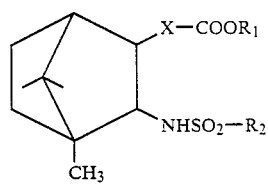

wherein $R_1$ is a hydrogen or $C_1$-$C_5$ alkyl; $R_2$ is an $C_1$-$C_{10}$ alkyl, aryl, aralkyl, or pyridyl, where the aryl, aralkyl, or pyridyl are unsubstituted or are substituted by $C_1$-$C_5$ alkyl, $C_1$-$C_5$ alkoxy, nitro, hydroxy, carboxy, amino, $C_1$-$C_5$ alkylamino, $C_1$-$C_5$ dialkylamino whose two alkyl groups may be different from each other, $C_1$-$C_3$ alkanoylamino, or halogen and X is an $C_1$-$C_7$ alkylene, $C_2$-$C_7$ alkenylene, 1-fluoro-2-hexenylene, trimethylenethioethylene, ethylenethiotrimethylene, phenyleneoxymethylene, or 2-propylene-m-phenylene, or its pharmaceutically acceptable salt.

3. A compound represented by the formula:

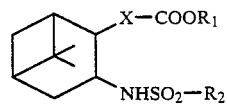

wherein $R_1$ is a hydrogen or $C_1$-$C_5$ alkyl; $R_2$ is an $C_1$-$C_{10}$ alkyl, aryl, aralkyl, or pyridyl, where the aryl, aralkyl, or pyridyl are unsubstituted or are substituted by $C_1$-$C_5$ alkyl, $C_1$-$C_5$ alkoxy, nitro, hydroxy, carboxy, amino, $C_1$-$C_5$ alkylamino, $C_1$-$C_5$ dialkylamino whose two alkyl groups may be different from each other, $C_1$-$C_3$ alkanoylamino, or halogen and X is an $C_1$-$C_7$ alkylene, $C_2$-$C_7$ alkenylene, 1-fluoro-2-hexenylene, trimethylenethioethylene, ethylenethiotrimethylene, phenyleneoxymethylene, or 2-propylene-m-phenylene, or its pharmaceutically acceptable salt.

4. The compound as claimed in claim 1, namely 5(Z)-7-(endo-3-benzenesulfonamidobicyclo[2.2.1]hept-exo-2-yl)-5-heptenoic acid.

5. The compound as claimed in claim 1, namely 5(Z)-7-[endo-3-(p-toluenesulfonamido)bicyclo[2.2.1]hept-exo-2-yl]-5-heptenoic acid.

6. The compound as claimed in claim 1, namely 5(Z)-7-[endo-3-(4-hydroxybenzenesulfonamido)bicyclo[2.2.1]hept-exo-2-yl]-5-heptenoic acid.

7. The compound as claimed in claim 1, namely 5(Z)-7-[endo-3-(4-fluorobenzenesulfonamido)bicyclo[2.2.1]hept-exo-2-yl]-5-heptenoic acid.

8. The compound as claimed in claim 1, namely 5(Z)-7-[endo-3-(4-chlorobenzenesulfonamido)bicyclo[2.2.1]hept-exo-2-yl]-5-heptenoic acid.

9. The compound as claimed in claim 1, namely 3(Z)-5-[endo-3-(p-toluenesulfonamido)bicyclo[2.2.1]hept-exo-2-yl]-3-pentenoic acid.

10. The compound as claimed in claim 1, namely 3(Z)-5-[endo-(4-fluorobenzenesulfonamido)bicyclo[2.2.1]hept-exo-2-yl]-3-pentenoic acid.

11. The compound as claimed in claim 1, namely 5(Z)-7-(exo-3-benzenesulfonamidobicyclo[2.2.1]hept-endo-2-yl)-5-heptenoic acid.

12. The compound as claimed in claim 3, namely 5(Z)-7-[(1S,2S,3S,5R)-3-benzenesulfonamide-6,6-dimethylbicyclo[3.1.1]hept-2-yl]-5-heptenoic acid.

13. The compound as claimed in claim 3, namely 5(Z)-7-[(1S,2S,3R,5R)-3-benzenesulfonamido-6,6-dimethylbicyclo[3.1.1]hept-2-yl]-5-heptenoic acid.

* * * * *